United States Patent
Hagel et al.

(10) Patent No.: US 12,187,679 B2
(45) Date of Patent: Jan. 7, 2025

(54) HYDROXYLATED PSILOCYBIN DERIVATIVES AND METHODS OF USING

(71) Applicant: Enveric Biosciences Canada Inc., Calgary (CA)

(72) Inventors: Jillian M. Hagel, Calgary (CA); Peter J. Facchini, Calgary (CA); Chang-Chun Ling, Calgary (CA)

(73) Assignee: Enveric Biosciences Canada Inc., Calgary (CA)

( * ) Notice: Subject to any disclaimer, the term of this patent is extended or adjusted under 35 U.S.C. 154(b) by 0 days.

(21) Appl. No.: 17/903,103

(22) Filed: Sep. 6, 2022

(65) Prior Publication Data

US 2023/0043896 A1 Feb. 9, 2023

Related U.S. Application Data

(63) Continuation of application No. PCT/CA2021/051210, filed on Sep. 1, 2021.

(60) Provisional application No. 63/073,076, filed on Sep. 1, 2020.

(51) Int. Cl.
C07D 209/16 (2006.01)

(52) U.S. Cl.
CPC .................................. *C07D 209/16* (2013.01)

(58) Field of Classification Search
CPC .................................................. C07D 209/16
See application file for complete search history.

(56) References Cited

U.S. PATENT DOCUMENTS

2018/0221396 A1  8/2018  Chadeayne

FOREIGN PATENT DOCUMENTS

| WO | WO2005039546 A2 | 5/2005 |
| WO | WO2019081764 A1 | 5/2019 |
| WO | WO 2019/173797 A1 * | 9/2019 |
| WO | WO2021016423 A1 | 1/2021 |
| WO | WO2022047580 A1 | 3/2022 |

OTHER PUBLICATIONS

Daniel, J. et al. Clinical potential of psilocybin as a treatment for mental health conditions. Mental Health Clin/, 2017;7(1): 24-28.
Grob, C. et al. Pilot study of psilocybin treatment for anxiety in patients with advanced-stage cancerArch. Gen. Psychiatry, 2011, 68(1) 71-78.
Cathart-Harris, R.L. et al. Psilocybin with psychological support for treatment-resistant depression: an open-label feasibility study. Lancet Psychiatry, 2016, 3: 619-627.
Devereux et al., A comprehensive set of sequence analysis programs for the VAX. Nucleic Acids Res., 1984, 12: 387.
Thompson, J D, Higgines, D G and Gibson T J. Clustal W: improving the sensitivity of progressive multiple sequence alignment through sequence weighting, position-specific gap penalties and weight matrix choice. 1994, Nucleic Acid Res 22(22): 4673-4680.
S. Kawai et al., Transformation of *Saccharomyces cerevisiae* and other fungi: methods and possible underlying mechanism. Bioeng Bugs. Nov.-Dec. 2010;1(6):395-403.
Henikoff S & Henikoff, J G, Amino acid substitution matrices from protein blocks. Proc Natl Acad Sci U S A. Nov. 15, 1992;89(22):10915-9.
Ross, S. et al. Acute and Sustained Reductions in Loss of Meaning and Suicidal Ideation Following Psilocybin-Assisted Psychotherapy for Psychiatric and Existential Distress in Life-Threatening Cancer. ACS Pharmacol Transl Sci. Apr. 9, 2021; 4(2): 553-562.
Durak L.J. et al. Late-Stage Diversification of Biologically Active Molecules via Chemoenzymatic C—H Functionalization ACS Catal. Mar. 4, 2016; 6(3): 1451-1454.
Corr M.J. et al. Sonogashira diversification of unprotected halotryptophans, halotryptophan containing tripeptides; and generation of a new to nature bromo-natural product and its diversification in water Chem Sci. Mar. 1, 2017;8(3):2039-2046.
Kikura-Hanajiri, R. et al. Simultaneous determination of nineteen hallucinogenic tryptamines/-calbolines and bhenethylamines using gas chromatography-mass spectrometry and liquid chromatography-electrospray ionisation-mass spectrometry. Journal of Chromatography B, 825 (2005) 29-37.
Chang et al., Isolation and Characterization of O-methyltransferases Involved in the Biosynthesis of Glaucine in Glaucium flavum. 2015, Plant Physiol. 169: 1127-1140.
Pyrgiotakis G. et al., Cell death discrimination with Raman spectroscopy and support vector machines. 2009, Ann. Biomed. Eng. 37: 1464-1473.
Jones et al. ePathOptimize: A Combinatorial Approach for Transcriptional Balancing of Metabolic Pathways. 2015, Sci Rep. 5: 11301.
Göthert, M. Serotonin discovery and stepwise disclosure of 5-HT receptor complexity over four decades. Part I. General background and discovery of serotonin as a basis for 5-HT receptor identification Pharmacol Rep. 2013;65(4):771-86.
Kim K. et al., Structure of a Hallucinogen-Activated Gq-Coupled 5-HT 2A Serotonin Receptor. 2020, Cell 182: 1574-1588.
Fasciani, I. et al., Allosteric Modulators of G Protein-Coupled Dopamine and Serotonin Receptors: A New Class of Atypical Antipsychotics. 2020, Pharmaceuticals 13: 388.
Gao Z. and Jacobsen K.A., Allosteric modulation and functional selectivity of G protein-coupled receptors2013, Drug Discov. Today Technol. 10: e237-e243.

(Continued)

*Primary Examiner* — Shawquia Jackson
(74) *Attorney, Agent, or Firm* — SMART & BIGGAR LP; Michael Fenwick

(57) ABSTRACT

Disclosed are novel hydroxylated psilocybin derivative compounds and pharmaceutical and recreational drug formulations containing the same. The compounds may be produced synthetically or biosynthetically.

26 Claims, 33 Drawing Sheets

Specification includes a Sequence Listing.

(56) References Cited

OTHER PUBLICATIONS

Sherwood, A.M. et al. Synthesis and Biological Evaluation of Tryptamines Found in Hallucinogenic Mushrooms: Norbaeocystin, Baeocystin, Norpsilocin, and Aeruginascin. J. Nat. Prod. 2020, 83, 461-467.

Sard, H. et al. SAR of psilocybin analogs: Discovery of a selective 5-HT2C agonist. Bioorganic & Medicinal Chemistry Letters 15 (2005) 4555-4559.

Altschul et al., Basic local alignment search tool. J Mol Biol. Oct. 5, 1990;215(3):403-10.

Needleman and Wunsch. A general method applicable to the search for similarities in the amino acid sequence of two proteins J. Mol. Biol., 1970, 48: 443.

Carillo and Lipton. SIAM J. Applied Math., 1988, 48:1073.

Finnin, B. and Morgan, T.M., Transdermal penetration enhancers: applications, limitations, and potential J Pharm Sci. Oct. 1999;88(10):955-8.

Schnepel C. et al. Enzymatic Halogenation: A Timely Strategy for Regioselective C—H Activation. Chemistry. Sep. 7, 2017;23(50):12064-12086.

Runguphan W. et al. Diversification of monoterpene indole alkaloid analogs through cross-coupling. Org Lett. Jun. 7, 2013;15(11):2850-3.

Roy A.D. et al. Development of fluorescent aryltryptophans by Pd mediated cross-coupling of unprotected halotryptophans in water. Chem Commun (Camb). Oct. 21, 2008;(39):4831-3.

Romeo, B. et al. Clinical and biological predictors of psychedelic response in the treatment of psychiatric and addictive disorders: A systematic review. J Psychiatr Res 137: 273, 2021.

Cregg et al., Recombinant protein expression in Pichia pastoris. Mol Biotechnol. (2000) 16(1): 23-52.

Mattanovich et al., Recombinant protein production in yeasts. Methods Mol. Biol., 2012, 824:329-58.

Romanos et al., Foreign gene expression in yeast: a review. Yeast. Jun. 1992;8(6):423-88.

Menéndez-Perdomo et al. Benzylisoquinoline alkaloid analysis using high-resolution Orbitrap LC-MS n2021, Mass Spectrom 56: e4683.

Servillo L. et al., Benzylisoquinoline alkaloid analysis using high-resolution Orbitrap LC-MS n J. Agric. Food Chem 61: 5156-5162.

Sherwood, A.M. et al An Improved, Practical, and Scalable Five-Step Synthesis of Psilocybin. Synthesis 2020, 52, 688-694.

Smith and Waterman. Adv. Appl. Math., 1981, 2: 482.

Fricke, Janis et al. Chemoenzymateic Synthesis of 5-Methylpsilocybin: A Tryptamine with Potential Psychedelic Activity. J. Nat. Prod. 2021, 84, 1404-1408.

* cited by examiner

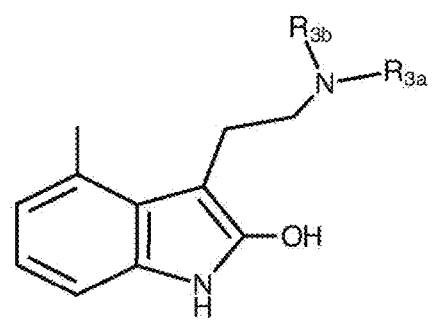
FIG. 3J
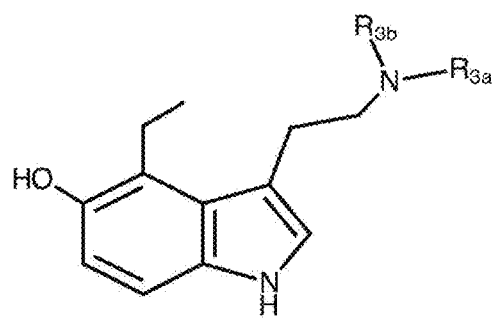
FIG. 3K
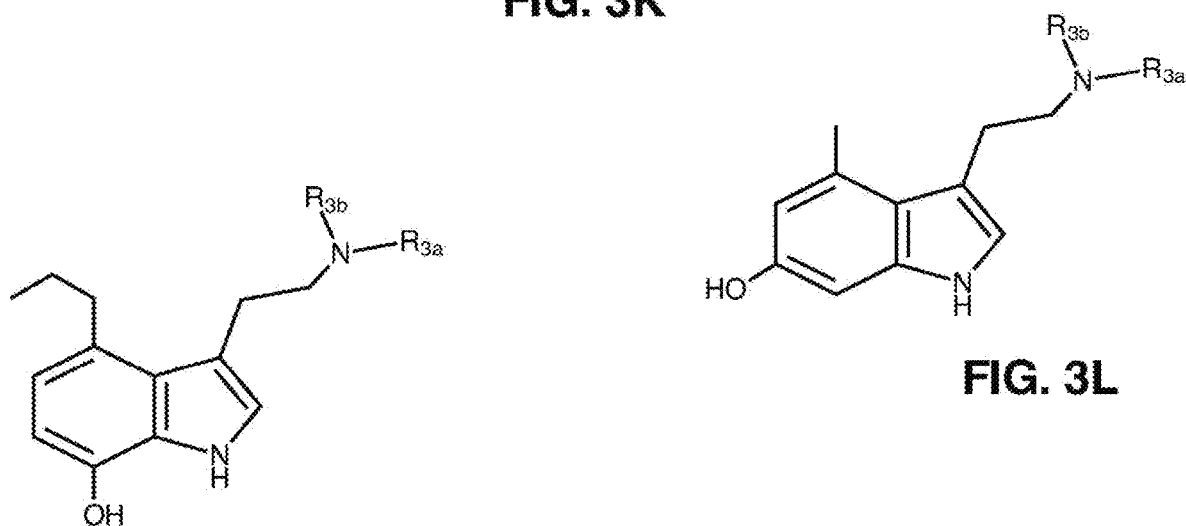
FIG. 3M
FIG. 3L

SEQUENCE LISTING

```
Sequence total quantity: 44
SEQ ID NO: 1            moltype = DNA  length = 1320
FEATURE                 Location/Qualifiers
source                  1..1320
                        mol_type = genomic DNA
                        organism = Psilocybe cubensis
SEQUENCE: 1
atgcaggtga tacccgcgtg caactcggca gcaataagat cactatgtcc tactcccgag   60
tcttttagaa acatgggatg gctctctgtc agcgatgcgg tctacagcga gttcatagga  120
```

```
gagttggcta  cccgcgcttc  caatcgaaat  tactccaacg  agttcggcct  catgcaaacct   180
atccaggaat  tcaaggcttt  cattgaaagc  gacccggtgg  tgcaccaaga  atttattgac   240
atgttcgagg  gcattcagga  ctctccaagg  aattatcagg  aactatgtaa  tatgttcaac   300
gatatctttc  gcaaagctcc  cgtctacgga  gaccttggcc  ctcccgttta  tatgattatg   360
gccaaattaa  tgaacacccg  agcgggcttc  tctgcattca  cgagacaaag  gttgaaccttt  420
cacttcaaaa  aacttttcga  tacctgggga  ttgttcctgt  cttcgaaaga  ttctcgaaat   480
gttcttgtgg  ccgaccagtt  cgacgacaga  cattgcggct  ggttaaacga  gcgggccttg   540
tctgctatgt  taaacatta   caatggacgc  gcatttgatg  aagtcttcct  ctgcgataaa   600
aatgccccat  actacggctt  caactcttac  gacgacttct  ttaatcgcag  atttcgaaac   660
cgagatatcg  accgacctgt  agtcggtgga  gttaacaaca  ccaccctcat  ttctgctgct   720
tgcgaatcac  tttcctacaa  cgtctcttat  gactcagt    ctctcgacac  tttagttttc   780
aaaggagaga  cttattcgct  taagcatttg  ctgaataatg  acccttttcac cccacaattc   840
gagcatggga  gtattctaca  aggattcttg  aacgtcaccg  cttaccaccg  atggcacgca   900
cccgtcaatg  ggacaatcgt  caaaatcatc  aacgttccag  gtacctactt  tgcgcaagcc   960
ccgagcacga  ttggcgaccc  tatcccggat  aacgattacg  acccaccttc  ttaccttaag  1020
tctcttgtct  acttctctaa  tattgccgca  aggcaaatta  tgtttattga  agccgacaac  1080
aaggaaattg  gcctcatttt  ccttgtgttc  atcggcatga  ccgaaatctc  gacatgtgaa  1140
gccacggtgt  ccgaaggtca  acacgtcaat  cgtggcgatg  acttgggaat  gttccatttc  1200
ggtggttctt  cgttcgcgct  tggtctgagg  aaggattgca  gggcagagat  cgttgaaaag  1260
ttcaccgaac  ccggaacagt  gatcagaatc  aacgaagtcg  tcgctgctct  aaaggcttag  1320

SEQ ID NO: 2       moltype = AA   length = 439
FEATURE            Location/Qualifiers
source             1..439
                   mol_type = protein
                   organism = Psilocybe cubensis
SEQUENCE: 2
MQVIPACNSA AIRSLCPTPE SFRNMGWLSV SDAVYSEFIG ELATRASNRN YSNEFGLMQP   60
IQEFKAFIES DPVVHQEFID MFEGIQDSPR NYQELCNMFN DIFRKAPVYG DLGPPVYMIM  120
AKLMNTRAGF SAFTRQRLNL HFKKLFDTWG LFLSSKDSRN VLVADQFDDR HCGWLNERAL  180
SAMVKHYNGR AFDEVFLCDK NAPYYGFNSY DDFFNRRFRN RDIDRPVVGG VNNTTLISAA  240
CESLSYNVSY DVQSLDTLVF KGETYSLKHL LNNDPFTPQF EHGSILQGFL NVTAYHRWHA  300
PVNGTIVKII NVPGTYFAQA PSTIGDPIPD NDYDPPPYLK SLVYFSNIAA RQIMFIEADN  360
KEIGLIFLVF IGMTEISTCE ATVSEGQHVN RGDDLGMFHF GGSSFALGLR KDCRAEIVEK  420
FTEPGTVIRI NEVVAALKA                                               439

SEQ ID NO: 3       moltype = DNA   length = 2155
FEATURE            Location/Qualifiers
source             1..2155
                   mol_type = genomic DNA
                   organism = Psilocybe cubensis
SEQUENCE: 3
atgatcgctg  tactattctc  cttcgtcatt  gcaggatgca  tatactacat  cgtttctcgt   60
agagtgaggc  ggtcgcgctt  gccaccaggg  ccgcctggca  ttcctattcc  cttcattggg  120
aacatgtttg  atatgcctga  agaatctcca  tggttaacat  ttctacaatg  gggacgggat  180
tacagtctgt  cttgccgcgt  tgacttctaa  tatatgaaca  gctaatatat  tgtcagacac  240
cgatattctc  tacgtggatg  ctggagggac  agaaatgact  tttaacca    cgttggagac  300
cattaccgat  ctattagaaa  agcgagggtc  catttattct  ggccggtgag  ctgatgttga  360
gttttttgca  attgaatttg  tggtcacacg  tttccagact  tgagagtaca  atggtcaacg  420
aacttatggg  gtgggagttt  gacttagggt  tcatcacata  cggcgacagg  tggcgcgaag  480
aaaggcgcat  gttcgccaag  gagttcagtg  agaagggcat  caagcaattt  gccatgctn  540
aagtgaaagc  tgcccatcag  cttgtccaac  agcttaccaa  aacgccagac  cgctgggcac  600
aacatattcg  ccagtaagta  ctacttgagg  aaaatagcgt  acgcttcgct  gaccggtccg  660
tacatcaaag  tcagatagcg  gcaatgtcac  tggatattgg  ttatggaatt  gatcttgcag  720
aagacgaccc  ttggctggaa  gcgacccatt  tggctaatga  aggcctcgcc  atagcatcag  780
tgccgggcaa  attttgggtc  gattcgttcc  cttctcgtga  gcatccttct  tctatgtagg  840
aagggaagga  gtctaacaag  tgttagtaaa  ataccttcct  gcttggttcc  caggtgctgt  900
cttcaagcgc  aaagcgaagg  tctggcgaga  agccgccgac  catatggttg  acatgcctta  960
tgaaactatg  aggaaattag  cagttagtca  aatgcgttct  ccccgtattt  tttcaatact  1020
ctaacttcag  ctcacagcct  caaggattga  ctcgtccgtc  gtatgcttca  gctcgtctgc  1080
aagccatgga  tctcaacggt  gaccttgagc  atcaagaaca  cgtaatcaag  aacacagccg  1140
cagaggttaa  tgtcggtaag  tcaaaagcgt  ccgtcggcaa  ttcaaaattc  aggcgctaaa  1200
gtgggtcttc  tcaccaaggt  ggaggcgata  ctgtaaggat  ttctcaatcg  ttagagtata  1260
agtgttctaa  tgcagtacat  actccaccaa  ccagactgtc  tctgctaagt  ctgcgttcat  1320
cttggccatg  gtgaagtacc  ctgaggtcca  gcgaaaggtt  caagcggagc  ttgatgctct  1380
gaccaataac  ggccaaattc  ctgactatga  cgaagaagtt  gactccttgc  catacctcac  1440
cgcatgtatc  aaggagcttt  tccggtgaaa  tcaaatcgca  cccctcgcta  taccgcacaa  1500
attaatgaag  gacgacgtgt  accgcgggta  tctgattccc  aagaacactc  tagtcttcgc  1560
aaacacctgg  tgaggctgtc  cattcattcc  tagtacatcc  gttgcccac   taatagcatc  1620
ttgataacag  ggcagtatta  aacgatccag  aagtctatcc  agatccctct  gtgttccgcc  1680
cagaaagata  tcttggtcct  gacgggaagc  ctgataacac  tgtacgcgac  ccacgtaaag  1740
cggcatttgg  ctatgacga   cgaaattggt  aagtgcgctt  tcagaacccc  ccttccgtt   1800
gactagtgcc  atgcgcgcat  acaatatcgc  tattgatctg  atataacttc  cctgcggcat  1860
ttattttggc  attcctttag  tcccggaatt  catctagcgc  agtcgacggt  ttggattgca  1920
ggggcaaccc  tcttatcagc  gttcaatatc  gagcgacctg  tcgatcagaa  tgggaagccc  1980
attgacatac  cggctgattt  tactacagga  ttccttcaggt  agctaatttc  cgtctttgtg  2040
tgcataaatac  ccctaacgac  gcacgtttac  cttttttgtaa  agacacccag  tgcctttcca  2100
gtgcaggttt  gttcctcgaa  cagagcaagt  ctcacagtcg  gtatccggac  cctga       2155
```

```
SEQ ID NO: 4              moltype = AA  length = 508
FEATURE                   Location/Qualifiers
source                    1..508
                          mol_type = protein
                          organism = Psilocybe cubensis
SEQUENCE: 4
MIAVLFSFVI AGCIYYIVSR RVRRSRLPPG PPGIPIPFIG NMFDMPEESP WLTFLQWGRD   60
YNTDILYVDA GGTEMVILNT LETITDLLEK RGSIYSGRLE STMVNELMGW EFDLGFITYG  120
DRWREERRMF AKEFSEKGIK QFRHAQVKAA HQLVQQLTKT PDRWAQHIRH QIAAMSLDIG  180
YGIDLAEDDP WLEATHLANE GLAIASVPGK FWVDSFPSLK YLPAWFPGAV FKRKAKVWRE  240
AADHMVDMPY ETMRKLAPQG LTRPSYASAR LQAMDLNGDL EHQEHVIKNT AAEVNVGGGD  300
TTVSAMSAFI LAMVKYPEVQ RKVQAELDAL TNNGQIPDYD EEDDSLPYLT ACIKELFRWN  360
QIAPLAIPHK LMKDDVYRGY LIPKNTLVFA NTWAVLNDPE VYPDPSVFRP ERYLGPDGKP  420
DNTVRDPRKA AFGYGRRNCP GIHLAQSTVW IAGATLLSAF NIERPVDQNG KPIDIPADFT  480
TGFFRHPVPF QCRFVPRTEQ VSQSVSGP                                    508

SEQ ID NO: 5              moltype = DNA  length = 1089
FEATURE                   Location/Qualifiers
source                    1..1089
                          mol_type = genomic DNA
                          organism = Psilocybe cubensis
SEQUENCE: 5
atggcgttcg atctcaagac tgaagacggc ctcatcacat atctcactaa acatctttct   60
ttggacgtcg acacgagcgg agtgaagcgc cttagcggag gctttgtcaa tgtaacctgg  120
cgcattaagc tcaatgctcc ttatcaaggt catacgagca tcatcctgaa gcatgctcag  180
ccgcacatgt ctacggatga ggattttaag ataggtgtag aacgttcggt ttacgaatac  240
caggctatca agctcatgat ggccaatcgg gaggttctgg gaggcgtgga tggcatagtt  300
tctgtgccag aaggcctgaa ctacgactta gagaataatg cattgatcat gaagatgtc   360
gggaagatga agacccttt agattatgtc accgccaaac cgccacttgc gacggatata  420
gcccgccttg ttgggacaga aattgggggg ttcgttgctc gactccataa cataggccgt  480
gagaggcgag acgatcctga gttcaaattc ttctctggaa atattgtcgg aaggacgact  540
tcagaccagc tgtatcaaac catcataccc aacgcagcga aatatggcgt cgatgacccc  600
ttgctgccta ctgtggttaa ggaccttgtg acgatgtca tgcacagcga agagaccctt  660
gtcatgcggc acctgtggag tggaaatatt cttctccagt tggaggaggg aaacccatcg  720
aagctgcaga agatatatat cctgattgg gaactttgca agtacggccc agcgtcgttg  780
gacctgggct attttcttgg tgactgctat ttgatatccc gctttcaaga cgagcaggtc  840
ggtacgacga tgcggcaagc ctacttgcaa agctatgcgc gtacgagcaa gcattcgatc  900
aactacgcca aagtcactgc aggtattgct gctcatattg tgatgtggac cgactttatg  960
cagtgggggg gcgaggaaga aaggataaat tttgtgaaaa aggggtagc tgcctttcac  1020
gacgccaggg gcaacaacga caatgggaa attacgtcta ccttactgaa ggaatcatcc  1080
actgcgtaa                                                         1089

SEQ ID NO: 6              moltype = AA  length = 309
FEATURE                   Location/Qualifiers
source                    1..309
                          mol_type = protein
                          organism = Psilocybe cubensis
SEQUENCE: 6
MHIRNPYRTP IDYQALSEAF PPLKPFVSVN ADGTSSVDLT IPEAQRAFTA ALLHRDFGLT   60
MTIPEDRLCP TVPNRLNYVL WIEDIFNYTN KTLGLSDDRP IKGVDIGTGA SAIYPMLACA  120
RPFKAWSMVGT EVERKCIDTA RLNVVANNLQ DRLSILETSI DGPILVPIFE ATEEYEYEFT  180
MCNPPFYDGA ADMQTSDAAK GFGFGVGAPH SGTVIEMSTE GGESAFVAQM VRESLKLRTR  240
CRWYTSNLGK LKSLKEIVGL LKELEISNYA INEYVQGSTR RYAVAWSFTD IQLPEELSRP  300
SNPELSSLF                                                          309

SEQ ID NO: 7              moltype = DNA  length = 930
FEATURE                   Location/Qualifiers
source                    1..930
                          mol_type = genomic DNA
                          organism = Psilocybe cubensis
SEQUENCE: 7
atgcatatca gaaatcctta ccgtacacca attgactatc aagcactttc agaggccttc   60
cctcccctca gccatttgt gtctgtcaat gcagatggta ccagttctgt tgacctcact  120
atcccagaag cccagagggc gttcacggcc gctcttcttc atcgtgactt cgggctcacc  180
atgaccatac cagaagaccg tctgtgccca acagtcccca taggttgaa ctacgttctg  240
tggattgaag atttttcaa ctacacgaac aaaaccctcg gcctgtcgga tgaccgtcct  300
attaaaggcg ttgatattgg tacaggagcc tccgcaattt atcctatgct tgcctgtgct  360
cggttcaagg catggtctat ggttggaaca gaggtcgaga ggaagtgcat tgacacggcc  420
cgcctcaatg tcgtcgcgaa caatctccaa gaccgtctct cgatattgaa gacatccatt  480
gatggtccta ttctcgtccc catttttgag gcgactgaag aatacgaata cgagtttact  540
atgtgtaacc ctccattcta cgacggtgct gccgatatgc agacttcgga tgctgccaaa  600
ggatttggat ttggcgtggg cgctccccat tctggaacag tcatcgaaat gtcgactgag  660
ggaggtgaat cggctttcgt cgctcagatg gtccgtgaga gcttgaagct tcgaacacga  720
tgcagatggt acacgagtaa cttgggaaag ctgaaatcgt tgaaagaact agtgggggtg  780
ctgaaagaac ttgagataag caactatgcc attaacgaat acgttcaggg gtccacacgt  840
cgttatgccg ttgcgtggtc tttcactgat attcaactgc ctgaggagct ttctcgtccc  900
tctaaccccg agctcagctc tcttttctag                                   930

SEQ ID NO: 8              moltype = AA  length = 309
```

```
FEATURE                 Location/Qualifiers
source                  1..309
                        mol_type = protein
                        organism = Psilocybe cubensis
SEQUENCE: 8
MHIRNPYRTP  IDYQALSEAF  PPLKPFVSVN  ADGTSSVDLT  IPEAQRAFTA  ALLHRDFGLT   60
MTIPEDRLCP  TVPNRLNYVL  WIEDIFNYTN  KTLGLSDDRP  IKGVDIGTGA  SAIYPMLACA  120
RFKAWSMVGT  EVERKCIDTA  RLNVVANNLQ  DRLSILETSI  DGPILVPIFE  ATEEYEYEFT  180
MCNPPFYDGA  ADMQTSDAAK  GFGFGVGAPH  SGTVIEMSTE  GGESAFVAQM  VRESLKLRTR  240
CRWYTSNLGK  LKSLKEIVGL  LKELEISNYA  INEYVQGSTR  RYAVAWSFTD  IQLPEELSRP  300
SNPELSSLF                                                               309

SEQ ID NO: 9            moltype = DNA  length = 3042
FEATURE                 Location/Qualifiers
source                  1..3042
                        mol_type = genomic DNA
                        organism = Psilocybe cubensis
SEQUENCE: 9
atgccttcca gtcaccctca cattactcat cgctatcggg ttccttcgag tgacgaccat    60
gaacgtatat ctgctctgtt cttgggtccc aaagcagaaa atgccgcatt tctccagcaa   120
tggttgacca cggtcgtcgc acagcaaaag gctgcccgcg atgcatactt cccggatgac   180
aatgcttttta ttactacaga catgcaaact tccccccgcct ttgctcagac tactaaagta   240
atcgcctcca atctcaccga attattgact gcactcggtg aaaggtcgat tcctttcttc   300
tcacctcggt acagcggcca tatgtctgtg gaccaaagtc tacctgccat tctcggattc   360
ttatcgacca cattttataa tcctaacaat gttgccttcg aggctagtcc attcacgacc   420
ctcatcgagg aagaagttgg cttgcaactc tctgaaatgt ctggttataa tcggctaaat   480
aacaccgaga aacctctcgc ctggggacat attgcatcag gtggaactgt tgcaaacttg   540
gaagcgatgt gggcggcgcg aaacctcaag ttttaccctc tctcactccg tgatgcttca   600
gccgaaggcg cagagatgga attcattcgt gacacattct ccgtcaaaac ctgtgttggt   660
gacaaaaaat tattaaagga ttgcagccca tgggaactcc tcaatttgca tgtttctact   720
atcttagaca tgcccgaccg tctgcacgac gagtacaata tttcacctcg gttcctcgaa   780
aaggttatgc gaaagtatat catccagtct accaacaaag cacgttgat gcagcgttgg    840
ggacttaccc aacaacctgt cgttttatcc ccgagcacaa accattattc ctggccaaag   900
gctgcagctg tgctcggtat tggctcagac aaccttcgca acgtcccagt agacatccat   960
gcccacatgg acataaacga actcgatcgt atgttaaaaa tttgcttgga cgaggagacg  1020
ccagtatatc aagtagttgc tgttatcggt accaccgaag agggcggtgt cgatcgcatt  1080
acggagatcc tgaagctgcg ccaaaagtat gaagctttgg ggctgtcttt tgccatccat  1140
gcagatgctg cttggggagg ctattttgca accatgctac ccaaagatac attgggtcga  1200
aaccggacta ggcttcccaa agaggacact acctcgggct ttgtccctca cgtcggtctg  1260
cgcgaggaga gcgcgttaca actcagccat ataaagtatg ccgattctat tactatcgac  1320
ccgcacaagg caggctatgt tccttacccc gctggggcac tctgttatcg cgacggaaga  1380
atgaggtacc tgcttacatg gtccgcgccc taccttgccc aaggcaacga gggcaaagt   1440
atcggaatat acgggatcga aggaagcaaa cctggtcagcagcatccgg ggtattcatg   1500
gcgcacgaaa ccattggcct gactccttct ggatacggga accttcttgg ccagcaatg   1560
tttacatgtc gccgatacgc tgctcactgg tctgcaatgt caacggatac taccagtttc  1620
actgtcaccc cgttcaatcc tatccctgct gacatcgacc ccaacgctga cccgcaaag   1680
gtcgaagagc aaaaacagtt catcagagat cgtatcttgt tcaaatcgaa cgaggaaata  1740
tacaacgatt ctgaggctat ggaactcttg caccaacttg ggtccgatct caatatcaac  1800
gttttcgcat gcaacttccg cgaccgcgat aataatctca caccgacgt cgaggaagcc   1860
aactggctca ataccgtat tttccaacgc ttttctgtta caagtgctga ggagaaccca   1920
ttggaaacgc cattcttcct cagctcaact acattgaaaa atccgaata cggcgtctag  1980
gcaaccgaag taaagagacg catgggactt gttggtgacc aggatgttat agtcctgagg  2040
aacgtcgtta tgtctccatt tactacaacg aacgactttg tgggaactct ggcaaacacc  2100
ttccaaagat cgttgagga ggaggtcgag tatgcacgga tccgcaacga tatgaaacct  2160
agcattcaca ccttccttct tcatggttca ggagagcaat actatcttgt ccacaccca   2220
acgatccata tggccagcgg ccgtcgccaa atcatccttt cagtaaatgt tgaaggccaa  2280
gttcggcagg cgatacatgc ccatgaaaga gttgaagcag tgattgtaca taacactgtg  2340
cccctccgcc ttgacgaaat cgttgacgga ggatcatttg acggcatact caccatcgga  2400
aagaggaaaa ctagtttcaa agtgaagatt tcaaacatta aagtagtcaa gaagcgctct  2460
ctgatgactg aggacctgga atctgcgtac ccatcgttga tgccattcta tttctacgag  2520
actcaaggac acgctcatct cgaccatgtc attactgtcg ttcctaacat ccatctgagt  2580
gctggcgaaa tacagtacaa attcgacgac gaggtgtcaa gcgaggacct cgccaagggc  2640
ctcattgttg ttgctgagaa cgtacacgag gcatccatgc agcccttccc gctcatgaaa  2700
gatttcaaga tcaccaacca attcttcttc agctccgggc aaatactccg tcctcaaagtg 2760
tacagagatc catacccggc atcgacaatg gatcccatcc ctctccacga catcaagaac  2820
cagcccgtcg tgcacaagg caccatcacg ctcgtcggaa atatttacgt cgattctgat  2880
gcgctcaacg tcgcttccga gcctactgcc gacgaagacg cggcgcatgt tcctcacgct  2940
cgcaacatgt acgcgagat gaccgctgga acgatcaaag gctggcaaaa cgctgttcgt  3000
catttccaca acaaattgga gactgttgct ccgacgaagt ag                     3042

SEQ ID NO: 10           moltype = AA  length = 1013
FEATURE                 Location/Qualifiers
source                  1..1013
                        mol_type = protein
                        organism = Psilocybe cubensis
SEQUENCE: 10
MPSSHPHITH  RYRVPSSDDH  ERISALFLGP  KAENAAFLQQ  WLTTVVAQQK  AARDAYFPDD   60
NAFITTDMQT  SPAFAQTTKV  IASNLTELLT  ALGERSIPFF  SPRYSGHMSV  DQSLPAILGF  120
LSTTFYNPNN  VAFEASPFTT  LIEEEVGLQL  SEMLGYNRLN  NTEKPLAWGH  IASGGTVANL  180
```

```
EAMWAARNLK FYPLSLRDAS AEGAEMEFIR DTFSVKTCVG DKKLLKDCSP WELLNLHVST    240
ILDMPDRLHD EYNISPQFLE KVMRKYIIQS TNKDTLMQRW GLTQQPVVLS PSTNHYSWPK    300
AAAVLGIGSD NLRNVPVDIQ AHMDINELDR MLKICLDEET PVYQVVAVIG TTEEGGVDRI    360
TEILKLRQKY EALGLSFAIH ADAAWGGYFA TMLPKDTLGR NRTRLPKEDT TSGFVPHVGL    420
REESALQLSH IKYADSITID PHKAGYVPYP AGALCYRDGR MRYLLTWSAP YLAQGNEGQS    480
IGIYGIEGSK PGAAASAVFM AHETIGLTPS GYGNLLGQAM FTCRRYAAHW SAMSTDTTSF    540
TVTPFNPIPA DIDPNADPAK VEEQKQFIRD RILFKSNEEI YNDSEAMELL HQLGSDLNIN    600
VFACNFRDRD NNLNTDVEEA NWLNNRIFQR FSVTSAEENP LETPFFLSST TLKQSEYGVC    660
ATEVKRRMGL VGDQDVIVLR NVVMSPFTTT NDFVGTLANT FQKIVEEEVE YARIRNDMKP    720
SIHTFLLHGS GEQYYLVHTP TIHMASGRRQ IILSVNVEGQ VRQAIHAHER VEAVIVHNTV    780
PLRLDEIVDG GSFDGILTIG KRKTSFKVKI SNIKVVKKRS LMTEDLESAY PSLMPFYFYG    840
TQGHAHLDHV ITVVPNIHLS AGEIQYKFDD EVSSEDLAKG LIVVAENVHE ASMQPFPLMK    900
DPFKITNQFFF SSGQILRVKV YRDPYPASTM DPIPLHDIKN QPVVTQGTIT LVGNIYVDSD    960
ALNVASEPTA DEDAAHVPHA RNMYGEMTAG TIKGWQNAVR HFHNKLETVA PTK          1013

SEQ ID NO: 11           moltype = DNA   length = 2103
FEATURE                 Location/Qualifiers
source                  1..2103
                        mol_type = genomic DNA
                        organism = Psilocybe cubensis
SEQUENCE: 11
atggaggcta tcaaaaaggt ttttgagaac aaaaaggcgg agggcattcc tgtgttggtg    60
accttttgtta ctgcaggata tcctcgtccc gaagatactg ttcccatctt gctggccatg   120
gaggccgtg gtgctgatat catcgagctt ggtatgccat tttcagaccc aattgcagat    180
ggtcctgtca tccaggaaac gaacacaatc gccgttgcaa accaggtaga ttataccact    240
gttctcggac aacttcggga agcccgcaaa caagggctca agcaccccgt tcttctgatg    300
ggatattata accccatatt ggcttacgga gaagacagat ctattcaaga tgccggctga    360
gctggagcca atgggtttat tatggtcgac cttccacccg aggaggctgt cgcttttcga    420
gagaaatgta tcaaatccaa cctctcatat gttcctctaa ttgcaccctc aacgactctg    480
tcgcgtataa agttcctctc aacaattgca gacacgttca tctatgtcgt gtctaaaatg    540
ggaaccaccg gatcctcaga gaaggttgcc atgaataacg cccttcccac catcatcgat    600
cgtattcgcg agtacgctga agttccttta gcagtcggat ttggagtcgc cactcgggct    660
cacttcaact acgtcgccga ttccggtgct gatggtgtcg ttattggcac caaactcgtt    720
aacgttatta aagagtcacc gcaagggaa gcacccaaca atgttgaggc atactgccgt    780
gagatgagcc aaaagggaga aacaaatcgc gtcaaatctc caccaactgc ccgtgctgcc    840
agctccgaat caattcctgt tgttgttcct tctgttctcc ccgcacgttt cggagaattc    900
ggaggacaat acgttcccga agctcttgtc gattgtctgg ttgaactaga agaagctcac    960
aaatctgcca tggctgatcc tgaattccag aaggaactac aatcgcatgc cggatatgca   1020
aatcgtcctt cacaaatata cctcgccgaa aatctcacca aggatgctgg gggtgcaaat   1080
atttggttga aacgtgaaga tttgaaccac acaggttccc acaaaatcaa taacgctttg   1140
ggacaaattc tgcttgcccg gagaatcgga aagaccagaa ttatcgcaga aacaggtgcc   1200
ggccagcatg gtgttgcaac agcgactgtt tgcgctaagt ttggaatgga atgtgttatc   1260
tacatggcg cagaagatgt gcgacgtcaa gctctaaatg tattcaggat tgagatgcta   1320
ggagcaaaag ttgttcctgt tacttcagga tcatgcacat tgaaggacgc tgtaaacgag   1380
gccttccgtg actgggtgac aaacctttct acgacgcatt atttggttgg ctctgtaatt   1440
ggacctcatc ccttcccac cattgtccga gatttccaaa aggtcattgg tcaagagatc   1500
aaggctcaga tgttggccgc ccgcggcaaa cttcctgatc gtcgtcgc ttgtgttggt    1560
ggaggaagca atgctatcgg tacgttctat gattttattg gcgacaagag tgtacgtcta   1620
gttggggtgg aagcaggagg agaaggtatt gacggagacc gacatagcgc cacactttcg   1680
atggggcaac cggagtact tcacggtgtt agaacatata ttctacaaga caaggccggt   1740
caaatcatcg agacgcactc aatcagcgct ggattgatt atcccggcgt tggaccagaa   1800
catgcttggc taaaggactc taaaagagca gaatatgttg tcgccacaga cgaagaagca   1860
cttcgcggtt tccgtatgct aacacaaagg gagggaatta ttcctgccct tgaatcttcc   1920
catgcgatct gggaggctgt caggattgcc cgcaccatgt cgaaggacca ggatcttgtt   1980
gtgtgtttgt ctggccgagg tgataaagac gttgagcaaa tttctcaact tcttcccaag   2040
tgggcggata ttctagactg gcatgtttct tcccatgccg ttggacacac aacaaaattc   2100
taa                                                                2103

SEQ ID NO: 12           moltype = AA    length = 700
FEATURE                 Location/Qualifiers
source                  1..700
                        mol_type = protein
                        organism = Psilocybe cubensis
SEQUENCE: 12
MEAIKKVFEN KKAEGIPVLV TFVTAGYPRP EDTVPILLAM EAGGADIIEL GMPFSDPIAD     60
GPVIQETNTI AVANQVDYTT VLGQLREARK QGLKAPVLLM GYYNPILAYG EDRSIQDAAE    120
AGANGFIMVD LPPEEAVAFR EKCIKSNLSY VPLIAPSTTL SRIKFLSTIA DTFIYVVSKM    180
GTTGSSEKVA MNNALPTIID RIREYAEVPL AVGFGVATRA HFNYVADSGA DGVVIGTKLV    240
NVIKESPQGE APKNVEAYCR EMSQKGETNR VKSPPTARAA SSESIPVVVP SVLPARFGEF    300
GGQYVPEALV DCLVELEEAH KSAMADPEFQ KELQSHAGYA NRPSQIYLAE NLTKDAGGAN    360
IWLKREDLNH TGSHKINNAL GQILLARRIG KTRIIAETGA GQHGVATATV CAKFGMECVI    420
YMGAEDVRRQ ALNVFRIEML GAKVVPVTSG SCTLKDAVNE AFRDWVTNLS TTHYLVGSVI    480
GPHPFPTIVR DFQKVIGQEI KAQMLAARGK LPDVVVACVG GGSNAIGTFY DFIGDKSVRL    540
VGVEAGGEGI DGDRHSATLS MGQPGVLHGV RTYILQDKAG QIIETHSISA GLDYPGVGPE    600
HAWLKDSKRA EYVVATDEEA LRGFRMLTQR EGIIPALESS HAIWEAVRIA RTMSKDQDLV    660
VCLSGRGDKD VEQISQLLPK WADILDWHVS SHAVGHTTKF                         700

SEQ ID NO: 13           moltype = DNA   length = 1572
FEATURE                 Location/Qualifiers
```

```
source                  1..1572
                        mol_type = genomic DNA
                        organism = Oryza sativa
SEQUENCE: 13
atggagctca ccatggcgtc gacgatgtcg ctcgcgctgc tcgtgctctc cgcggcgtac   60
gtgttggtcg cgttgaggag gagccggtcg tcgtcgtcaa agccacggcg gctgccgccg  120
tcgccgccgg ggtggccggt gatcgggcac ctccacctca tgtccggcat gccgcaccac  180
gcgctggcgg agctggcgcg caccatgcgc gcgccgctgt tccggatgcg gctggggagc  240
gtgccggcgg tggtgatctc caagccggac ctcgcccgcg ccgcgctcac caccaacgac  300
gccgcgctcg cgtcgcggcc gcacctgctc tccggccagt tcctgtcgtt cggctgctcc  360
gacgtgacgt tcgcgccggc ggggccgtac caccggatgg cgccgcgt ggtggtgtcg    420
gagctcctgt cggcgcgtcg cgtcgccacg tacggcgccg tcagggtcaa ggagctccgc  480
cgcctgctcg cgcacctcac caagaacacc tcgccggcga agcccgtcga cctcagcgag  540
tgcttcctca acctcgccaa cgacgtgctc tgccgctcgc cgttcggccg ccggttcccg  600
cacggcgagg gcgacaagct cggcgcggtg ctcgccgagg cgcaggacct cttcgccggg  660
ttcaccatcg gcgacttctt ccccgagctc gagcccgtcg ccagcaccgt caccggactc  720
cgccgccgcc tcaagaagtg cctcgccgac tccgcgagg cctgcgacgt gatcgtggac   780
gaacacatca gcggcaaccg ccagcgccgc atc ccggcgac gcgacgagga cttcgtcgac  840
gtcctcctcc gcgtcagaa atcccccgac ctcgaggtcc ccctaaccga cgacaatctc   900
aagggccctcg tcctggacat gttcgtcgcc ggcacggaca ccacgttcgc gacgctggag  960
tgggtgatga cggagctagt ccgccaccca cggatcctca gaaggcgca ggaggaggtc  1020
cggcagtcg tcggcgacag cggccgcgtc gaggagtccc acctcggcga gctccactac  1080
atgcgcgcca tcatcaagga gacgttccgc ctgcacccgg cggtgccgtt gctagtgccg  1140
cgcgagtccg tcgcgccgtg cacgctgggc ggctacgaca tcccggcgag gacgcgggtg  1200
ttcatcaaca cgttcgccat ggggcgcgac ccggagatct gggacaaccc gctggagtac  1260
tcgccggaga ggttcgagag cgccggcggc ggcgagggaa tcgacctcaa ggaccccgac  1320
tacaagctgc tgccgttcgg cggcgggcgg cgagggtgcc ccggctacac gttcgcgctc  1380
gccaccgtgc aggtgtcgct cgccagcttg ctctaccact cgagtgggc gctgcccgcc  1440
ggcgtgcgcg ccgaggacgt caacctcgac gagacgttcg gcctcgccac gaggaagaag  1500
gagccgctct tcgtcgccgt caggaagagc gacgcgtacg agtttaaggg agaggagctt  1560
agtgaggttt aa                                                     1572

SEQ ID NO: 14           moltype = AA    length = 522
FEATURE                 Location/Qualifiers
source                  1..522
                        mol_type = protein
                        organism = Oryza sativa
SEQUENCE: 14
MELTMASTMS LALLVLSAAY VLVALRRSRS SSSKPRRLPP SPPGWPVIGH LHLMSGMPHH   60
ALAELARTMR APLFRMRLGS VPAVVISKPD LARAALTTND AALASRPHLL SGQFLSFGCS  120
DVTFAPAGPY HRMARRVVVS ELLSARRVAT YGAVRVKELR RLLAHLTKNT SPAKPVDLSE  180
CFLNLANDVL CRVAFGRRFP HGEGDKLGAV LAEAQDLFAG FTIGDFFPEL EPVASTVTGL  240
RRRLKKCLAD LREACDVIVD EHISGNRQRI PGDRDEDFVD VLLRVQKSPD LEVPLTDDNL  300
KALVLDMFVA GTDTTFATLE WVMTELVRHP RILKKAQEEV RRVVGDSGRV EESHLGELYM  360
RAIIKETFRL HPAVPLLVPR ESVAPCTLGG YDIPARTRVF INTFAMGRDP EIWDNPLEYS  420
PERFESAGGG GEIDLKDPDY KLLPFGGGRR GCPGYTFALA TVQVSLASLL YHFEWALPAG  480
VRAEDVNLDE TFGLATRKKE PLFVAVRKSD AYEFKGEELS EV                    522

SEQ ID NO: 15           moltype = DNA    length = 1335
FEATURE                 Location/Qualifiers
source                  1..1335
                        mol_type = genomic DNA
                        organism = Rattus norvegicus
SEQUENCE: 15
atgattgaag acaacaagga gaacaaagac cattcctcag aaaggggggag agtgactctc   60
atcttttcct tgaagaatga agttggagga ctcataaaag cactgaaaat cttccaggag  120
aaccacgtga acctgttaca tattgagtcc cggaaatcga agcgaagaaa ctcagaattt  180
gagattttg tggactgcga catcaaccga gaacagctga atgacatctt tcccctgctg  240
aagtcccaca ccacggtcct ctctgtggac tcgcccgatc agctccctga aaaggaagat  300
gttatggaga ctgtcccttg gttcccaaag aagatttctg acctggactt ctgcgccaac  360
agagtgctgt tgtacggatc cgaactcgac gcggaccatc ctggcttcaa agacaatgtc  420
taccgtagaa gacgaaagta tttcgcagag ctggctatga actacaaaca tggggacccc  480
attcccaaga ttgaattcac ggaagaggag attaagacct ggggggaccat cttccgagag  540
ctgaacaaac tctacccaac ccacgcctgc agggagtacc tcagaaacct tcctctgctc  600
tcaaaatact gtggctatcg ggaagacaac gtcccgcaac tggaagatgt ctccaactt   660
ttaaaagaac gcacagggtt ttccatccgt cctgtggctg gttaccctc accgagagat  720
ttcctgtcag ggttagcctt tcgagtcttt cactgcactc agtatgtgag acacagttcg  780
gatcctctct ataccccaga gccagacacc tgccacgaac tgccacgac ccgtccctct   840
ttggctgaac ccagttttgc tcaattctcc caagaaattg gcctggcttc tcttggagct  900
tcagaggaga cggttcagaa actggcaacg tgctacttct tcactgtgga gttttggactg  960
tgcaagcaag atgggcagct gagagtcttt ggtgccggcc tgcttcttc catcagtgag 1020
ctcagacatg cactttctgg acatgccaag gttaagccc ttgatcccaa ggttgcctgc  1080
aaacaggaat gtcatcatc aagcttccag gatgtcact ttgtatcgga gagctttgaa  1140
gatgcaaagg agaagatgag agaaatttgcc aaaccgtga tggagtgaag 1200
tacaatccgt acacacagag cattcaggtt ctgagagaca gcaagagcat aaccagcgcc  1260
atgaatgagt tgcggcatga cctcgatgtc gtcaatgatg cccttgctag agtcagcagg  1320
tggcccagtg tgtga                                                  1335

SEQ ID NO: 16           moltype = AA    length = 444
```

```
FEATURE                 Location/Qualifiers
source                  1..444
                        mol_type = protein
                        organism = Rattus norvegicus
SEQUENCE: 16
MIEDNKENKD HSSERGRVTL IFSLKNEVGG LIKALKIFQE NHVNLLHIES RKSKRRNSEF   60
EIFVDCDINR EQLNDIFPLL KSHTTVLSVD SPDQLPEKED VMETVPWFPK KISDLDFCAN  120
RVLLYGSELD ADHPGFKDNV YRRRRKYFAE LAMNYKHGDP IPKIEFTEEE IKTWGTIFRE  180
LNKLYPTHAC REYLRNLPLL SKYCGYREDN VPQLEDVSNF LKERTGFSIR PVAGYLSPRD  240
FLSGLAFRVF HCTQYVRHSS DPLYTPEPDT CHELLGHVPL LAEPSFAQFS QEIGLASLGA  300
SEETVQKLAT CYFFTVEFGL CKQDGQLRVF GAGLLSSISE LRHALSGHAK VKPFDPKVAC  360
KQECLITSFQ DVYFVSESFE DAKEKMREFA KTVKRPFGVK YNPYTQSIQV LRDSKSITSA  420
MNELRHDLDV VNDALARVSR WPSV                                        444

SEQ ID NO: 17           moltype = DNA  length = 1002
FEATURE                 Location/Qualifiers
source                  1..1002
                        mol_type = genomic DNA
                        organism = Oryza sativa
SEQUENCE: 17
atgcccgccg tggccgggag cttgtacatg gcgagccagc acaagggagt gcctccgccg   60
ctgccgccgc cgccgcggcc attgccggtg atcaacctgg gccggctcac catggacagt  120
gcctcgcggg cgctcgccgt gcgggatatc gtgctggcgt gccgtgaacg tggctgcttt  180
gaggtggtga accatggcat cagcaggtct tgcatgaatg gcgccctcga agccgcctcc  240
gagttcttcc agctatcgac ggagcgcaag gaggagttcg cgtcggacga catccggcag  300
cccatcaggt acgacacgag ctcgagggac gggatccaga tgtccaggtc atttctgaag  360
cactatgcca atcccctgga cgactggatc aagttctggc cgacgcagcc accaacttac  420
agggagaaaa tgggtgagta cgccgtggag acgcagcgag tgtcaatgca gctcatggaa  480
gcaatcctgc agggcctggg attagggcca tcgtacctgc aagaaaagct tgaaggaggg  540
gtgcagttcg tggccttgaa caactacccg cagtcatcgg cgaagaaagc cgacaagatc  600
ggcttggctc ctcactctga ttatggcttc ctcaccatcc tgttgcagag ctccccaggg  660
cttgaggtga tgcaccatga ggatgatgcc tggacatctg tccctgctat ccctggggct  720
ctccatgtcc atgtaggaga ccacctggaa gtgttgagca atggccagct caagtccctt  780
gtccatcgag ccgttctcaa cccaaacgag tcaaggattt ctattgccag catccatggt  840
ctctcgatgg atgaagaggt ccactgcgcc gaagagctcg tcgatgaaca ccaccccaaa  900
atgtacaggg gaagcagctt ccaggacttc ctggacttcc tgccagcaga catgaacagg  960
tataggaggt atgtcgagag cctcaggatc gacaaaccct ga                    1002

SEQ ID NO: 18           moltype = AA  length = 333
FEATURE                 Location/Qualifiers
source                  1..333
                        mol_type = protein
                        organism = Oryza sativa
SEQUENCE: 18
MPAVAGSLYM ASQHKGVPPP LPPPPRPLPV INLGRLTMDS ASRALAVRDI VLACRERGCF   60
EVVNHGISRS CMNGALEAAS EFFQLSTERK EEFASDDIRQ PIRYDTSSRD GISMSRSFLK  120
HYANPLDDWI KFWPTQPPTY REKMGEYAVE TQRVSMQLME AILQGLGLGP SYLQEKLEGG  180
VQFVALNNYP QSSAKKADKI GLAPHSDYGF LTILLQSSPG LEVMHHEDDA WTSVPAIPGA  240
LHVHVGDHLE VLSNGQLKSL VHRAVLNPNE SRISIASIHG LSMDEEVHCA EELVDEHHPK  300
MYRGSSFQDF LDFLPADMNR YRRYVESLRI DKP                              333

SEQ ID NO: 19           moltype = DNA  length = 1539
FEATURE                 Location/Qualifiers
source                  1..1539
                        mol_type = genomic DNA
                        organism = Aspergillus nidulans
SEQUENCE: 19
atgctgagtc tcgacctagt attctctttc ccagcatggg cgctcctcct agtcctaacc   60
ctcttgtata cactatacct agccacaacg cgctcctccc tgagcccccat tcgccatatt  120
cccggcccaa ctctagccgc actgtcgttt tggcctgaat tctactacga cgtcgtccaa  180
cggggacagt attttcgaca aattgacaag atgcatcaga catcggtcc gctagtccgc  240
attaacccat tcgaaatcca catccaagac ccctccttct atcccgtgct gtacacaggc  300
ccaactcgtc gacgacataa atggctctgg gctgcacgaa tgttcgggaa caacacctct  360
gcctttgcaa ccgtccggca cgaacaccac agactaagaa gcggtgcatt gaaccctctc  420
ttctcaaaga gcgctatcca gcggctaaca ccgcacctgc aacatacccct agcgcggcta  480
tgtagtcggc tcgatgggtt cgcttttaca agacaggatg tggacttggg gatcggactt  540
acagcgttcg cggccgacgt catcacagag tactgtttcg acagtcact ggagttgatt   600
gggaaagata actttggaaa ggagtggatt gatatggtaa gcgctccgtc agagctcggc  660
catctggtaa agcagtgtcc gtggatcttg gtggtttgta aatgggcgcc gaaagctcgc  720
gttagggctt tgctgccggg ggttgcgttg ttgtttcaaa tacaagagag aatgagcgcc  780
cagattcaac cgcttgttga tcgagccgcc gccgttgaca agccagctga ccctttgacc  840
gtcttcgact tcctcctctc gagtacccctc ccacagcacg aaaagacagt ggaccgactc  900
aagggcgaag gcagacgct catcggcgcg gggacattaa cgaccgggaa tgcattgaag  960
acgatatct tccacgtcct caatgatccc gacatctttc ggaaacttcg agcagaggtc 1020
gacggtgctc tagaaaatat ggatattctg tccatgtctg atacggccta cctcgaacgc 1080
ctcccgtacc tgtcagcgtg cataaaggaa ggtctacgga tttcctacgg cgtcacgcat 1140
agactccaac tgatcgccga agagccccta atatactcag gagtgaccat cccagcagga 1200
acaccagttg gaatgacatc gatcttcatg cacgacaatc cagtagtatt ccctcagccg 1260
cgggaattcc gtccagagcg ctggttcgag gcagattttg agactgtgca ggcaatgaat 1320
```

```
cgccacttcg tcccttcag caagggcagc cgcatgtgtc tgggaatgaa cctggcgtat  1380
gcggagattt acttggtgct ggcagtactt tttcgacggt atgagatttc tctgagcggg  1440
gtgacgaggg aggatattga gatggcacat gatttttcg atcctgcgcc aaaggagggg   1500
gcaagaggat tgatcgttca actgcagaag aggggtga                         1539
```

SEQ ID NO: 20          moltype = AA  length = 512
FEATURE                Location/Qualifiers
source                 1..512
                       mol_type = protein
                       organism = Aspergillus nidulans
SEQUENCE: 20
```
MLSLDLVFSF PAWALLLVLT LLYTLYLATT RLLLSPIRHI PGPTLAALSF WPEFYYDVVQ   60
RGQYFRQIDK MHQTYGPLVR INPFEIHIQD PSFYPVLYTG PTRRRHKWLW AARMFGNNTS  120
AFATVRHEHH RLRRSALNPL FSKSAIQRLT PHLQHTLARL CSRLDGFAFT RQDVDLGIGL  180
TAFAADVITE YCFGQSLELI GKDNFGKEWI DMVSAPSELG HLVKQCPWIL VVCKWAPKAL  240
VRALLPGVAL LFQIQERMSA QIQPLVDRAA AVDKPADPLT VFDFLLSSTL PQHEKTVDRL  300
KGEGQTLIGA GTLTTGNALK TIIFHVLNDP DIFRKLRAEV DGALENMDIL SMSDTAYLER  360
LPYLSACIKE GLRISYGVTH RLQLIAEEPL IYSGVTIPAG TPVGMTSIFM HDNPVVFPQP  420
REFRPERWFE ADFETVQAMN RHFVPFSKGS RMCLGMNLAY AEIYLVLAVL FRRYEISLSG  480
VTREDIEMAH DFFDPAPKEG ARGLIVQLQK RG                               512
```

SEQ ID NO: 21          moltype = DNA  length = 3810
FEATURE                Location/Qualifiers
misc_feature           1..3810
                       note = pCDM4 vector
source                 1..3810
                       mol_type = other DNA
                       organism = synthetic construct
SEQUENCE: 21
```
gctaacagcg cgatttgctg gtgacccaat gcgaccagat gctccacgcc cagtcgcgta   60
ccgtcttcat gggagaaaat aatactgttg atgggtgtct ggtcagagac atcaagaaat  120
aacgccggaa cattagtgca ggcagcttcc acagcaatgg catcctggtc atccagcgga  180
tagttaatga tcagcccact gacgcgttgc gcgagaagat tgtgcaccgc cgctttacag  240
gcttcgacgc cgcttcgttc taccatcgac accaccagtc tggcacccag ttgatcggcg  300
cgagatttaa tcgccgcgac aatttgcgac ggcgcgtgca gggcagact ggaggtggca   360
acgccaatca gcaacgactg tttgcccgcc agttgttgtg ccacgcggtt gggaatgtaa  420
ttcagctccg ccatcgccgc ttccactttt tcccgcgttt tcgcagaaac gtggctggcc  480
tggttcacca cgcgggaaac ggtctgataa gagacaccgg catactctgc gacatcgtat  540
aacgttactg gtttcacatt caccaccctg aattgactct cttccgggcg ctatcatgcc  600
ataccgcgaa aggttttgcg ccattgcatg gtgtccggga tctcgacgct ctcccttatg  660
cgactcctgc attaggaagc agcccagtag taggttgagg ccgttgagca ccgccgccgc  720
aaggaatggt gcatgcaagg agatggcgcc caacagtccc ccggcacgg ggcctgccac    780
catcccacg ccgaaacaag cgctcatgag cccgaagtgg gcgccgat cttccccatc     840
ggtgatgtcg gcgatatagg cgccagcaac cgcacctgtg gcgccggtga tgccggccac  900
gatgcgtccg gcgtagccta ggatcgagat cgatctcgat cccgcgaaat taatacgact  960
cactataggg gaattgtgag cggataacaa ttcccctcta gaaataattt tgtttaactt  1020
taagaaggag atatacatat ggcagatctc aattggataa gccggccca cgcgatcgct   1080
gacgtcggta ccctcgagtc tggtaaagaa accgctgctg cgaaatttga acgccagcac  1140
atggactcgt ctactagtcg cagcttaatt aaccctaaact gctgccaccg ctgagcaata  1200
actagcataa ccccttgggg cctctaaacg ggtcttgagg ggttttttgc tagcgaaagg  1260
aggagtcgac actgcttccg gtagtcaata aaccggtaaa ccagcaatag acataagcgg  1320
ctatttaacg accctgccct gaaccgacga ccggtcatc gtggccggat cttgcggccc   1380
ctcggcttga acgaattgtt agacattatt tgccgactac cttggtgatc tcgcctttca  1440
cgtagtggac aaattcttcc aactgatctg cgcgcgaggc caagcgatct tcttcttgtc  1500
caagataagc ctgtctagct tcaagtatga cgggctgata ctgggccgcc aggcgctcca  1560
ttgcccagtc ggcagcgaca tccttcggcg cgattttgcc ggttactgcg ctgtaccaaa  1620
tgcgggacaa cgtaagcact acatttcgct catcgccagc ccagtcgggc ggcgagttcc  1680
atagcgttaa ggtttcattt agcgcctcaa atagatcctg ttcaggaacc ggatcaaaga  1740
gttcctccgc cgctggacct accaaggcaa cgctatgttc tcttgctttt gtcagcaaga  1800
tagccagatc aatgtcgatc gtggctggct cgaagatacc tgcaagaatg tcattgcgct  1860
gccattctcc aaattgcagt tcgcgcttag ctggataacg ccacgaatg atgtcgtcgt   1920
gcacaacaat ggtgacttct acagcgcgga gaatctcgct ctctcagggg aagccgaag   1980
tttccaaaag gtcgttgatc aaagctcgcc gcgttgtttc atcaagcctt acggtcaccg  2040
taaccagcaa atcaatatca ctgtgtggct tcaggccgcc atccactgcg gagccgtaca  2100
aatgtacggc cagcaacgtc ggttcgagat ggcgctcgat gacgccaact acctctgata  2160
gttgagtcga tacttcggcg atcaccgctt ccctcatact cttccttttt caatattatt  2220
gaagcattta tcagggttat tgtctcatga gcggatacat atttgaatgt atttagaaaa  2280
ataaacaaat agcagctca ctcggtcgct acgctccggg cgtgagactg cggcgggcgc    2340
tgcggacaca tacaaagtta cccacagatt ccgtggataa gcaggggact aacatgtgga  2400
gcaaaacagc agggccgcgc cggtggcgtt tttccatagg ctccgccctc ctgccagagt  2460
tcacataaac agacgctttt ccggtgcatc tgtgggagcc gtgaggctca accatgaatc  2520
tgacagtacg ggcgaaaccc gacaggactt aaagatcccc accgtttccg gcgggtcgct  2580
ccctcttgcg ctctcctgtt ccgaccctgc cgtttaccgg atacctgttc cgcctttctc  2640
ccttacggga agtgtggcgc tttctcatag ctcacacact ggtatctcgg ttcagcccga  2700
gtcgttcgct ccaagctggg ctgtaagcaa gaactcccgc ttcagcccga ctgctgcgcc  2760
ttatccggta actgttcact tgagtccaac ccggaaaagc acgtaaaaac gccactggca  2820
gcagccattg gtaactggga gttcgcagag gatttgttta gctaaacacg cggttgctct  2880
tgaagtgtgc gccaaagtcc ggctacactg gaaggacaga tttggttgct gtgctctgcg  2940
aaagccagtt accacggtta gcagttccc caactgactt aaccttcgat caaaccacct   3000
```

```
ccccaggtgg ttttttcgtt tacagggcaa aagattacgc gcagaaaaaa aggatctcaa  3060
gaagatcctt tgatcttttc tactgaaccg ctctagattt cagtgcaatt tatctcttca  3120
aatgtagcac ctgaagtcag ccccatacga tataagttgt aattctcatg ttagtcatgc  3180
cccgcgccca ccggaaggag ctgactgggt tgaaggctct caagggcatc ggtcgagatc  3240
ccggtgccta atgagtgagc taacttacat taattgcgtt gcgctcactg cccgctttcc  3300
agtcgggaaa cctgtcgtgc cagctgcatt aatgaatcgg ccaacgcgcg gggagaggcg  3360
gtttgcgtat tgggcgccag ggtggttttt cttttcacca gtgagacggg caacagctga  3420
ttgcccttca ccgcctggcc ctgagagagt tgcagcaagc ggtccacgct ggtttgcccc  3480
agcaggcgaa aatcctgttt gatggtggtt aacggcggga tataacatga gctgtcttcg  3540
gtatcgtcgt atcccactac cgagatgtcc gcaccaacgc gcagcccgga ctcggtaatg  3600
gcgcgcattg cgcccagcgc catctgatcg ttggcaacca gcatcgcagt gggaacgatg  3660
ccctcattca gcatttgcat ggtttgttga aaaccggaca tggcactcca gtcgccttcc  3720
cgttccgcta tcggctgaat ttgattgcga gtgatatatt tatgccagcc agccagacgc  3780
agacgcgccg agacagaact taatgggccc                                    3810

SEQ ID NO: 22          moltype = DNA   length = 24
FEATURE                Location/Qualifiers
misc_feature           1..24
                       note = Synthetic FLAG epitope tag polypeptide
source                 1..24
                       mol_type = other DNA
                       organism = synthetic construct
SEQUENCE: 22
gactacaagg atgacgatga caaa                                           24

SEQ ID NO: 23          moltype = AA   length = 8
FEATURE                Location/Qualifiers
REGION                 1..8
                       note = Synthetic FLAG epitope tag polypeptide
source                 1..8
                       mol_type = protein
                       organism = synthetic construct
SEQUENCE: 23
DYKDDDDK                                                              8

SEQ ID NO: 24          moltype = DNA   length = 549
FEATURE                Location/Qualifiers
source                 1..549
                       mol_type = genomic DNA
                       organism = Streptomyces griseofuscus
SEQUENCE: 24
atgaacacct tcagaacagc cactgccaga gacatacctg atgtagcagc aactcttacg   60
gaagccttcg caactgatcc acccacgcag tgggtgttcc ccgacggtac tgccgccgtc  120
agcaggttct ttacacatgt tgcagatagg gttcacacgg ccgtggtat tgttgagcta  180
ctaccagaca gagccgccat gattgcattg ccaccacacg tgaggctgcc aggagaagct  240
gccgacggaa ggcaggcgga aattcagaga aggctggcag acaggcaccc gctgacacct  300
cactactacc tgctgtttta cggagttaga acggcacacg aggttcgggg attgggcgga  360
agaatgctgg ccagattaac tagcagagct gataggaca gggtgggtac atatactgag  420
gcatccacct ggcgtggcgc tagactgatg ctgagacatg gattccatgc tacaaggcca  480
ctaagattgc cagatggacc cagcatgttt ccactttgga gagatccaat ccatgatcat  540
tctgattag                                                          549

SEQ ID NO: 25          moltype = AA   length = 182
FEATURE                Location/Qualifiers
source                 1..182
                       mol_type = protein
                       organism = Streptomyces griseofuscus
SEQUENCE: 25
MNTFRTATAR DIPDVAATLT EAFATDPPTQ WVFPDGTAAV SRFFTHVADR VHTAGGIVEL   60
LPDRAAMIAL PPHVRLPGEA ADGRQAEIQR RLADRHPLTP HYYLLFYGVR TAHQGSGLGG  120
RMLARLTSRA DRDRVGTYTE ASTWRGARLM LRHGFHATRP LRLPDGPSMF PLWRDPIHDH  180
SD                                                                 182

SEQ ID NO: 26          moltype = DNA   length = 1170
FEATURE                Location/Qualifiers
source                 1..1170
                       mol_type = genomic DNA
                       organism = Thermotoga maritima
SEQUENCE: 26
atgaaaggat atttcggacc atacggtggc cagtacgtac cagaaatatt aatgggtgcc   60
ttagaggagt tagaggcagc atacgaggag attatgaagg atgagagctt ctggaaggag  120
ttcaacgatc tactgaggga ttcgcaggc agaccaacgc cattgtactt tgccaggaga  180
ttgtctgaga agtacggcgc ccgtgtttac ttgaagcgtg aggatctgct gcacactgga  240
gcacacaaga taataacgc tatccgacag gttttattgg ccaaattaat gggaagaca  300
cgtatcatag ccgagacggg agctgggcag catggagtcg ctactgctac cgctgctgcc  360
ctgttcggaa tggaatgtgt gatctacatg ggtgaagagg acacaatcag acagaagttg  420
aacgtggagc gtatgaaatt attaggggct aagttgtcc ctgttaagtc tggcagtagg  480
accttgaagg atgcgataga cgaggctttg agagactgga ttactaattt acagacaaca  540
tattatgtta tcggatctgt tgttggtccc caccccttacc caattatcgt aaggaatttc  600
```

```
cagaaggtta tcggtgagga gaccaagaag caaataccag aaaaggaagg tcgtttgcca    660
gactatatag ttgcctgcgt aggcggcggt agcaatgccg caggtatatt ttacccattc    720
atagactctg gagtaaagct gataggtgtt gaggcaggtg gcgagggatt ggagacaggt    780
aaacacgcag cctcgttatt aaagggtaaa attggctatt tacatggatc gaagaccttt    840
gttctacaag atgactgggg tcaagtccaa gtgagccatt cggtgtcagc tggtcttgac    900
tattcaggag taggacctga gcatgctat tggagagaga cagggaaggt tctgtacgac     960
gcagtgactg acgaagaggc tttggacgca tttatagagt tatcaagact agagggcatt   1020
ataccgctt tagagtcatc gcatgctcta gcatatttga agaagataaa tataaaaggt    1080
aaggttgtgg tggtcaacct atcagggaga ggggataaaa acctggagtc agtcttaaac    1140
catccatacg tgagagaaag aattagatga                                    1170

SEQ ID NO: 27           moltype = AA   length = 389
FEATURE                 Location/Qualifiers
source                  1..389
                        mol_type = protein
                        organism = Thermotoga maritima
SEQUENCE: 27
MKGYFGPYGG QYVPEILMGA LEELEAAYEE IMKDESFWKE FNDLLRDYAG RPTPLYFARR     60
LSEKYGARVY LKREDLLHTG AHKINNAIGQ VLLAKLMGKT RIIAETGAGQ HGVATATAAA    120
LFGMECVIYM GEEDTIRQKL NVERMKLLGA KVVPVKSGSR TLKDAIDEAL RDWITNLQTT    180
YYVIGSVVGP HPYPIIVRNF QKVIGEETKK QIPEKEGRLP DYIVACVGGG SNAAGIFYPF    240
IDSGVKLIGV EAGGEGLETG KHAASLLKGK IGYLHGSKTF VLQDDWGQVQ VSHSVSAGLD    300
YSGVGPEHAY WRETGKVLYD AVTDEEALDA FIELSRLEGI IPALESSHAL AYLKKINIKG    360
KVVVVNLSGR GDKDLESVLN HPYVRERIR                                     389

SEQ ID NO: 28           moltype = DNA   length = 42
FEATURE                 Location/Qualifiers
misc_feature            1..42
                        note = Synthetic V5 epitope tag polypeptide
source                  1..42
                        mol_type = other DNA
                        organism = synthetic construct
SEQUENCE: 28
ggtaagccaa ttccaaatcc tttgttgggt ttggactcca cc                        42

SEQ ID NO: 29           moltype = AA   length = 14
FEATURE                 Location/Qualifiers
REGION                  1..14
                        note = Synthetic V5 epitope tag polypeptide
source                  1..14
                        mol_type = protein
                        organism = synthetic construct
SEQUENCE: 29
GKPIPNPLLG LDST                                                      14

SEQ ID NO: 30           moltype = DNA   length = 5203
FEATURE                 Location/Qualifiers
misc_feature            1..5203
                        note = pETM6-H10 vector
source                  1..5203
                        mol_type = other DNA
                        organism = synthetic construct
SEQUENCE: 30
gaagaattgt gagcggataa caattcccct ctagaaataa ttttgtttaa ctttaagaag     60
gagatataca tatggcagat ctcaattgga tatcggccgg ccacgcgatc gctgacgtcg    120
gtaccctcga gtctggtaaa gaaaccgctg ctgcgaaatt tgaacgccag cacatggact    180
cgtctactag tcgcagctta attaacctaa actgctgcca ccgctgagca ataactagca    240
taaccccttg gggcctctaa acgggtcttg aggggttttt tgctagcgaa aggaggagtc    300
gactatatcc ggattggcga atgggacgcg ccctgtagcg cgcattaagc cgctcgcttt    360
gtggtggtta cgcgcagcgt gaccgctaca cttgccagcg ccctagcgcc cgctcctttc    420
gctttcttcc cttcctttct cgccacgttc gccggctttc ccgtcaagc tctaaatcgg    480
gggctccctt tagggttccg atttagtgct ttacggcacc tcgaccccaa aaacttgat    540
tagggtgatg gttcacgtag tgggccatcg ccctgataga cggttttcg ccctttgacg    600
ttggagtcca cgttctttaa tagtggactc ttgttccaaa ctggaacaac actcaaccct    660
atctcggtct attcttttga tttataaggg attttgccga tttcggccta ttggttaaaa    720
aatgagctga tttaacaaaa atttaacgcg aattttaaca aaatattaac gtttacaatt    780
tctggcggca cgatggcatg agattatcaa aaaggatctt cacctagatc cttttaaatt    840
aaaaatgaag ttttaaatca atctaaagta tatatgagta aacttggtct gacagttacc    900
aatgcttaat cagtgaggca cctatctcag cgatctgtct atttcgttca tccatagttg    960
cctgactccc cgtcgtgtag ataactacga tacgggaggg cttaccatct ggccccagtg   1020
ctgcaatgat accgcgagac ccacgctcac cggctccaga tttatcagca ataaaccagc   1080
cagccggaag ggccgagcgc agaagtggtc ctgcaacttt atccgcctcc atccagtcta   1140
ttaattgttg ccgggaagct agagtaagta gttcgccagt taatagtttg cgcaacgttg   1200
ttgccattgc tacaggcatc gtggtgtcac gctcgtcgtt tggtatggct tcattcagct   1260
ccggttccca acgatcaagg cgagttacat gatccccat gttgtgcaaa aaagcggtta   1320
gctcctccgg tcctccgatc gttgtcagaa gtaagttggc cgcagtgtta tcactcatgg   1380
ttatggcagc actgcataat tctcttactg tcatgccatc cgtaagatgc ttttctgtga   1440
ctggtgagta ctcaaccaag tcattctgag aatagtgtat gcggcgaccg agttgctctt   1500
gcccggcgtc aatacgggat aataccgcgc cacatagcag aactttaaaa gtgctcatca   1560
```

```
ttggaaaacg ttcttcgggg cgaaaactct caaggatctt accgctgttg agatccagtt    1620
cgatgtaacc cactcgtgca cccaactgat cttcagcatc ttttactttc accagcgttt    1680
ctgggtgagc aaaaacagga aggcaaaatg ccgcaaaaaa gggaataagg gcgacacgga    1740
aatgttgaat actcatactc ttccttttc aatcatgatt gaagcattta tcagggttat    1800
tgtctcatga gcggatacat atttgaatgt atttagaaaa ataaacaaat aggtcatgac    1860
caaaatccct taacgtgagt tttcgttcca ctgagcgtca gaccccgtag aaaagatcaa    1920
aggatcttct tgagatcctt ttttttctgcg cgtaatctgc tgcttgcaaa caaaaaaacc    1980
accgctacca gcggtggttt gtttgccgga tcaagagcta ccaactcttt ttccgaaggt    2040
aactggcttc agcagagcgc agataccaaa tactgtcctt ctagtgtagc cgtagttagg    2100
ccaccacttc aagaactctg tagcaccgcc tacataccctc gctctgctaa tcctgttacc    2160
agtggctgct gccagtggcg ataagtcgtg tcttaccggg ttggactcaa gacgatagtt    2220
accgataag gcgcagcgt cgggctgaac ggggggttcg tgcacacagc ccagcttgga    2280
gcgaacgacc tacaccgaac tgagatacct acagcgtgag ctatgagaaa gcgccacgct    2340
tcccgaaggg agaaaggcgg acaggtatcc ggtaagcgat agggtcggaa caggagacgg    2400
cacgagggag cttccagggg gaaacgcctg gtatctttat agtcctgtcg ggtttcgcca    2460
cctctgactt gagcgtcgat ttttgtgatg ctcgtcaggg gggcggagcc tatgaaaaa    2520
cgccagcaac gcggccttt tacggttcct ggccttttgc tggccttttg ctcacatgtt    2580
ctttcctgcg ttatccctg attctgtgga taaccgtatt accgcctttg agtgagctga    2640
taccgctcgc cgcagccgaa cgaccgagcg cagcgagtca gtgagcgagg aagcggaaga    2700
gcgcctgatg cggtatttc tccttacgca tctgtgcggt atttcacacc gcatatatgg    2760
tgcactctca gtacaatctg ctctgatgcc gcatagttaa gccagtatac actccgctat    2820
cgctacgtga ctgggtcatg gctgcccc gacacccgcc aacacccgct gacgcgcct    2880
gacgggcttg tctgctcccg gcatccgctt acagacaagc tgtgaccgtc tccgggagct    2940
gcatgtgtca gaggttttca ccgtcatcac cgaaacgcgc gaggcagctg cggtaaagct    3000
catcagcgtg gtcgtgaagc gattcacaga tgtctgcctg ttcatccgcg tccagctcgt    3060
tgagtttctc cagaagcgtt aatgtctggc ttctgataaa gcgggccatg ttaagggcgg    3120
ttttttcctg tttggtcact gatgcctccg tgtaagggg atttctgttc atggggtaa    3180
tgataccgat gaaacgagag aggatgctca cgatacgggt tactgatgat gaacatgccc    3240
ggttactgga acgttgtgag ggtaaacaac tggcggtatg gatgcggcgg gaccagagaa    3300
aaatcactca gggtcaatgc cagcgcttcg ttaatacaga tgtaggtgtt ccacagggta    3360
gccagcagca tcctgcgatg cagatccgga acataatggt gcagggcgct gacttccgcg    3420
tttccagact ttacgaaaca cggaaaccga agaccattca tgttgttgct caggtcgcag    3480
acgttttgca gcagcagtcg cttcacgttc gctcgcgtat cggtgattca ttctgctaac    3540
cagtaaggca accccgccag cctagccggg tcctcaacga caggagcagg atcatgcgga    3600
tcatgccccg cgcccaccgg aaggagctga ctgggttgaa ggctctcaag ggcatcggtc    3660
gagatcccgg tgcctaatga gtgagctaac ttacattaat tgcgttgcgc tcactgcccg    3720
ctttccagtc gggaaacctg tcgtgccagc tgcattaatg aatcggccaa cgcgcgggga    3780
gaggcggttt gcgtattggg cgccagggtg ttttttcttt tcaccagtga cgggcaac    3840
agctgattgc ccttcaccgc ctggccctga gagagttgca gcaagcggtc cacgctggtt    3900
tgccccagca ggcgaaaatc ctgtttgatg gtggttaacg gcgggatata acatgagctg    3960
tcttcggtat cgtcgtatcc cactaccgag atgtccgcac caacgcgcag cccggactcg    4020
gtaatggcgc gcattgcgcc cagcgccatc tgatcgttgg caaccagcat cgcagtggga    4080
acgatgccct cattcagcat ttgcatggtt tgttgaaaac cggacattgg actccagtcg    4140
ccttcccgtt ccgctatcgg ctgaatttga ttgcgagtga gatatttatg ccagccagcc    4200
agacgcagac gcgccgagac agaacttaat gggcccgcta acagcgcgat ttgctggtga    4260
cccaatgcga ccagatgctc cacgcccagt cgcgtaccgt cttcatggga gaaaataata    4320
ctgttgatgg gtgtctggtc agagacatca agaaataacg ccggaacatt agtgcaggca    4380
gcttccacag caatggcatc ctggtcatcc agcggatagt taatgatcag cccactgacg    4440
cgttgcgcga agattgtg caccgccgct tacaggcctt cgacgccgct tcgttctacc    4500
atcgacacca ccacgctggc acccagttga tcggcgcgag atttaatcgc cgcgacaatt    4560
tgcgacggcg cgtgcagggc cagactggag gtggcaacgc caatcagcaa cgactgtttg    4620
cccgccagtt gttgtgccac gcggttggga atgtaattca gctccgccat cgccgcttcc    4680
acttttcc gcgttttcgc agaaacgtgg ctggcctggt tcaccacgcg ggaaacggtc    4740
tgataagaga caccggcata ctctgcgaca tcgtataacg ttactggttt cacattcacc    4800
accctgaatt gactctcttc cgggcgctat catgccatac cgcgaaaggt tttgcgccat    4860
tcgatggtgt ccgggatctc gacgctctcc cttatgcgac tcctgcatta ggaagcagcc    4920
cagtagtagg ttgaggccgt tgagcaccgc cgccgcaagg aatggtgcat gcaaggagat    4980
ggcgcccaac agtcccccgg ccacggggcc tgccaccata cccacgccga acaagcgct    5040
catgagcccg aagtggcgag cccgatcttc cccatccggtg atgtcggcga tataggcgcc    5100
agcaaccgcc cctgtggcgc cggtgatgcc ggccacgatg cgtccggcgt agcctaggat    5160
cgagatcgat ctcgatcccg cgaaattaat acgactcact acg                     5203
SEQ ID NO: 31           moltype = DNA  length = 1446
FEATURE                 Location/Qualifiers
source                  1..1446
                        mol_type = genomic DNA
                        organism = Bacillus atrophaeus
SEQUENCE: 31
atgatgtctg aaaatttgca attgtcagct gaagaaatga gacaattggg ttaccaagca      60
gttgatttga tcatcgatca catgaaccat ttgaagtcta agccagtttc agaaacaatc     120
gattctgata tcttgagaaa taagttgact gaatctatcc cagaaaatgg ttcagatcca     180
aaggaattgt tgcatttctt gaacagaaac gttttttaatc aaattacaca tgttgatcat     240
ccacatttct tggcttttgt tccaggtcca ataaattacg ttggtgttgt tgcagatttc     300
ttggccttctg gttttaatgt ttttccaact gcatggattg tgcaggtgct gctgaacaa     360
atcgaattga ctacaattaa ttggttgaaa tctatgttgg gttttccaga ttcagctgaa     420
ggtttatttg tttctggtgg ttcaatggca aatttgacag ctttgactgt tgcaagacag     480
gctaagttga caacgatatc gaaaatgct gttgttact tctctgatca aacacatttc     540
tcagttgata gagcattgaa ggtttaggt tttaaacatc atcaaatctg tagaatcgaa     600
acagatgaac atttgagaat ctctgtttca gctttgaaga aacaaattaa agaagataga     660
```

```
actaagggta aaaagccatt ctgtgttatt gcaaatgctg gtactacaaa ttgtggtgct   720
gttgattctt tgaacgaatt agcagatttg tgtaacgatg aagatgtttg gttgcatgct   780
gatggttctt atggtgctcc agctatcttg tctgaaaagg gttcagctat gttgcaaggt   840
attcatagag cagattcttt gactttagat ccacataagt ggttgttcca accatacgat   900
gttggttgtg ttttgatcag aaactctcaa tatttgtcaa agactttag aatgatgcca    960
gaatacatca aggattcaga aactaacgtt gaaggtgaaa ttaatttcgg tgaatgtggt  1020
atcgaattgt caagaagatt cagagctttg aaggtttggt tgtcttttaa agttttcggt  1080
gttgctgctt ttagacaagc aatcgatcat ggtatcatgt tagcagaaca agttgaagca  1140
tttttgggta aagcaaaaga tgggaagtt gttacaccag ctcaattggg tatcgttact   1200
tttagataca ttccatctga attggcatca acagatacta ttaatgaaat taataagaaa  1260
ttggttaagg aaatcacaca tagaggtttc gctatgttat ctactacaga attgaaggaa  1320
aaggttgtta ttagattgtg ttcaattaat ccaagaacta caactgaaga aatgttgcaa  1380
atcatgatga agattaaagc attggctgaa gaagtttcta tttcatacccc atgtgttgct  1440
gaataa                                                              1446

SEQ ID NO: 32           moltype = AA   length = 481
FEATURE                 Location/Qualifiers
source                  1..481
                        mol_type = protein
                        organism = Bacillus atrophaeus
SEQUENCE: 32
MMSENLQLSA EEMRQLGYQA VDLIIDHMNH LKSKPVSETI DSDILRNKLT ESIPENGSDP   60
KELLHFLNRN VFNQITHVDH PHFLAFVPGP NNYVGVVADF LASGFNVFPT AWIAGAGAEQ  120
IELTTINWLK SMLGFPDSAE GLFVSGGSMA NLTALTVARQ AKLNNDIENA VVYFSDQTHF  180
SVDRALKVLG FKHHQICRIE TDEHLRISVS ALKKQIKEDR TKGKKPFCVI ANAGTTNCGA  240
VDSLNELADL CNDEDVWLHA DGSYGAPAIL SEKGSAMLQG IHRADSLTLD PHKWLFQPYD  300
VGCVLIRNSQ YLSKTFRMMP EYIKDSETNV EGEINFGECG IELSRRFRAL KVWLSFKVFG  360
VAAFRQAIDH GIMLAEQVEA FLGKAKDWEV VTPAQLGIVT FRYIPSELAS TDTINEINKK  420
LVKEITHRGF AMLSTTELKE KVVIRLCSIN PRTTTEEMLQ IMMKIKALAE EVSISYPCVA  480
E                                                                  481

SEQ ID NO: 33           moltype = DNA   length = 18
FEATURE                 Location/Qualifiers
misc_feature            1..18
                        note = Synthetic HIS epitope tag polypeptide
source                  1..18
                        mol_type = other DNA
                        organism = synthetic construct
SEQUENCE: 33
catcatcatc atcatcat                                                 18

SEQ ID NO: 34           moltype = AA   length = 6
FEATURE                 Location/Qualifiers
REGION                  1..6
                        note = Synthetic HIS epitope tag polypeptide
source                  1..6
                        mol_type = protein
                        organism = synthetic construct
SEQUENCE: 34
HHHHHH                                                              6

SEQ ID NO: 35           moltype = DNA   length = 5369
FEATURE                 Location/Qualifiers
misc_feature            1..5369
                        note = pET28a(+) vector
source                  1..5369
                        mol_type = other DNA
                        organism = synthetic construct
SEQUENCE: 35
atccggatat agttcctcct ttcagcaaaa aaccccctcaa gacccgttta gaggccccaa   60
ggggttatgc tagttattgc tcagcggtgg cagcagccaa ctcagcttcc tttcgggctt  120
tgttagcagc cggatctcag tggtggtggt ggtggtgctc gagtgcggcc gcaagcttgt  180
cgacggagct cgaattcgga tccgcgaccc atttgctgtc caccagtcat gctagccata  240
tggctgccgc gcggcaccag gccgctgctg tgatgatgat gatgatgctg gctgcccatg  300
gtatatctcc ttcttaaagt taaacaaaat tatttctaga ggggaattgt tatccgctca  360
caattcccct atagtgagtc gtattaattt cgcgggatcg agatctcgat cctctacgcc  420
ggacgcatcg tggccggcat caccggcgcc acaggtgcgg ttgctggcgc ctatatcgcc  480
gacatcaccg atggggaaga tcgggctcgc cacttcgggc tcatgagcgc ttgtttcggc  540
gtgggtatgg tggcaggccc cgtggccggg gactgttggg cgccatctcc ttgcatgcac  600
ccattccttg cggcggcggt gctcaacggc ctcaacctac tactgggctg cttcctaatg  660
caggagtcgc ataagggaga gcgtcgagat cccggacacc atcgaatggc gcaaaacctt  720
tcgcggtatg gcatgatagc gcccggaaga gagtcaattc agggtggtga atgtgaaacc  780
agtaacgtta tacgatgtcg cagagtatgc cggtgtctct tatcagaccg tttcccgcgt  840
ggtgaaccag gccagccacg tttctgcgaa aacgcgggaa aaagtggaag cggcgatggc  900
ggagctgaat tacattccca accgcgtggc acaacaactg gcgggcaaac agtcgttgct  960
gattggcgtt gccacctcca gtctggccct gcacgcgccg tcgcaaattg tcgcggcgat 1020
taaatctcgc gccgatcaac tgggtgccag cgtggtggtg tcgatggtag aacgaagcgg 1080
cgtcgaagcc tgtaaagcgg cggtgcacaa tcttctcgcg caacgcgtca gtgggctgat 1140
cattaactat ccgctggatg accaggatgc cattgctgtg gaagctgcct gcactaatgt 1200
```

```
tccggcgtta tttcttgatg tctctgacca gacacccatc aacagtatta ttttctccca   1260
tgaagacggt acgcgactgg gcgtggagca tctggtcgca ttgggtcacc agcaaatcgc   1320
gctgttagcg ggcccattaa gttctgtctc ggcgcgtctg cgtctggctg gctggcataa   1380
atatctcact cgcaatcaaa ttcagccgat agcggaacgg gaaggcgact ggagtgccat   1440
gtccggtttt caacaaacca tgcaaatgct gaatgggcag atcgttccca ctgcgatgct   1500
ggttgccaac gatcagatgg cgctgggcgc aatgcgcgcc attaccgagt ccgggctgcg   1560
cgttggtgcg gatatctcgg tagtgggata cgacgatacc gaagacagct catgttatat   1620
cccgccgtta accaccatca aacaggattt tcgcctgctg gggcaaacca gcgtggaccg   1680
cttgctgcaa ctctctcagg gccaggcggt gaagggcaat cagctgttgc ccgtctcact   1740
ggtgaaaaga aaaaccaccc tggcgcccaa tacgcaaacc gcctctcccc gcgcgttggc   1800
cgattcatta atgcagctgg cacgacaggt tcccgactg gaaagcgggc agtgagcgca   1860
acgcaattaa tgtaagttag ctcactcatt aggcaccggg atctcgaccg atgcccttga   1920
gagccttcaa cccagtcagc tccttccggt gggcgcgggg catgactatc gtcgccgcac   1980
ttatgactgt cttctttatc atgcaactcg taggacaggt gccggcagcg ctctgggtca   2040
ttttcggcga ggaccgcttt cgctggagcg cgacgatgat cggcctgtcg cttgcgtat   2100
tcggaatctt gcacgccctc gctcaagcct tcgtcactgg tcccgccacc aaacgtttcg   2160
gcgagaagca ggcattatc gccggcatgg cggcccacg ggtgcgcatg atcgtgctcc   2220
tgtcgttgag gacccggcta ggctggcggg gttgccttac tggttagcag aatgaatcac   2280
cgatacgcga gcgaacgtga agcgactgct gctgcaaaac gtctgcgacc tgagcaacaa   2340
catgaatggt cttcggtttc cgtgtttcgt aaagtctgga aacgcggaag tcagcgccct   2400
gcaccattat gttccggatc tgcatcgcag gatgctgctg gctaccctgt ggaacaccta   2460
catctgtatt aacgaagcgc tggcattgac cctgagtgat ttttctctgg tcccgccgca   2520
tccataccgc cagttgttta ccctcacaac gttccagtaa ccgggcatgt tcatcatcag   2580
taacccgtat cgtgagcatc ctctctcgtt tcatcggtat cattacccc atgaacagaa   2640
atccccctta cacggaggca tcagtgacca acaggaaaa aaccgccctt aacatggccc   2700
gctttatcag aagccagaca ttaacgcttc tggagaaact caacgacgtg gacgcggatg   2760
aacaggcaga catctgtgaa tcgcttcacg accacgctga tgagcttttac cgcagctgcc   2820
tcgcgcgttt cggtgatgac ggtgaaaacc tctgacacat gcagctcccg gagacggtca   2880
cagcttgtct gtaagcggat gccgggagca gacaagcccg tcagggcgcg tcagcggggtg   2940
ttggcgggtg tcggggcgca gccatgaccc agtcacgtag cgatagccgga gtgtatactg   3000
gcttaactat gcggcatcag agcagattgt actgagagtg caccatatat gcggtgtgaa   3060
ataccgcaca gatgcgtaag gagaaaatac cgcatcaggc gctcttccgc ttcctcgctc   3120
actgactcgc tgcgctcggt cgttcggctg cggcgagcgg tatcagctca ctcaaaggcg   3180
gtaatacggt tatccacaga atcaggggat aacgcaggaa agaacatgtg agcaaaaggc   3240
cagcaaaagg ccaggaaccg taaaaaggcc gcgttgctgg cgtttttcca taggctccgc   3300
ccccctgacg agcatcacaa aaatcgacgc tcaagtcaga ggtggcgaaa cccgacagga   3360
ctataaagat accaggcgtt tccccctgga agctccctcg tgcgctctcc tgttccgacc   3420
ctgccgctta ccggatacct gtccgccttt ctcccttcgg gaagcgtggc gctttctcat   3480
agctcacgct gtaggtatct cagttcggtg taggtcgttc gctccaagct gggctgtgtg   3540
cacgaacccc ccgttcagcc cgaccgctgc gccttatccg gtaactatcg tcttgagtcc   3600
aacccggtaa gacacgactt atcgccactg gcagcagcca ctggtaacag gattagcaga   3660
gcgaggtatg taggcggtgc tacagagttc ttgaagtggt ggcctaacta cggctacact   3720
agaaggacag tatttggtat ctgcgctctg ctgaagccag ttaccttcgg aaaaagagtt   3780
ggtagctctt gatccggcaa acaaaccacc gctggtagcg gtggtttttt tgtttgcaag   3840
cagcagatta cgcgcagaaa aaaaggatct caagaagatc ctttgatctt ttctacgggg   3900
tctgacgctc agtggaacga aaactcacgt taagggattt tggtcatgaa caataaaact   3960
gtctgcttac ataaacagta ataccaagggg tgttatgagc catattcaac gggaaacgtc   4020
ttgctctagg ccgcgattaa attccaacat ggatgctgat ttatatgggt ataaatgggc   4080
tcgcgataat gtcgggcaat caggtgcgac aatctatcga ttgtatggga agcccgatgc   4140
gccagagttg tttctgaaac atggcaaagg tagcgttgcc aatgatgtta cagatgagat   4200
ggtcagacta aactggctga cggaatttat gcctcttccg accatcaagc attttatccg   4260
tactcctgat gatgcatggt tactcaccac tgcgatcccc gggaaaacag cattccaggt   4320
attagaagaa tatcctgatt caggtgaaaa tattgttgat gcgctggcag tgttcctgcg   4380
ccggttgcat tcgattcctg tttgtaattg tccttttaac agcgatcgcg tatttcgtct   4440
cgctcaggcg caatcacgaa tgaataacgg tttggttgat gcgagtgatt ttgatgacga   4500
gcgtaatggc tggcctgttg aacaagtctg gaaagaaatg cataaacttt tgccattctc   4560
accggattca gtcgtcactc atggtgattt ctcacttgat aaccttattt ttgacgaggg   4620
gaaattaata ggttgtattg atgttggacg agtcggaatc gcagaccgat accaggatct   4680
tgccatccta tggaactgcc tcggtgagtt ttctccttca ttacagaaac ggctttttca   4740
aaaatatggt attgataatc ctgatatgaa taaattgcag tttcatttga tgctcgatga   4800
gttttttcta a gaattaattc atgagcggat acatatttga atgtatttag aaaaataaac   4860
aaataggggt tccgcgcaca tttccccgaa aagtgccacc tgaaattgta acgttaata   4920
ttttgttaaa attcgcgtta aatttttgtt aaatcagctc atttttttaac caataggccg   4980
aaatcggcaa aatcccttat aaatcaaaag aatagaccga gatagggttg agtgttgttc   5040
cagtttggaa caagagtcca ctattaaaga acgtggactc caacgtcaaa gggcgaaaaa   5100
ccgtctatca gggcgatggc ccactacgtg aaccatcacc taatcaagt ttttttgggt   5160
cgaggtgccg taaagcacta atcggaacc ctaagggag cccccgattt agagcttgac   5220
ggggaaagcc ggcgaacgtg gcgagaaagg aagggaagaa agcgaaagga gcgggcgcta   5280
gggcgctggc aagtgtagcg tcacgctgcg cgtaaccac cacacccgcc gcgcttaatg   5340
cgccgctaca gggcgcgtcc cattcgcca                                     5369

SEQ ID NO: 36         moltype = DNA   length = 33
FEATURE               Location/Qualifiers
misc_feature          1..33
                      note = Synthetic c-MYC epitope tag polypeptide
source                1..33
                      mol_type = other DNA
                      organism = synthetic construct
SEQUENCE: 36
```

```
gaacaaaagt taatttctga agaagatttg gaa                              33
```

SEQ ID NO: 38          moltype = DNA   length = 2160
FEATURE                Location/Qualifiers
source                 1..2160
                       mol_type = genomic DNA
                       organism = Oryza sativa
SEQUENCE: 37
EQKLISEEDL                                                        10

SEQ ID NO: 38          moltype = DNA   length = 2160
FEATURE                Location/Qualifiers
source                 1..2160
                       mol_type = genomic DNA
                       organism = Oryza sativa
SEQUENCE: 38
```
atggagtcgt cggcggggcc gatggagctg gtggcggcgc tgctgcgggg gctgacgccg   60
cgggcggagc agctgctgca gctgtcgtcc gggggagggg aggccgccgc cggtggcgcg  120
gcggaggcga gggccgcggt ggccacggtg gccgccgcgc tgctcgggtg cgcgttcttg  180
gtgttatgga ggcgggtctc ggcggggcgg aagcggaaga ggaggaggcc agaaggtcg   240
gcggcggccg tggctggggt ggggaagggc gggaagaatg cctccgcggc ggccggggag  300
gaggccggcg cgccgacgg gaggaagcgg gtcaccgtct tcttcggcac gcagaccggc   360
accgccgagg gcttcgccaa ggcactcgct gaggaggcta agtcaagata cgacaaggcg  420
atattcaaag ttgtggactt ggatgagtat gcgatgagg atggaggaga ga           480
ttgaagaagg agaagatatc gttgttcttc gttgcaacgt acggagatgg tgaaccgact  540
gacaatgctg ctaggttcta taaatggttc actgagggaa atgagagggg tgtttggttg  600
aatgacttcc agtatgctat ttttggtctt ggcaatcggc agtatgagca tttcaacaag  660
gttgcaaagg ttgttgatga gctcctagtt gagcaaggtg gaaaacgtct tgttccgagtt  720
ggtcttggag atgatgatca atgcattgag gatgacttca acgcatggaa agaaactctc   780
tggccagaat tggatcagtt acttcgggat gaaaatgatg tttcaacagg cactacctac   840
acagctgcca ttcctgaata ccgggttgaa tttgttaagc ctgatgaggc agcccatttg   900
gagagaaatt tcagtcttgc aaacggttat gcggttcatg atgctcaagca tccttgccgg   960
gccaacgtgg ctgtgcgacg ggaactccac actcctgctt ctgatcgttc atgcactcac  1020
ttggagtttg acattgctgg cactggtctt acgtatgaaa ccggtgacca tgttggtgta  1080
tacacagaga actgcctcga ggttgtagag gaggcagaga ggttgttagg ctactcccca  1140
gaggcttttt tcaccatcca tgcagacaaa gaggacggta caccactagg tggtggttct  1200
ctggctcctc cattcccttc ccgattact gtgaggaatg gcttgctag atatgcggat    1260
cttctgaatt cgccgaagaa gagtgctttg gttgcattag ctacttatgc ttcagattct   1320
actgaagctg atcgtctgag gttcttggcc tctcctgctg gaaaggatga gtatgctcaa   1380
tggggttgttg cgagtcaaag aagtctatta gaagtgatgg cagagttccc ttcagcaaag   1440
cctccactag gagtcttctt tgcagccgtt gctcctcgtc ttcagccgag atactactca   1500
atttcatctt cacctagcat ggcacctacc agaattcatg ttacatgtgc acttgtccat   1560
gaaaaaacac ctgctggaag ggtacataag ggagtctgct caacatggat taagaatgct   1620
attccatcag aagagacaaa ggactgcagc tgggctccag ttttttgtgag acaatcaaac   1680
ttcaaactgc ctgctgatcc ttcagtaccg gttatcatga ttggcccagg aactggtctt   1740
gctcctttcc gcggattctt gcaggagagg ctgtctcaaa acaatcagg agctgagctt    1800
ggtcgctccg tattcttctt tggatgcaga aacagcaaga tggactttcat ctatgaggat   1860
gagctgaaca ctttccttga ggaaggagca ttgtccgagc tggttctcgc cttctctcgt   1920
gagggcccta cgaaggaata cgtgcagcac aaaatgtcgc agaaagcttc cgaaatctgg   1980
gacatgatct cccagggtgg ttacattta gtctgtggtg atgccaaagg catggccaga   2040
gatgtacata gagttctcca caccattgta caggaacagg gatcacttga cagctctaag   2100
gctgagagct ttgtgaagag cctccaaacg gagggtaggt atctgagaga tgtgtggtga   2160
```

SEQ ID NO: 39          moltype = AA   length = 719
FEATURE                Location/Qualifiers
source                 1..719
                       mol_type = protein
                       organism = Oryza sativa
SEQUENCE: 39
```
MESSAGPMEL VAALLRGLTP RAEQLLQLSS GGGEAAAGGA AEARAAVATV AAALLGCAFL   60
VLWRRVSAGR KRKREEAERS AAAVAGVGKG GKNASAAAGE EAGGADGRKR VTVFFGTQTG  120
TAEGFAKALA EEAKSRYDKA IFKVVDLDEY AMEDEEYEER LKKEKISLFF VATYGDGEPT  180
DNAARFYKWF TEGNERGVWL NDFQYAIFGL GNRQYEHFNK VAKVVDELLV EQGGKRLVPV  240
GLGDDDQCIE DDFNAWKETL WPELDQLLRD ENDVSTGTTY TAAIPEYRVE FVKPDEAAHL  300
ERNFSLANGY AVHDAQHPCR ANVAVRRELH TPASDRSCTH LEFDIAGTGL TYETGDHVGV  360
YTENCLEVVE EAERLLGYSP EAFFTIHADK EDGTPLGGGS LAPPFPSPIT VRNALARYAD  420
LLNSPKKSAL VALATYASDS TEADRLRFLA SPAGKDEYAQ WVVASQRSLL EVMAEFPSAK  480
PPLGVFFAAV APRLQPRYYS ISSSPSMAPT RIHVTCALVH EKTPAGRVHK GVCSTWIKNA  540
IPSEETKDCS WAPVFVRQSN FKLPADPSVP VIMIGPGTGL APFRGFLQER LSQKQSGAEL  600
GRSVFFFGCR NSKMDFIYED ELNTFLEEGA LSELVLAFSR EGPTKEYVQH KMSQKASEIW  660
DMISQGGYIY VCGDAKGMAR DVHRVLHTIV QEQGSLDSSK AESFVKSLQT EGRYLRDVW   719
```

SEQ ID NO: 40          moltype = DNA   length = 27
FEATURE                Location/Qualifiers
misc_feature           1..27
                       note = Synthetic HA epitope tag polypeptide
source                 1..27

```
                        mol_type = other DNA
                        organism = synthetic construct
SEQUENCE: 40
tacccatacg acgttccaga ctacgcc                                        27

SEQ ID NO: 41           moltype = AA   length = 9
FEATURE                 Location/Qualifiers
REGION                  1..9
                        note = Synthetic HA epitope tag polypeptide
source                  1..9
                        mol_type = protein
                        organism = synthetic construct
SEQUENCE: 41
YPYDVPDYA                                                             9

SEQ ID NO: 42           moltype = DNA   length = 2169
FEATURE                 Location/Qualifiers
source                  1..2169
                        mol_type = genomic DNA
                        organism = Oryza sativa
SEQUENCE: 42
atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acgttgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatgaccc caaatgtgcctg gatgcgttcc caaaattagt ttgttttaaa    540
aaacgtattg aagctatccc acaaattgat aagtacttga aatccagcaa gtatatagca    600
tggcctttgc agggctggca agccacgttt ggtggtggcg accatcctcc aaaatcggat    660
ctggaagttc tgttccaggg gcccctggga tccccgatgc tgccgccgtc gccgccgggg    720
tggccggtga tcgggcacct ccacctcatg tccggcatgc cgcaccacgc gctggccgag    780
ctggcgcgca ccatgcgcgc cggctgttc cggatgcgcg tggggagcgt gccggcggtg    840
gtgatctcca gccggacct cgcccgcgcc gcgctcacca ccaacgacgc cgcgctggcg    900
tcgcggccgc acctgctctc cggccagttc ctgtcgttcg gctgctccga cgtgacgttc    960
gcgccggcgg ggccgtacca ccggatggcg cgccgcgtgg tggtgtcgga gctcctgtcg   1020
gcgcgtcgcg tcgccacgta cggcgccgtc agggtcaagg agctccgcg cctgctcgcg   1080
cacctcacca gaacacctc gccggcgaag cccgtcgacc tcagcgagtg cttcctcaac   1140
ctcgccaacg acgtgctctg ccgcgtcgcg ttcggccgcc ggttcccgca cggcgagggc   1200
gacaagctcg gcgcggtgct cgccgaggcg caggacctct cgccgggtt caccatcggc   1260
gacttcttcc ccgagctcga gccgctcgcc agcaccgtca ccggactccg ccgccgccgcacg   1320
aagaagtgcc tcgccgacct ccgcgaggcc tgcgacgtga tcgtggacga acacatcagc   1380
ggcaaccgcc agcgcatccc cggcgaccgc gacgaggact cgtcgacgt cctcctccgc   1440
gtccagaaat cccccgacct cgaggtcccc ctaaccgacg acaatctcaa ggccctcgtc   1500
ctggacatgt tcgtcgccgg cacggacacc acgttccgca cgttcgccgag tggtgatgacg   1560
gagctagtcc gccacccacg gatcctcaag aaggcgcagg aggaggtccg gcgagtcgtc   1620
ggcgacagcg gccgcgtcga ggagtcccac ctcggcgagc tccactacat gcgcgccatc   1680
atcaaggaga cgttccggct gcacccggcg gtgccgttgc tagtgccgcg cgagtccgtc   1740
gcgccgtgca cgctgggcgg ctacgacatc ccggcgagga cgcgggtgtt catcaacacg   1800
ttcgccatgg ggcgcgaccc ggagatctgg gacaacccgc tggagtactc gccggagagg   1860
ttcgagagcg ccggcggcgg cggcgagatc gacctcaagg acccggacta caagctgctg   1920
ccgttcggcg gcgggcggcg agggtgcccc ggctacacgt tcgcgctcgc caccgtgcag   1980
gtgtcgctcg ccagcttgct ctaccacttc gagtgggcgc tgcccgccgg cgtgcgccca   2040
gaggacgtca acctcgacga gacgttcggc ctcgccacga ggaagaagga gccgctcttc   2100
gtcgccgtca ggaagagcga cgcgtacgag tttaagggag aggagcttag tgaggtttac   2160
ccatactga                                                          2169

SEQ ID NO: 43           moltype = AA   length = 722
FEATURE                 Location/Qualifiers
source                  1..722
                        mol_type = protein
                        organism = Oryza sativa
SEQUENCE: 43
MSPILGYWKI KGLVQPTRLL LEYLEEKYEE HLYERDEGDK WRNKKFELGL EFPNLPYYID    60
GDVKLTQSMA IIRYIADKHN MLGGCPKERA EISMLEGAVL DIRYGVSRIA YSKDFETLKV   120
DFLSKLPEML KMFEDRLCHK TYLNGDHVTH PDFMLYDALD VVLYMDPMCL DAFPKLVCFK   180
KRIEAIPQID KYLKSSKYIA WPLQGWQATF GGGDHPPKSD LEVLFQGPLG SPMLPPSPPG   240
WPVIGHLHLM SGMPHHALAE LARTMRAPLF RMRLGSVPAV VISKPDLARA ALTTNDAALA   300
SRPHLLSGQF LSFGCSDVTF APAGPYHRMA RRVVVSELLS ARRVATYGAV RVKELRRLLA   360
HLTKNTSPAK PVDLSECFLN LANDVLCRVA FGRRFPHGEG DKLGAVLAEA QDLFAGFTIG   420
DFFPELEPVA STVTGLRRRL KKCLADLREA CDVIVDEHIS GNRQRIPGDR DEDFVDLLR   480
VQKSPDLEVP LTDDNLKALV LDMFVAGTDT TFATLEWVMT ELVRHPRILK KAQEEVRRVV   540
GDSGRVEESH LGELHYMRAI IKETFRLHPA VPLLVPRESV APCTLGGYDI PARTRVFINT   600
FAMGRDPEIW DNPLEYSPER FESAGGGGEI DLKDPDYKLL PFGGGRRGCP GYTFALATVQ   660
VSLASLLYHF EWALPAGVRA EDVNLDETFG LATRKKEPLF VAVRKSDAYE FKGEELSEVY   720
PY                                                                 722
```

| SEQ ID NO: 44 | moltype = DNA   length = 3781 |
|---|---|
| FEATURE | Location/Qualifiers |
| misc_feature | 1..3781 |
| | note = pCDFDuet-1 vector |
| source | 1..3781 |
| | mol_type = other DNA |
| | organism = synthetic construct |

SEQUENCE: 44

```
ggggaattgt gagcggataa caattcccct gtagaaataa ttttgtttaa ctttaataag    60
gagatatacc atgggcagca gccatcacca tcatcaccac agccaggatc cgaattcgag   120
ctcggcgcgc ctgcaggtcg acaagcttgc ggccgcataa tgcttaagtc gaacagaaag   180
taatcgtatt gtacacggcc gcataatcga aattaatacg actcactata ggggaattgt   240
gagcggataa caattcccca tcttagtata ttagttaagt ataagaagga gatatacata   300
tggcagatct caattggata tcggccggcc acgcgatcgc tgacgtcggt accctcgagt   360
ctggtaaaga aaccgctgct gcgaaatttg aacgccagca catggactcg tctactagcg   420
cagcttaatt aacctaggct gctgccaccg ctgagcaata actagcataa ccccttgggg   480
cctctaaacg ggtcttgagg ggttttttgc tgaaacctca ggcatttgag aagcacacgg   540
tcacactgct tccggtagtc aataaaccgg taaaccagca atagacataa gcggctattt   600
aacgaccctg ccctgaaccg acgacccggt catcgtggcc ggatcttgcg gcccctcggc   660
ttgaacgaat tgttagacat tatttgccga ctaccttggt gatctcgcct ttcacgtagt   720
ggacaaattc ttccaactga tctgcgcgcg aggccaagtc atcttcttct tgtccaagat   780
aagcctgtct agcttcaagt atgacgggct gatactgacg gcggcaggcg tccattgccc   840
agtcggcagc gacatccttc ggcgcgattt tgccggttac tgcgctgtac caaatgcggg   900
acaacgtaag cactacattt cgctcatcgc cagcccagtc gggcggcgag ttccatagcg   960
ttaaggtttc atttagcgcc tcaaatagat cctgttcagg aaccggatca agagttcct  1020
ccgccgctgg acctaccaag gcaacgctat gttctcttgc ttttgtcagc aagatagcca  1080
gatcaatgtc gatcgtggct ggctcgaaga tacctgcaaa aatgtcattg cgctgccatt  1140
ctccaaattg cagttcgcgc ttagctggat aacgccacgg aatgatgtcg tcgtgcacaa  1200
caatggtgac ttctacagcg cggagaatct cgctctctcc aggggaagcc gaagtttcca  1260
aaaggtcgtt gatcaaagct cgccgcgttg tttcatcaag ccttacgtca ccgtaaccga  1320
gcaaatcaat atcactgtgt ggcttcaggc cgccatccac tgcggagccg tacaaatgta  1380
cggccagcaa cgtcggttcg agatggcgct cgatgacgcg aactacctct gatagttgag  1440
tcgatacttc ggcgatcacc gcttccctca tactcttcct ttttcaatat tattgaagca  1500
tttatcaggg ttattgtctc atgagcggat acatatttga atgtatttag aaaaataaac  1560
aaatagctag ctcactcggt cgctacgctc cgggcgtgag actgcggcgg gcgctgcgga  1620
cacatacaaa gttacccaca gattccgtgg ataagcaggg gactaacatg tgaggcaaaa  1680
cagcagggcc gcgccggtgg cgttttttcca taggctccgc cctcctgcca gagttcacat  1740
aaacagtc ttttcggtg catctgtggg agccgtgagg ctcaaccatg aatctgacag  1800
tacgggcgaa acccgacagg acttaaagat ccccaccgtt tccggcgggt cgctccctct  1860
tgcgctctcc tgttccgacc ctgccgttta ccggatacct gttccgcctt tctcccttac  1920
gggaagtgtg gcgctttctc atagctcaca cactggtatc tcggctcggt gtaggtcgtt  1980
cgctccaagc tgggctgtaa gcaagaactc ccgttcagc cgactgctg cgccttatcc  2040
ggtaactgtt cacttgagtc caacccggaa aagcacggta aaacgccact ggcagcagcc  2100
attggtaact gggagttcgc agaggatttg tttagctaaa cacgcggttg ctcttgaagt  2160
gtgcgccaaa gtccggctac actggaagga cagatttggt tgctgtgctc tgcgaaagcc  2220
agttaccacg gttaagcagt tccccaactg acttaacctt cgatcaaacc acctccccag  2280
gtggtttttt cgtttacagg gcaaaagatt acgcgcagaa aaaaaggatc tcaagaagat  2340
cctttgatct tttctactga accgctctag atttcagtgc aatttatctc ttcaaatgta  2400
gcacctgaag tcagccccat acgatataag ttgtaattct catgttagtc atgcccgcg  2460
cccaccggaa ggagctgact gggttgaagg ctctcaaggg catcggtcga tcccggtg  2520
cctaatgagt gagctaactt acattaattg cgttgcgctc actgcccgct ttccagtcgg  2580
gaaacctgtc gtgccagctg cattaatgaa tcggccaaca gcggggggaga gcggtttgc  2640
gtattgggcg ccagggtggt tttcttttc accagtgaga cgggcaacag ctgattgccc  2700
ttcaccgcct ggccctgaga gagttgcagc aagcggtcca cgctggtttg ccccagcagg  2760
cgaaaatcct gtttgatggt ggttaacggc gggatataac atgagctgtc ttcggtatcg  2820
tcgtatccca ctaccgagat gtccgcacca acgcgcagcc cggactcggt aatgcgcgc  2880
attgcgccca cgccatctg atcgttgca ccagcatcg cagtgggaac gatgccctca  2940
ttcagcattt gcatggtttg ttgaaaaccg gacatggcac tccagtcgcc ttcccgttcc  3000
gctatcggct gaatttgatt gcgagtgaga tattatgcc accagccag acgcagacgc  3060
gccgagacag aacttaatgg gcccgctaac agcgcgattt gctggtgacc caatgcgacc  3120
agatgctcca cgcccagtcg cgtaccgtct tcatgggaga aaataatact gttgatgggt  3180
gtctggtcag agacatcaag aaataacgcc ggaacattag tgcaggcagc ttccacagca  3240
atggcatcct ggtcatccag cggatagtta atgatcagcc cactgacgcg ttgcgcgaga  3300
agattgtgca ccgccgcttt acaggcttcg acgccgcttc gttctaccat cgacaccacc  3360
acgctggcac ccagttgatc ggcgcgagat taatcgccg cgacaatttg cgacggcgcg  3420
tgcagggcca gactggaggt ggcaacgcca atcagcaacg actgtttgcc cgccagttgt  3480
tgtgccacgc ggttgggaat gtaattcagc tccgccatcg ccgcttccac ttttcccgcg  3540
gttttcgcag aaacgtggct ggcctggttc accacgcggg aaacggtctg ataagagaca  3600
ccggcatact ctgcgacatc gtataacgtt actggtttca cattcaccac cctgaattga  3660
ctctcttccg ggcgctatca tgccataccg cgaaaggttt tgcgccattc gatggtgtcc  3720
gggatctcga cgctctccct tatgcgactc ctgcattagg aaattaatac gactcactat  3780
a                                                                  3781
```

HYDROXYLATED PSILOCYBIN DERIVATIVES AND METHODS OF USING

RELATED APPLICATION

This application is a continuation of PCT Application No. PCT/CA2021/051210 filed Sep. 1, 2021, which claims the benefit of U.S. Provisional Application No. 63/073,076 filed Sep. 1, 2020; the entire contents of Patent Application Nos. PCT/CA2021/051210 and 63/073,076 are hereby incorporated by reference.

INCORPORATION OF SEQUENCE LISTING

A computer readable form of the Sequence Listing "29664-P62367US02_SequenceListing.xml" (124,749 bytes), submitted via EFS-WEB and created on Sep. 2, 2022, is herein incorporated by reference.

FIELD OF THE DISCLOSURE

The compositions and methods disclosed herein relate to a chemical compound known as psilocybin. Furthermore, the compositions and methods disclosed herein relate in particular to hydroxylated forms of psilocybin.

BACKGROUND OF THE DISCLOSURE

The following paragraphs are provided by way of background to the present disclosure. They are not however an admission that anything discussed therein is prior art or part of the knowledge of a person of skill in the art.

The biochemical pathways in the cells of living organisms may be classified as being part of primary metabolism, or as being part of secondary metabolism. Pathways that are part of a cell's primary metabolism are involved in catabolism for energy production or in anabolism for building block production for the cell. Secondary metabolites, on the other hand, are produced by the cell without having an obvious anabolic or catabolic function. It has long been recognized that secondary metabolites can be useful in many respects, including as therapeutic compounds.

Psilocybin, for example, is a secondary metabolite that is naturally produced by certain mushrooms which taxonomically can be classified as belonging the Basidiomycota division of the fungi kingdom. Mushroom species which can produce psilocybin include species belonging to the genus *Psilocybe*, such as *Psilocybe azurescens, Psilocybe semilanceata, Psilocybe serbica, Psilocybe mexicana*, and *Psilocybe cyanescens*, for example. The interest of the art in psilocybin is well established. Thus, for example, psilocybin is a psychoactive compound and is therefore used as a recreational drug. Furthermore, psilocybin is used as a research tool in behavioral and neuro-imaging studies in psychotic disorders, and has been evaluated for its clinical potential in the treatment of mental health conditions (Daniel, J. et al. Mental Health Clin/, 2017; 7(1): 24-28), including to treat anxiety in terminal cancer patients (Grob, C. et al. Arch. Gen. Psychiatry, 2011, 68(1) 71-78) and to alleviate symptoms of treatment-resistant depression (Cathart-Harris, R. L. et al. Lancet Psychiatry, 2016, 3: 619-627).

Although the toxicity of psilocybin is low, adverse side effects, including, for example, panic attacks, paranoia and psychotic states, sometimes together or individually referred to as "a bad trip", are not infrequently experienced by recreational psilocybin users.

There exists therefore a need in the art for improved psilocybin compounds.

SUMMARY OF THE DISCLOSURE

The following paragraphs are intended to introduce the reader to the more detailed description, not to define or limit the claimed subject matter of the present disclosure.

In one aspect, the present disclosure relates to psilocybin and derivative compounds.

In another aspect, the present disclosure relates to hydroxylated psilocybin derivative compounds and methods of making and using these compounds.

Accordingly, in one aspect, the present disclosure provides, in at least one embodiment, in accordance with the teachings herein, a chemical compound or salt thereof having formula (I):

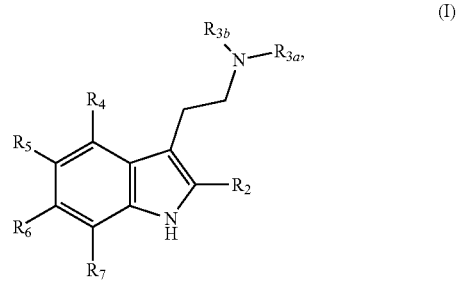

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a hydrogen atom, an alkyl group or a phosphate group, and wherein $R_{3A}$ and $R_{3B}$ are a hydrogen atom, an alkyl group, a cycloalkyl group, an aryl group, an alkaryl group or an acyl group.

In at least one embodiment, in an aspect, $R_2$ can be a hydroxy group, $R_5$, $R_6$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_4$ can be a hydroxy group and $R_2$, $R_5$, $R_6$ and $R_7$ can each be a hydrogen atom or an alkyl group or O-alkyl group.

In at least one embodiment, in an aspect, $R_5$ can be a hydroxy group, $R_2$, $R_6$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_6$ can be a hydroxy group, $R_2$, $R_5$ and $R_7$ can each be a hydrogen atom or an alkyl group or O-alkyl group, and $R_4$ can be a phosphate group, a hydrogen atom or an alkyl group or O-alkyl group.

In at least one embodiment, in an aspect, $R_7$ can be a hydroxy group, $R_2$, $R_5$ and $R_6$ can each be a hydrogen atom or an alkyl group or O-alkyl group, and $R_4$ can be a phosphate group, a hydrogen atom or an alkyl group or O-alkyl group.

In at least one embodiment, in an aspect, at least two of $R_2$, $R_4$, $R_5$, $R_6$ or $R_7$ can be a hydroxy group.

In at least one embodiment, in an aspect, $R_2$ and $R_4$ can be a hydroxy group, and $R_5$, $R_6$ and $R_7$ can be a hydrogen atom or an alkyl group or O-alkyl group.

In at least one embodiment, in an aspect, $R_2$ and $R_5$ can be a hydroxy group, $R_6$ and $R_7$ can be a hydrogen atom, and $R_4$ can be a hydrogen atom, an alkyl group or a phosphate group.

In at least one embodiment, in an aspect, $R_2$ and $R_6$ can be a hydroxy group, $R_5$ and $R_7$ can be a hydrogen atom or an alkyl group or O-alkyl group, and $R_4$ can be a hydrogen atom, an alkyl group or a phosphate group.

In at least one embodiment, in an aspect, $R_2$ and $R_7$ can be a hydroxy group, $R_5$ and $R_6$ can be a hydrogen atom or an alkyl group or O-alkyl group, and $R_4$ can be a hydrogen atom, an alkyl group an alkyl group or a phosphate group.

In at least one embodiment, in an aspect, $R_4$ and $R_5$ can be a hydroxy group, and $R_2$, $R_6$ and $R_7$ can be a hydrogen atom or an alkyl group or O-alkyl group.

In at least one embodiment, in an aspect, $R_4$ and $R_6$ can be a hydroxy group, and $R_2$, $R_5$ and $R_7$ can be a hydrogen atom or an alkyl group or O-alkyl group.

In at least one embodiment, in an aspect, $R_4$ and $R_7$ can be a hydroxy group and $R_2$, $R_5$ and $R_6$ can be a hydrogen atom or an alkyl group or O-alkyl group.

In at least one embodiment, in an aspect, $R_5$ and $R_6$ can be a hydroxy group, $R_2$ and $R_7$ can be a hydrogen atom or an alkyl group or O-alkyl group, and $R_4$ can be a hydrogen atom, an alkyl group or a phosphate group.

In at least one embodiment, in an aspect, $R_5$ and $R_7$ can be a hydroxy group, $R_2$ and $R_6$ can be a hydrogen atom or an alkyl group or O-alkyl group, and $R_4$ can be a hydrogen atom, an alkyl group or a phosphate group.

In at least one embodiment, in an aspect, $R_6$ and $R_7$ can be a hydroxy group, $R_2$ and $R_5$ can be a hydrogen atom or an alkyl group or O-alkyl group, and $R_4$ can be a hydrogen atom, an alkyl group or a phosphate group.

In at least one embodiment, in an aspect, $R_4$ when it is not hydroxylated can be a hydrogen atom.

In at least one embodiment, in an aspect, $R_4$ when it is not hydroxylated can be an alkyl group.

In at least one embodiment, in an aspect, $R_4$ when it is not hydroxylated can be an O-alkyl group.

In at least one embodiment, in an aspect, $R_4$ when it is not hydroxylated can be a phosphate group.

In at least one embodiment, in an aspect, three, four or all five of $R_2$, $R_4$, $R_5$, $R_6$ or $R_7$ can be a hydroxy group.

In at least one embodiment, in an aspect, the chemical compound can be selected from the group consisting of compounds having formulas (III), (IV); (V); (VI); (VII); (VIII); (IX); (X); (XI), (XII); (XIII); (XIV); (XV); (XVI); (XVII); (XVIII); (XIX); (XX); (XXI); (XXII); (XXIII); (XXIV); (XXV); (XXVI); (XXVII); (XXVIII); (XXIX); (XXX); (XXXI), and (XXXII):

(III)
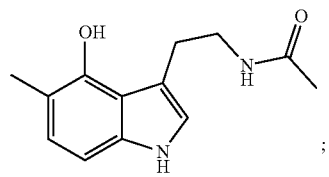

(IV)
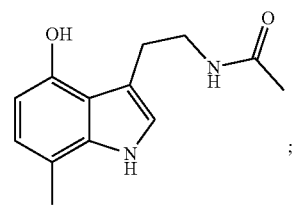

(V)
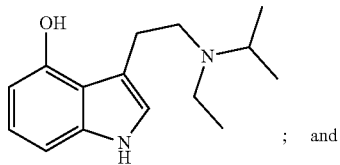

and (VI)
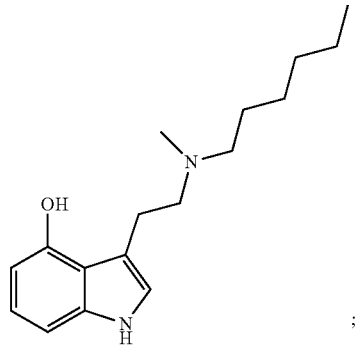

(VII)
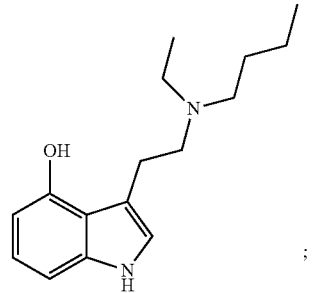

(VIII)
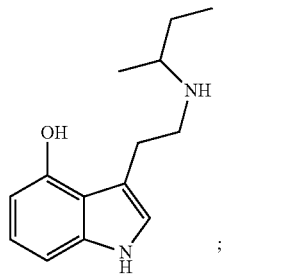

(IX)
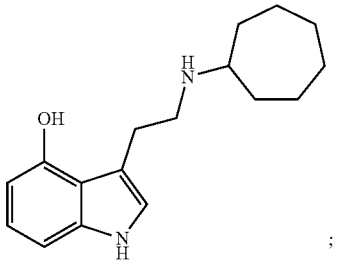

-continued
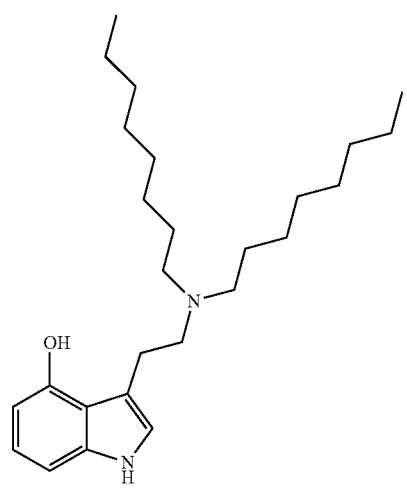
(X)
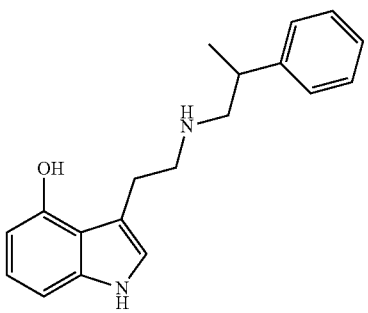
(XI)
(XII)
(XIII)
-continued
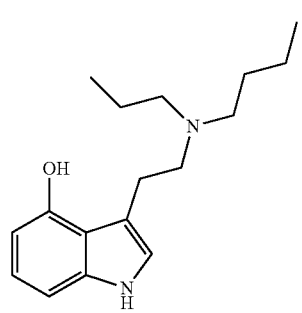
(XIV)
(XV)
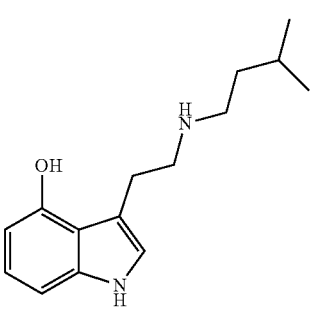
(XVI)
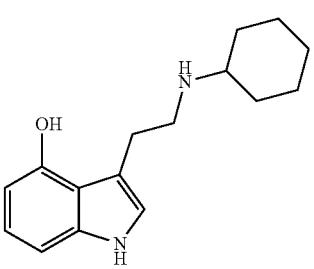
(XVII)
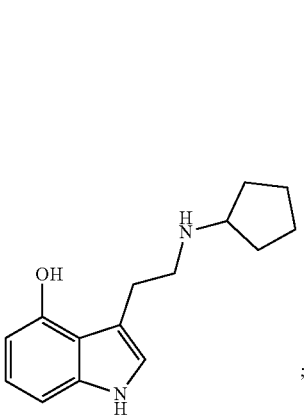
(XVIII)

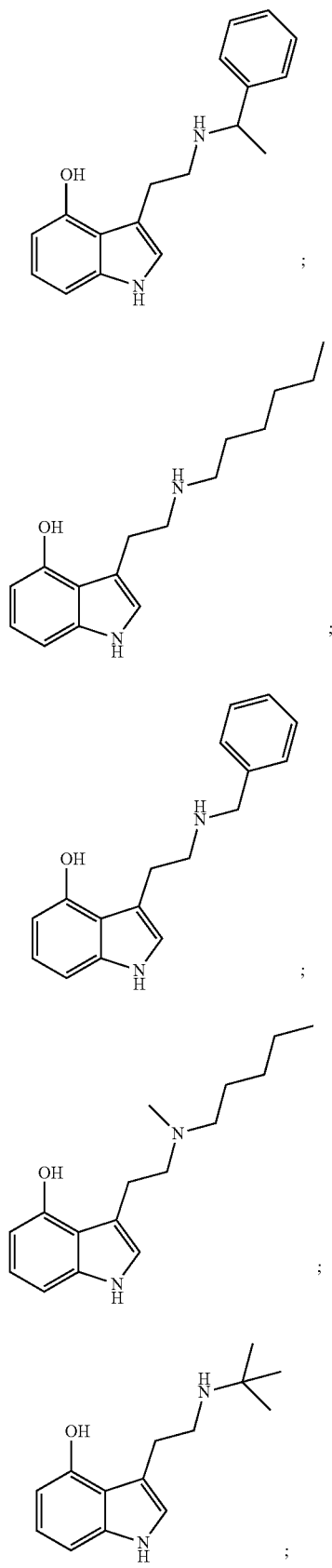
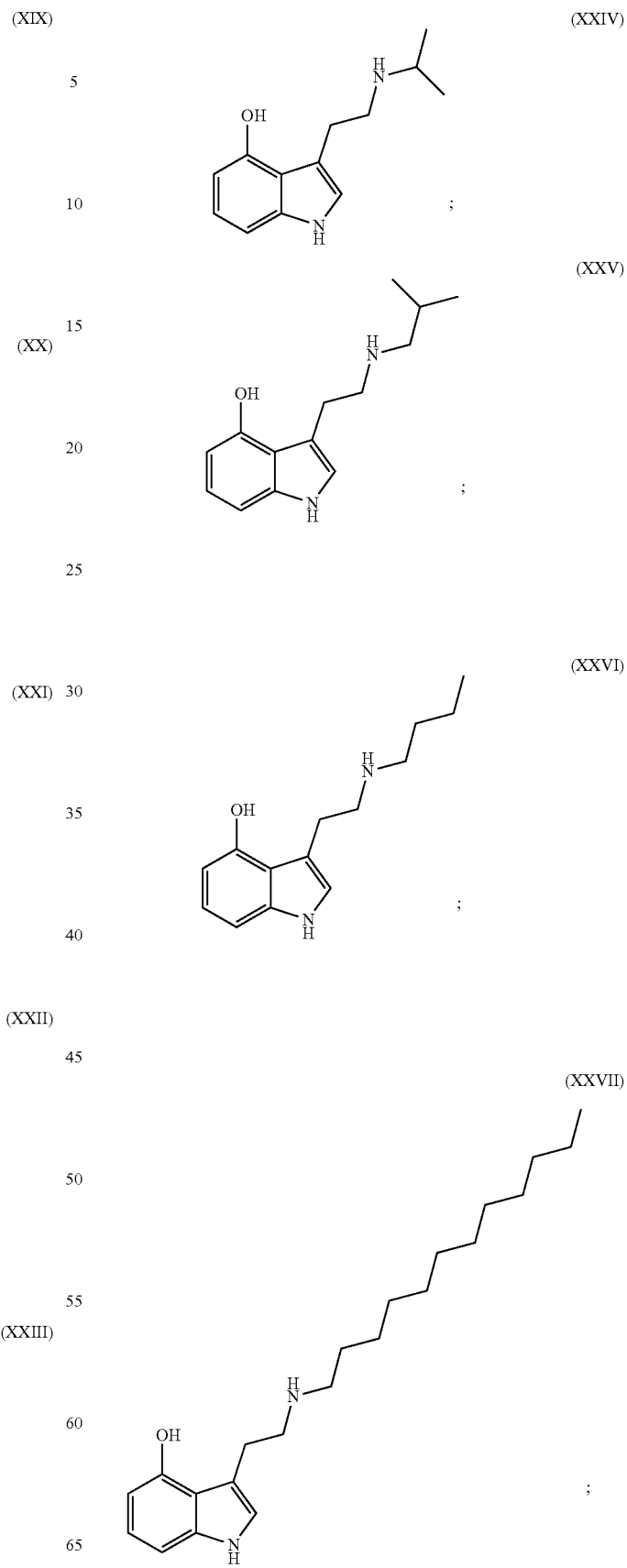

(XXVIII)
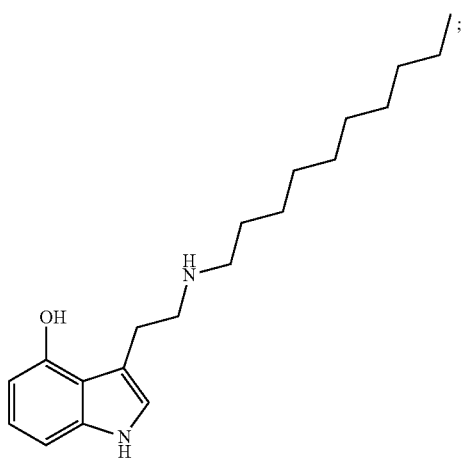

(XXIX)
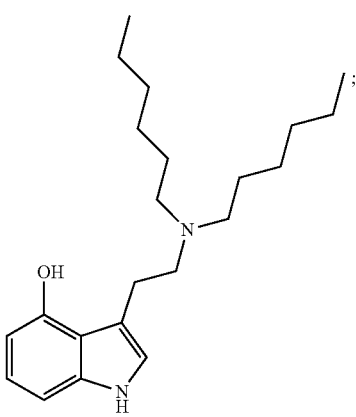

(XXX)
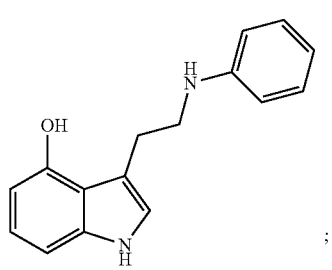

(XXXI)
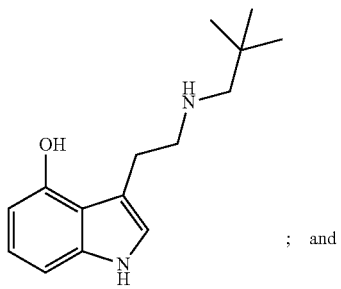
; and (XXXII)
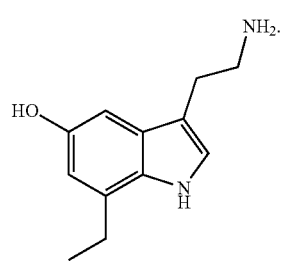

In another aspect, the present disclosure relates to pharmaceutical and recreational drug formulations comprising hydroxylated psilocybin derivatives. Accordingly, in one aspect, the present disclosure provides, in at least one embodiment, a pharmaceutical or recreational drug formulation comprising an effective amount of a chemical compound or salt thereof having formula (I):

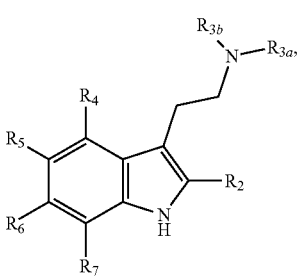
(I)

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a hydrogen atom, an alkyl group or a phosphate group, and wherein $R_{3A}$ and $R_{3B}$ are a hydrogen atom, an alkyl group, a cycloalkyl group, an aryl group, an alkaryl group, or an acyl group, together with a pharmaceutically acceptable carrier, diluent or excipient.

In another aspect, the present disclosure relates to methods of treatment of psychiatric disorders. Accordingly, the present disclosure further provides, in at least one embodiment, a method for treating a psychiatric disorder, the method comprising administering to a subject in need thereof a pharmaceutical formulation comprising a chemical compound or salt thereof having formula (I):

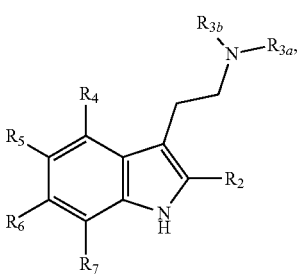
(I)

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a hydrogen atom, an alkyl group or a phosphate group, and wherein $R_{3A}$ and $R_{3B}$ are a hydrogen atom, an alkyl group, a cycloalkyl group, an aryl group, an alkaryl group, or an acyl group, wherein the pharmaceutical formulation is administered in an effective amount to treat the psychiatric disorder in the subject.

In at least one embodiment, in an aspect, the disorder can be a 5-$HT_{2A}$ receptor mediated disorder.

In at least one embodiment, in an aspect, a dose can be administered of about 0.001 mg to about 5,000 mg.

In another aspect, the present disclosure relates to methods of making hydroxylated psilocybin derivatives. Accordingly, in one aspect, the present disclosure provides, in at least one embodiment, a method of making a hydroxylated psilocybin derivative the method comprising:
(a) contacting a psilocybin precursor compound with a host cell comprising a psilocybin biosynthetic enzyme complement; and
(b) growing the host cell to produce a hydroxylated psilocybin derivative compound having the formula (I):

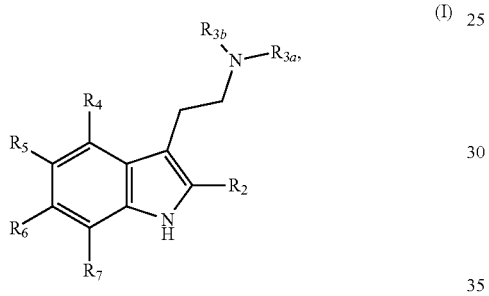

wherein, at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a phosphate group, a hydrogen atom, or an alkyl group, and wherein $R_{3A}$ and $R_{3B}$ are a hydrogen atom, an alkyl group, a cycloalkyl group, an aryl group, an alkaryl group, or an acyl group.

In at least one embodiment, in an aspect, the psilocybin precursor compound can be a hydroxy-derivative psilocybin derivative compound selected from hydroxylated indole or an alkyl or O-alkyl derivative thereof, hydroxylated tryptophan or an alkyl or O-alkyl derivative thereof, and hydroxylated tryptamine or an alkyl or O-alkyl derivative thereof and the hydroxy-derivative psilocybin derivative compound is included in a medium to grow the host cell.

In at least one embodiment, in an aspect, the psilocybin precursor compound can be a hydroxy-derivative psilocybin derivative compound selected from hydroxylated indole or an alkyl or O-alkyl derivative thereof and hydroxylated tryptophan or an alkyl or O-alkyl derivative thereof, and the psilocybin biosynthetic enzyme complement can comprise at least one of TrpB and PsiD wherein TrpB is encoded by a nucleic acid sequence selected from:
(a) SEQ. ID NO: 11 or SEQ. ID NO: 26;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ. ID NO: 12 and SEQ. ID NO: 27;
(f) a nucleic acid sequence that encodes a functional variant of any one of the amino acid sequences set forth in SEQ. ID NO: 12 and SEQ. ID NO: 27; and
(g) a nucleic acid sequence that hybridizes under stringent conditions to any one of the nucleic acid sequences set forth in (a), (b), (c), (d), (e) or (f); and
wherein the PsiD is encoded by a nucleic acid sequence selected from:
(a) SEQ. ID NO: 1, SEQ. ID NO: 9 or SEQ. ID NO: 31;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ. ID NO: 2, SEQ. ID NO: 10 and SEQ. ID NO: 32;
(f) a nucleic acid sequence that encodes a functional variant of any one of the amino acid sequences set forth in SEQ. ID NO: 2, SEQ. ID NO: 10 and SEQ. ID NO: 32; and
(g) a nucleic acid sequence that hybridizes under stringent conditions to any one of the nucleic acid sequences set forth in (a), (b), (c), (d), (e) or (f).

In at least one embodiment, in an aspect, the psilocybin precursor compound can be a hydroxy-derivative psilocybin derivative compound selected from hydroxylated tryptamine or an alkyl or O-alkyl derivative thereof and hydroxylated tryptophan or an alkyl or O-alkyl derivative thereof, and the psilocybin biosynthetic enzyme complement can comprise at least one of PsiH and PsiD wherein PsiH is encoded by a nucleic acid sequence selected from:
(a) SEQ. ID NO: 3;
(b) a nucleic acid sequence that is substantially identical to SEQ. ID NO: 3;
(c) a nucleic acid sequence that is substantially identical to SEQ. ID NO: 3 but for the degeneration of the genetic code;
(d) a nucleic acid sequence that is complementary to SEQ. ID NO: 3;
(e) a nucleic acid sequence encoding a polypeptide having the amino acid sequences set forth in SEQ. ID NO: 4;
(f) a nucleic acid sequence that encodes a functional variant of any the amino acid sequence set forth in SEQ. ID NO: 4; and
(g) a nucleic acid sequence that hybridizes under stringent conditions to any one of the nucleic acid sequences set forth in (a), (b), (c), (d), (e) or (f); and
wherein the PsiD is encoded by a nucleic acid sequence selected from:
(a) SEQ. ID NO: 1, SEQ. ID NO: 9 or SEQ. ID NO: 31;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ. ID NO: 2, SEQ. ID NO: 10 and SEQ. ID NO: 32;

(f) a nucleic acid sequence that encodes a functional variant of any one of the amino acid sequences set forth in SEQ. ID NO: 2, SEQ. ID NO: 10 and SEQ. ID NO: 32; and (g) a nucleic acid sequence that hybridizes under stringent conditions to any one of the nucleic acid sequences set forth in (a), (b), (c), (d), (e) or (f).

In at least one embodiment, in aspect, the psilocybin biosynthetic enzyme complement can further comprise an acetyl transferase wherein the acetyl transferase is encoded by a nucleic acid sequence selected from:

(a) SEQ. ID NO: 24;

(b) a nucleic acid sequence that is substantially identical to SEQ. ID NO: 24;

(c) a nucleic acid sequence that is substantially identical to SEQ. ID NO: 24 but for the degeneration of the genetic code;

(d) a nucleic acid sequence that is complementary to SEQ. ID NO: 24;

(e) a nucleic acid sequence encoding a polypeptide having the amino acid sequences set forth in SEQ. ID NO: 25;

(f) a nucleic acid sequence that encodes a functional variant of the amino acid sequences set forth in SEQ. ID NO: 25; and (g) a nucleic acid sequence that hybridizes under stringent conditions to any one of the nucleic acid sequences set forth in (a), (b), (c), (d), (e) or (f).

In at least one embodiment, in an aspect, the psilocybin biosynthetic enzyme complement can further comprise at least one enzyme encoded by a nucleic acid selected from:

(a) SEQ. ID NO: 5 and SEQ. ID NO: 7;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ. ID NO: 6 and SEQ. ID NO: 8;

(f) a nucleic acid sequence that encodes a functional variant of any one of the amino acid sequences set forth in SEQ. ID NO: 6 and SEQ. ID NO: 8; and (g) a nucleic acid sequence that hybridizes under stringent conditions to any one of the nucleic acid sequences set forth in (a), (b), (c), (d), (e) or (f).

In at least one embodiment, in an aspect, the psilocybin precursor compound can be selected from 4-hydroxy-5 methyl indole and 4-hydroxy-7-methyl-indole, and the hydroxylated psilocybin derivative can be a compound having the chemical formula (III) or (IV):

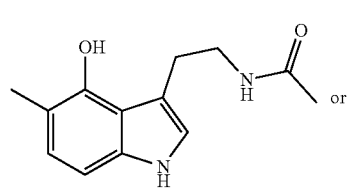

(III)

or

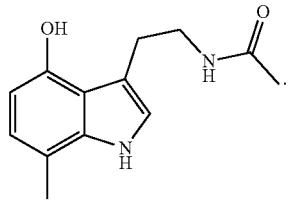

(IV)

In at least one embodiment, in an aspect, the psilocybin precursor compound can be a hydroxy-derivative psilocybin derivative compound selected from a hydroxylated indole or an alkyl or O-alkyl derivative thereof, a hydroxylated tryptophan or an alkyl or O-alkyl derivative thereof, or a hydroxylated tryptamine or an alkyl or O-alkyl derivative which is formed by contacting the host cell with a non-hydroxy-derivative psilocybin precursor compound, wherein the non-hydroxy-derivative psilocybin precursor compound is selected from indole or an alkyl or O-alkyl derivative thereof, tryptophan or an alkyl or O-alkyl derivative or tryptamine or an alkyl or O-alkyl derivative thereof, the host cell further comprising a hydroxylase capable of hydroxylating the non-hydroxylated psilocybin compound and forming the hydroxy-derivative psilocybin precursor compound.

In at least one embodiment, in an aspect, the hydroxylase can be encoded by a nucleic acid selected from:

(a) SEQ. ID NO: 13, SEQ. ID NO: 15, SEQ. ID NO: 17, SEQ. ID NO: 19, SEQ. ID NO: 38 and SEQ. ID NO: 42;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ. ID NO: 14, SEQ. ID NO: 16, SEQ. ID NO: 18, SEQ. ID NO: 39, and SEQ. ID NO: 43;

(f) a nucleic acid sequence that encodes a functional variant of any one of the amino acid sequences set forth in SEQ. ID NO: 14, SEQ. ID NO: 16, SEQ. ID NO: 18, SEQ. ID NO: 39 and SEQ. ID NO: 43; and (g) a nucleic acid sequence that hybridizes under stringent conditions to any one of the nucleic acid sequences set forth in (a), (b), (c), (d), 1 or (f).

In at least one embodiment, the biosynthetic enzyme complement can further comprise at least one of TrpB and PsiD wherein TrpB is encoded by a nucleic acid sequence selected from:

(a) SEQ. ID NO: 11 or SEQ. ID NO: 26;

(b) a nucleic acid sequence that is substantially identical to any one of the nucleic acid sequences of (a);

(c) a nucleic acid sequence that is substantially identical to any one of the nucleic acid sequences of (a) but for the degeneration of the genetic code;

(d) a nucleic acid sequence that is complementary to any one of the nucleic acid sequences of (a);

(e) a nucleic acid sequence encoding a polypeptide having any one of the amino acid sequences set forth in SEQ. ID NO: 12 and SEQ. ID NO: 27;

(f) a nucleic acid sequence that encodes a functional variant of any one of the amino acid sequences set forth in SEQ. ID NO: 12 and SEQ. ID NO: 27; and
(g) a nucleic acid sequence that hybridizes under stringent conditions to any one of the nucleic acid sequences set forth in (a), (b), (c), (d), (e) or (f); and
wherein the PsiD is encoded by a nucleic acid sequence selected from:
(a) SEQ. ID NO: 1, SEQ. ID NO: 9 or SEQ. ID NO: 31;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ. ID NO: 2, SEQ. ID NO: 10 and SEQ. ID NO: 32;
(f) a nucleic acid sequence that encodes a functional variant of any one of the amino acid sequences set forth in SEQ. ID NO: 2, SEQ. ID NO: 10 and SEQ. ID NO: 32; and
(g) a nucleic acid sequence that hybridizes under stringent conditions to any one of the nucleic acid sequences set forth in (a), (b), (c), (d), (e) or (f).

In at least one embodiment, in an aspect, the psilocybin biosynthetic enzyme complement can further comprise at least one of PsiH and PsiD wherein PsiH is encoded by a nucleic acid sequence selected from:
(a) SEQ. ID NO: 3;
(b) a nucleic acid sequence that is substantially identical to SEQ. ID NO: 3;
(c) a nucleic acid sequence that is substantially identical to SEQ. ID NO: 3 but for the degeneration of the genetic code;
(d) a nucleic acid sequence that is complementary to SEQ. ID NO: 3;
(e) a nucleic acid sequence encoding a polypeptide having the amino acid sequences set forth in SEQ. ID NO: 4;
(f) a nucleic acid sequence that encodes a functional variant of any the amino acid sequence set forth in SEQ. ID NO: 4; and
(g) a nucleic acid sequence that hybridizes under stringent conditions to any one of the nucleic acid sequences set forth in (a), (b), (c), (d), (e) or (f); and
wherein the PsiD is encoded by a nucleic acid sequence selected from:
(a) SEQ. ID NO: 1, SEQ. ID NO: 9 or SEQ. ID NO: 31;
(b) a nucleic acid sequence that is substantially identical to any one of the nucleic acid sequences of (a);
(c) a nucleic acid sequence that is substantially identical to any one of the nucleic acid sequences of (a) but for the degeneration of the genetic code;
(d) a nucleic acid sequence that is complementary to any one of the nucleic acid sequences of (a);
(e) a nucleic acid sequence encoding a polypeptide having any one of the amino acid sequences set forth in SEQ. ID NO: 2, SEQ. ID NO: 10 and SEQ. ID NO: 32;
(f) a nucleic acid sequence that encodes a functional variant of any one of the amino acid sequences set forth in SEQ. ID NO: 2, SEQ. ID NO: 10 and SEQ. ID NO: 32; and
(g) a nucleic acid sequence that hybridizes under stringent conditions to any one of the nucleic acid sequences set forth in (a), (b), (c), (d), (e) or (f).

In at least one embodiment, in aspect, the psilocybin biosynthetic enzyme complement can further comprise an acetyl transferase wherein the acetyl transferase is encoded by a nucleic acid sequence selected from:
(a) SEQ. ID NO: 24;
(b) a nucleic acid sequence that is substantially identical to SEQ. ID NO: 24;
(c) a nucleic acid sequence that is substantially identical to SEQ. ID NO: 24 but for the degeneration of the genetic code;
(d) a nucleic acid sequence that is complementary to SEQ. ID NO: 24;
(e) a nucleic acid sequence encoding a polypeptide having the amino acid sequences set forth in SEQ. ID NO: 25;
(f) a nucleic acid sequence that encodes a functional variant of the amino acid sequences set forth in SEQ. ID NO: 25; and
(g) a nucleic acid sequence that hybridizes under stringent conditions to any one of the nucleic acid sequences set forth in (a), (b), (c), (d), (e) or (f).

In at least one embodiment, in an aspect, the psilocybin precursor compound can be 7-ethyl indole and the hydroxylated psilocybin derivative can be a compound having the chemical formula (XXXII):

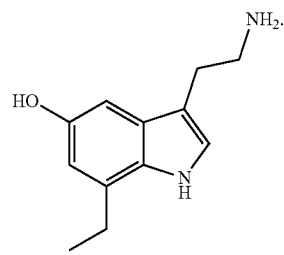

(XXXII)

In at least one embodiment, in an aspect, the method can further include a step comprising isolating the hydroxylated psilocybin derivative compound.

In at least one embodiment, in an aspect, the host cell can be a microbial cell.

In at least one embodiment, in an aspect, the host cell can be a bacterial cell or a yeast cell.

In another aspect, the present disclosure provides, in at least one embodiment, a method for modulating a 5-$HT_{2A}$ receptor, the method comprising contacting a 5-$HT_{2A}$ receptor with a chemical compound or salt thereof having formula (I)

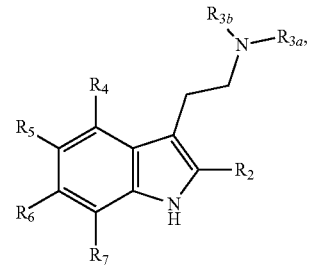

(I)

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein R₄ when it is not hydroxylated is a hydrogen atom, an alkyl group or O-alkyl group or a phosphate group, and wherein $R_{3A}$ and $R_{3B}$ are a hydrogen atom, an alkyl group, a cycloalkyl group, an aryl group, an alkaryl group, or an acyl group under reaction conditions sufficient to thereby modulate receptor activity.

In some embodiments, in an aspect, the reaction conditions can be in vitro reaction conditions.

In some embodiments, in an aspect, the reaction conditions can be in vivo reaction conditions.

In another aspect, the present disclosure provides, in at least one embodiment, a use of a chemical compound having the formula (I):

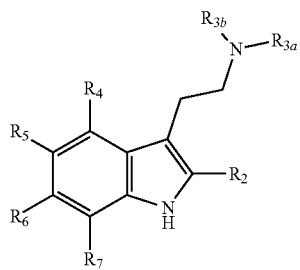

(I)

wherein, at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a phosphate group, a hydrogen atom, or an alkyl group and wherein $R_{3A}$ and $R_{3B}$ are a hydrogen atom, an alkyl group, a cycloalkyl group, an alkyl group, an alkaryl group or an acyl group, in the manufacture of a pharmaceutical or recreational drug formulation.

In at least one embodiment, in an aspect, the manufacture can comprise formulating the chemical compound with an excipient, diluent or carrier.

In at least one embodiment, in an aspect, the manufacture can further include a step comprising derivatizing the chemical compound having the formula (I) by substituting the hydroxy group with another group or an atom.

In another aspect, the present disclosure provides, in at least one embodiment, a use of a chemical compound having the formula (I):

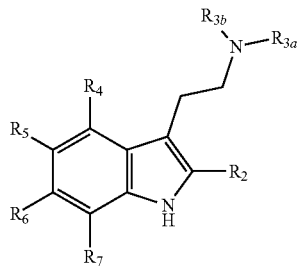

(I)

wherein, at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a phosphate group, a hydrogen atom or an alkyl group or O-alkyl group, and wherein $R_{3A}$ and $R_{3B}$ are a hydrogen atom, an alkyl group, a cycloalkyl group, an alkyl group, an alkaryl group or an acyl group, together with a diluent, carrier, or excipient as a pharmaceutical or recreational drug formulation.

Other features and advantages will become apparent from the following detailed description. It should be understood, however, that the detailed description, while indicating preferred implementations of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described, by way of example, in relation to the attached figures. The figures provided herein are provided for a better understanding of the example embodiments and to show more clearly how the various embodiments may be carried into effect. The figures are not intended to limit the present disclosure.

FIGS. 3A, 3B, 3C, 3D, 3E, 3F, 3G, 3H, 3I, 3J, 3K, 3L, 3M, 3N, 3O, 3P and 3Q depict the chemical structures of certain example hydroxylated psilocybin derivative compounds, notably a 2-hydroxy psilocybin derivative (FIG. 3A); a 4-hydroxy derivative (FIG. 3B); a 5-hydroxy psilocybin derivative (FIG. 3C); a 6-hydroxy psilocybin derivative (FIG. 3D); a 4-phospho-7-hydroxy psilocybin derivative (FIG. 3E); a 2-hydroxy-4-phospho psilocybin derivative (FIG. 3F); a 4-phospho-5-hydroxy psilocybin derivative (FIG. 3G); a 4-phospho-6-hydroxy psilocybin derivative (FIG. 3H); a 4-phospho-7-hydroxy psilocybin derivative (FIG. 3I); a 2-hydroxy-4-methyl psilocybin derivative (FIG. 3J); a 4-ethyl-5-hydroxy psilocybin derivative (FIG. 3K); a 4-methyl-6-hydroxy psilocybin derivative (FIG. 3L); a 4-propyl-7-hydroxy psilocybin derivative (FIG. 3M); a 2-hydroxy-4-O-methyl psilocybin derivative (FIG. 3N); a 4-O-ethyl-5-hydroxy psilocybin derivative (FIG. 3O); a 4-O-methyl-6-hydroxy psilocybin derivative (FIG. 3P); and a 4-O-propyl-7-hydroxy psilocybin derivative (FIG. 3Q) It is noted that in each of FIGS. 3A, 3B, 3C, 3D, 3E, 3F, 3G, 3H, 3I, 3J, 3K, 3L, 3M, 3N, 3O, 3P and 3Q, $R_{3a}$ and $R_{3b}$ can be a hydrogen atom, an alkyl group, a cycloalkyl group, an aryl group, an alkaryl group, or an acyl group.

Figure 1:
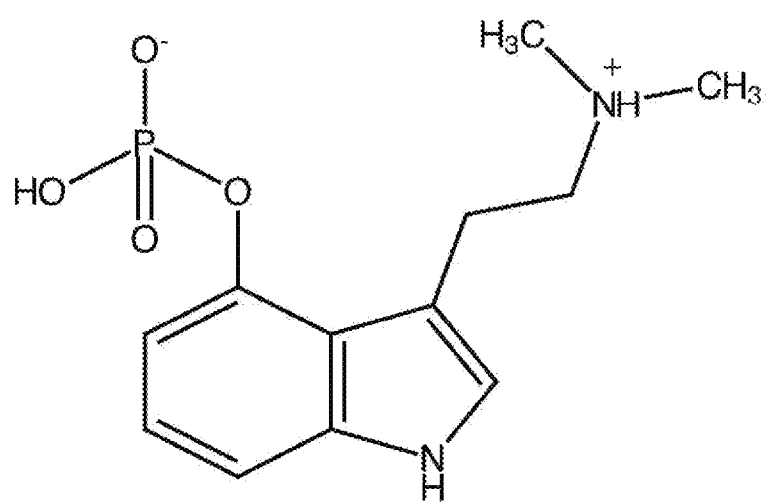
FIG. 1 depicts the chemical structure of psilocybin.

The figures together with the following detailed description make apparent to those skilled in the art how the disclosure may be implemented in practice.

DETAILED DESCRIPTION

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

As used herein and in the claims, the singular forms, such "a", "an" and "the" include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers.

Various compositions, systems or processes will be described below to provide an example of an embodiment of each claimed subject matter. No embodiment described below limits any claimed subject matter and any claimed subject matter may cover processes, compositions or systems that differ from those described below. The claimed subject matter is not limited to compositions, processes or systems having all of the features of any one composition, system or process described below or to features common to multiple or all of the compositions, systems or processes described below. It is possible that a composition, system or process described below is not an embodiment of any claimed subject matter. Any subject matter disclosed in a composition, system or process described below that is not claimed in this document may be the subject matter of another protective instrument, for example, a continuing patent application, and the applicant(s), inventor(s) or owner(s) do not intend to abandon, disclaim or dedicate to the public any such subject matter by its disclosure in this document.

When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context. Furthermore any range of values described herein is intended to specifically include the limiting values of the range, and any intermediate value or sub-range within the given range, and all such intermediate values and sub-ranges are individually and specifically disclosed (e.g. a range of 1 to 5 includes 1, 1.5, 2, 2.75, 3, 3.90, 4, and 5). Similarly, other terms of degree such as "substantially" and "approximately" as used herein mean a reasonable amount of deviation of the modified term such that the end result is not significantly changed. These terms of degree should be construed as including a deviation of the modified term if this deviation would not negate the meaning of the term it modifies.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present invention, which is defined solely by the claims.

All publications, patents and patent applications are herein incorporated by reference in their entirety to the same extent as if each individual publication, patent or patent application was specifically and individually indicated to be incorporated by reference in its entirety.

Terms and Definitions

The term "psilocybin", refers to a chemical compound having the structure set forth in FIG. 1.

Figure 2:
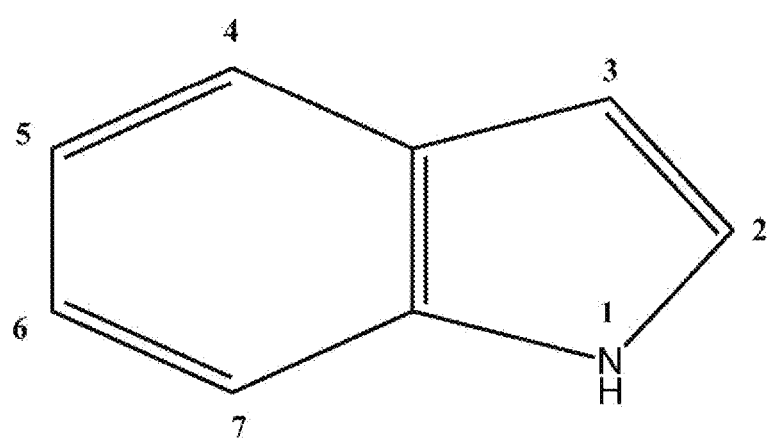
FIG. 2 depicts a certain prototype structure of psilocybin and psilocybin derivative compounds, namely an indole. Certain carbon and nitrogen atoms may be referred to herein by reference to their position within the indole structure, i.e. $N_1$, $C_2$, $C_3$ etc. The pertinent atom numbering is shown.

The term "indole prototype structure" refers to the chemical structure shown in FIG. 2. It is noted that specific carbon atoms and a nitrogen atom in the indole prototype structure are numbered. Reference may be made to these carbon and nitrogen numbers herein, for example $C_2$, $C_4$, $N_1$, and so forth. Furthermore, reference may be made to chemical groups attached to the indole prototype structure in accordance with the same numbering, for example $R_4$ and $R_6$ reference chemical groups attached to the $C_4$ and $C_6$ atom, respectively. In addition, $R_{3A}$ and $R_{3B}$, in this respect, reference chemical groups extending from the 2-aminoethyl group extending in turn from the $C_3$ atom of the prototype indole structure.

The terms "hydroxy-containing psilocybin derivative" or hydroxy-containing psilocybin derivative compound" refer to a psilocybin derivative compound comprising one or more hydroxy groups. Reference may be made to specific carbon atoms which may be hydroxylated. For example, a 7-hydroxy-psilocybin derivative refers to a hydroxylated psilocybin derivative in which carbon atom number 7 (as identified in the indole prototype structure) is hydroxylated, or, similarly, 2-hydroxy-psilocybin derivative refers to a hydroxylated psilocybin derivative in which carbon atom number 2 (as identified in the indole prototype structure) is hydroxylated. Thus, for example, hydroxy-containing psilocybin derivatives include, single hydroxy derivatives, 2-hydroxy, 4-hydroxy, 5-hydroxy, 6-hydroxy and 7-hydroxy psilocybin derivatives, for example, and multiple hydroxy derivatives, such as, for example, 4,7-dihydroxy-psilocybin derivatives, and 2,5,7-tri-hydroxy-psilocybin derivatives. The term hydroxy-containing psilocybin derivatives further includes chemical compounds having the chemical formula (I):

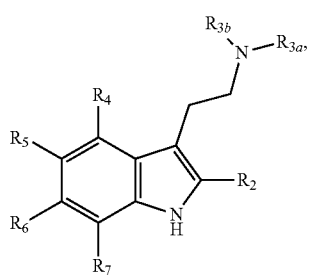

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a hydrogen atom, an alkyl group or a phosphate group, and wherein $R_{3A}$ and $R_{3B}$ are a hydrogen, an alkyl group, an aryl group, or an acyl group. The term further includes salts of hydroxy-containing psilocybin derivatives, such as a sodium salt, a potassium salt etc.

The term "psilocybin precursor compound", as used herein, refers to hydroxy-derivative psilocybin precursor compounds (as herein defined) and non-hydroxy-derivative psilocybin precursor compounds (as herein defined), together.

The term "hydroxy-derivative psilocybin precursor compound" refers to psilocybin precursor compounds possessing or derivatized to possess at least one hydroxy group and includes compounds selected from a hydroxylated tryptophan, a hydroxylated tryptamine and a hydroxylated indole, and further includes alkyl or O-alkyl derivatives thereof (e.g. $C_2$, $C_4$, $C_5$, $C_6$, or $C_7$ methyl, ethyl, propyl, O-methyl, O-ethyl, O-propyl derivatives). It is further noted that reference may be made to specific carbon atoms of the hydroxy-derivative psilocybin precursor compound which may be hydroxylated, for example, 6-hydroxy-tryptophan refers to a hydroxylated tryptophan in which carbon atom number 6 (as identified in the indole prototype structure) is hydroxylated, or, similarly, 2,4-di-hydroxytryptamine refers to a hydroxytryptamine in which carbon atom numbers 2 and 4 (as identified in the indole prototype structure) are hydroxylated. Further hydroxy-derivative psilocybin precursor compounds include 4-hydroxy-indole, 4-hydroxy-tryptophan, 4-hydroxy-tryptamine, 4-hydroxy-5-methyl-indole, and 4-hydroxy-7-methyl-indole.

The term "non-hydroxy-derivative psilocybin precursor compound" refers to any one of the psilocybin precursor compounds selected from tryptophan, tryptamine, and indole, and alkyl or O-alkyl derivatives thereof (e.g. $C_2$, $C_4$, $C_5$, $C_6$, or $C_7$ methyl, ethyl, propyl, O-methyl, O-ethyl, O-propyl derivatives). It is noted that non-hydroxy-derivative psilocybin precursor compound do not possess a hydroxy group. Further non-hydroxy-derivative psilocybin precursor compounds include 7-ethyl-indole, 7-ethyl-tryptophan, 5-methyl-indole.

The term "phosphate group", as used herein, is a molecule containing one atom of phosphorus, covalently bound to four oxygen atoms (three single bonds and one double bond). Of the four oxygen atoms one oxygen atom may be a hydroxy group, and one of the non-hydroxylated oxygen atom may be chemically bonded to another entity.

The terms "hydroxy group", and "hydroxy", as used herein refers to a molecule containing one atom of oxygen bonded to one atom of hydrogen, and having the formula —OH. A hydroxy group through its oxygen atom may be chemically bonded to another entity.

The term "alkyl" as used herein refers to a straight and/or branched chain, saturated alkyl radical containing from one to "p" carbon atoms ("$C_1$-$C_p$-alkyl") and includes, depending on the identity of "p", methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable p is an integer representing the largest number of carbon atoms in the alkyl radical. Alkyl groups further include hydrocarbon groups arranged in a chain having the chemical formula —$C_nH_{2n+1}$, including, without limitation, methyl groups (—$CH_3$), ethyl groups (—$O_2H_5$), propyl groups (—$O_3H_7$), and butyl groups (—$O_4H_9$).

The term "alkylene" as used herein, whether alone or as part of another group, means an alkyl group (as defined herein) that is bivalent; i.e. that is substituted on two ends with another group. The term $C_{0-2}$alkylene means an alkylene group having 0, 1 or 2 carbon atoms.

The term "cycloalkyl" as used herein refers to a cyclic alkyl radical containing from three to "r" carbon atoms ("$C_1$-$C_r$-cycloalkyl") and includes, depending on the identity of "r", cyclopropyl, cyclobutyl, cyclopentyl, cyclohexyl, cycloheptyl, and the like, where the variable r is an integer representing the largest number of carbon atoms in the cycloalkyl radical.

The term "O-alkyl", as used herein, refers to a hydrocarbon group arranged in a chain having the chemical formula —O—$C_nH_{2n+1}$. O-alkyl groups include, without limitation, O-methyl groups (—O—$CH_3$), O-ethyl groups (—O—$C_2H_5$), O-propyl groups (—O—$C_3H_7$) and O-butyl groups (—O—$C_4H_9$).

The term "aryl" as used herein refers to a monocyclic, bicyclic or tricyclic aromatic ring system containing, depending on the number of atoms in the rings, for example, from 6 to 14 carbon atoms ($C_6$-$C_{14}$-aryl) or from 6 to 10 carbons ($C_6$-$C_{10}$-aryl), and at least 1 aromatic ring and includes phenyl, naphthyl, anthracenyl, 1,2-dihydronaphthyl, 1,2,3,4-tetrahydronaphthyl, fluorenyl, phenanthrenyl, biphenylenyl, indanyl, indenyl and the like.

The term "alkaryl" as used herein refers to an aryl group, as defined herein, attached to the parent molecular group through an alkylene group as defined herein. In Some embodiments, the alkylene and the aryl each can be further substituted with 1, 2, 3, or 4 substituent groups as defined herein for the respective groups.

The term "acyl" refers to a carbon atom double bonded to an oxygen and single bonded to an alkyl group. The carbon atom further can be bonded to another entity. An acyl group can be described by the chemical formula: —C(=O)—$C_nH_{2n+1}$.

The term "5-HT$_{2A}$ receptor", as used herein, refers to a subclass of a family of receptors for the neurotransmitter and peripheral signal mediator serotonin. 5-HT$_{2A}$ receptors can mediate a plurality of central and peripheral physiologic functions of serotonin. Central nervous system effects can include mediation of hallucinogenic effects of hallucinogenic compounds.

The term "modulating 5-HT$_{2A}$ receptors", as used herein, refers to the ability of a compound disclosed herein to alter the function of 5-HT$_{2A}$ receptors. A 5-HT$_{2A}$ receptor modulator may activate the activity of a 5-HT$_{2A}$ receptor, may activate or inhibit the activity of a 5-HT$_{2A}$ receptor depending on the concentration of the compound exposed to the 5-HT$_{2A}$ receptor, or may inhibit the activity of a 5-HT$_{2A}$ receptor. Such activation or inhibition may be contingent on the occurrence of a specific event, such as activation of a signal transduction pathway, and/or maybe manifest only in particular cell types. The term "modulating 5-HT$_{2A}$ receptors" also refers to altering the function of a 5-HT$_{2A}$ receptor by increasing or decreasing the probability that a complex forms between a 5-HT$_{2A}$ receptor and a natural binding partner to form a multimer. A 5-HT$_{2A}$ receptor modulator may increase the probability that such a complex forms between the 5-HT$_{2A}$ receptor and the natural binding partner, may increase or decrease the probability that a complex forms between the 5-HT$_{2A}$ receptor and the natural binding partner depending on the concentration of the compound exposed to the 5-HT$_{2A}$ receptor, and or may decrease the probability that a complex forms between the 5-HT$_{2A}$ receptor and the natural binding partner. Furthermore, the term includes allosteric modulation of the receptor 5-HT$_{2A}$, i.e. modulation of the 5-HT$_{2A}$ receptor through interaction with the 5-HT$_{2A}$ receptor that is topographically different than the orthosteric site recognized by the cell's endogenous agonist, such modulation further including positive allosteric modulation (PAM), negative allosteric modulation (NAM) and silent allosteric modulation (SAM).

The term "5-HT$_{2A}$ receptor-mediated disorder", as used herein, refers to a disorder that is characterized by abnormal 5-HT$_{2A}$ receptor activity. A 5-HT$_{2A}$ receptor-mediated disorder may be completely or partially mediated by modulating 5-HT$_{2A}$ receptors. In particular, a 5-HT$_{2A}$ receptor-mediated disorder is one in which modulation of 5-HT$_{2A}$ receptors results in some effect on the underlying disorder e.g., administration of a 5-HT$_{2A}$ receptor modulator results in some improvement in at least some of the subjects being treated.

The term "pharmaceutical formulation", as used herein, refers to a preparation in a form which allows an active ingredient, including a psychoactive ingredient, contained therein to provide effective treatment, and which does not contain any other ingredients which cause excessive toxicity, an allergic response, irritation, or other adverse response commensurate with a reasonable risk/benefit ratio. The pharmaceutical formulation may contain other pharmaceutical ingredients such as excipients, carriers, diluents, or auxiliary agents.

The term "recreational drug formulation", as used herein, refers to a preparation in a form which allows a psychoactive ingredient contained therein to be effective for administration as a recreational drug, and which does not contain any other ingredients which cause excessive toxicity, an allergic response, irritation, or other adverse response commensurate with a reasonable risk/benefit ratio. The recreational drug formulation may contain other ingredients such as excipients, carriers, diluents, or auxiliary agents.

The term "effective for administration as a recreational drug", as used herein, refers to a preparation in a form which allows a subject to voluntarily induce a psychoactive effect for non-medical purposes upon administration, generally in the form of self-administration. The effect may, include an altered state of consciousness, satisfaction, pleasure, euphoria, perceptual distortion; or hallucination.

The term "effective amount", as used herein, refers to an amount of an active agent, pharmaceutical formulation or recreational drug formulation, sufficient to induce a desired biological or therapeutic effect, including a prophylactic effect, and further including a psychoactive effect. Such effect can include an effect with respect to the signs, symptoms or causes of a disorder, or disease or any other desired alteration of a biological system. The effective amount can vary depending, for example, on the health condition, injury stage, disorder stage, or disease stage, weight, or sex of a subject being treated, timing of the administration, manner of the administration, age of the subject, and the like, all of which can be determined by those of skill in the art.

The terms "treating" and "treatment", and the like, as used herein, are intended to mean obtaining a desirable physiological, pharmacological, or biological effect, and includes prophylactic and therapeutic treatment. The effect may result in the inhibition, attenuation, amelioration, or reversal of a sign, symptom or cause of a disorder, or disease, attributable to the disorder, or disease, which includes mental and psychiatric diseases and disorders. Clinical evidence of the prevention or treatment may vary with the disorder, or disease, the subject and the selected treatment.

The term "pharmaceutically acceptable", as used herein, refers to materials, including excipients, carriers, diluents, or auxiliary agents, that are compatible with other materials in a pharmaceutical or recreational drug formulation and within the scope of reasonable medical judgement suitable for use in contact with a subject without excessive toxicity, allergic response, irritation, or other adverse response commensurate with a reasonable risk/benefit ratio.

The term "psilocybin biosynthetic enzyme complement", as used herein, refers to one or more polypeptides which alone or together are capable of facilitating the chemical conversion of a psilocybin precursor compound and form another psilocybin precursor compound or psilocybin or a hydroxylated form thereof. A psilocybin biosynthetic enzyme complement can include, for example, PsiD, PsiH, PsiK, PsiM, PsiP, Psi-ncAAAD and TrpB.

The term "PsiD" as used herein, refers to any and all enzymes comprising a sequence of amino acid residues which is (i) substantially identical to the amino acid sequences constituting any PsiD polypeptide set forth herein, including, for example, SEQ. ID NO: 2, SEQ. ID NO: 10 and SEQ. ID NO: 32, or (ii) encoded by a nucleic acid sequence capable of hybridizing under at least moderately stringent conditions to any nucleic acid sequence encoding any PsiD set forth herein, but for the use of synonymous codons.

The term "PsiH" as used herein, refers to any and all enzymes comprising a sequence of amino acid residues which is (i) substantially identical to the amino acid sequences constituting any PsiH polypeptide set forth herein, including, for example, SEQ. ID NO: 4, or (ii) encoded by a nucleic acid sequence capable of hybridizing under at least moderately stringent conditions to any nucleic acid sequence encoding any PsiH set forth herein, but for the use of synonymous codons.

The term "PsiK" as used herein, refers to any and all enzymes comprising a sequence of amino acid residues which is (i) substantially identical to the amino acid sequences constituting any PsiK polypeptide set forth herein, including, for example, SEQ. ID NO: 6, or (ii) encoded by a nucleic acid sequence capable of hybridizing under at least moderately stringent conditions to any nucleic acid sequence encoding any PsiK set forth herein, but for the use of synonymous codons.

The term "PsiM" as used herein, refers to any and all enzymes comprising a sequence of amino acid residues which is (i) substantially identical to the amino acid sequences constituting any PsiM polypeptide set forth herein, including, for example, SEQ. ID NO: 8, or (ii) encoded by a nucleic acid sequence capable of hybridizing under at least moderately stringent conditions to any nucleic acid sequence encoding any PsiM set forth herein, but for the use of synonymous codons.

The term "Psi-ncAAAD" as used herein, refers to any and all enzymes comprising a sequence of amino acid residues which is (i) substantially identical to the amino acid sequences constituting any Psi-ncAAAD polypeptide set forth herein, including, for example, SEQ. ID NO: 10, or (ii) encoded by a nucleic acid sequence capable of hybridizing under at least moderately stringent conditions to any nucleic acid sequence encoding any Psi-ncAAAD set forth herein, but for the use of synonymous codons.

The term "TrpB" as used herein, refers to any and all enzymes comprising a sequence of amino acid residues which is (i) substantially identical to the amino acid sequences constituting any TrpB polypeptide set forth herein, including, for example, SEQ. ID NO: 12 and SEQ. ID NO: 27, or (ii) encoded by a nucleic acid sequence capable of hybridizing under at least moderately stringent conditions to any nucleic acid sequence encoding any TrpB set forth herein, but for the use of synonymous codons.

The term "hydroxylase" as used herein, refers to any and all enzymes comprising a sequence of amino acid residues which is (i) substantially identical to the amino acid sequences constituting any hydroxylase polypeptide set forth herein, including, for example, SEQ. ID NO: 14, SEQ. ID NO: 16, SEQ. ID NO: 18, SEQ. ID NO: 20, SEQ. ID NO: 39 and SEQ. ID NO: 43, or (ii) encoded by a nucleic acid sequence capable of hybridizing under at least moderately stringent conditions to any nucleic acid sequence encoding any hydroxylase set forth herein, but for the use of synonymous codons.

The term "acetyl transferase" as used herein, refers to any and all enzymes comprising a sequence of amino acid residues which is (i) substantially identical to the amino acid sequences constituting any acetyl transferase polypeptide set forth herein, including, for example, SEQ. ID NO: 24, or (ii) encoded by a nucleic acid sequence capable of hybridizing under at least moderately stringent conditions to any nucleic acid sequence encoding any acetyl transferase set forth herein, but for the use of synonymous codons.

The terms "nucleic acid sequence encoding PsiD", and "nucleic acid sequence encoding a PsiD polypeptide", as may be used interchangeably herein, refer to any and all nucleic acid sequences encoding a PsiD polypeptide, including, for example, SEQ. ID NO: 1, SEQ. ID NO: 9 and SEQ. ID NO: 31. Nucleic acid sequences encoding a PsiD polypeptide further include any and all nucleic acid sequences which (i) encode polypeptides that are substantially identical to the PsiD polypeptide sequences set forth herein; or (ii) hybridize to any PsiD nucleic acid sequences set forth herein under at least moderately stringent hybridization conditions or which would hybridize thereto under at least moderately stringent conditions but for the use of synonymous codons.

The terms "nucleic acid sequence encoding PsiH", and "nucleic acid sequence encoding a PsiH polypeptide", as may be used interchangeably herein, refer to any and all nucleic acid sequences encoding a PsiH polypeptide, including, for example, SEQ. ID NO: 3. Nucleic acid sequences encoding a PsiH polypeptide further include any and all nucleic acid sequences which (i) encode polypeptides that are substantially identical to the PsiH polypeptide sequences set forth herein; or (ii) hybridize to any PsiH nucleic acid sequences set forth herein under at least moderately stringent hybridization conditions or which would hybridize thereto under at least moderately stringent conditions but for the use of synonymous codons.

The terms "nucleic acid sequence encoding PsiK", and "nucleic acid sequence encoding a PsiK polypeptide", as may be used interchangeably herein, refer to any and all nucleic acid sequences encoding a PsiK polypeptide, including, for example, SEQ. ID NO: 5. Nucleic acid sequences encoding a PsiK polypeptide further include any and all nucleic acid sequences which (i) encode polypeptides that are substantially identical to the PsiK polypeptide sequences set forth herein; or (ii) hybridize to any PsiK nucleic acid sequences set forth herein under at least moderately stringent hybridization conditions or which would hybridize thereto under at least moderately stringent conditions but for the use of synonymous codons.

The terms "nucleic acid sequence encoding PsiM", and "nucleic acid sequence encoding a PsiM polypeptide", as may be used interchangeably herein, refer to any and all nucleic acid sequences encoding a PsiD polypeptide, including, for example, SEQ. ID NO: 7. Nucleic acid sequences encoding a PsiM polypeptide further include any and all nucleic acid sequences which (i) encode polypeptides that are substantially identical to the PsiM polypeptide sequences set forth herein; or (ii) hybridize to any PsiM nucleic acid sequences set forth herein under at least moderately stringent hybridization conditions or which would hybridize thereto under at least moderately stringent conditions but for the use of synonymous codons.

The terms "nucleic acid sequence encoding Psi-ncAAAD", and "nucleic acid sequence encoding a Psi-ncAAAD polypeptide", as may be used interchangeably herein, refer to any and all nucleic acid sequences encoding a PsiD polypeptide, including, for example, SEQ. ID NO: 9. Nucleic acid sequences encoding a Psi-ncAAAD polypeptide further include any and all nucleic acid sequences which (i) encode polypeptides that are substantially identical to the Psi-ncAAAD polypeptide sequences set forth herein; or (ii) hybridize to any Psi-ncAAAD nucleic acid sequences set forth herein under at least moderately stringent hybridization conditions or which would hybridize thereto under at least moderately stringent conditions but for the use of synonymous codons.

The terms "nucleic acid sequence encoding TrpB", and "nucleic acid sequence encoding a TrpB polypeptide", as may be used interchangeably herein, refer to any and all nucleic acid sequences encoding a TrpB polypeptide, including, for example, SEQ. ID NO: 11 and SEQ. ID NO: 26. Nucleic acid sequences encoding a TrpB polypeptide further include any and all nucleic acid sequences which (i) encode polypeptides that are substantially identical to the TrpB polypeptide sequences set forth herein; or (ii) hybridize to any TrpB nucleic acid sequences set forth herein under at least moderately stringent hybridization conditions or which would hybridize thereto under at least moderately stringent conditions but for the use of synonymous codons.

The terms "nucleic acid sequence encoding a hydroxylase", and "nucleic acid sequence encoding a hydroxylase polypeptide", as may be used interchangeably herein, refer to any and all nucleic acid sequences encoding a hydroxylase polypeptide, including, for example, SEQ. ID NO: 13, SEQ. ID NO: 15, SEQ. ID NO: 17, SEQ. ID NO: 19, SEQ. ID NO: 38 and SEQ. ID NO: 42. Nucleic acid sequences encoding a hydroxylase polypeptide further include any and all nucleic acid sequences which (i) encode polypeptides that are substantially identical to the hydroxylase polypeptide sequences set forth herein; or (ii) hybridize to any hydroxylase nucleic acid sequences set forth herein under at least moderately stringent hybridization conditions or which would hybridize thereto under at least moderately stringent conditions but for the use of synonymous codons.

The terms "nucleic acid sequence encoding acetyl transferase", and "nucleic acid sequence encoding an acetyl. transferase polypeptide", as may be used interchangeably herein, refer to any and all nucleic acid sequences encoding an acetyl transferase polypeptide, including, for example, SEQ. ID NO: 25. Nucleic acid sequences encoding an acetyl transferase polypeptide further include any and all nucleic acid sequences which (i) encode polypeptides that are substantially identical to the acetyl transferase polypeptide sequences set forth herein; or (ii) hybridize to any acetyl transferase nucleic acid sequences set forth herein under at least moderately stringent hybridization conditions or which would hybridize thereto under at least moderately stringent conditions but for the use of synonymous codons.

The terms "nucleic acid", or "nucleic acid sequence", as used herein, refer to a sequence of nucleoside or nucleotide monomers, consisting of naturally occurring bases, sugars and intersugar (backbone) linkages. The term also includes modified or substituted sequences comprising non-naturally occurring monomers or portions thereof. The nucleic acids of the present disclosure may be deoxyribonucleic nucleic acids (DNA) or ribonucleic acids (RNA) and may include naturally occurring bases including adenine, guanine, cytosine, thymidine and uracil. The nucleic acids may also contain modified bases. Examples of such modified bases include aza and deaza adenine, guanine, cytosine, thymidine and uracil, and xanthine and hypoxanthine. A sequence of nucleotide or nucleoside monomers may be referred to as a polynucleotide sequence, nucleic acid sequence, a nucleotide sequence or a nucleoside sequence.

The term "polypeptide", as used herein in conjunction with a reference SEQ. ID NO, refers to any and all polypeptides comprising a sequence of amino acid residues which is (i) substantially identical to the amino acid sequence constituting the polypeptide having such reference SEQ. ID NO, or (ii) encoded by a nucleic acid sequence capable of hybridizing under at least moderately stringent conditions to any nucleic acid sequence encoding the polypeptide having such reference SEQ. ID NO, but for the use of synonymous codons. A sequence of amino acid residues may be referred to as an amino acid sequence, or polypeptide sequence.

The term "nucleic acid sequence encoding a polypeptide", as used herein in conjunction with a reference SEQ. ID NO, refers to any and all nucleic acid sequences encoding a polypeptide having such reference SEQ. ID NO. Nucleic acid sequences encoding a polypeptide, in conjunction with a reference SEQ. ID NO, further include any and all nucleic acid sequences which (i) encode polypeptides that are substantially identical to the polypeptide having such reference SEQ. ID NO; or (ii) hybridize to any nucleic acid sequences encoding polypeptides having such reference SEQ. ID NO under at least moderately stringent hybridization conditions or which would hybridize thereto under at least moderately stringent conditions but for the use of synonymous codons.

By the term "substantially identical" it is meant that two amino acid sequences preferably are at least 70% identical, and more preferably are at least 85% identical and most preferably at least 95% identical, for example 96%, 97%, 98% or 99% identical. In order to determine the percentage of identity between two amino acid sequences the amino acid sequences of such two sequences are aligned, using for example the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Mol. Biol., 1990: 215:403). A particularly preferred method for determining the percentage identity between two polypeptides involves the Clustal W algorithm (Thompson, J D, Higgines, D G and Gibson T J, 1994, Nucleic Acid Res 22(22): 4673-4680 together with the BLOSUM 62 scoring matrix (Henikoff S & Henikoff, J G, 1992, Proc. Natl. Acad. Sci. USA 89: 10915-10919 using a gap opening penalty of 10 and a gap extension penalty of 0.1, so that the highest order match obtained between two sequences wherein at least 50% of the total length of one of the two sequences is involved in the alignment.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.-16.6 (Log 10 [Na+])+0.41(% (G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation) −5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1.-6.3.6 and in: Sambrook et al., Molecular Cloning, a Laboratory Manual, Cold Spring Harbor Laboratory Press, 1989, Vol. 3.

The term "functional variant", as used herein in reference to polynucleotides or polypeptides, refers to polynucleotides or polypeptides capable of performing the same function as a noted reference polynucleotide or polypeptide. Thus, for example, a functional variant of the polypeptide set forth in SEQ. ID NO: 2, refers to a polypeptide capable of performing the same function as the polypeptide set forth in SEQ. ID NO: 2. Functional variants include modified a polypeptide wherein, relative to a noted reference polypeptide, the modification includes a substitution, deletion or addition of one or more amino acids. In some embodiments, substitutions are those that result in a replacement of one amino acid with an amino acid having similar characteristics. Such substitutions include, without limitation (i) glutamic acid and aspartic acid; (i) alanine, serine, and threonine; (iii) isoleucine, leucine and valine, (iv) asparagine and glutamine, and (v) tryptophan, tyrosine and phenylalanine. Functional variants further include polypeptides having retained or exhibiting an enhanced psilocybin biosynthetic bioactivity.

The term "chimeric", as used herein in the context of nucleic acids, refers to at least two linked nucleic acids which are not naturally linked. Chimeric nucleic acids include linked nucleic acids of different natural origins. For example, a nucleic acid constituting a microbial promoter linked to a nucleic acid encoding a plant polypeptide is considered chimeric. Chimeric nucleic acids also may comprise nucleic acids of the same natural origin, provided they are not naturally linked. For example a nucleic acid constituting a promoter obtained from a particular cell-type may be linked to a nucleic acid encoding a polypeptide obtained from that same cell-type, but not normally linked to the nucleic acid constituting the promoter. Chimeric nucleic acids also include nucleic acids comprising any naturally occurring nucleic acids linked to any non-naturally occurring nucleic acids.

The terms "substantially pure" and "isolated", as may be used interchangeably herein describe a compound, e.g., a secondary metabolite, psilocybin or a psilocybin derivative, polynucleotide or a polypeptide, which has been separated from components that naturally accompany it. Typically, a compound is substantially pure when at least 60%, more preferably at least 75%, more preferably at least 90%, 95%, 96%, 97%, or 98%, and most preferably at least 99% of the total material (by volume, by wet or dry weight, or by mole percent or mole fraction) in a sample is the compound of interest. Purity can be measured by any appropriate method, e.g., in the case of polypeptides, by chromatography, gel electrophoresis or HPLC analysis.

The term "recovered" as used herein in association with an enzyme, protein, a secondary metabolite or a chemical compound, refers to a more or less pure form of the enzyme, protein, secondary metabolite, or chemical compound.

General Implementation

As hereinbefore mentioned, the present disclosure relates to psilocybin derivatives. In particular, the present disclosure provides novel hydroxylated psilocybin derivatives. In general, the herein provided compositions exhibit functional properties which deviate from the functional properties of psilocybin. Thus, for example, the hydroxylated psilocybin derivatives, can exhibit pharmacological properties which deviate from psilocybin. Furthermore, the hydroxylated derivatives may psilocybin derivatives may exhibit physicochemical properties which differ from psilocybin. Thus, for example, hydroxylated psilocybin derivatives may exhibit superior solubility in a solvent, for example, an aqueous solvent. The hydroxylated psilocybin derivatives in this respect are useful in the formulation of pharmaceutical and recreational drug formulations. Furthermore, the hydroxylated psilocybin compounds of the present disclosure may be used as a feedstock material for deriving further psilocybin derivatives. In one embodiment, the hydroxylated psilocybin derivatives of the present disclosure can conveniently be biosynthetically produced. The practice of this method avoids the extraction of psilocybin from mushrooms and the performance of subsequent chemical reactions to achieve hydroxylated derivatives. Furthermore, the growth of mushrooms can be avoided thus limiting the dependence on climate and weather, and potential legal and social challenges associated with the cultivation of mushrooms containing psychoactive compounds. The method can efficiently yield substantial quantities of hydroxylated psilocybin derivatives.

In what follows selected embodiments are described with reference to the drawings.

Initially example hydroxylated psilocybin derivatives will be described. Thereafter example methods of using and making the hydroxylated psilocybin derivatives will be described.

Accordingly, in one aspect the present disclosure provides derivatives of a compound known as psilocybin of which the chemical structure is shown in FIG. 1. The derivatives herein provided are, in particular, derivatives of psilocybin including a hydroxy group.

Thus, in one aspect, the present disclosure provides, in accordance with the teachings herein, in at least one embodiment, a chemical compound or salt thereof having formula (I):

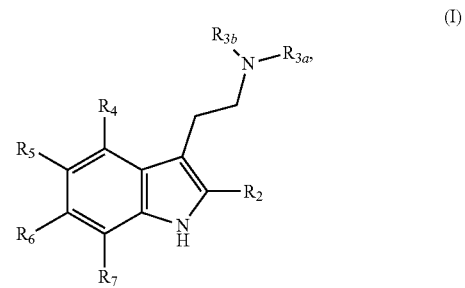

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a hydrogen atom, an alkyl group or a phosphate group, and wherein $R_{3A}$ and $R_{3B}$ are a hydrogen, an alkyl group, a cycloalkyl group, an aryl group, an alkaryl group or an acyl group.

Thus, referring to the chemical compound having formula (I), initially it is noted that, in an aspect thereof, at least one of $R_2$, $R_4$, $R_5$, $R_6$, or $R_7$ is a hydroxy group.

Figure 3A:
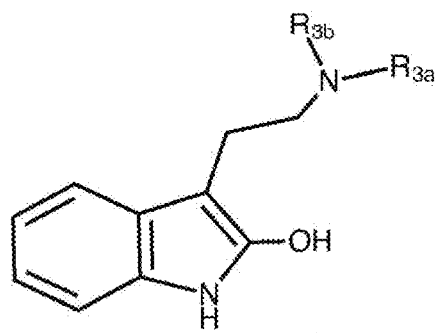

Continuing to refer to the chemical compound having formula (I), in one embodiment, one of $R_2$, $R_4$, $R_5$, $R_6$ and $R_7$ can be a hydroxy group. Thus, in one embodiment, $R_2$ can be a hydroxy group, each of $R_5$, $R_6$ and $R_7$ can be a hydrogen atom or an alkyl group or O-alkyl group, and $R_4$ can be a phosphate group, a hydrogen atom or an alkyl group or O-alkyl group (see: the example hydroxylated psilocybin derivatives shown in FIG. 3A ($R_2$ is a hydroxy group; $R_4$ is a hydrogen atom; $R_5$, $R_6$ and $R_7$ are a hydrogen atom; $R_{3a}$ and $R_{3b}$ are a hydrogen atom, an alkyl group, a cycloalkyl group, an alkaryl group, an aryl group, or an acyl group); FIG. 3F ($R_2$ is a hydroxy group; $R_4$ is a phosphate group; $R_5$, $R_6$ and $R_7$ are a hydrogen atom; $R_{3a}$ and $R_{3b}$ are a hydrogen atom, an alkyl group, a cycloalkyl group, an alkaryl group, an aryl group, or an acyl group); FIG. 3J ($R_2$ is a hydroxy group; $R_4$ is a methyl group; $R_5$, $R_6$ and $R_7$ are a hydrogen atom; $R_{3a}$ and $R_{3b}$ are a hydrogen atom, an alkyl group, a cycloalkyl group, an alkaryl group, an aryl group, or an acyl group); and FIG. 3N ($R_2$ is a hydroxy group; $R_4$ is an O-methyl group; $R_5$, $R_6$ and $R_7$ are a hydrogen atom; $R_{3a}$ and $R_{3b}$ are a hydrogen atom, an alkyl group, a cycloalkyl group, an alkaryl group, an aryl group, or an acyl group)).

Figure 3B:
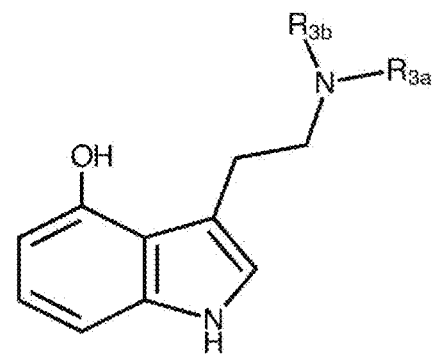

Continuing to refer to the chemical compound having formula (I), in one embodiment, $R_4$ can be a hydroxy group, and each of $R_2$, $R_5$, $R_6$ and $R_7$ can be a hydrogen atom or an alkyl group or O-alkyl group (see: the example hydroxylated psilocybin derivative shown in FIG. 3B ($R_4$ is a hydroxy group; $R_2$, $R_5$, $R_6$ and $R_7$ are a hydrogen atom; $R_{3a}$ and $R_{3b}$ are a hydrogen atom, an alkyl group, a cycloalkyl group, an alkaryl group, an aryl group, or an acyl group)).

Figure 3C:
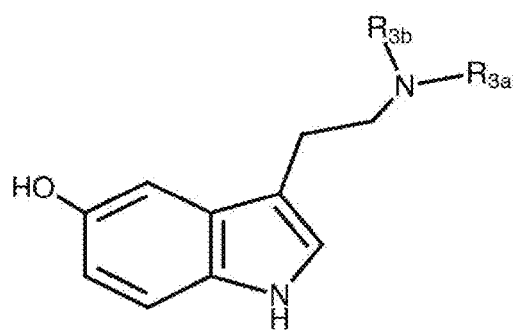

Continuing to refer to the chemical compound having formula (I), in one embodiment, $R_5$ can be a hydroxy group, and each of $R_2$, $R_6$ and $R_7$ can be a hydrogen atom or an alkyl group or O-alkyl group, and $R_4$ can be a phosphate group, a hydrogen atom or a hydroxy group (see: the example hydroxylated psilocybin derivatives shown in FIG. 3C ($R_5$ is a hydroxy group; $R_4$ is a hydrogen atom; $R_2$, $R_6$ and $R_7$ are a hydrogen atom; $R_{3a}$ and $R_{3b}$ are a hydrogen atom, an alkyl group, a cycloalkyl group, an alkaryl group, an aryl group, or an acyl group); FIG. 3G ($R_5$ is a hydroxy group; $R_4$ is a phosphate group; $R_4$, $R_6$ and $R_7$ are a hydrogen atom; $R_{3a}$ and $R_{3b}$ are a hydrogen atom, an alkyl group, a cycloalkyl group, an alkaryl group, an aryl group, or an acyl group); FIG. 3K ($R_5$ is a hydroxy group; $R_4$ is a ethyl group; $R_4$, $R_6$ and $R_7$ are a hydrogen atom; $R_{3a}$ and $R_{3b}$ are a hydrogen atom, an alkyl group, a cycloalkyl group, an alkaryl group, an aryl group, or an acyl group); and FIG. 3O ($R_5$ is a hydroxy group; $R_4$ is an O-ethyl group; $R_4$, $R_6$ and $R_7$ are a hydrogen atom; $R_{3a}$ and $R_{3b}$ are a hydrogen atom, an alkyl group, a cycloalkyl group, an alkaryl group, an aryl group, or an acyl group).

Figure 3D:
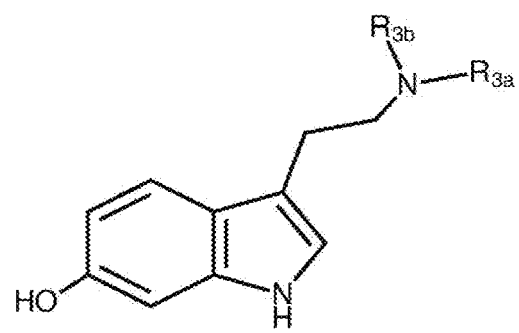

Continuing to refer to the chemical compound having formula (I), in one embodiment, $R_6$ can be a hydroxy group, and each of $R_2$, $R_5$ and $R_7$ can be a hydrogen atom or an alkyl group or O-alkyl group, and $R_4$ can be a phosphate group, a hydrogen atom or an alkyl group or O-alkyl group (see: the example hydroxylated psilocybin derivatives shown in FIG. 3D ($R_6$ is a hydroxy group; $R_4$ is a phosphate group; $R_2$, $R_5$ and $R_7$ are a hydrogen atom; $R_{3a}$ and $R_{3b}$ are a hydrogen atom, an alkyl group, a cycloalkyl group, an alkaryl group, an aryl group, or an acyl group) and FIG. 3H ($R_6$ is a hydroxy group; $R_4$ is a phosphate group; $R_2$, $R_5$ and $R_7$ are a hydrogen atom; $R_{3a}$ and $R_{3b}$ are a hydrogen atom, an alkyl group, a cycloalkyl group, an alkaryl group, an aryl group, or an acyl group); FIG. 3L ($R_6$ is a hydroxy group; $R_4$ is a methyl group; $R_2$, $R_5$ and $R_7$ are a hydrogen atom; $R_{3a}$ and $R_{3b}$ are a hydrogen atom, an alkyl group, a cycloalkyl group, an alkaryl group, an aryl group, or an acyl group); and FIG. 3P ($R_6$ is a hydroxy group; $R_4$ is an O-methyl group; $R_2$, $R_5$ and $R_7$ are a hydrogen atom; $R_{3a}$ and $R_{3b}$ are a hydrogen atom, an alkyl group, a cycloalkyl group, an alkaryl group, an aryl group, or an acyl group)).

Figure 3E:
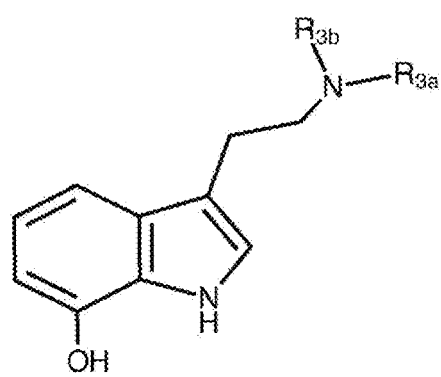
Figure 3F:
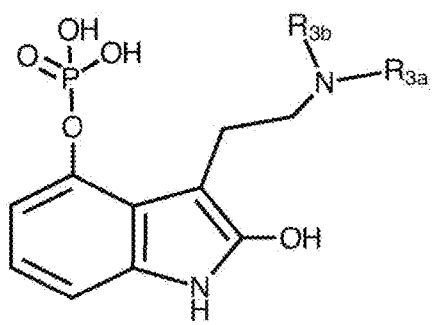
Figure 3G:
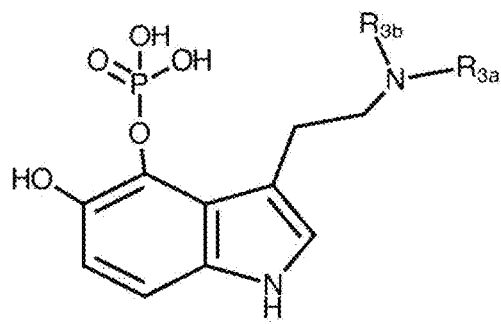
Figure 3H:
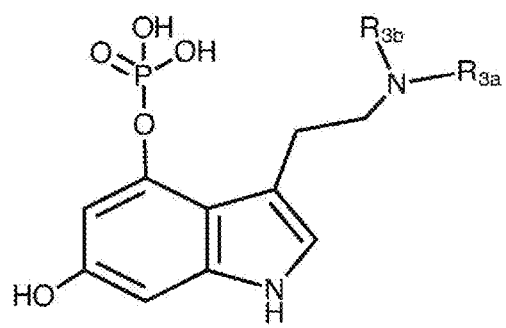
Figure 3I:
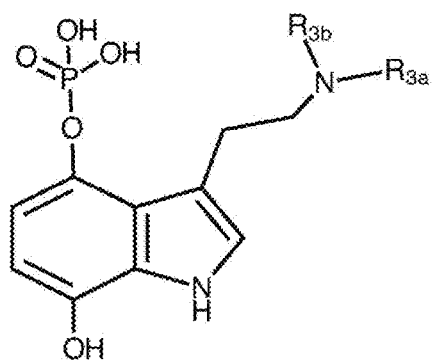
Figure 3N:
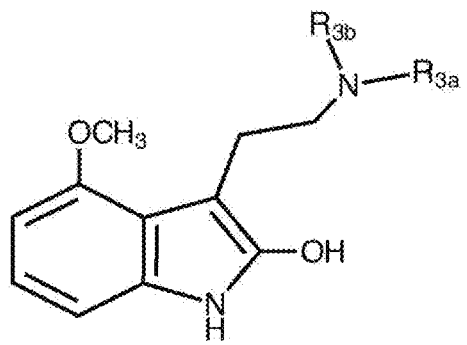
Figure 3O:
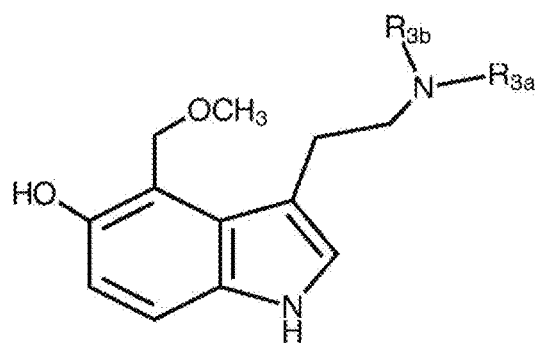
Figure 3P:
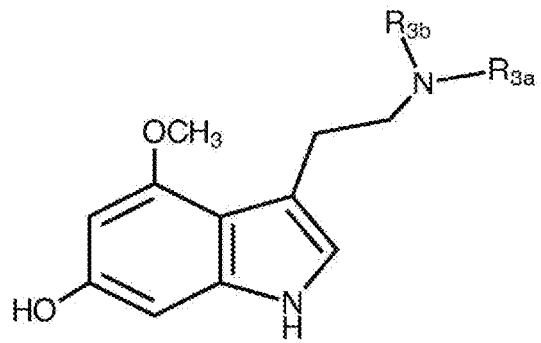
Figure 3Q:
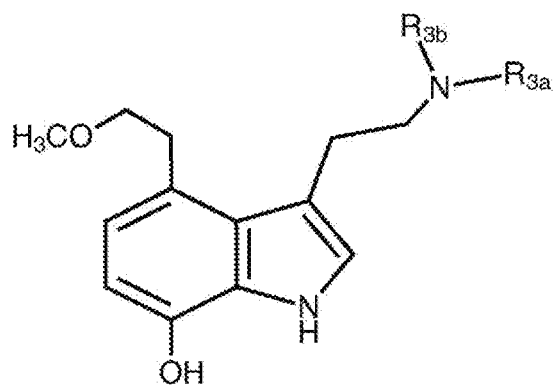

Continuing to refer to the chemical compound having formula (I), in one embodiment, $R_7$ can be a hydroxy group, and each of $R_2$, $R_5$ and $R_6$ can be a hydrogen atom or an alkyl group or O-alkyl group, and $R_4$ can be a phosphate group, a hydrogen atom or an alkyl group or O-alkyl group (see: the example hydroxylated psilocybin derivatives shown in FIG. 3E ($R_7$ is a hydroxy group; $R_4$ is a hydrogen atom; $R_2$, $R_5$ and $R_6$ are a hydrogen atom $R_{3a}$ and $R_{3b}$ are a hydrogen atom, an alkyl group, a cycloalkyl group, an alkaryl group, an aryl group, or an acyl group); FIG. 3I ($R_7$ is a hydroxy group; $R_4$ is a phosphate group; $R_2$, $R_5$ and $R_6$ are a hydrogen atom; $R_{3a}$ and $R_{3b}$ are a hydrogen atom, an alkyl group, a cycloalkyl group, an alkaryl group, an aryl group, or an acyl group); FIG. 3M ($R_7$ is a hydroxy group; $R_4$ is a propyl group; $R_2$, $R_5$ and $R_6$ are a hydrogen atom; $R_{3a}$ and $R_{3b}$ are a hydrogen atom, an alkyl group, a cycloalkyl group, an alkaryl group, an aryl group, or an acyl group); and FIG. 3Q ($R_7$ is a hydroxy group; $R_4$ is an O-propyl group; $R_2$, $R_5$ and $R_6$ are a hydrogen atom; $R_{3a}$ and $R_{3b}$ are a hydrogen atom, an alkyl group, a cycloalkyl group, an alkaryl group, an aryl group, or an acyl group)).

In some embodiments, two of $R_2$, $R_4$, $R_5$, $R_6$ and $R_7$ of the chemical compound having formula (I) can be hydroxy groups. Thus, continuing to refer to the chemical compound having formula (I), in one embodiment, two of $R_2$, $R_4$, $R_5$, $R_6$ and $R_7$ can be a hydroxy group, wherein each non-hydroxylated $R_2$, $R_5$, $R_6$ and $R_7$ is a hydrogen atom or an alkyl group or O-alkyl group, and wherein $R_4$, when it is not a hydroxy group, is a phosphate group, a hydrogen atom or an alkyl group or O-alkyl group.

Figure 4A:
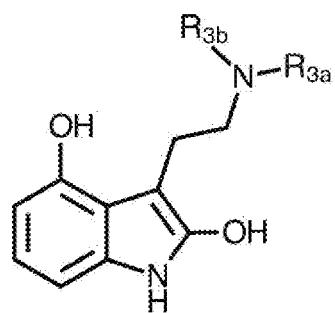
FIGS. 4A, 4B, 4C, 4D, 4E, 4F, 4G, 4H, 4I and 4J depict the chemical structures of certain further example hydroxylated psilocybin derivative compounds, notably a 2,4-di-hydroxy psilocybin derivative (FIG. 4A); a 2,5-hydroxy psilocybin derivative (FIG. 4B); a 2,6-di-hydroxy-4-methyl psilocybin derivative (FIG. 4C); a 2,7-di-hydroxy-4-phospho psilocybin derivative (FIG. 4D); a 4,5-di-hydroxy psilocybin derivative (FIG. 4E); a 4,6-di-hydroxy psilocybin derivative (FIG. 4F); a 4,7-di-hydroxy psilocybin derivative (FIG. 4G); a 4-phospho-5,6-di-hydroxy psilocybin derivative (FIG. 4H) a 4-phospho-5,7-di-hydroxy psilocybin derivative (FIG. 4I); and a 6,7-di-hydroxy psilocybin derivative (FIG. 4J). It is noted that in each of FIGS. 4A, 4B, 4C, 4D, 4E, 4F, 4G, 4H, 4I and 4J $R_{3a}$ and $R_{3b}$ can be a hydrogen atom, an alkyl group, a cycloalkyl group, an aryl group, an alkaryl group, or an acyl group.

Still continuing to refer to the chemical compound having formula (I), in one embodiment, $R_2$ and $R_4$ can be hydroxy groups and $R_5$, $R_6$ and $R_7$ can be hydrogen atoms or alkyl groups (see: the example hydroxylated psilocybin derivative shown in FIG. 4A ($R_2$ and $R_4$ are each a hydroxy group; $R_5$, $R_6$ and $R_7$ are hydrogen atoms; and $R_{3a}$ and $R_{3b}$ are a hydrogen atom, an alkyl group, a cycloalkyl group, an alkaryl group, an aryl group, or an acyl group)).

Figure 4B:
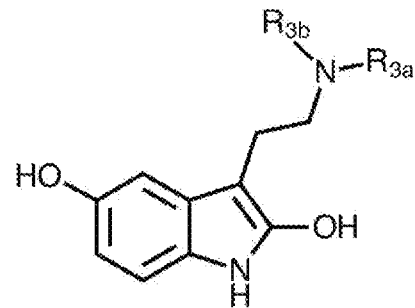

Continuing to refer to the chemical compound having formula (I), in one embodiment, $R_2$ and $R_5$ can be hydroxy groups, and $R_6$ and $R_7$ can be hydrogen atoms or alkyl groups and $R_4$ can be a phosphate group, a hydrogen atom or an alkyl group or O-alkyl group (see: the example hydroxylated psilocybin derivative shown in FIG. 4B ($R_2$ and $R_5$ are each a hydroxy group; $R_4$, $R_6$ and $R_7$ are hydrogen atoms; and $R_{3a}$ and $R_{3b}$ are a hydrogen atom, an alkyl group, a cycloalkyl group, an alkaryl group, an aryl group, or an acyl group)).

Figure 4C:
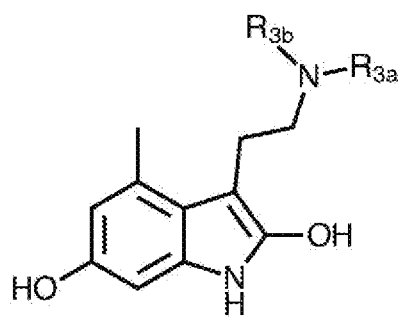

Continuing to refer to the chemical compound having formula (I), in one embodiment, $R_2$ and $R_6$ can hydroxy groups, and $R_5$ and $R_7$ can be hydrogen atoms, and $R_4$ can be a phosphate group, a hydrogen atom or an alkyl group or O-alkyl group (see: the example hydroxylated psilocybin derivative shown in FIG. 4C ($R_2$ and $R_6$ are each a hydroxy group; $R_4$ is a methyl group, $R_5$ and $R_7$ are hydrogen atoms; and $R_{3a}$ and $R_{3b}$ are a hydrogen atom, an alkyl group, a cycloalkyl group, an alkaryl group, an aryl group, or an acyl group)).

Figure 4D:
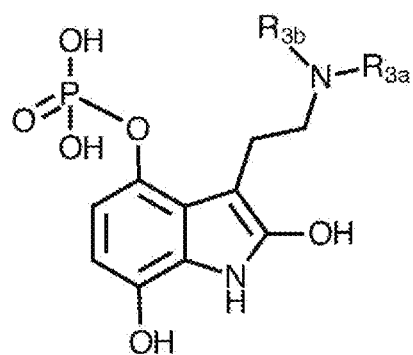

Continuing to refer to the chemical compound having formula (I), in one embodiment, $R_2$ and $R_7$ can be hydroxy groups, and $R_5$ and $R_6$ can be hydrogen atoms or alkyl group and $R_4$ can be a phosphate group, a hydrogen atom or an alkyl group or O-alkyl group (see: the example hydroxylated psilocybin derivative shown in FIG. 4D ($R_2$ and $R_7$ are each hydroxy groups; $R_4$ is a phosphate group; $R_5$ and $R_6$ are hydrogen atoms; and $R_{3a}$ and $R_{3b}$ are a hydrogen atom, an alkyl group, a cycloalkyl group, an alkaryl group, an aryl group, or an acyl group)).

Figure 4E:
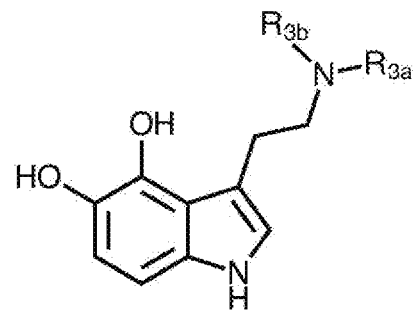

In one embodiment, $R_4$ and $R_5$ can be hydroxy groups, $R_2$, $R_6$ and $R_7$ can be hydrogen atoms or alkyl groups (see: the example hydroxylated psilocybin derivative shown in FIG. 4E ($R_4$ and $R_5$ are each hydroxy groups; $R_2$, $R_6$ and $R_7$ are hydrogen atoms; and $R_{3a}$ and $R_{3b}$ are a hydrogen atom, an alkyl group, a cycloalkyl group, an alkaryl group, an aryl group, or an acyl group)).

Figure 4F:
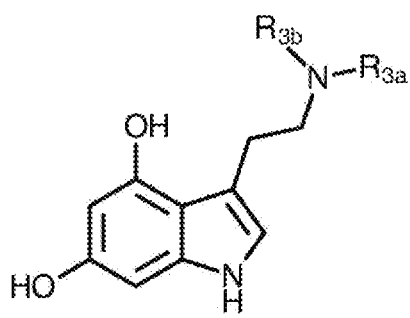

Continuing to refer to the chemical compound having formula (I), in one embodiment, $R_4$ and $R_6$ can be hydroxy groups, and $R_2$, $R_5$ and $R_7$ can be hydrogen atoms or alkyl groups (see: the example hydroxylated psilocybin derivative shown in FIG. 4F ($R_4$ and $R_6$ are each hydroxy groups; $R_2$, $R_5$ and $R_7$ are hydrogen atoms; and $R_{3a}$ and $R_{3b}$ are a hydrogen atom, an alkyl group, a cycloalkyl group, an alkaryl group, an aryl group, or an acyl group)).

Figure 4G:
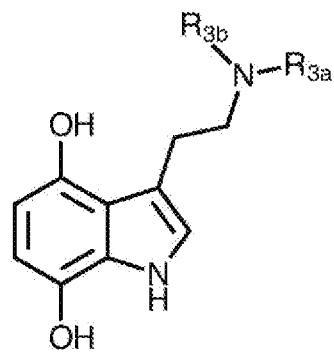

Continuing to refer to the chemical compound having formula (I), in one embodiment, $R_4$ and $R_7$ can be hydroxy groups, and $R_2$, $R_5$ and $R_6$ can be hydrogen atoms or alkyl groups (see: the example hydroxy psilocybin derivative shown in FIG. 4G ($R_4$ and $R_7$ are each hydroxy groups; $R_2$, $R_5$ and $R_6$ are hydrogen atoms; and $R_{3a}$ and $R_{3b}$ are a hydrogen atom, an alkyl group, a cycloalkyl group, an alkaryl group, an aryl group, or an acyl group)).

Figure 4H:
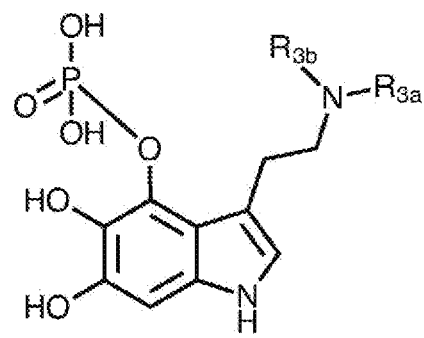

Continuing to refer to the chemical compound having formula (I), in one embodiment, $R_5$ and $R_6$ can be hydroxy groups and $R_2$ and $R_7$ can be hydrogen atoms or alkyl groups and $R_4$ can be a phosphate group, a hydrogen atom or an alkyl group or O-alkyl group (see: the example hydroxylated psilocybin derivative shown in FIG. 4H ($R_5$ and $R_6$ are each hydroxy groups; $R_4$ is a phosphate group; $R_2$ and $R_7$ are hydrogen atoms; and $R_{3a}$ and $R_{3b}$ are a hydrogen atom, an alkyl group, a cycloalkyl group, an alkaryl group, an aryl group, or an acyl group)).

Figure 4I:
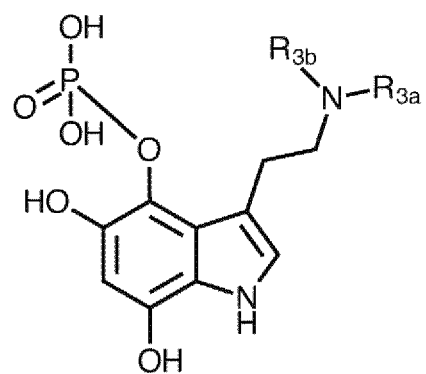

Continuing to refer to the chemical compound having formula (I), in one embodiment, $R_5$ and $R_7$ can be hydroxy groups, and $R_2$ and $R_6$ can be hydrogen atoms or alkyl groups and $R_4$ can be a phosphate group, a hydrogen atom or an alkyl group or O-alkyl group (see: the example hydroxylated psilocybin derivative shown in FIG. 4I ($R_5$ and $R_7$ are each hydroxy groups; $R_4$ is a phosphate group; $R_2$ and $R_6$ are hydrogen atoms; and $R_{3a}$ and $R_{3b}$ are a hydrogen atom, an alkyl group, a cycloalkyl group, an alkaryl group, an aryl group, or an acyl group)).

Figure 4J:
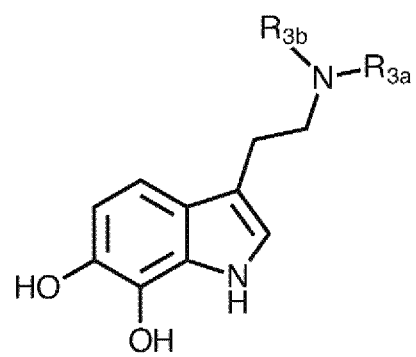

Continuing to refer to the chemical compound having formula (I), in one embodiment, $R_6$ and $R_7$ can be hydroxy groups, and $R_2$ and $R_5$ can be hydrogen atoms or alkyl groups and $R_4$ can be a phosphate group, a hydrogen atom or an alkyl group or O-alkyl group (see: the example hydroxylated psilocybin derivative shown in FIG. 4J ($R_6$ and $R_7$ are each hydroxy groups; $R_2$, $R_4$ and $R_5$ are hydrogen atoms; and $R_{3a}$ and $R_{3b}$ are a hydrogen atom, an alkyl group, a cycloalkyl group, an alkaryl group, an aryl group, or an acyl group)).

Referring again to the chemical compound having formula (I), in one further embodiment, three of $R_2$, $R_4$, $R_5$, $R_6$ and $R_7$ can be a hydroxy group, wherein the non-hydroxylated $R_2$, $R_5$, $R_6$, or $R_7$ substituents are a hydrogen atom or an alkyl group or O-alkyl group, and wherein $R_4$, when it is not a hydroxy group, is a phosphate group, hydrogen atom or an alkyl group or O-alkyl group.

Figure 5A:
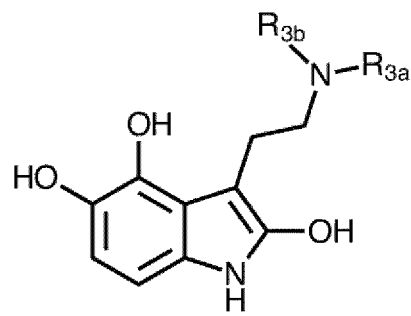
FIGS. 5A, 5B, 5C, 5D, 5E, and 5F depict the chemical structures of certain further example hydroxylated psilocybin derivative compounds, notably a 2,4,5-tri-hydroxy psilocybin derivative (FIG. 5A); a 2-5,6-tri-hydroxy-4-methyl psilocybin derivative (FIG. 5B); a 2,5,7-tri-hydroxy psilocybin derivative (FIG. 5C); a 4,5,6-tri-hydroxy psilocybin derivative (FIG. 5D); a 4,5,7-tri-hydroxy psilocybin derivative (FIG. 5E); and a 4-phospho-5,6,7-tri-hydroxy psilocybin derivative (FIG. 5F). It is noted that in each of FIGS. 5A, 5B, 5C, 5D, 5E, and 5F $R_{3a}$ and $R_{3b}$ can be a hydrogen atom, an alkyl group, a cycloalkyl group, an aryl group, an alkaryl group or an acyl group.

Thus, referring to the chemical compound having formula (I) again, in one embodiment $R_2$, $R_4$, and $R_5$ can be a hydroxy group, and $R_6$ and $R_7$ can be a hydrogen atom or an alkyl group or O-alkyl group (see: the example hydroxylated psilocybin derivative shown in FIG. 5A ($R_2$, $R_4$ and $R_5$ are each hydroxy groups; $R_6$ and $R_7$ are hydrogen atoms; and $R_{3a}$ and $R_{3b}$ are a hydrogen atom, an alkyl group, a cycloalkyl group, an alkaryl group, an aryl group, or an acyl group)).

Figure 5B:
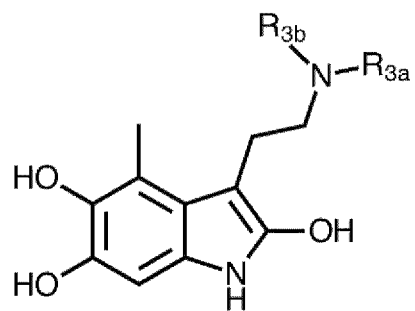

Referring to the chemical compound having formula (I), in one embodiment, $R_2$, $R_5$, and $R_6$ can be a hydroxy groups, and $R_7$ can be a hydrogen atom or alkyl group, and $R_4$ can a phosphate group, a hydrogen atom or an alkyl group or O-alkyl group (see: the example hydroxylated psilocybin derivative shown in FIG. 5B ($R_2$, $R_5$ and $R_6$ are each hydroxy groups; $R_4$ is a methyl group; $R_7$ is a hydrogen atom; and $R_{3a}$ and $R_{3b}$ are a hydrogen atom, an alkyl group, a cycloalkyl group, an alkaryl group, an aryl group, or an acyl group)).

Figure 5C:
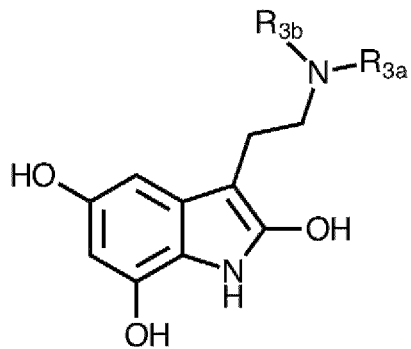

Referring to the chemical compound having formula (I), in one embodiment, $R_2$, $R_5$, and $R_7$ can be a hydroxy group and $R_6$ can be a hydrogen atom or alkyl group, and $R_4$ can a phosphate group, a hydrogen atom or alkyl group (see: the example hydroxylated psilocybin derivative shown in FIG. 5C ($R_2$, $R_5$ and $R_7$ are each hydroxy groups; $R_4$ and $R_6$ are hydrogen atoms; and $R_{3a}$ and $R_{3b}$ are a hydrogen atom, an alkyl group, a cycloalkyl group, an alkaryl group, an aryl group, or an acyl group)).

Figure 5D:
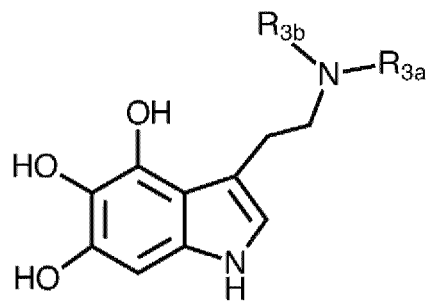

Referring to the chemical compound having formula (I), in one embodiment, $R_4$, $R_5$, and $R_6$ can be a hydroxy group, and $R_2$ and $R_7$ can be a hydrogen atom or alkyl group (see: the example hydroxylated psilocybin derivative shown in FIG. 5D ($R_4$, $R_5$ and $R_6$ are each a hydroxy group; $R_2$ and $R_7$ are hydrogen atoms; and $R_{3a}$ and $R_{3b}$ are a hydrogen atom, an alkyl group, a cycloalkyl group, an alkaryl group, an aryl group, or an acyl group)).

Figure 5E:
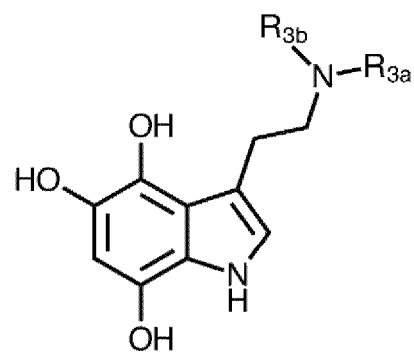

Referring to the chemical compound having formula (I), in one embodiment, $R_4$, $R_5$, and $R_7$ can be a hydroxy group, and $R_2$ and $R_6$ can be a hydrogen atom or alkyl group (see: the example hydroxylated psilocybin derivative shown in FIG. 5E ($R_4$, $R_5$ and $R_7$ are each a hydroxy group; $R_2$ and $R_6$ are hydrogen atoms; and $R_{3a}$ and $R_{3b}$ are a hydrogen atom, an alkyl group, a cycloalkyl group, an alkaryl group, an aryl group, or an acyl group)).

Figure 5F:
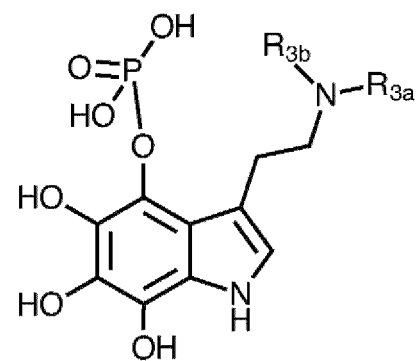

Referring to the chemical compound having formula (I), in one embodiment, $R_5$, $R_6$, and $R_7$ can a hydroxy group, and $R_2$ can be a hydrogen atom or an alkyl group or O-alkyl group, and $R_4$ can be a phosphate group, a hydrogen atom or an alkyl group or O-alkyl group (see: the example hydroxylated psilocybin derivative shown in FIG. 5F ($R_5$, $R_6$ and $R_7$ are each a hydroxy group; $R_4$ is a phosphate group; $R_2$ is a hydrogen atom; and $R_{3a}$ and $R_{3b}$ are a hydrogen atom, an alkyl group, a cycloalkyl group, an alkaryl group, an aryl group, or an acyl group)).

Referring again to the chemical compound having formula (I), in one embodiment, four of $R_2$, $R_4$, $R_5$, $R_6$ and $R_7$ can be a hydroxy group and wherein the non-hydroxylated $R_2$, $R_5$, $R_6$, or $R_7$ is a hydrogen atom or an alkyl group or O-alkyl group, and wherein $R_4$, when it is not a hydroxy group, is a phosphate group, a hydrogen atom or an alkyl group or O-alkyl group.

Figure 6A:
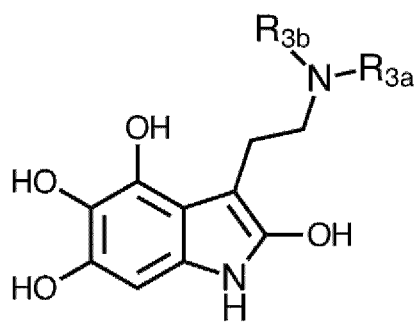
FIGS. 6A, 6B, 6C, 6D, and 6E depict the chemical structures of certain further example hydroxylated psilocybin derivative compounds, notably a 2,4,5,6-tetrhydroxy psilocybin derivative (FIG. 6A); a 4,5,6,7-tetra hydroxy psilocybin derivative (FIG. 6B); a 2,5,6-7-tetra-hydroxy-4-phospho psilocybin derivative (FIG. 6C); a 2,4,6,7-tetra hydroxy psilocybin derivative (FIG. 6D); and a 2,4,5,7-tetra-hydroxy psilocybin derivative (FIG. 6E). It is noted that in each of FIGS. 6A, 6B, 6C, 6D, and 6E $R_{3a}$ and $R_{3b}$ can be a hydrogen atom, an alkyl group, a cycloalkyl group, an alkaryl group, an aryl group, or an acyl group.

Thus, referring to the chemical compound having formula (I), in one embodiment, $R_2$, $R_4$, $R_5$ and $R_6$ can be a hydroxy group and $R_7$ can be a hydrogen atom or an alkyl group or O-alkyl group (see: the example hydroxylated psilocybin derivative shown in FIG. 6A ($R_2$, $R_4$, $R_5$ and $R_6$ are each hydroxy groups; $R_7$ is a hydrogen atom; and $R_{3a}$ and $R_{3b}$ are a hydrogen atom, an alkyl group, a cycloalkyl group, an alkaryl group, an aryl group, or an acyl group)).

Figure 6B:
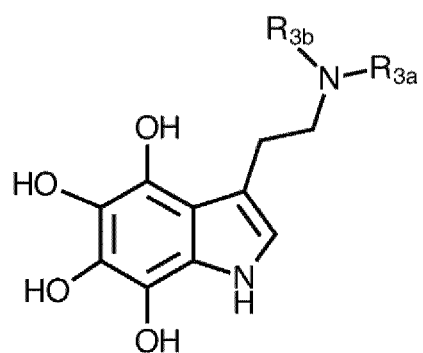

Referring to the chemical compound having formula (I), in one embodiment, $R_4$, $R_5$, $R_6$ and $R_7$ can be a hydroxy group and $R_2$ can be a hydrogen atom or an alkyl group or O-alkyl group (see: the example hydroxylated psilocybin derivative shown in FIG. 6B ($R_4$, $R_5$, $R_6$ and $R_7$ are each hydroxy groups; $R_2$ is a hydrogen atom; and $R_{3a}$ and $R_{3b}$ are a hydrogen atom, an alkyl group, a cycloalkyl group, an alkaryl group, an aryl group, or an acyl group)).

Figure 6C:
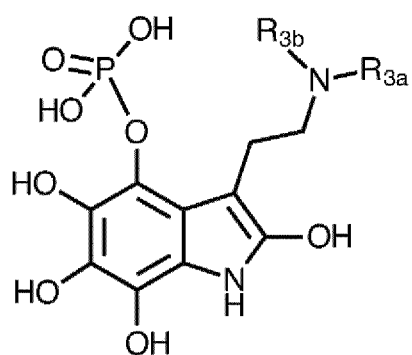

Referring to the chemical compound having formula (I), in one embodiment, $R_2$, $R_5$, $R_6$ and $R_7$ can be a hydroxy group, $R_4$ can be a phosphate group, a hydrogen atom or an alkyl group or O-alkyl group (see: the example hydroxylated psilocybin derivative shown in FIG. 6C ($R_2$, $R_5$, $R_6$ and $R_7$ are each hydroxy groups; $R_4$ is a phosphate group; and $R_{3a}$ and $R_{3b}$ are a hydrogen atom, an alkyl group, a cycloalkyl group, an alkaryl group, an aryl group, or an acyl group)).

Figure 6D:
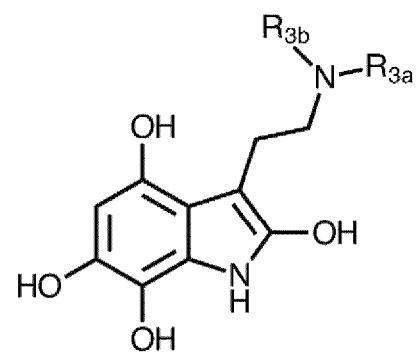

Referring to the chemical compound having formula (I), in one embodiment $R_2$, $R_4$, $R_6$ and $R_7$ can be a hydroxy group and $R_5$ can be a hydrogen atom or alkyl group (see: the example hydroxylated psilocybin derivative shown in FIG. 6D ($R_2$, $R_4$, $R_6$, and $R_7$ are hydroxy groups; $R_5$ is a hydrogen atom; and $R_{3a}$ and $R_{3b}$ are a hydrogen atom, an alkyl group, a cycloalkyl group, an alkaryl group, an aryl group, or an acyl group)).

Figure 6E:
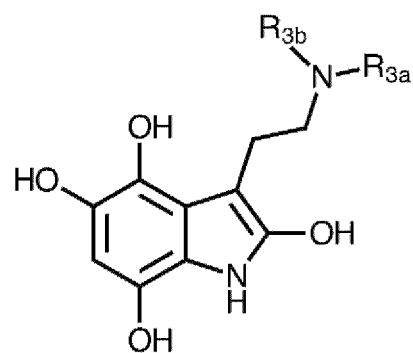

Referring to the chemical compound having formula (I), in one embodiment $R_2$, $R_4$, $R_5$ and $R_7$ can be hydroxy groups and $R_6$ can be a hydrogen atom or alkyl group (see: the example hydroxylated psilocybin derivative shown in FIG. 6E ($R_2$, $R_4$, $R_5$ and $R_7$ are each hydroxy groups; $R_6$ is a hydrogen atom; and $R_{3a}$ and $R_{3b}$ are a hydrogen atom, an alkyl group, a cycloalkyl group, an alkaryl group, an aryl group, or an acyl group)).

In one embodiment, all five of $R_2$, $R_4$, $R_5$, $R_6$ and $R_7$ can be a hydroxy group.

It is noted that, in a further aspect hereof, $R_{3A}$ and $R_{3B}$ can be a hydrogen atom, an alkyl group, a cycloalkyl group, an alkaryl group, an aryl group or an acyl group. Thus, for example, $R_{3A}$ and $R_{3B}$ can each be a hydrogen atom, or $R_{3A}$ and $R_{3B}$ can each be an alkyl group, such as a methyl group, ethyl group, propyl group, or longer chain alkyl group, or $R_{3A}$ and $R_{3B}$ can each be a cycloalkyl group, such as cyclopentyl group, a cyclohexyl group, or a cycloheptyl group, or $R_{3A}$ and $R_{3B}$ can each be an alkaryl group such as —$CH_2CH_2$-phenyl, —$CH_2CH(CH_3)$-phenyl, —$CH_2$-phenyl, or —$CH(CH_3)$-phenyl, or $R_{3A}$ and $R_{3B}$ can each be an aryl group, such as a phenyl group or a naphthyl group, or $R_{3A}$ and $R_{3B}$ can each be an acyl group, such as an acetyl group. Furthermore, one of $R_{3A}$ and $R_{3B}$ can be a hydrogen atom, and one of $R_{3A}$ and $R_{3B}$ can be an alkyl group, a cycloalkyl group, an alkaryl group, aryl group, or an acyl group. Furthermore, $R_{3A}$ and $R_{3B}$ can be an aryl group and an alkyl group, an aryl group and an acyl group, or an alkyl group and an acyl group.

In one further embodiment of the disclosure, a chemical compound or salt thereof having formula (I) is included:

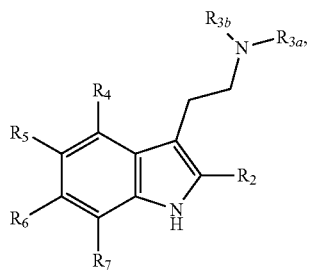

(I)

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a hydrogen atom, alkyl group, or a phosphate group, and wherein $R_{3A}$ and $R_{3B}$ are a hydrogen atom, an alkyl group, a cycloalkyl group, an alkaryl group, an aryl group, or an acyl group.

In one embodiment, at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or a ($C_1$-$C_{20}$)-alkyl group, wherein $R_4$ when it is not hydroxylated is a hydrogen atom, a ($C_1$-$C_{20}$)-alkyl group, or a phosphate group. In another embodiment, each non-hydroxylated $R_2$, $R_5$, $R_6$, or $R_7$ is a hydrogen atom or a ($C_1$-$C_{10}$)-alkyl group. In another embodiment, each non-hydroxylated $R_2$, $R_5$, $R_6$, or $R_7$ is a hydrogen atom or a ($C_1$-$C_6$)-alkyl group. In another embodiment, each non-hydroxylated $R_2$, $R_5$, $R_6$, or $R_7$ is a hydrogen atom, a methyl group, an ethyl group or a propyl group.

In another embodiment, when $R_4$ is not hydroxylated, $R_4$ is a hydrogen atom, a ($C_1$-$C_{20}$)-alkyl group, or a phosphate group. In another embodiment, when $R_4$ is not hydroxylated, $R_4$ is a hydrogen atom, a ($C_1$-$C_{10}$)-alkyl group, or a phosphate group. In another embodiment, when $R_4$ is not hydroxylated, $R_4$ is a hydrogen atom, a ($C_1$-$C_6$)-alkyl group, or a phosphate group. In another embodiment, when $R_4$ is not hydroxylated, $R_4$ is a hydrogen atom, a methyl group, an ethyl group, a propyl group, or a phosphate group.

In another embodiment, $R_{3A}$ and $R_{3B}$ are a hydrogen atom, a ($C_1$-$C_{20}$)-alkyl group, a ($C_3$-$C_{20}$)-cycloalkyl group, a ($C_1$-$C_{20}$)-alk-($C_6$-$C_{14}$)-aryl group, a ($C_6$-$C_{14}$-aryl group, or a —$C(=O)$($C_1$-$C_{20}$)-alkyl group. In another embodiment, $R_{3A}$ and $R_{3B}$ are a hydrogen atom, a ($C_1$-$C_{10}$)-alkyl group, a ($C_3$-$C_{10}$)-cycloalkyl group, a ($C_1$-$C_{10}$)-alk-($C_6$-$C_{10}$)-aryl group a ($C_6$-$C_{10}$)-aryl group, or a —$C(=O)$($C_1$-$C_{10}$)-alkyl group. In another embodiment, $R_{3A}$ and $R_{3B}$ are a hydrogen atom, a ($C_1$-$C_6$)-alkyl group, a ($C_3$-$C_7$)-cycloalkyl group, a ($C_1$-$C_6$)-alk-phenyl group, a phenyl group, or a —$C(=O)$($C_1$-$C_6$)-alkyl group. In another embodiment, $R_{3A}$ and $R_{3B}$ are a hydrogen atom, a methyl group, an ethyl group, a propyl group, a cyclopentyl group, a cyclohexyl group, a cycloheptyl group, —$CH_2CH_2$-phenyl, —$CH_2CH(CH_3)$-phenyl, —$CH_2$-phenyl, —$CH(CH_3)$-phenyl, a phenyl group, —$C(=O)$—$CH_3$, —$C(=O)$—$CH_2CH_3$, or —$C(=O)$—$CH_2CH_2CH_3$.

In one embodiment of the disclosure, a chemical compound or salt thereof having formula (I) is included:

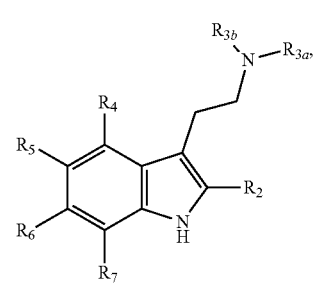

(I)

wherein
$R_2$, $R_5$, $R_6$, and $R_7$ are independently or simultaneously H, an alkyl group or a hydroxy group, $R_{3A}$ and $R_{3B}$ are a hydrogen atom, an alkyl group, a cycloalkyl group, an alkaryl group, an aryl group, or an acyl group; and $R_4$ is hydrogen atom, alkyl group, a hydroxy group or a phosphate group;

wherein at least one of $R_2$, $R_4$, $R_5$, $R_6$, and $R_7$ is a hydroxy group.

In one embodiment, $R_2$, $R_5$, $R_6$, and $R_7$ are independently or simultaneously H, $(C_1-C_{20})$-alkyl group or a hydroxy group. In one embodiment, $R_2$, $R_5$, $R_6$, and $R_7$ are independently or simultaneously H, $(C_1-C_{10})$-alkyl group or a hydroxy group. In one embodiment, $R_2$, $R_5$, $R_6$, and $R_7$ are independently or simultaneously H, $(C_1-C_6)$-alkyl group or a hydroxy group. In one embodiment, $R_2$, $R_5$, $R_6$, and $R_7$ are independently or simultaneously H, methyl, ethyl, propyl or a hydroxy group.

In one embodiment, $R_4$ is H, $(C_1-C_{20})$-alkyl group, a hydroxy group or a phosphate group. In one embodiment, $R_4$ is H, $(C_1-C_{10})$-alkyl group, a hydroxy group or a phosphate group. In one embodiment, $R_4$ is H, $(C_1-C_6)$-alkyl group, a hydroxy group or a phosphate group. In one embodiment, $R_4$ is H, methyl, ethyl, propyl, a hydroxy group or a phosphate group.

In another embodiment, $R_{3A}$ and $R_{3B}$ are a hydrogen atom, a $(C_1-C_{20})$-alkyl group, a $(C_3-C_{20})$-cycloalkyl group, a $(C_1-C_{20})$-alk-$(C_6-C_{14})$-aryl group, a $(C_6-C_{14})$-aryl group, or a —C(=O)($C_1-C_{20}$)-alkyl group. In another embodiment, $R_{3A}$ and $R_{3B}$ are a hydrogen atom, a $(C_1-C_{10})$-alkyl group, a $(C_3-C_{10})$-cycloalkyl group, a $(C_1-C_{10})$-alk-$(C_6-C_{10})$-aryl group a $(C_6-C_{10})$-aryl group, or a —C(=O)($C_1-C_{10}$)-alkyl group. In another embodiment, $R_{3A}$ and $R_{3B}$ are a hydrogen atom, a $(C_1-C_6)$-alkyl group, a $(C_3-C_7)$-cycloalkyl group, a $(C_1-C_6)$-alk-phenyl group, a phenyl group, or a —C(=O)($C_1-C_6$)-alkyl group. In another embodiment, $R_{3A}$ and $R_{3B}$ are a hydrogen atom, a methyl group, an ethyl group, a propyl group, a cyclopentyl group, a cyclohexyl group, a cycloheptyl group, —$CH_2CH_2$-phenyl, —$CH_2CH(CH_3)$-phenyl, —$CH_2$-phenyl, —$CH(CH_3)$-phenyl, a phenyl group, —C(=O)—$CH_3$, —C(=O)—$CH_2CH_3$, or —C(=O)—$CH_2CH_2CH_3$.

Furthermore, in one embodiment, a hydroxylated psilocybin derivative according to the present disclosure can be a chemical compound having the formula (III):

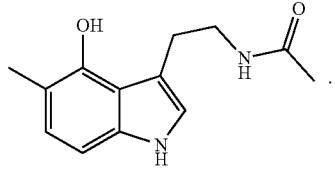

(III)

Furthermore, in one embodiment, a hydroxylated psilocybin derivative according to the present disclosure can be a chemical compound having the formula (IV):

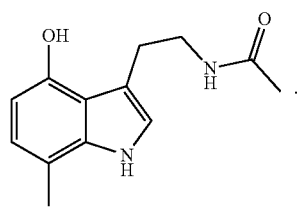

(IV)

Furthermore, in one embodiment, a hydroxylated psilocybin derivative according to the present disclosure can be a chemical compound having the formula (V):

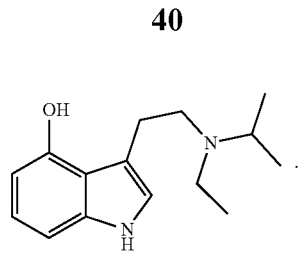

(V)

Furthermore, in one embodiment, a hydroxylated psilocybin derivative according to the present disclosure can be a chemical compound having the formula (VI):

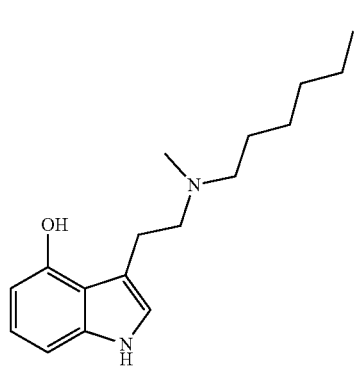

(VI)

Furthermore, in one embodiment, a hydroxylated psilocybin derivative according to the present disclosure can be a chemical compound having the formula (VII):

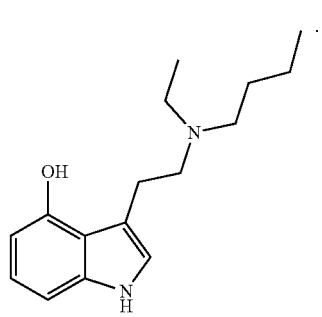

(VII)

Furthermore, in one embodiment, a hydroxylated psilocybin derivative according to the present disclosure can be a chemical compound having the formula (VIII):

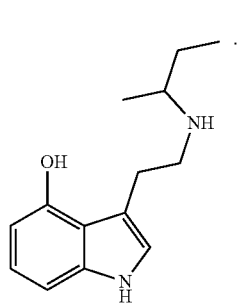

(VIII)

Furthermore, in one embodiment, a hydroxylated psilocybin derivative according to the present disclosure can be a chemical compound having the formula (IX):

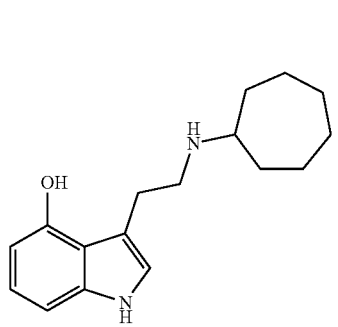

(IX)

Furthermore, in one embodiment, a hydroxylated psilocybin derivative according to the present disclosure can be a chemical compound having the formula (X):

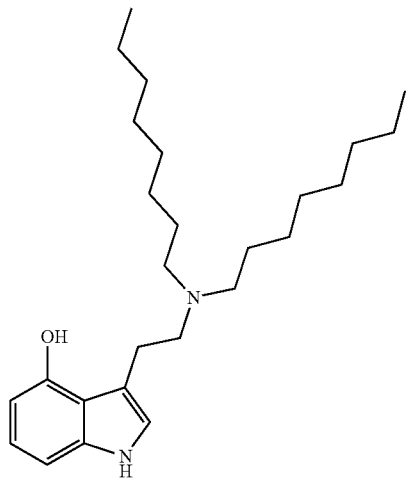

(X)

Furthermore, in one embodiment, a hydroxylated psilocybin derivative according to the present disclosure can be a chemical compound having the formula (XI):

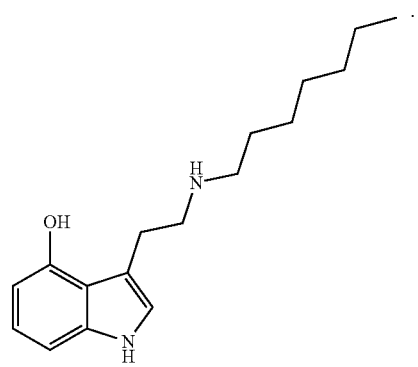

(XI)

Furthermore, in one embodiment, a hydroxylated psilocybin derivative according to the present disclosure can be a chemical compound having the formula (XII):

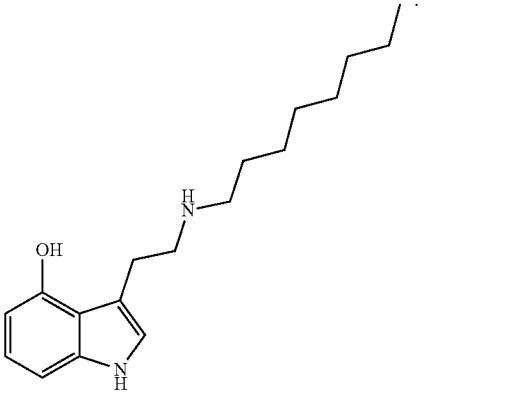

(XII)

Furthermore, in one embodiment, a hydroxylated psilocybin derivative according to the present disclosure can be a chemical compound having the formula (XIII):

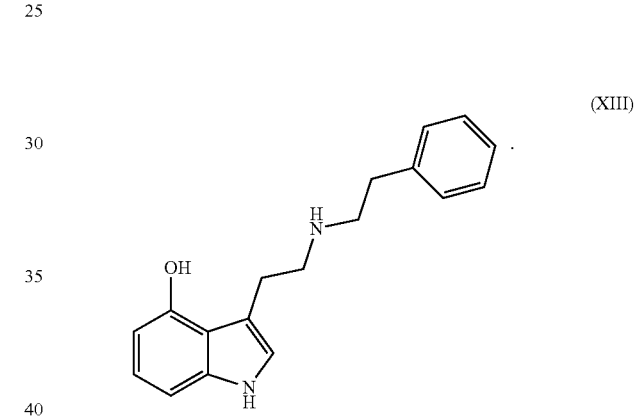

(XIII)

Furthermore, in one embodiment, a hydroxylated psilocybin derivative according to the present disclosure can be a chemical compound having the formula (XIV):

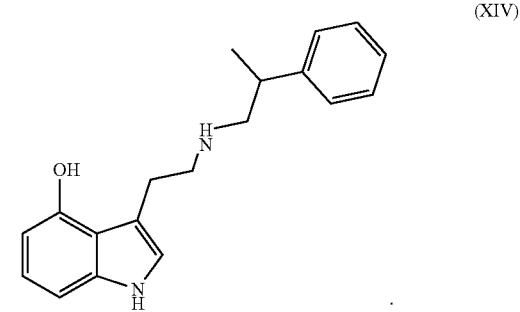 [SMILES: CC(CNCCc1c[nH]c2cccc(O)c12)c1ccccc1]

(XIV)

Furthermore, in one embodiment, a hydroxylated psilocybin derivative according to the present disclosure can be a chemical compound having the formula (XV):

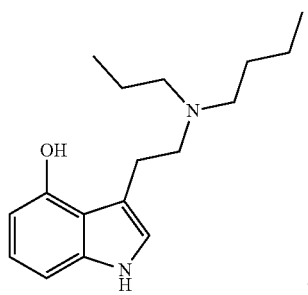

(XV)

Furthermore, in one embodiment, a hydroxylated psilocybin derivative according to the present disclosure can be a chemical compound having the formula (XVI):

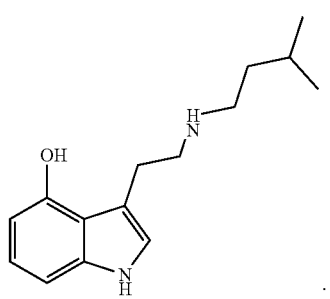

(XVI)

Furthermore, in one embodiment, a hydroxylated psilocybin derivative according to the present disclosure can be a chemical compound having the formula (XVII):

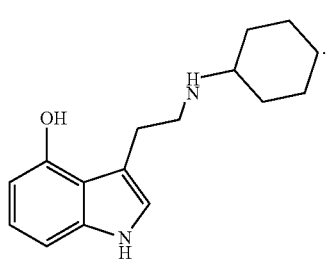

(XVII)

Furthermore, in one embodiment, a hydroxylated psilocybin derivative according to the present disclosure can be a chemical compound having the formula (XVIII):

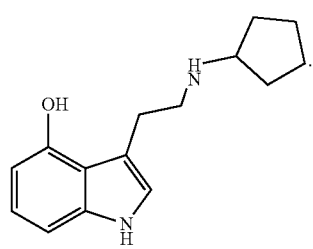

(XVIII)

Furthermore, in one embodiment, a hydroxylated psilocybin derivative according to the present disclosure can be a chemical compound having the formula (XIX):

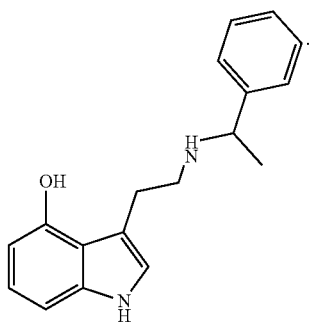

(XIX)

Furthermore, in one embodiment, a hydroxylated psilocybin derivative according to the present disclosure can be a chemical compound having the formula (XX):

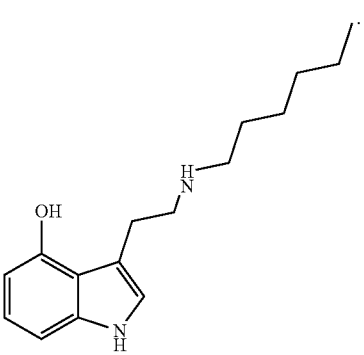

(XX)

Furthermore, in one embodiment, a hydroxylated psilocybin derivative according to the present disclosure can be a chemical compound having the formula (XXI):

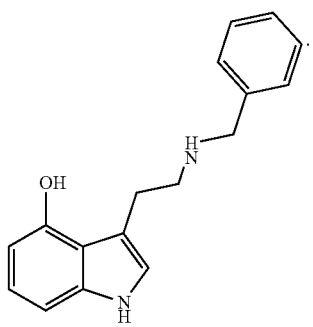

(XXI)

Furthermore, in one embodiment, a hydroxylated psilocybin derivative according to the present disclosure can be a chemical compound having the formula (XXII):

(XXII)

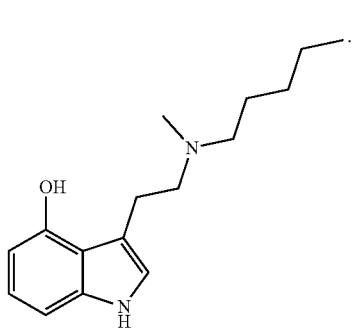

Furthermore, in one embodiment, a hydroxylated psilocybin derivative according to the present disclosure can be a chemical compound having the formula (XXIII):

(XXIII)

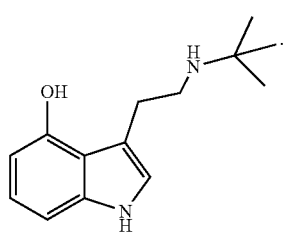

Furthermore, in one embodiment, a hydroxylated psilocybin derivative according to the present disclosure can be a chemical compound having the formula (XXIV):

(XXIV)

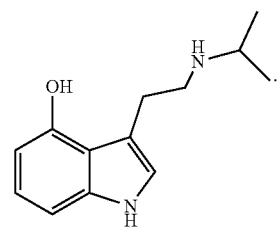

Furthermore, in one embodiment, a hydroxylated psilocybin derivative according to the present disclosure can be a chemical compound having the formula (XXV):

(XXV)

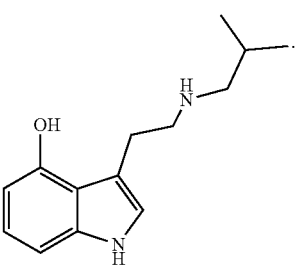

Furthermore, in one embodiment, a hydroxylated psilocybin derivative according to the present disclosure can be a chemical compound having the formula (XXVI):

(XXVI)

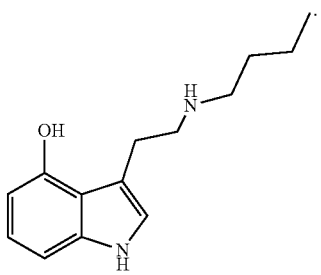

Furthermore, in one embodiment, a hydroxylated psilocybin derivative according to the present disclosure can be a chemical compound having the formula (XXVII):

(XXVII)

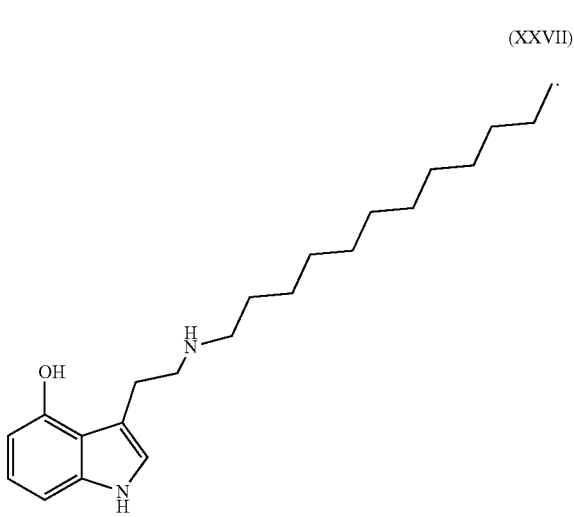 [SMILES: CCCCCCCCCCCCNCCc1c[nH]c2cccc(O)c12]

Furthermore, in one embodiment, a hydroxylated psilocybin derivative according to the present disclosure can be a chemical compound having the formula (XXVIII):

(XXVIII)

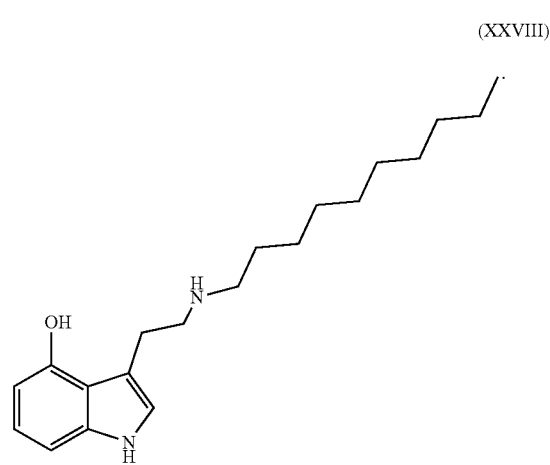 [SMILES: CCCCCCCCCCNCCc1c[nH]c2cccc(O)c12]

Furthermore, in one embodiment, a hydroxylated psilocybin derivative according to the present disclosure can be a chemical compound having the formula (XXIX):

(XXIX)

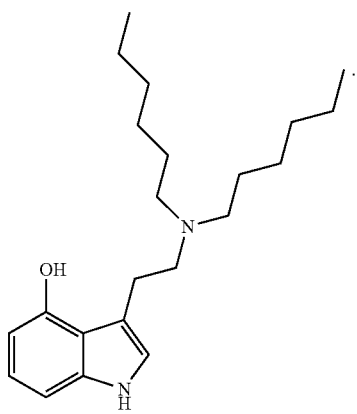

Furthermore, in one embodiment, a hydroxylated psilocybin derivative according to the present disclosure can be a chemical compound having the formula (XXX):

(XXX)

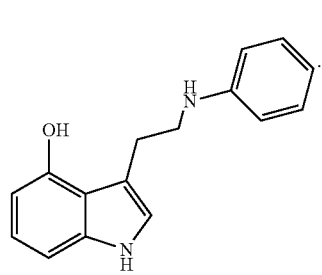

Furthermore, in one embodiment, a hydroxylated psilocybin derivative according to the present disclosure can be a chemical compound having the formula (XXXI):

(XXXI)

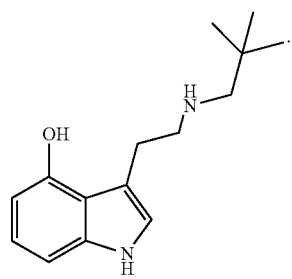

Furthermore, in one embodiment, a hydroxylated psilocybin derivative according to the present disclosure can be a chemical compound having the formula (XXXII):

(XXXII)

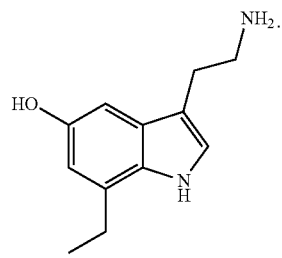

Furthermore, it is noted that the hydroxylated psilocybin derivatives of the present disclosure include salts thereof, including pharmaceutically acceptable salts. Thus, the nitrogen atom of the 2-aminoethyl group extending in turn from the $C_3$ atom may be protonated, and the positive charge may be balanced by, for example, chloride or sulfate ions, to thereby form a chloride salt or a sulfate salt. Furthermore, in compounds wherein $R_4$ is a phosphate group, the phosphate group may be de-protonated, and the negative charge may be balanced by, for example, sodium ions or potassium ions, to thereby form a sodium salt or a potassium salt.

Furthermore, it is noted that when $R_4$ is a phosphate group, the term hydroxylated psilocybin derivative also includes compounds having the formula (XXXIII):

(XXXIII)

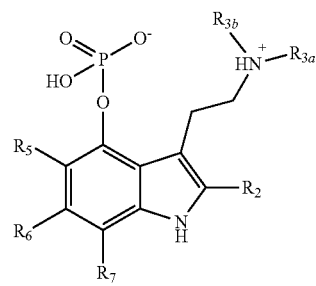

wherein at least one of $R_2$, $R_5$, $R_6$, or $R_7$ is a hydroxy group, and wherein any $R_2$, $R_5$, $R_6$, or $R_7$ which are not a hydroxy group are a hydrogen atom or an alkyl group or O-alkyl group, and wherein $R_{3A}$ and $R_{3B}$ are a hydrogen atom, an alkyl group, a cycloalkyl group, an alkaryl group, and aryl group or an acyl group. Further included are salts of hydroxylated psilocybins having the formula (VII), such as a sodium salt, a potassium salt etc.

Thus, to briefly recap, the present disclosure provides hydroxylated psilocybin derivatives. The disclosure provides, in particular, a chemical compound or salt thereof having formula (I):

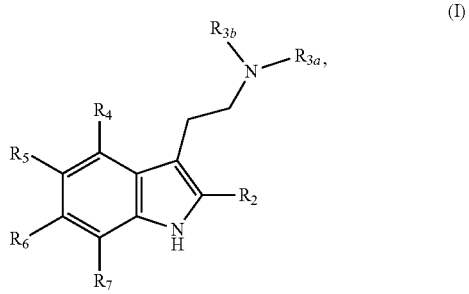

wherein in an aspect, at least one of $R_2$, $R_4$, $R_5$, $R_6$, or $R_7$ is a hydroxy group. In an aspect, in formula (I), each non-hydroxylated $R_2$, $R_5$, $R_6$, or $R_7$ is a hydrogen atom or an alkyl group or O-alkyl group. In a further aspect, in formula (I), $R_4$ when it is not hydroxylated is a hydrogen atom, an alkyl group or a phosphate group. Yet in a further aspect, $R_{3A}$ and $R_{3B}$ are a hydrogen atom, an alkyl group, a cycloalkyl group, an alkaryl group, an aryl group, or an acyl group.

In one embodiment of the disclosure, a chemical compound or salt thereof having formula (I) is included:

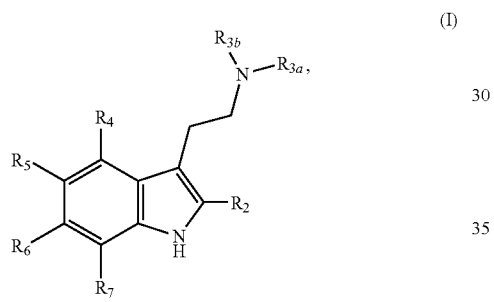

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a hydrogen atom, an alkyl group or a phosphate group, and wherein $R_{3A}$ and $R_{3B}$ are a hydrogen atom an alkyl group, a cycloalkyl group, an alkaryl group, an aryl group, or an acyl group.

In one embodiment, at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or a $(C_1-C_{20})$-alkyl group or $(C_1-C_{20})$—O-alkyl group, wherein $R_4$ when it is not hydroxylated is a hydrogen atom, a $(C_1-C_{20})$-alkyl group or $(C_1-C_{20})$—O-alkyl group, or a phosphate group.

In another embodiment, each non-hydroxylated $R_2$, $R_5$, $R_6$, or $R_7$ is a hydrogen atom or a $(C_1-C_{10})$-alkyl group or $(C_1-C_{10})$—O-alkyl group. In another embodiment, each non-hydroxylated $R_2$, $R_5$, $R_6$, or $R_7$ is a hydrogen atom or a $(C_1-C_6)$-alkyl group or $(C_1-C_6)$—O-alkyl group. In another embodiment, each non-hydroxylated $R_2$, $R_5$, $R_6$, or $R_7$ is a hydrogen atom, a methyl group, ethyl group, a propyl group, an O-methyl group, an O-ethyl group, or an O-propyl group.

In another embodiment, when $R_4$ is not hydroxylated, $R_4$ is a hydrogen atom, a $(C_1-C_{20})$-alkyl group or $(C_1-C_{20})$—O-alkyl group, or a phosphate group. In another embodiment, when $R_4$ is not hydroxylated, $R_4$ is a hydrogen atom, a $(C_1-C_{10})$-alkyl group or $(C_1-C_{10})$—O-alkyl group, or a phosphate group. In another embodiment, when $R_4$ is not hydroxylated, $R_4$ is a hydrogen atom, a $(C_1-C_6)$-alkyl group or $(C_1-C_6)$—O-alkyl group, or a phosphate group. In another embodiment, when $R_4$ is not hydroxylated, $R_4$ is a hydrogen atom, a methyl group, an ethyl group, a propyl group, a phosphate group, an O-methyl group, an O-ethyl group, or an O-propyl group.

In another embodiment, $R_{3A}$ and $R_{3B}$ are a hydrogen atom, a $(C_1-C_{20})$-alkyl group, a $(C_3-C_{20})$-cycloalkyl group, a $(C_1-C_{20})$-alk-$(C_6-014)$-aryl group, a (06-014)-aryl group, or a —C(=O)($C_1-C_{20}$)-alkyl group. In another embodiment, $R_{3A}$ and $R_{3B}$ are a hydrogen atom, a $(C_1-C_{10})$-alkyl group, a $(C_3-C_{10})$-cycloalkyl group, a $(C_1-C_{10})$-alk-$(C_6-C_{10})$-aryl group a $(C_6-C_{10})$-aryl group, or a —C(=O)($C_1-C_{10}$)-alkyl group. In another embodiment, $R_{3A}$ and $R_{3B}$ are a hydrogen atom, a $(C_1-C_6)$-alkyl group, a $(C_3-C_7)$-cycloalkyl group, a $(C_1-C_6)$-alk-phenyl group, a phenyl group, or a —C(=O)($C_1-C_6$)-alkyl group. In another embodiment, $R_{3A}$ and $R_{3B}$ are a hydrogen atom, a methyl group, an ethyl group, a propyl group, a cyclopentyl group, a cyclohexyl group, a cycloheptyl group, —$CH_2CH_2$-phenyl, —$CH_2CH(CH_3)$-phenyl, —$CH_2$-phenyl, —$CH(CH_3)$-phenyl, a phenyl group, —C(=O)—$CH_3$, —C(=O)—$CH_2CH_3$, or —C(=O)—$CH_2CH_2CH_3$.

In one embodiment of the disclosure, a chemical compound or salt thereof having formula (I) is included:

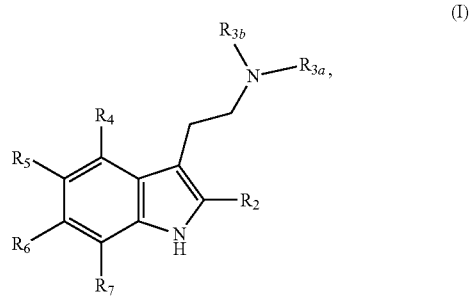

wherein $R_2$, $R_5$, $R_6$, and $R_7$ are independently or simultaneously H, an alkyl group or O-alkyl group or a hydroxy group, $R_{3A}$ and $R_{3B}$ are a hydrogen atom, an alkyl group, a cycloalkyl group, an alkaryl group, an aryl group, or an acyl group; and $R_4$ is hydrogen atom, alkyl group or O-alkyl group, a hydroxy group or a phosphate group; wherein at least one of $R_2$, $R_4$ $R_5$, $R_6$, and $R_7$ is a hydroxy group.

In one embodiment, $R_2$, $R_5$, $R_6$, and $R_7$ are independently or simultaneously H, $(C_1-C_{20})$-alkyl group or $(C_1-C_{20})$—O-alkyl group or a hydroxy group. In one embodiment, $R_2$, $R_5$, $R_6$, and $R_7$ are independently or simultaneously H, $(C_1-C_{10})$-alkyl group or $(C_1-C_{10})$—O-alkyl group or a hydroxy group. In one embodiment, $R_2$, $R_5$, $R_6$, and $R_7$ are independently or simultaneously H, $(C_1-06)$-alkyl group or $(C_1-C_6)$—O-alkyl group or a hydroxy group. In one embodiment, $R_2$, $R_5$, $R_6$, and $R_7$ are independently or simultaneously H, methyl, ethyl, propyl, O-methyl, O-ethyl, O-propyl, or a hydroxy group.

In one embodiment, $R_4$ is H, $(C_1-C_{20})$-alkyl group or $(C_1-C_{20})$—O-alkyl group, a hydroxy group or a phosphate group. In one embodiment, $R_4$ is H, $(C_1-C_{10})$-alkyl group or $(C_1-C_{10})$—O-alkyl group, a hydroxy group or a phosphate group. In one embodiment, $R_4$ is H, $(C_1-C_6)$-alkyl group or $(C_1-C_6)$—O-alkyl group, a hydroxy group or a phosphate group. In one embodiment, $R_4$ is H, methyl, ethyl, propyl, O-methyl, O-ethyl, O-propyl, a hydroxy group, or a phosphate group.

In another embodiment, $R_{3A}$ and $R_{3B}$ are a hydrogen atom, a ($C_1$-$C_{20}$-alkyl group, a ($C_3$-$C_{20}$)-cycloalkyl group, a ($C_1$-$C_{20}$)-alk-($C_6$-$C_{14}$)-aryl group, a ($C_6$-$C_{14}$-aryl group, or a —C(=O)($C_1$-$C_{20}$)-alkyl group. In another embodiment, $R_{3A}$ and $R_{3B}$ are a hydrogen atom, a ($C_1$-$C_{10}$)-alkyl group, a ($C_3$-$C_{10}$)-cycloalkyl group, a ($C_1$-$C_{10}$)-alk-($C_6$-$C_{10}$)-aryl group a ($C_6$-$C_{10}$)-aryl group, or a —C(=O)($C_1$-$C_{10}$)-alkyl group. In another embodiment, $R_{3A}$ and $R_{3B}$ are a hydrogen atom, a ($C_1$-$C_6$)-alkyl group, a ($C_3$-$C_7$)-cycloalkyl group, a ($C_1$-$C_6$)-alk-phenyl group, a phenyl group, or a —C(=O)($C_1$-$C_6$)-alkyl group. In another embodiment, $R_{3A}$ and $R_{3B}$ are a hydrogen atom, a methyl group, an ethyl group, a propyl group, a cyclopentyl group, a cyclohexyl group, a cycloheptyl group, —$CH_2CH_2$-phenyl, —$CH_2CH(CH_3)$-phenyl, —$CH_2$-phenyl, —$CH(CH_3)$-phenyl, a phenyl group, —C(=O)—$CH_3$, —C(=O)—$CH_2CH_3$, or —C(=O)—$CH_2CH_2CH_3$.

The hydroxylated psilocybin derivatives of the present disclosure may be used to prepare a pharmaceutical or recreational drug formulation. Thus in one embodiment, the present disclosure further provides in another aspect, pharmaceutical and recreational drug formulations comprising hydroxylated psilocybin derivatives. Accordingly, in one aspect, the present disclosure provides in a further embodiment a pharmaceutical or recreational drug formulation comprising a chemical compound having formula (I):

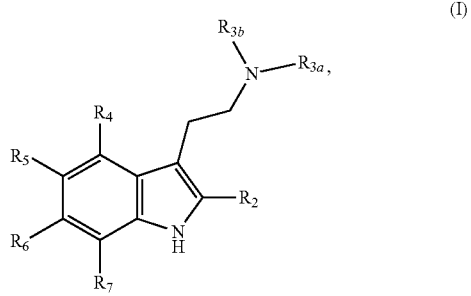

(I)

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a hydrogen atom, an alkyl group or a phosphate group, and wherein $R_{3A}$ and $R_{3B}$ are a hydrogen atom an alkyl group, a cycloalkyl group, an alkaryl group, an aryl group, or an acyl group, or a salt of the chemical compound, together with a diluent, carrier or excipient.

The dose when using the compounds of the present disclosure can vary within wide limits, and as is customary and is known to those of skill in the art, the dose can be tailored to the individual conditions in each individual case. The dose depends, for example, on the nature and severity of the illness to be treated, on the condition of the patient, on the compound employed or on whether an acute or chronic disease state is treated or prophylaxis is conducted, on the mode of delivery of the compound, or on whether further active compounds are administered in addition to the compounds of the present disclosure. Representative doses of the present invention include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to about 100 mg, about 0.001 mg to about 50 mg, and about 0.001 mg to about 25 mg. Representative doses of the present disclosure include, but are not limited to, about 0.0001 to about 1,000 mg, about 10 to about 160 mg, about 10 mg, about 20 mg, about 40 mg, about 80 mg or about 160 mg. Multiple doses may be administered during the day, especially when relatively large amounts are deemed to be needed, for example 2, 3 or 4, doses. Depending on the subject and as deemed appropriate from the patient's physician or care giver it may be necessary to deviate upward or downward from the doses described herein.

The pharmaceutical or recreational drug formulations may be prepared as liquids, tablets, capsules, microcapsules, nanocapsules, trans-dermal patches, gels, foams, oils, aerosols, nanoparticulates, powders, creams, emulsions, micellar systems, films, sprays, ovules, infusions, teas, decoctions, suppositories, etc. and include a pharmaceutically acceptable salt or solvate of the hydroxylated psilocybin compound together with an excipient. The term "excipient" as used herein means any ingredient other than the chemical compound of the disclosure. As will readily be appreciated by those of skill in art, the selection of excipient may depend on factors such as the particular mode of administration, the effect of the excipient on solubility of the chemical compounds of the present disclosure and methods for their preparation will be readily apparent to those skilled in the art. Such compositions and methods for their preparation may be found, for example, in "Remington's Pharmaceutical Sciences", 22nd Edition (Pharmaceutical Press and Philadelphia College of Pharmacy at the University of the Sciences, 2012).

The pharmaceutical and drug formulations comprising the hydroxylated psilocybin derivatives of the present disclosure may be administered orally. Oral administration may involve swallowing, so that the compound enters the gastrointestinal tract, or buccal or sublingual administration may be employed by which the compound enters the blood stream directly from the mouth. Formulations suitable for oral administration include both solid and liquid formulations.

Solid formulations include tablets, capsules (containing particulates, liquids, microcapsules, or powders), lozenges (including liquid-filled lozenges), chews, multi- and nano-particulates, gels, solid solutions, liposomal preparations, microencapsulated preparations, creams, films, ovules, suppositories and sprays.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose.

Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80. When present, surface active agents may comprise from 0.2% (w/w) to 5% (w/w) of the tablet.

Tablets may further contain lubricants such as magnesium stearate, calcium stearate, zinc stearate, sodium stearyl fumarate, and mixtures of magnesium stearate with sodium lauryl sulphate. Lubricants generally comprise from 0.25% (w/w) to 10% (w/w), from 0.5% (w/w) to 3% (w/w) of the tablet.

In addition to the hydroxylated psilocybin derivative, tablets may contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1% (w/w) to 25% (w/w) or from 5% (w/w) to 20% (w/w) of the dosage form.

Other possible auxiliary ingredients include anti-oxidants, colourants, flavouring agents, preservatives and taste-masking agents.

For tablet dosage forms, depending on the desired effective amount of the chemical compound, the chemical compound of the present disclosure may make up from 1% (w/w) to 80% (w/w) of the dosage form, more typically from 5% (w/w) to 60% (w/w) of the dosage form.

Exemplary tablets contain up to about 80% (w/w) of the chemical compound, from about 10% (w/w) to about 90% (w/w) binder, from about 0% (w/w) to about 85% (w/w) diluent, from about 2% (w/w) to about 10% (w/w) disintegrant, and from about 0.25% (w/w) to about 10% (w/w) lubricant.

The formulation of tablets is discussed in "Pharmaceutical Dosage Forms: Tablets", Vol. 1-Vol. 3, by CRC Press (2008).

The pharmaceutical and recreational drug formulations comprising the hydroxylated psilocybin derivatives of the present disclosure may also be administered directly into the blood stream, into muscle, or into an internal organ. Thus, the pharmaceutical and recreational drug formulations can be administered parenterally (for example, by subcutaneous, intravenous, intraarterial, intrathecal, intraventricular, intracranial, intramuscular, or intraperitoneal injection). Parenteral formulations are typically aqueous solutions which may contain excipients such as salts, carbohydrates and buffering agents (in one embodiment, to a pH of from 3 to 9), but, for some applications, they may be more suitably formulated as a sterile non-aqueous solution or as a dried form to be used in conjunction with a suitable vehicle such as sterile water.

Formulations comprising the hydroxylated psilocybin derivatives of the present disclosure for parenteral administration may be formulated to be immediate and/or modified release. Modified release formulations include delayed-, sustained-, pulsed-, controlled-, targeted and programmed release. Thus the chemical compounds of the disclosure may be formulated as a solid, semi-solid, or thixotropic liquid for administration as an implanted depot providing modified release of the active compound. Examples of such formulations include drug-coated stents and poly(dl-lactic-coglycolic)acid (PGLA) microspheres.

The pharmaceutical or recreational drug formulations of the present disclosure also may be administered topically to the skin or mucosa, i.e. dermally or transdermally. Example pharmaceutical and recreational drug formulations for this purpose include gels, hydrogels, lotions, solutions, creams, ointments, dusting powders, cosmetics, oils, eye drops, dressings, foams, films, skin patches, wafers, implants, sponges, fibres, bandages and microemulsions. Liposomes may also be used. Example carriers include alcohol, water, mineral oil, liquid petrolatum, white petrolatum, glycerin, polyethylene glycol and propylene glycol. Penetration enhancers may be incorporate (see: for example, Finnin, B. and Morgan, T. M., 1999 J. Pharm. Sci, 88 (10), 955-958).

Other means of topical administration include delivery by electroporation, iontophoresis, phonophoresis, sonophoresis and microneedle or needle-free (e.g., Powderject™, Bioject™, etc.) injection.

Pharmaceutical and recreational drug formulations for inhalation or insufflation include solutions and suspensions in pharmaceutically acceptable, aqueous or organic solvents, or mixtures thereof, and powders. The liquid or solid pharmaceutical compositions can contain suitable pharmaceutically acceptable excipients. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

In further embodiments, in which the hydroxylated psilocybin compounds of present disclosure are used as a recreational drug, the compounds may be included in compositions such as a food or food product, a beverage, a food seasoning, a personal care product, such as a cosmetic, perfume or bath oil, or oils (both for topical administration as massage oil, or to be burned or aerosolized). The chemical compounds of the present disclosure may also be included in a "vape" product, which may also include other drugs, such as nicotine, and flavorings.

The pharmaceutical formulations comprising the chemical compounds of the present disclosure may be used to treat a subject, and in particular to treat a psychiatric disorder in a subject. Accordingly, the present disclosure includes in a further embodiment, a method for treating a psychiatric disorder, the method comprising administering to a subject in need thereof a pharmaceutical formulation comprising a chemical compound or salt thereof having formula (I):

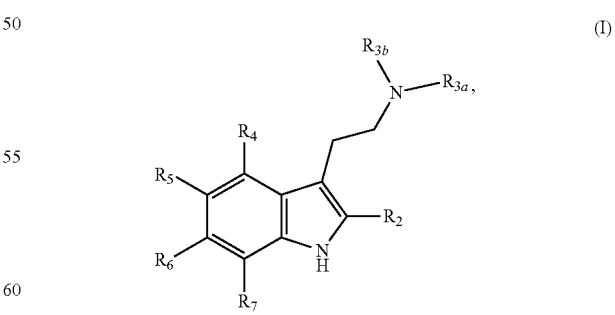

wherein at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a hydrogen atom, an alkyl group or a phosphate group, and wherein $R_{3A}$ and $R_{3B}$ are a hydrogen atom, an alkyl group, a cycloalkyl group, an alkaryl group, an aryl group, or an acyl group, together with a diluent, carrier or excipient.

Psychiatric disorders that may be treated include, for example, neurodevelopmental disorders such as intellectual disability, global development delay, communication disorders, autism spectrum disorder, and attention-deficit hyperactivity disorder (ADHD); bipolar and related disorders, such as mania, and depressive episodes; anxiety disorder, such as generalized anxiety disorder (GAD), agoraphobia, social anxiety disorder, specific phobias (natural events, medical, animal, situational, for example), panic disorder, and separation anxiety disorder; stress disorders, such as acute stress disorder, adjustment disorders, post-traumatic stress disorder (PTSD), and reactive attachment disorder; dissociative disorders, such as dissociative amnesia, dissociative identity disorder, and depersonalization/derealization disorder; somatoform disorders, such as somatic symptom disorders, illness anxiety disorder, conversion disorder, and factitious disorder; eating disorders, such as anorexia nervosa, bulimia nervosa, rumination disorder, pica, and binge-eating disorder; sleep disorders, such as narcolepsy, insomnia disorder, hypersomnolence, breathing-related sleep disorders, parasomnias, and restless legs syndrome; disruptive disorders, such as kleptomania, pyromania, intermittent explosive disorder, conduct disorder, and oppositional defiant disorder; depressive disorders, such as disruptive mood dysregulation disorder, major depressive disorder, persistent depressive disorder (dysthymia), premenstrual dysphoric disorder, substance/medication-induced depressive disorder, postpartum depression, and depressive disorder caused by another medical condition, for example, psychiatric and existential distress within life-threatening cancer situations (ACS Pharmacol. Transl. Sci. 4: 553-562; J Psychiatr Res 137: 273-282); substance-related disorders, such as alcohol-related disorders, cannabis related disorders, inhalant-use related disorders, stimulant use disorders, and tobacco use disorders; neurocognitive disorders, such as delirium; schizophrenia; compulsive disorders, such as obsessive compulsive disorders (OCD), body dysmorphic disorder, hoarding disorder, trichotillomania disorder, excoriation disorder, substance/medication induced obsessive-compulsive disorder, and obsessive-compulsive disorder related to another medical condition; and personality disorders, such as antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder.

In an aspect, the compounds of the present disclosure may be used to be contacted with a 5-$HT_{2A}$ receptor to thereby modulate the 5-$HT_{2A}$ receptor. Such contacting includes bringing a compound of the present disclosure and 5-$HT_{2A}$ receptor together under in vitro conditions, for example, by introducing the compounds in a sample containing a 5-$HT_{2A}$ receptor, for example, a sample containing purified 5-$HT_{2A}$ receptors, or a sample containing cells comprising 5-$HT_{2A}$ receptors. In vitro conditions further include the conditions described in Example 3 hereof. Contacting further includes bringing a compound of the present disclosure and 5-$HT_{2A}$ receptor together under in vivo conditions. Such in vivo conditions include the administration to an animal or human subject, for example, of a pharmaceutically effective amount of the compound of the present disclosure, when the compound is formulated together with a pharmaceutically active carrier, diluent or excipient, as hereinbefore described, to thereby treat the subject. Upon having contacted the 5-$HT_{2A}$ receptor, the compound may activate the 5-$HT_{2A}$ receptor or inhibit the 5-$HT_{2A}$ receptor.

Thus, in a further aspect, the condition that may be treated in accordance herewith can be any 5-$HT_{2A}$ receptor mediated disorder. Such disorders include, but are not limited to schizophrenia, psychotic disorder, attention deficit hyperactivity disorder, autism, and bipolar disorder.

The chemical compounds of the present disclosure may also be used as a feedstock material for other psilocybin derivatives. Thus in one embodiment, the chemical compounds of the present disclosure may be in used manufacture of a pharmaceutical or recreational drug formulation, wherein the manufacture may comprise derivatizing a chemical compound having the formula

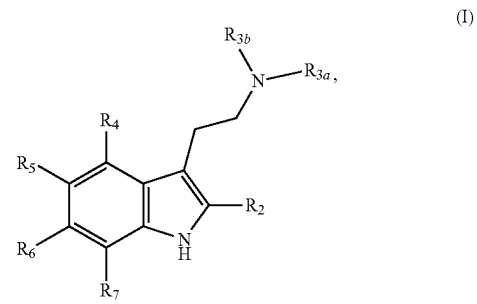

(I)

wherein, at least one of $R_2$, $R_4$, $R_5$, $R_6$ or $R_7$ is a hydroxy group, wherein each non-hydroxylated $R_2$, $R_5$, $R_6$, or $R_7$ is a hydrogen atom, wherein $R_4$ when it is not hydroxylated is a phosphate group, a hydrogen atom or an alkyl group or O-alkyl group, and wherein $R_{3A}$ and $R_{3B}$ are a hydrogen atom, an alkyl group, a cycloalkyl group, an alkaryl group, an aryl group, or an acyl group, or a salt of the chemical compound.

In order to use the compound having formula (I) as a feedstock, one or more hydroxy groups may be replaced by any atoms or groups, for example hydrocarbon groups. Those of skill in the art will be generally familiar with methods that may be used to substitute hydroxy groups. In this respect, guidance may be found in Schnepel C. et al. (2017) Chem. Eur. J. 23:12064-12086; Durak L. J. et al. (2016) ACS Catal. 6: 1451; Runguphan W. et al. (2013) Org Lett 15: 2850; Corr M. J. et al. (2017) Chem. Sci. 8: 2039; and Roy A. D. et al. Chem. Comm. 4831.

Turning now to methods of making the hydroxylated psilocybin derivatives, it is noted that the psilocybin compounds of the present disclosure may be prepared in any suitable manner, including any organic chemical synthesis methods, biosynthetic methods, or a combination thereof. Synthesis generally may involve selecting a psilocybin precursor compound, and modifying the psilocybin precursor compound to form a hydroxylated psilocybin derivative. In this respect, it is noted that a non-hydroxylated psilocybin derivative may be selected and modified to form psilocybin, which subsequently may be hydroxylated, or, alternatively, a hydroxylated psilocybin derivative may be selected to subsequently form a hydroxylated psilocybin derivative. Suitable psilocybin precursor compounds include compounds comprising an indole prototype structure (see: FIG. 2), including, for example tryptophan, tryptamine, 4-hydroxyindole, 4-hydroxytryptophan, 4-hydroxytryptamine, norbaeocystin and baeocystin, and hydroxylated forms thereof, notably, with respect to the indole prototype structure, 2-, 4-, 5-, 6-, 7-hydroxylated forms thereof. The hydroxy-derivative psilocybin precursor compounds may be provided in a more or less chemically pure form, for example, in the form of a psilocybin precursor preparation having a purity of at least about 95%, at least about 96%, at least about 97%, at least about 98%, at least about 99%, or at least 99.9%. The psilocybin precursor compounds may be chemically synthesized, or obtained from a fine chemical manufacturer.

In one embodiment of the present disclosure the hydroxylated psilocybin derivatives may be formed biosynthetically. Accordingly, the present disclosure further includes in one embodiment, a method of making a hydroxylated psilocybin derivative the method comprising:
(a) contacting a psilocybin precursor compound with a host cell comprising a psilocybin biosynthetic enzyme complement; and
(b) growing the host cell to produce a hydroxylated psilocybin derivative compound having the formula (I):

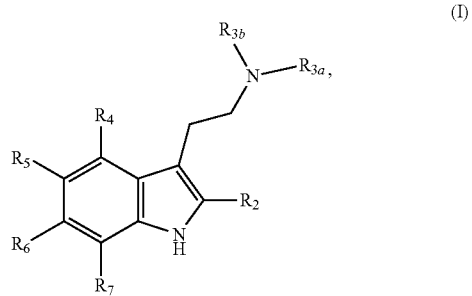

wherein, at least one of $R_2$, $R_4$, $R_5$, $R_6$, or $R_7$ is a hydroxy group, and wherein each non-hydroxylated $R_2$, $R_5$, $R_6$, or $R_7$ is a hydrogen atom or an alkyl group or O-alkyl group, wherein $R_4$ when it is not hydroxylated is a phosphate group, a hydrogen atom or an alkyl group or O-alkyl group, and wherein $R_{3A}$ and $R_{3B}$ are a hydrogen atom, an alkyl group, a cycloalkyl group, an alkaryl group, an aryl group, or an acyl group.

Implementation of the foregoing example embodiment initially involves providing psilocybin precursor compounds and host cells having a psilocybin biosynthetic enzyme complement. Accordingly, next, exemplary psilocybin precursor compounds and example host cells that may be selected and used in accordance with the present disclosure will be described. Thereafter, example methodologies and techniques will be described to contact and use the psilocybin precursor compounds and cells to produce example hydroxylated psilocybin compounds.

In some embodiments, hydroxy-derivative psilocybin precursor compounds may be selected, prepared and used, i.e. psilocybin precursor compounds possessing or derivatized to possess one or more hydroxy groups, including a hydroxylated tryptophan, e.g. $C_2$, $C_4$, $C_5$, $C_6$, and/or $C_7$ hydroxylated tryptophan, a hydroxylated indole, e.g. $C_2$, $C_4$, $C_5$, $C_6$, and/or $C_7$ hydroxylated indole, or a hydroxylated tryptamine e.g. $C_2$, $C_4$, $C_5$, $C_6$, and/or $C_7$ hydroxylated tryptamine, and further includes alkyl or O-alkyl derivatives thereof e.g. $C_2$, $C_4$, $C_5$, $C_6$, and/or $C_7$ methyl, ethyl, propyl, O-methyl, O-ethyl, O-propyl hydroxylated tryptophan derivatives, hydroxylated indole derivatives and hydroxylated tryptamine derivatives. Hydroxy-derivative psilocybin precursor compounds that may be used in accordance herewith further include 2-hydroxy-indole, 2-hydroxy-tryptophan, 2-hydroxy-tryptamine, 4-hydroxy-indole, 4-hydroxy-tryptophan, 4-hydroxy-tryptamine, 5-hydroxy-indole, 5-hydroxy-tryptophan, 5-hydroxy-tryptamine, 6-hydroxy-indole, 6-hydroxy-tryptophan, 6-hydroxy-tryptamine, 7-hydroxy-indole, 7-hydroxy-tryptophan, 7-hydroxy-tryptamine, 2-hydroxy-5-methyl-indole, 4-hydroxy-5-methyl-indole, 6-hydroxy-5-methyl-indole and 4-hydroxy-7-methyl-indole, 2-hydroxy-5-O-methyl-indole, 4-hydroxy-5-O-methyl-indole, 6-hydroxy-5-O-methyl-indole and 4-hydroxy-7-O-methyl-indole, 2-hydroxy-5-ethyl-indole, 4-hydroxy-5-ethyl-indole, 6-hydroxy-5-ethyl-indole and 4-hydroxy-7-ethyl-indole, 2-hydroxy-5-O-ethyl-indole, 4-hydroxy-5-O-ethyl-indole, 6-hydroxy-5-O-ethyl-indole and 4-hydroxy-7-O-ethyl-indole.

In some embodiments, non-hydroxy-derivative psilocybin precursor compounds may be selected, prepared and used, i.e. any one of the psilocybin precursor compounds selected from tryptophan, tryptamine, and indole, and alkyl or O-alkyl derivatives thereof (e.g. $C_2$, $C_4$, $C_5$, $C_6$, or $C_7$ methyl, ethyl, propyl, O-methyl, O-ethyl, O-propyl derivatives). Further non-hydroxy-derivative psilocybin precursor compounds include 2-methyl-indole, 4-methyl-indole, 5-methyl-indole, 6-methyl indole, 7-methyl indole, 2-ethyl-indole, 4-ethyl-indole, 5-ethyl-indole, 6-ethyl indole, 7-ethyl indole, 2-methyl-tryptophan, 4-methyl-tryptophan, 5-methyl-tryptophan, 6-methyl tryptophan, 7-methyl tryptophan, 2-ethyl-tryptophan, 4-ethyl-tryptophan, 5-ethyl-tryptophan, 6-ethyl-tryptophan, 7-ethyl-tryptophan, 2-methyl-tryptamine, 4-methyl-tryptamine, 5-methyl-tryptamine, 6-methyl tryptamine, 7-methyl tryptamine, 2-ethyl-tryptamine 4-ethyl-tryptamine, 5-ethyl-tryptamine, 6-ethyl-tryptamine, 7-ethyl-tryptamine Turning now to the host cells that can be used in accordance with the present disclosure, it is initially noted that a variety of host cells may be selected in accordance with the present disclosure, including microorganism host cells, plant host cells, and animal host cells.

In accordance herewith the host cell includes a psilocybin biosynthetic enzyme complement. Such cells can be obtained in at least two ways. First, in some embodiments, host cells may be selected in which a psilocybin biosynthetic enzyme complement is naturally present. Generally cells naturally producing psilocybin for example, cells of fungal species belonging to the genus *Psilocybe*, are suitable in this respect. Second, in some embodiments, a host cell that not naturally produces psilocybin may be modulated to produce a psilocybin biosynthetic enzyme complement. Thus, for example, a nucleic acid sequence encoding a psilocybin biosynthetic enzyme complement may be introduced into a host cell, and upon cell growth the host cells can make the psilocybin biosynthetic enzyme complement.

Typically a nucleic acid sequence encoding one or more enzymes constituting a psilocybin biosynthetic enzyme complement further includes one or more additional nucleic acid sequences, for example, a nucleic acid sequences controlling expression of the one or more enzymes, and these one or more additional nucleic acid sequences together with the nucleic acid sequence encoding the one or more enzymes can be said to form a chimeric nucleic acid sequence.

A host cell which upon cultivation expresses the chimeric nucleic acid can be selected and used in accordance with the present disclosure. Suitable host cells in this respect include, for example, microbial cells, such as bacterial cells, yeast cells, for example, and algal cells or plant cells. A variety of techniques and methodologies to manipulate host cells to introduce nucleic acid sequences in cells and attain expression exists and are well known to the skilled artisan. These methods include, for example, cation based methods, for example, lithium ion or calcium ion based methods, electroporation, biolistics, and glass beads based methods. As will be known to those of skill in the art, depending on the host cell selected, the methodology to introduce nucleic acid material in the host cell may vary, and, furthermore, methodologies may be optimized for uptake of nucleic acid material by the host cell, for example, by comparing uptake of nucleic acid material using different conditions. Detailed guidance can be found, for example, in Sambrook et al., Molecular Cloning, a Laboratory Manual, Cold Spring Harbor Laboratory Press, 2012, Fourth Ed. It is noted that the chimeric nucleic acid is a non-naturally occurring chimeric nucleic acid sequence and can be said to be heterologous to the host cell.

In some embodiments, the one or more enzymes constituting a psilocybin enzyme complement can be selected from by a nucleic acid sequence selected from the nucleic acid sequences consisting of:
 (a) SEQ. ID NO: 1, SEQ. ID NO: 3, SEQ. ID NO: 5, SEQ. ID NO: 7, SEQ. ID NO: 9, SEQ. ID NO 11, SEQ. ID NO: 13, SEQ. ID NO: 15, SEQ. ID NO: 17, SEQ. ID NO: 19, SEQ. ID NO: 24, SEQ. ID NO: 26, SEQ. ID NO: 31, SEQ. ID NO: 38 and SEQ. ID NO: 42;
 (b) a nucleic acid sequence that is substantially identical to any one of the nucleic acid sequences of (a);
 (c) a nucleic acid sequence that is substantially identical to any one of the nucleic acid sequences of (a) but for the degeneration of the genetic code;
 (d) a nucleic acid sequence that is complementary to any one of the nucleic acid sequences of (a);
 (e) a nucleic acid sequence encoding a polypeptide having any one of the amino acid sequences set forth in SEQ. ID NO: 2, SEQ. ID NO: 4, SEQ. ID NO: 6, SEQ. ID NO: 8, SEQ. ID NO: 10, SEQ. ID NO 12, SEQ. ID NO: 14, SEQ. ID NO: 16, SEQ. ID NO: 18, SEQ. ID NO: 20, SEQ. ID NO: 25, SEQ. ID NO: 27, SEQ. ID NO: 32, SEQ. ID NO: 39 and SEQ. ID NO: 43;
 (f) a nucleic acid sequence that encodes a functional variant of any one of the amino acid sequences set forth in SEQ. ID NO: 2, SEQ. ID NO: 4, SEQ. ID NO: 6, SEQ. ID NO: 8, SEQ. ID NO: 10, SEQ. ID NO 12, SEQ. ID NO: 14, SEQ. ID NO: 16, SEQ. ID NO: 18, SEQ. ID NO: 20, SEQ. ID NO: 25, SEQ. ID NO: 27, SEQ. ID NO: 32, SEQ. ID NO: 39 and SEQ. ID NO: 43; and
 (g) a nucleic acid sequence that hybridizes under stringent conditions to any one of the nucleic acid sequences set forth in (a), (b), (c), (d), (e) or (f).

Thus any of the nucleic acid sequences set forth in (a), (b), (c), (d), (e), (f) or (g) may be selected and introduced into a host cell. In general, however the nucleic acid sequence is selected in conjunction with the selected psilocybin precursor compound, as hereinafter further discussed in reference with FIG. 7.

One example host cell that conveniently may be used is *Escherichia coli*. The preparation of the *E. coli* vectors may be accomplished using commonly known techniques such as restriction digestion, ligation, gel electrophoresis, DNA sequencing, the polymerase chain reaction (PCR) and other methodologies. A wide variety of cloning vectors is available to perform the necessary steps required to prepare a recombinant expression vector. Among the vectors with a replication system functional in *E. coli*, are vectors such as pBR322, the pUC series of vectors, the M13 mp series of vectors, pBluescript etc. Suitable promoter sequences for use in *E. coli* include, for example, the T7 promoter, the T5 promoter, tryptophan (trp) promoter, lactose (lac) promoter, tryptophan/lactose (tac) promoter, lipoprotein (lpp) promoter, and λ phage PL promoter. Typically, cloning vectors contain a marker, for example, an antibiotic resistance marker, such as ampicillin or kanamycin resistance marker, allowing selection of transformed cells. Nucleic acid sequences may be introduced in these vectors, and the vectors may be introduced in *E. coli* by preparing competent cells, electroporation or using other well known methodologies to a person of skill in the art. *E. coli* may be grown in an appropriate medium, such as Luria-Broth medium and harvested. Recombinant expression vectors may readily be recovered from cells upon harvesting and lysing of the cells.

Another example host cell that may be conveniently used is a yeast cell. Example yeast host cells that can be used are yeast cells belonging to the genus *Candida, Kluyveromyces, Saccharomyces, Schizosaccharomyces, Pichia, Hansenula*, and *Yarrowia*. In specific example embodiments, the yeast cell can be a *Saccharomyces cerevisiae* cell, a *Yarrowia lipolytica* cell, or *Pichia pastoris* cell.

A number of vectors exist for the expression of recombinant proteins in yeast host cells. Examples of vectors that may be used in yeast host cells include, for example, Yip type vectors, YEp type vectors, YRp type vectors, YCp type vectors, pGPD-2, pAO815, pGAPZ, pGAPZα, pHIL-D2, pHIL-S1, pPIC3.5K, pPIC9K, pPICZ, pPICZα, pPIC3K, pHWO10, pPUZZLE and 2 μm plasmids. Such vectors are known to the art and are, for example, described in Cregg et al., Mol Biotechnol. (2000) 16(1): 23-52. Suitable promoter sequences for use in yeast host cells are also known and described, for example, in Mattanovich et al., Methods Mol. Biol., 2012, 824:329-58, and in Romanos et al.; 1992, Yeast 8: 423-488. Examples of suitable promoters for use in yeast host cells include promoters of glycolytic enzymes, like triosephosphate isomerase (TPI), phosphoglycerate kinase (PGK), glyceraldehyde-3-phosphate dehydrogenase (GAPDH or GAP) and variants thereof, lactase (LAC) and galactosidase (GAL), *P. pastoris* glucose-6-phosphate isomerase promoter (PPG), the 3-phosphoglycerate kinase promoter (PPGK), the glycerol aldehyde phosphate dehydrogenase promoter (PGAP), translation elongation factor promoter (PTEF), *S. cerevisiae* enolase (ENO-1), *S. cerevisiae* galactokinase (GAD), *S. cerevisiae* alcohol dehydrogenase/glyceraldehyde-3-phosphate dehydrogenase (ADH1, ADH2/GAP), *S. cerevisiae* triose phosphate isomerase (TPI), *S. cerevisiae* metallothionein (CUP1), and *S. cerevisiae* 3-phosphoglycerate kinase (PGK), and the maltase gene promoter (MAL). Marker genes suitable for use in yeast host cells are also known to the art. Thus, antibiotic resistance markers, such as ampicillin resistance markers, can be used in yeast, as well as marker genes providing genetic functions for essential nutrients, for example, leucine (LEU2), tryptophan (TRP1 and TRP2), uracil (URA3, URA5, URA6), histidine (HIS3), and the like. Methods for introducing vectors into yeast host cells can, for example, be found in S. Kawai et al., 2010, Bioeng. Bugs 1(6): 395-403.

Further, guidance with respect to the preparation of expression vectors and introduction thereof into host cells, including in *E. coli* cells, yeast cells, and other host cells, may be found in, for example: Sambrook et al., Molecular Cloning, a Laboratory Manual, Cold Spring Harbor Laboratory Press, 2012, Fourth Ed.

Thus, to briefly recap, a host cell comprising a chimeric nucleic acid comprising (i) a nucleic acid sequence controlling expression in a host cell and (ii) a nucleic acid sequence encoding a psilocybin biosynthetic enzyme complement, can be prepared in accordance with the present disclosure.

In accordance herewith, host cells are grown to multiply and to express a chimeric nucleic acid. Expression of the chimeric nucleic acid results in the biosynthetic production in the host cell of a psilocybin biosynthetic enzyme complement. Growth media and growth conditions can vary depending on the host cell that is selected, as will be readily appreciated to those of ordinary skill in the art. Growth media typically contain a carbon source, one or several nitrogen sources, essential salts including salts of potassium, sodium, magnesium, phosphate and sulphate, trace metals, water soluble vitamins, and process aids including but not limited to antifoam agents, protease inhibitors, stabilizers, ligands and inducers. Example carbon sources are e.g. mono- or disaccharides. Example nitrogen sources are, e.g. ammonia, urea, amino acids, yeast extract, corn steep liquor and fully or partially hydrolyzed proteins. Example trace metals are e.g. Fe, Zn, Mn, Cu, Mo and $H_3BO_3$. Example water soluble vitamins are e.g. biotin, pantothenate, niacin, thiamine, p-aminobenzoic add, choline, pyridoxine, folic; add, riboflavin and ascorbic acid. Further, specific example media include liquid culture media for the growth of yeast cells and bacterial cells including, Luria-Bertani (LB) broth for bacterial cell cultivation, and yeast extract peptone dextrose (YEPD or YPD), for yeast cell cultivation. Further media and growth conditions can be found in Sambrook et al., Molecular Cloning, a Laboratory Manual, Cold Spring Harbor Laboratory Press, 2012, Fourth Ed.

In order for the host cells to produce the hydroxylated psilocybin or psilocin compounds, the cells are provided with a psilocybin precursor compound. Thus, in accordance herewith, host cells may be contacted with a psilocybin precursor compound. In some embodiments, a psilocybin precursor compound can be exogenously supplied, for example, by including a psilocybin precursor compound in the growth medium of the host cells, and growing the host cells in a medium including the psilocybin precursor compound.

Figure 7:
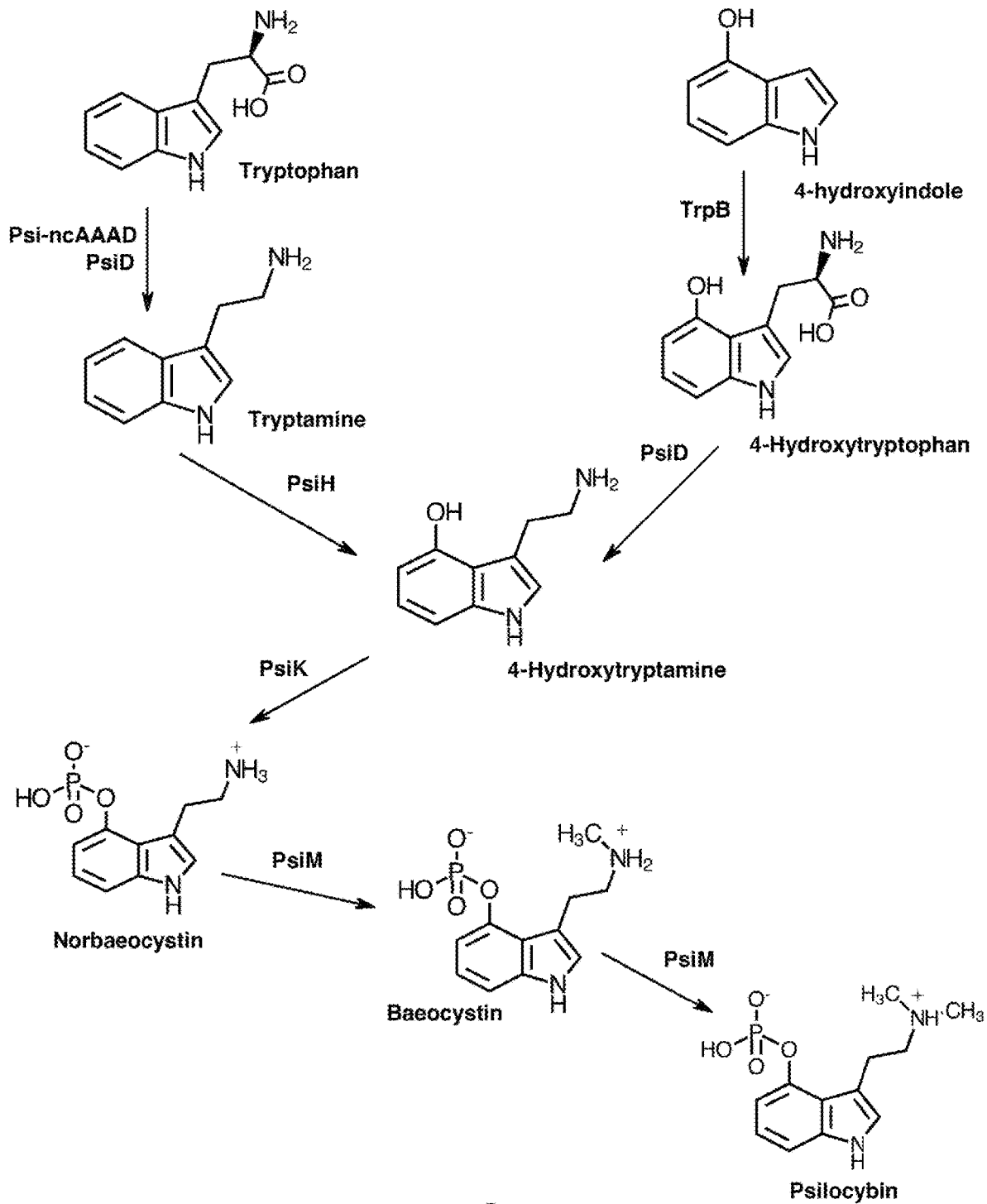
FIG. 7 depicts a biosynthesis pathway for the synthesis of psilocybin.

Referring next to FIG. 7, shown therein is an example natural biosynthetic pathway showing the conversion of example psilocybin precursor compounds to form psilocybin. Thus, as can be appreciated from FIG. 7, various psilocybin precursor compounds may be selected and prepared in hydroxylated and non-hydroxylated form, in conjunction with a psilocybin biosynthetic enzyme complement.

Thus, referring further to FIG. 7, by way of example, 4-hydroxy-5-methyl indole may be selected as hydroxy-derivative psilocybin precursor compound and contacted with a host cell comprising a psilocybin biosynthetic enzyme complement comprising (i) a nucleic acid sequence encoding TrpB selected from SEQ. ID NO: 11 and SEQ. ID NO: 26 or a sequence substantially identical thereto; (ii) a nucleic acid sequence encoding PsiD selected from SEQ. ID NO: 1, SEQ. ID NO: 9 and SEQ. ID NO: 31 or a sequence substantially identical thereto; and (iii) a nucleic acid sequence encoding an acetyl transferase having SEQ. ID NO: 24 or a sequence substantially identical thereto, and upon growth of the cells 4-hydroxy-5-methyl-tryptamine can be formed, which can further be acetylated by the acetyl transferase (not shown in FIG. 7) to form the hydroxylated psilocybin derivative compound having chemical formula (III):

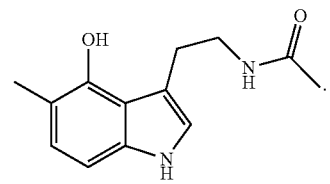

(III)

Thus, referring further to FIG. 7, by way of a further example, 4-hydroxy-7-methyl indole may be selected as hydroxy-derivative psilocybin precursor compound and contacted with a host cell comprising a psilocybin biosynthetic enzyme complement comprising (i) a nucleic acid sequence encoding TrpB selected from SEQ. ID NO: 11 and SEQ. ID NO: 26 or a sequence substantially identical thereto; (ii) a nucleic acid sequence encoding PsiD selected from SEQ. ID NO: 1, SEQ. ID NO: 9 and SEQ. ID NO: 31 or a sequence substantially identical thereto; and (iii) a nucleic acid sequence encoding an acetyl transferase having SEQ. ID NO: 24 or a sequence substantially identical thereto and upon growth of the cells 4-hydroxy-7-methyl-tryptamine can be formed, which can further be acetylated by the acetyl transferase (not shown in FIG. 7) to form the hydroxylated psilocybin derivative compound having chemical formula (IV):

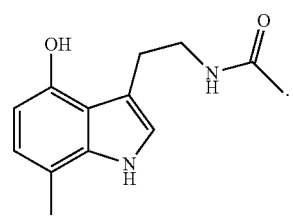

(IV)

It is noted that in some embodiments, the host cells may include a hydroxylase. In such embodiments, the cell may be contacted with a non-hydroxy-derivative psilocybin precursor compound, and hydroxylation may occur in vivo in the host cells. Thus, referring again to FIG. 7, by way of example, tryptophan, indole or tryptamine may be selected and contacted with a host cell including a hydroxylase, and upon growth of the host cells a hydroxylated psilocybin derivative compound can be formed.

Accordingly, in one embodiment the hydroxylase can be encoded by a nucleic acid selected from:
  (a) SEQ. ID NO: 13, SEQ. ID NO: 15, SEQ. ID NO: 17, SEQ. ID NO: 19, SEQ. ID NO: 38 or SEQ. ID NO: 42;
  (b) a nucleic acid sequence that is substantially identical to any one of the nucleic acid sequences of (a);
  (c) a nucleic acid sequence that is substantially identical to any one of the nucleic acid sequences of (a) but for the degeneration of the genetic code;
  (d) a nucleic acid sequence that is complementary to any one of the nucleic acid sequences of (a);
  (e) a nucleic acid sequence encoding a polypeptide having any one of the amino acid sequences set forth in SEQ. ID NO: 14, SEQ. ID NO: 16, SEQ. ID NO: 18, SEQ. ID NO: 20, SEQ. ID NO: 39 and SEQ. ID NO: 43;
  (f) a nucleic acid sequence that encodes a functional variant of any one of the amino acid sequences set forth in SEQ. ID NO: 14, SEQ. ID NO: 16, SEQ. ID NO: 18, SEQ. ID NO: 20, SEQ. ID NO: 39 and SEQ. ID NO: 43; and (g) a nucleic acid sequence that hybridizes under stringent conditions to any one of the nucleic acid sequences set forth in (a), (b), (c), (d), (e) or (f).

Thus, referring further to FIG. 7, by way of example, 7-ethyl-indole may be selected as a non-hydroxy-derivative psilocybin precursor compound and contacted with a host cell comprising a psilocybin biosynthetic enzyme complement comprising (i) a nucleic acid sequence encoding TrpB selected from SEQ. ID NO: 11 and SEQ. ID NO: 26 or a sequence substantially identical thereto; (ii) a nucleic acid sequence encoding PsiD selected from SEQ. ID NO: 1, SEQ. ID NO: 9 and SEQ. ID NO: 31 or a sequence substantially identical thereto; and (iii) a nucleic acid sequence encoding a hydroxylase selected from SEQ. ID NO: 14, SEQ. ID NO: 16, SEQ. ID NO: 18, SEQ. ID NO: 20, SEQ. ID NO: 39 and SEQ. ID NO: 43 or a sequence substantially identical thereto, and upon growth of the cells the hydroxylated psilocybin derivative compound having chemical formula (XXXII):

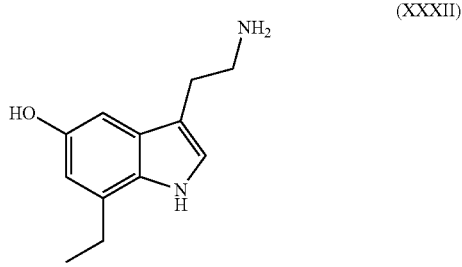

can be formed.

It will be clear to those of skill in the art that a significant variety of different hydroxy- and non-hydroxy-derivative psilocybin precursor compounds may be selected. FIG. 7 in this respect provides guidance and allows a person of skill in the art to select appropriate psilocybin precursor compounds and a matching a psilocybin biosynthetic enzyme complement.

Upon production by the host cells of the hydroxylated psilocybin compounds in accordance with the methods of the present disclosure, the hydroxylated psilocybin compounds may be extracted from the host cell suspension, and separated from other constituents within the host cell suspension, such as media constituents and cellular debris. Separation techniques will be known to those of skill in the art and include, for example, solvent extraction (e.g. butane, chloroform, ethanol), column chromatography based techniques, high-performance liquid chromatography (HPLC), for example, and/or countercurrent separation (CCS) based systems. The recovered hydroxylated psilocybin compounds may be obtained in a more or less pure form, for example, a preparation of hydroxylated psilocybin compounds of at least about 60% (w/v), about 70% (w/v), about 80% (w/v), about 90% (w/v), about 95% (w/v) or about 99% (w/v) purity may be obtained. Thus, in this manner, hydroxylated psilocybin derivatives in more or less pure form may be prepared.

In further embodiments, in accordance herewith hydroxylated psilocybin compounds may be chemically synthesized, using, for example, 4-benzyloxyindole as a starting compound. Example techniques for chemically synthesizing the hydroxylated psilocybin compounds of the present disclosure are further hereinafter described in Examples 4 to 14.

It will now be clear form the foregoing that novel hydroxylated psilocybin derivatives are disclosed herein. The hydroxylated psilocybin compounds may be formulated for use as a pharmaceutical drug or recreational drug. The hydroxylated psilocybin compounds may also be used as a feedstock to produce other psilocybin derivatives.

SUMMARY OF SEQUENCES

SEQ. ID NO: 1 sets forth a *Psilocybe cubensis* nucleic acid sequence encoding a PsiD polypeptide.

SEQ. ID NO: 2 sets forth a deduced amino acid sequence of a *Psilocybe cubensis* PsiD polypeptide.

SEQ. ID NO: 3 sets forth a *Psilocybe cubensis* nucleic acid sequence encoding a PsiH polypeptide.

SEQ. ID NO: 4 sets forth a deduced amino acid sequence of a *Psilocybe cubensis* PsiH polypeptide.

SEQ. ID NO: 5 sets forth a *Psilocybe cubensis* nucleic acid sequence encoding a PsiK polypeptide.

SEQ. ID NO: 6 sets forth a deduced amino acid sequence of a *Psilocybe cubensis* PsiK polypeptide.

SEQ. ID NO: 7 sets forth a *Psilocybe cubensis* nucleic acid sequence encoding a PsiM polypeptide.

SEQ. ID NO: 8 sets forth a deduced amino acid sequence of a *Psilocybe cubensis* PsiM polypeptide.

SEQ. ID NO: 9 sets forth a *Psilocybe cubensis* nucleic acid sequence encoding a Psi-ncAAAD polypeptide.

SEQ. ID NO: 10 sets forth a deduced amino acid sequence of a *Psilocybe cubensis* Psi-ncAAAD polypeptide.

SEQ. ID NO: 11 sets forth a *Psilocybe cubensis* nucleic acid sequence encoding a TrpB polypeptide.

SEQ. ID NO: 12 sets forth a deduced amino acid sequence of a *Psilocybe cubensis* TrpB polypeptide.

SEQ. ID NO: 13 sets forth an *Oryza sativa* nucleic acid sequence encoding tryptamine 5-hydroxylase polypeptide.

SEQ. ID NO: 14 sets forth a deduced amino acid sequence of an *Oryza sativa* tryptamine 5-hydroxylase polypeptide.

SEQ. ID NO: 15 sets forth a *Rattus norvegicus* nucleic acid sequence encoding tryptophan 5-hydroxylase polypeptide.

SEQ. ID NO: 16 sets forth a deduced amino acid sequence of a *Rattus norvegicus* tryptophan 5-hydroxylase polypeptide.

SEQ. ID NO: 17 sets forth an *Oryza sativa* nucleic acid sequence encoding melatonin 2-hydroxylase polypeptide.

SEQ. ID NO: 18 sets forth a deduced amino acid sequence of an *Oryza sativa* melatonin 2-hydroxylase polypeptide.

SEQ. ID NO: 19 sets forth an *Aspergillus nidulans* nucleic acid sequence encoding tryptamine N-acetyltryptophan 6-hydroxylase polypeptide.

SEQ. ID NO: 20 sets forth a deduced amino acid sequence of an *Aspergillus nidulans* N-acetyltryptophan 6-hydroxylase polypeptide.

SEQ. ID NO: 21 sets forth a nucleic acid sequence of pCDM4 vector.

SEQ. ID NO: 22 sets forth a nucleic acid sequence encoding a synthetic FLAG epitope tag polypeptide SEQ. ID NO: 23 sets forth a deduced amino acid sequence of a synthetic FLAG epitope tag polypeptide SEQ. ID NO: 24 sets forth a nucleic acid sequence encoding a *Streptomyces griseofuscus* PsmF N-acetyltransferase polypeptide.

SEQ. ID NO: 25 sets forth a deduced amino acid sequence of a *Streptomyces griseofuscus* PsmF N-acetyltransferase polypeptide.

SEQ. ID NO: 26 sets forth a nucleic acid sequence encoding a mutated *Thermotoga maritima* TmTrpB-2F3 tryptophan synthase subunit B polypeptide.

SEQ. ID NO: 27 sets forth a deduced amino acid sequence of a mutated *Thermotoga maritima* TmTrpB-2F3 tryptophan synthase subunit B polypeptide.

SEQ. ID NO: 28 sets forth a nucleic acid sequence encoding a synthetic V5 epitope tag polypeptide SEQ. ID NO: 29 sets forth a deduced amino acid sequence of a synthetic V5 epitope tag polypeptide SEQ. ID NO: 30 sets forth a nucleic acid sequence of pETM6-H10 vector SEQ. ID NO: 31 sets forth a nucleic acid sequence encoding a *Bacillus atrophaeus* BaTDC tryptophan decarboxylase polypeptide.

SEQ. ID NO: 32 sets forth a deduced amino acid sequence of a *Bacillus atrophaeus* BaTDC tryptophan decarboxylase polypeptide.

SEQ. ID NO: 33 sets forth a nucleic acid sequence encoding a synthetic HIS epitope tag polypeptide SEQ. ID NO: 34 sets forth a deduced amino acid sequence of a synthetic HIS epitope tag polypeptide SEQ. ID NO: 35 sets forth a nucleic acid sequence of pET28a(+) vector SEQ. ID NO: 36 sets forth a nucleic acid sequence encoding a synthetic c-MYC epitope tag polypeptide SEQ. ID NO: 37 sets forth a deduced amino acid sequence of a synthetic c-MYC epitope tag polypeptide SEQ. ID NO: 38 sets forth a nucleic acid sequence encoding an *Oryza sativa* OsCPR2 cytochrome P450 reductase-2 polypeptide, SEQ. ID NO: 39 sets forth a deduced amino acid sequence of an *Oryza sativa* OsCPR2 cytochrome P450 reductase-2 polypeptide.

SEQ. ID NO: 40 sets forth a nucleic acid sequence encoding a synthetic HA epitope tag polypeptide SEQ. ID NO: 41 sets forth a deduced amino acid sequence of a synthetic HA epitope tag polypeptide SEQ. ID NO: 42 sets forth a nucleic acid sequence encoding an N-terminal GST tagged *Oryza sativa* OsCYP71p cytochrome P450 polypeptide.

SEQ. ID NO: 43 sets forth deduced amino acid sequence of an N-terminal GST tagged *Oryza sativa* OsCYP71p cytochrome P450 polypeptide.

SEQ. ID NO: 44 sets forth a nucleic acid sequence of pCDFDuet-1 vector

SEQUENCE LISTING

```
SEQ. ID NO: 1
ATGCAGGTGATACCCGCGTGCAACTCGGCAGCAATAAGATCACTATGTCCTACTCCCGAGTCTTTTAGAAACATGGGATGG

CTCTCTGTCAGCGATGCGGTCTACAGCGAGTTCATAGGAGAGTTGGCTACCCGCGCTTCCAATCGAAATTACTCCAACGAG

TTCGGCCTCATGCAACCTATCCAGGAATTCAAGGCTTTCATTGAAAGCGACCCGGTGGTGCACCAAGAATTTATTGACATG

TTCGAGGGCATTCAGGACTCTCCAAGGAATTATCAGGAACTATGTAATATGTTCAACGATATCTTTCGCAAAGCTCCCGTC

TACGGAGACCTTGGCCCTCCCGTTTATATGATTATGGCCAAATTAATGAACACCCGAGCGGGCTTCTCTGCATTCACGAGA

CAAAGGTTGAACCTTCACTTCAAAAAACTTTTCGATACCTGGGGATTGTTCCTGTCTTCGAAAGATTCTCGAAATGTTCTT

GTGGCCGACCAGTTCGACGACAGACATTGCGGCTGGTTGAACGAGCGGGCCTTGTCTGCTATGGTTAAACATTACAATGGA

CGCGCATTTGATGAAGTCTTCCTCTGCGATAAAAATGCCCCATACTACGGCTTCAACTCTTACGACGACTTCTTTAATCGC

AGATTTCGAAACCGAGATATCGACCGACCTGTAGTCGGTGGAGTTAACAACACCACCCTCATTTCTGCTGCTTGCGAATCA

CTTTCCTACAACGTCTCTTATGACGTCCAGTCTCTCGACACTTTAGTTTTCAAAGGAGAGACTTATTCGCTTAAGCATTTG

CTGAATAATGACCCTTTCACCCCACAATTCGAGCATGGGAGTATTCTACAAGGATTCTTGAACGTCACCGCTTACCACCGA

TGGCACGCACCCGTCAATGGGACAATCGTCAAAATCATCAACGTTCCAGGTACCTACTTTGCGCAAGCCCCGAGCACGATT

GGCGACCCTATCCCGGATAACGATTACGACCCACCTCCTTACCTTAAGTCTCTTGTCTACTTCTCTAATATTGCCGCAAGG

CAAATTATGTTTATTGAAGCCGACAACAAGGAAATTGGCCTCATTTTCCTTGTGTTCATCGGCATGACCGAAATCTCGACA

TGTGAAGCCACGGTGTCCGAAGGTCAACACGTCAATCGTGGCGATGACTTGGGAATGTTCCATTTCGGTGGTTCTTCGTTC

GCGCTTGGTCTGAGGAAGGATTGCAGGGCAGAGATCGTTGAAAAGTTCACCGAACCCGGAACAGTGATCAGAATCAACGAA

GTCGTCGCTGCTCTAAAGGCTTAG

SEQ. ID NO: 2
MQVIPACNSAAIRSLCPTPESFRNMGWLSVSDAVYSEFIGELATRASNRNYSNEFGLMQPIQEFKAFIESDPVVHQEFIDM

FEGIQDSPRNYQELCNMFNDIFRKAPVYGDLGPPVYMIMAKLMNTRAGFSAFTRQRLNLHFKKLFDTWGLFLSSKDSRNVL

VADQFDDRHCGWLNERALSAMVKHYNGRAFDEVFLCDKNAPYYGFNSYDDFFNRRFRNRDIDRPVVGGVNNTTLISAACES

LSYNVSYDVQSLDTLVFKGETYSLKHLLNNDPFTPQFEHGSILQGFLNVTAYHRWHAPVNGTIVKIINVPGTYFAQAPSTI

GDPIPDNDYDPPPYLKSLVYFSNIAARQIMFIEADNKEIGLIFLVFIGMTEISTCEATVSEGQHVNRGDDLGMFHFGGSSF

ALGLRKDCRAEIVEKFTEPGTVIRINEWAALKA
```

SEQ. ID NO: 3

ATGATCGCTGTACTATTCTCCTTCGTCATTGCAGGATGCATATACTACATCGTTTCTCGTAGAGTGAGGCGGTCGCGCTTG
CCACCAGGGCCGCCTGGCATTCCTATTCCCTTCATTGGGAACATGTTTGATATGCCTGAAGAATCTCCATGGTTAACATTT
CTACAATGGGGACGGGATTACAGTCTGTCTTGCCGCGTTGACTTCTAATATATGAACAGCTAATATATTGTCAGACACCGA
TATTCTCTACGTGGATGCTGGAGGGACAGAAATGGTTATTCTTAACACGTTGGAGACCATTACCGATCTATTAGAAAAGCG
AGGGTCCATTTATTCTGGCCGGTGAGCTGATGTTGAGTTTTTTGCAATTGAATTTGTGGTCACACGTTTCCAGACTTGAGA
GTACAATGGTCAACGAACTTATGGGGTGGGAGTTTGACTTAGGGTTCATCACATACGGCGACAGGTGGCGCGAAGAAAGGC
GCATGTTCGCCAAGGAGTTCAGTGAGAAGGGCATCAAGCAATTTCGCCATGCTCAAGTGAAAGCTGCCCATCAGCTTGTCC
AACAGCTTACCAAAACGCCAGACCGCTGGGCACAACATATTCGCCAGTAAGTACTACTTGAGGAAAATAGCGTACGCTTCG
CTGACCGGTCCGTACATCAAAGTCAGATAGCGGCAATGTCACTGGATATTGGTTATGGAATTGATCTTGCAGAAGACGACC
CTTGGCTGGAAGCGACCCATTTGGCTAATGAAGGCCTCGCCATAGCATCAGTGCCGGGCAAATTTTGGGTCGATTCGTTCC
CTTCTCGTGAGCATCCTTCTTCTATGTAGGAAGGGAAGGAGTCTAACAAGTGTTAGTAAAATACCTTCCTGCTTGGTTCCC
AGGTGCTGTCTTCAAGCGCAAAGCGAAGGTCTGGCGAGAAGCCGCCGACCATATGGTTGACATGCCTTATGAAACTATGAG
GAAATTAGCAGTTAGTCAAATGCGTTCTCCCCGTATTTTTTCAATACTCTAACTTCAGCTCACAGCCTCAAGGATTGACTC
GTCCGTCGTATGCTTCAGCTCGTCTGCAAGCCATGGATCTCAACGGTGACCTTGAGCATCAAGAACACGTAATCAAGAACA
CAGCCGCAGAGGTTAATGTCGGTAAGTCAAAAGCGTCCGTCGGCAATTCAAAATTCAGGCGCTAAAGTGGGTCTTCTCACC
AAGGTGGAGGCGATACTGTAAGGATTTCTCAATCGTTAGAGTATAAGTGTTCTAATGCAGTACATACTCCACCAACCAGAC
TGTCTCTGCTATGTCTGCGTTCATCTTGGCCATGGTGAAGTACCCTGAGGTCCAGCGAAAGGTTCAAGCGGAGCTTGATGC
TCTGACCAATAACGGCCAAATTCCTGACTATGACGAAGAAGATGACTCCTTGCCATACCTCACCGCATGTATCAAGGAGCT
TTTCCGGTGGAATCAAATCGCACCCCTCGCTATACCGCACAAATTAATGAAGGACGACGTGTACCGCGGGTATCTGATTCC
CAAGAACACTCTAGTCTTCGCAAACACCTGGTGAGGCTGTCCATTCATTCCTAGTACATCCGTTGCCCCACTAATAGCATC
TTGATAACAGGGCAGTATTAAACGATCCAGAAGTCTATCCAGATCCCTCTGTGTTCCGCCCAGAAAGATATCTTGGTCCTG
ACGGGAAGCCTGATAACACTGTACGCGACCCACGTAAAGCGGCATTTGGCTATGGACGACGAAATTGGTAAGTGCGCTTTC
AGAACCCCCCCTTCCGTTGACTAGTGCCATGCGCGCATACAATATCGCTATTGATCTGATATAACTTCCCTGCGGCATTTA
TTTTGGCATTCCTTTAGTCCCGGAATTCATCTAGCGCAGTCGACGGTTTGGATTGCAGGGGCAACCCTCTTATCAGCGTTC
AATATCGAGCGACCTGTCGATCAGAATGGGAAGCCCATTGACATACCGGCTGATTTTACTACAGGATTCTTCAGGTAGCTA
ATTTCCGTCTTTGTGTGCATAATACCCCTAACGACGCACGTTTACCTTTTTGTAAAGACACCCAGTGCCTTTCCAGTGCAG
GTTTGTTCCTCGAACAGAGCAAGTCTCACAGTCGGTATCCGGACCCTGA

SEQ. ID NO: 4

MIAVLFSFVIAGCIYYIVSRRVRRSRLPPGPPGIPIPFIGNMFDMPEESPWLTFLQWGRDYNTDILYVDAGGTEMVILNTL
ETITDLLEKRGSIYSGRLESTMVNELMGWEFDLGFITYGDRWREERRMFAKEFSEKGIKQFRHAQVKAAHQLVQQLTKTPD
RWAQHIRHQIAAMSLDIGYGIDLAEDDPWLEATHLANEGLAIASVPGKFWVDSFPSLKYLPAWFPGAVFKRKAKVWREAAD
HMVDMPYETMRKLAPQGLTRPSYASARLQAMDLNGDLEHQEHVIKNTAAEVNVGGGDTTVSAMSAFILAMVKYPEVQRKVQ
AELDALTNNGQIPDYDEEDDSLPYLTACIKELFRWNQIAPLAIPHKLMKDDVYRGYLIPKNTLVFANTWAVLNDPEVYPDP
SVFRPERYLGPDGKPDNTVRDPRKAAFGYGRRNCPGIHLAQSTVWIAGATLLSAFNIERPVDQNGKPIDIPADFTTGFFRH
PVPFQCRFVPRTEQVSQSVSGP

SEQ. ID NO: 5

ATGGCGTTCGATCTCAAGACTGAAGACGGCCTCATCACATATCTCACTAAACATCTTTCTTTGGACGTCGACACGAGCGGA
GTGAAGCGCCTTAGCGGAGGCTTTGTCAATGTAACCTGGCGCATTAAGCTCAATGCTCCTTATCAAGGTCATACGAGCATC
ATCCTGAAGCATGCTCAGCCGCACATGTCTACGGATGAGGATTTTAAGATAGGTGTAGAACGTTCGGTTTACGAATACCAG
GCTATCAAGCTCATGATGGCCAATCGGAGGTTCTGGGAGGCGTGGATGGCATAGTTTCTGTGCCAGAAGGCCTGAACTAC
GACTTAGAGAATAATGCATTGATCATGCAAGATGTCGGGAAGATGAAGACCCTTTTAGATTATGTCACCGCCAAACCGCCA

-continued

```
CTTGCGACGGATATAGCCCGCCTTGTTGGGACAGAAATTGGGGGGTTCGTTGCCAGACTCCATAACATAGGCCGCGAGAGG

CGAGACGATCCTGAGTTCAAATTCTTCTCTGGAAATATTGTCGGAAGGACGACTTCAGACCAGCTGTATCAAACCATCATA

CCCAACGCAGCGAAATATGGCGTCGATGACCCCTTGCTGCCTACTGTGGTTAAGGACCTTGTGGACGATGTCATGCACAGC

GAAGAGACCCTTGTCATGGCGGACCTGTGGAGTGGAAATATTCTTCTCCAGTTGGAGGAGGGAAACCCATCGAAGCTGCAG

AAGATATATATCCTGGATTGGGAACTTTGCAAGTACGGCCCAGCGTCGTTGGACCTGGGCTATTTCTTGGGTGACTGCTAT

TTGATATCCCGCTTTCAAGACGAGCAGGTCGGTACGACGATGCGGCAAGCCTACTTGCAAAGCTATGCGCGTACGAGCAAG

CATTCGATCAACTACGCCAAAGTCACTGCAGGTATTGCTGCTCATATTGTGATGTGGACCGACTTTATGCAGTGGGGAGC

GAGGAAGAAAGGATAAATTTTGTGAAAAAGGGGGTAGCTGCCTTTCACGACGCCAGGGGCAACAACGACAATGGGGAAATT

ACGTCTACCTTACTGAAGGAATCATCCACTGCGTAA
```

SEQ. ID NO: 6

```
MHIRNPYRTPIDYQALSEAFPPLKPFVSVNADGTSSVDLTIPEAQRAFTAALLHRDFGLTMTIPEDRLCPTVPNRLNYVLW

IEDIFNYTNKTLGLSDDRPIKGVDIGTGASAIYPMLACARFKAWSMVGTEVERKCIDTARLNVVANNLQDRLSILETSIDG

PILVPIFEATEEYEYEFTMCNPPFYDGAADMQTSDAAKGFGFGVGAPHSGTVIEMSTEGGESAFVAQMVRESLKLRTRCRW

YTSNLGKLKSLKEIVGLLKELEISNYAINEYVQGSTRRYAVAWSFTDIQLPEELSRPSNPELSSLF
```

SEQ. ID NO: 7

```
ATGCATATCAGAAATCCTTACCGTACACCAATTGACTATCAAGCACTTTCAGAGGCCTTCCCTCCCCTCAAGCCATTTGTG

TCTGTCAATGCAGATGGTACCAGTTCTGTTGACCTCACTATCCCAGAAGCCCAGAGGGCGTTCACGGCCGCTCTTCTTCAT

CGTGACTTCGGGCTCACCATGACCATACCAGAAGACCGTCTGTGCCCAACAGTCCCCAATAGGTTGAACTACGTTCTGTGG

ATTGAAGATATTTTCAACTACACGAACAAAACCCTCGGCCTGTCGGATGACCGTCCTATTAAAGGCGTTGATATTGGTACA

GGAGCCTCCGCAATTTATCCTATGCTTGCCTGTGCTCGGTTCAAGGCATGGTCTATGGTTGGAACAGAGGTCGAGAGGAAG

TGCATTGACACGGCCCGCCTCAATGTCGTCGCGAACAATCTCCAAGACCGTCTCTCGATATTAGAGACATCCATTGATGGT

CCTATTCTCGTCCCCATTTTCGAGGCGACTGAAGAATACGAATACGAGTTTACTATGTGTAACCCTCCATTCTACGACGGT

GCTGCCGATATGCAGACTTCGGATGCTGCCAAAGGATTTGGATTTGGCGTGGGCGCTCCCCATTCTGGAACAGTCATCGAA

ATGTCGACTGAGGGAGGTGAATCGGCTTTCGTCGCTCAGATGGTCCGTGAGAGCTTGAAGCTTCGAACACGATGCAGATGG

TACACGAGTAACTTGGGAAAGCTGAAATCCTTGAAAGAAATAGTGGGGCTGCTGAAAGAACTTGAGATAAGCAACTATGCC

ATTAACGAATACGTTCAGGGGTCCACACGTCGTTATGCCGTTGCGTGGTCTTTCACTGATATTCAACTGCCTGAGGAGCTT

TCTCGTCCCTCTAACCCCGAGCTCAGCTCTCTTTTCTAG
```

SEQ. ID NO: 8

```
MHIRNPYRTPIDYQALSEAFPPLKPFVSVNADGTSSVDLTIPEAQRAFTAALLHRDFGLTMTIPEDRLCPTVPNRLNYVLW

IEDIFNYTNKTLGLSDDRPIKGVDIGTGASAIYPMLACARFKAWSMVGTEVERKCIDTARLNVVANNLQDRLSILETSIDG

PILVPIFEATEEYEYEFTMCNPPFYDGAADMQTSDAAKGFGFGVGAPHSGTVIEMSTEGGESAFVAQMVRESLKLRTRCRW

YTSNLGKLKSLKEIVGLLKELEISNYAINEYVQGSTRRYAVAWSFTDIQLPEELSRPSNPELSSLF
```

SEQ. ID NO: 9

```
ATGCCTTCCAGTCACCCTCACATTACTCATCGCTATCGGGTTCCTTCGAGTGACGACCATGAACGTATATCTGCTCTGTTC

TTGGGTCCCAAAGCAGAAAATGCCGCATTTCTCCAGCAATGGTTGACCACGGTCGTCGCACAGCAAAAGGCTGCCCGCGAT

GCATACTTCCCGGATGACAATGCTTTTATTACTACAGACATGCAAACTTCCCCCGCCTTTGCTCAGACTACTAAAGTAATC

GCCTCCAATCTCACCGAATTATTGACTGCACTCGGTGAAAGGTCGATTCCTTTCTTCTCACCTCGGTACAGCGGCCATATG

TCTGTGGACCAAAGTCTACCTGCCATTCTCGGATTCTTATCGACCACATTTTATAATCCTAACAATGTTGCCTTCGAGGCT

AGTCCATTCACGACCCTCATCGAGGAAGAAGTTGGCTTGCAACTCTCTGAAATGCTGGGTTATAATCGGCTAAATAACACC

GAGAAACCTCTCGCCTGGGGACATATTGCATCAGGTGGAACTGTTGCAAACTTGGAAGCGATGTGGGCGGCGCGAAACCTC

AAGTTTTACCCTCTCTCACTCCGTGATGCTTCAGCCGAAGGCGCAGAGATGGAATTCATTCGTGACACATTCTCCGTCAAA

ACCTGTGTTGGTGACAAAAAATTATTAAAGGATTGCAGCCCATGGGAACTCCTCAATTTGCATGTTTCTACTATCTTAGAC
```

-continued

```
ATGCCCGACCGTCTGCACGACGAGTACAATATTTCACCTCAGTTCCTCGAAAAGGTTATGCGAAAGTATATCATCCAGTCT

ACCAACAAAGACACGTTGATGCAGCGTTGGGGACTTACCCAACAACCTGTCGTTTTATCCCCGAGCACAAACCATTATTCC

TGGCCAAAGGCTGCAGCTGTGCTCGGTATTGGCTCAGACAACCTTCGCAACGTCCCAGTAGACATCCAAGCCCACATGGAC

ATAAACGAACTCGATCGTATGTTAAAAATTTGCTTGGACGAGGAGACGCCAGTATATCAAGTAGTTGCTGTTATCGGTACC

ACCGAAGAGGGCGGTGTCGATCGCATTACGGAGATCCTGAAGCTGCGCCAAAAGTATGAAGCTTTGGGGCTGTCTTTTGCC

ATCCATGCAGATGCTGCTTGGGGAGGCTATTTTGCAACCATGCTACCCAAAGATACATTGGGTCGAAACCGGACTAGGCTT

CCCAAAGAGGACACTACCTCGGGCTTTGTCCCTCACGTCGGTCTGCGCGAGGAGAGCGCGTTACAACTCAGCCATATAAAG

TATGCCGATTCTATTACTATCGACCCGCACAAGGCAGGCTATGTTCCTTACCCCGCTGGGGCACTCTGTTATCGCGACGGA

AGAATGAGGTACCTGCTTACATGGTCCGCGCCCTACCTTGCCCAAGGCAACGAGGGCCAAAGTATCGGAATATACGGGATC

GAAGGAAGCAAACCTGGTGCAGCAGCATCCGCGGTATTCATGGCGCACGAAACCATTGGCCTGACTCCTTCTGGATACGGG

AACCTTCTTGGCCAGGCAATGTTTACATGTCGCCGATACGCTGCTCACTGGTCTGCAATGTCAACGGATACTACCAGTTTC

ACTGTCACCCCGTTCAATCCTATCCCTGCTGACATCGACCCCAACGCTGACCCCGCAAAGGTCGAAGAGCAAAAACAGTTC

ATCAGAGATCGTATCTTGTTCAAATCGAACGAGGAAATATACAACGATTCTGAGGCTATGGAACTCTTGCACCAACTTGGG

TCCGATCTCAATATCAACGTTTTCGCATGCAACTTCCGCGACCGCGATAATAATCTCAACACCGACGTCGAGGAAGCCAAC

TGGCTCAATAACCGTATTTTCCAACGCTTTTCTGTTACAAGTGCTGAGGAGAACCCATTGGAAACGCCATTCTTCCTCAGC

TCAACTACATTGAAACAATCCGAATACGGCGTCTGCGCAACCGAAGTAAAGAGACGCATGGGACTTGTTGGTGACCAGGAT

GTTATAGTCCTGAGGAACGTCGTTATGTCTCCATTTACTACAACGAACGACTTTGTGGGAACTCTGGCAAACACCTTCCAA

AAGATCGTTGAGGAGGAGGTCGAGTATGCACGGATCCGCAACGATATGAAACCTAGCATTCACACCTTCCTTCTTCATGGT

TCAGGAGAGCAATACTATCTTGTCCACACCCCAACGATCCATATGGCCAGCGGCCGTCGCCAAATCATCCTTTCAGTAAAT

GTTGAAGGCCAAGTTCGGCAGGCGATACATGCCCATGAAAGAGTTGAAGCAGTGATTGTACATAACACTGTGCCCCTCCGC

CTTGACGAAATCGTTGACGGAGGATCATTTGACGGCATACTCACCATCGGAAAGAGGAAAACTAGTTTCAAAGTGAAGATT

TCAAACATTAAAGTAGTCAAGAAGCGCTCTCTGATGACTGAGGACCTGGAATCTGCGTACCCATCGTTGATGCCATTCTAT

TTCTACGGGACTCAAGGACACGCTCATCTCGACCATGTCATTACTGTCGTTCCTAACATCCATCTGAGTGCTGGCGAAATA

CAGTACAAATTCGACGACGAGGTGTCAAGCGAGGACCTCGCCAAGGGCCTCATTGTTGTTGCTGAGAACGTACACGAGGCA

TCCATGCAGCCCTTCCCGCTCATGAAAGATTTCAAGATCACCAACCAATTCTTCTTCAGCTCCGGGCAAATACTCCGCGTC

AAAGTGTACAGAGATCCATACCCGGCATCGACAATGGATCCCATCCCTCTCCACGACATCAAGAACCAGCCCGTCGTGACA

CAAGGCACCATCACGCTCGTCGGAAATATTTACGTCGATTCTGATGCGCTCAACGTCGCTTCCGAGCCTACTGCCGACGAA

GACGCGGCGCATGTTCCTCACGCTCGCAACATGTACGGCGAGATGACCGCTGGAACGATCAAAGGCTGGCAAAACGCTGTT

CGTCATTTCCACAACAAATTGGAGACTGTTGCTCCGACGAAGTAG
```

SEQ. ID NO: 10

```
MPSSHPHITHRYRVPSSDDHERISALFLGPKAENAAFLQQWLTTVVAQQKAARDAYFPDDNAFITTDMQTSPAFAQTTKVI

ASNLTELLTALGERSIPFFSPRYSGHMSVDQSLPAILGFLSTTFYNPNNVAFEASPFTTLIEEEVGLQLSEMLGYNRLNNT

EKPLAWGHIASGGTVANLEAMWAARNLKFYPLSLRDASAEGAEMEFIRDTFSVKTCVGDKKLLKDCSPWELLNLHVSTILD

MPDRLHDEYNISPQFLEKVMRKYIIQSTNKDTLMQRWGLTQQPVVLSPSTNHYSWPKAAAVLGIGSDNLRNVPVDIQAHMD

INELDRMLKICLDEETPVYQVVAVIGTTEEGGVDRITEILKLRQKYEALGLSFAIHADAAWGGYFATMLPKDTLGRNRTRL

PKEDTTSGFVPHVGLREESALQLSHIKYADSITIDPHKAGYVPYPAGALCYRDGRMRYLLTWSAPYLAQGNEGQSIGIYGI

EGSKPGAAASAVFMAHETIGLTPSGYGNLLGQAMFTCRRYAAHWSAMSTDTTSFTVTPFNPIPADIDPNADPAKVEEQKQF

IRDRILFKSNEEIYNDSEAMELLHQLGSDLNINVFACNFRDRDNNLNTDVEEANWLNNRIFQRFSVTSAEENPLETPFFLS

STTLKQSEYGVCATEVKRRMGLVGDQDVIVLRNVVMSPFTTTNDFVGTLANTFQKIVEEEVEYARIRNDMKPSIHTFLLHG

SGEQYYLVHTPTIHMASGRRQIILSVNVEGQVRQAIHAHERVEAVIVHNTVPLRLDEIVDGGSFDGILTIGKRKTSFKVKI

SNIKVVKKRSLMTEDLESAYPSLMPFYFYGTQGHAHLDHVITWPNIHLSAGEIQYKFDDEVSSEDLAKGLIWAENVHEASM
```

-continued

QPFPLMKDFKITNQFFFSSGQILRVKVYRDPYPASTMDPIPLHDIKNQPVVTQGTITLVGNIYVDSDALNVASEPTADEDA
AHVPHARNMYGEMTAGTIKGWQNAVRHFHNKLETVAPTK

SEQ. ID NO: 11
ATGGAGGCTATCAAAAAGGTTTTTGAGAACAAAAAGGCGGAGGGCATTCCTGTGTTGGTGACCTTTGTTACTGCAGGATAT
CCTCGTCCCGAAGATACTGTTCCCATCTTGCTGGCCATGGAGGCCGGTGGTGCTGATATCATCGAGCTTGGTATGCCATTT
TCAGACCCAATTGCAGATGGTCCTGTCATCCAGGAAACGAACACAATCGCCGTTGCAAACCAGGTAGATTATACCACTGTT
CTCGGACAACTTCGGGAAGCCCGCAAACAAGGGCTCAAGGCACCCGTTCTTCTGATGGGATATTATAACCCCATATTGGCT
TACGGAGAAGACAGATCTATTCAAGATGCGGCTGAAGCTGGAGCCAATGGGTTTATTATGGTCGACCTTCCACCCGAGGAG
GCTGTCGCTTTTCGAGAGAAATGTATCAAATCCAACCTCTCATATGTTCCTCTAATTGCACCCTCAACGACTCTGTCGCGT
ATAAAGTTCCTCTCAACAATTGCAGACACGTTCATCTATGTCGTGTCTAAAATGGGAACCACCGGATCCTCAGAGAAGGTT
GCCATGAATAACGCCCTTCCCACCATCATCGATCGTATTCGCGAGTACGCTGAAGTTCCTTTAGCAGTCGGATTTGGAGTC
GCCACTCGGGCTCACTTCAACTACGTCGCCGATTCCGGTGCTGATGGTGTCGTTATTGGCACCAAACTCGTTAACGTTATT
AAAGAGTCACCGCAAGGGGAAGCACCCAAAAATGTTGAGGCATACTGCCGTGAGATGAGCCAAAAGGGAGAAACAAATCGC
GTCAAATCTCCACCAACTGCCCGTGCTGCCAGCTCCGAATCAATTCCTGTTGTTGTTCCTTCTGTTCTCCCCGCACGTTTC
GGAGAATTCGGAGGACAATACGTTCCCGAAGCTCTTGTCGATTGTCTGGTTGAACTAGAAGAAGCTCACAAATCTGCCATG
GCTGATCCTGAATTCCAGAAGGAACTACAATCGCATGCCGGATATGCAAATCGTCCTTCACAAATATACCTCGCCGAAAAT
CTCACCAAGGATGCTGGGGGTGCAAATATTTGGTTGAAACGTGAAGATTTGAACCACACAGGTTCCCACAAAATCAATAAC
GCTTTGGGACAAATTCTGCTTGCCCGGAGAATCGGAAAGACCAGAATTATCGCAGAAACAGGTGCCGGCCAGCATGGTGTT
GCAACAGCGACTGTTTGCGCTAAGTTTGGAATGGAATGTGTTATCTACATGGGCGCAGAAGATGTGCGACGGCAAGCTCTA
AATGTATTCAGGATTGAGATGCTAGGAGCAAAAGTTGTTCCTGTTACTTCAGGATCATGCACATTGAAGGACGCTGTAAAC
GAGGCCTTCCGTGACTGGGTGACAAACCTTTCTACGACGCATTATTTGGTTGGCTCTGTAATTGGACCTCATCCCTTCCCC
ACCATTGTCCGAGATTTCCAAAAGGTCATTGGTCAAGAGATCAAGGCTCAGATGTTGGCCGCCCGCGGCAAACTTCCTGAT
GTCGTCGTCGCTTGTGTTGGTGGAGGAAGCAATGCTATCGGTACGTTCTATGATTTTATTGGCGACAAGAGTGTACGTCTA
GTTGGGGTGGAAGCAGGAGGAGAAGGTATTGACGGAGACCGACATAGCGCCACACTTTCGATGGGGCAACCGGGAGTACTT
CACGGTGTTAGAACATATATTCTACAAGACAAGGCCGGTCAAATCATCGAGACGCACTCAATCAGCGCTGGATTGGATTAT
CCCGGCGTTGGACCAGAACATGCTTGGCTAAAGGACTCTAAAAGAGCAGAATATGTTGTCGCCACAGACGAAGAAGCACTT
CGCGGTTTCCGTATGCTAACACAAAGGGAGGGAATTATTCCTGCCCTTGAATCTTCCCATGCGATCTGGGAGGCTGTCAGG
ATTGCCCGCACCATGTCGAAGGACCAGGATCTTGTTGTGTGTTTGTCTGGCCGAGGTGATAAAGACGTTGAGCAAATTTCT
CAACTTCTTCCCAAGTGGGCGGATATTCTAGACTGGCATGTTTCTTCCCATGCCGTTGGACACAACAAAATTCTAA

SEQ. ID NO: 12
MEAIKKVFENKKAEGIPVLVTFVTAGYPRPEDTVPILLAMEAGGADIIELGMPFSDPIADGPVIQETNTIAVANQVDYTTV
LGQLREARKQGLKAPVLLMGYYNPILAYGEDRSIQDAAEAGANGFIMVDLPPEEAVAFREKCIKSNLSYVPLIAPSTTLSR
IKFLSTIADTFIYVVSKMGTTGSSEKVAMNNALPTIIDRIREYAEVPLAVGFGVATRAHFNYVADSGADGVVIGTKLVNVI
KESPQGEAPKNVEAYCREMSQKGETNRVKSPPTARAASSESIPVVVPSVLPARFGEFGGQYVPEALVDCLVELEEAHKSAM
ADPEFQKELQSHAGYANRPSQIYLAENLTKDAGGANIWLKREDLNHTGSHKINNALGQILLARRIGKTRIIAETGAGQHGV
ATATVCAKFGMECVIYMGAEDVRRQALNVFRIEMLGAKVVPVTSGSCTLKDAVNEAFRDWVTNLSTTHYLVGSVIGPHPFP
TIVRDFQKVIGQEIKAQMLAARGKLPDVVVACVGGGSNAIGTFYDFIGDKSVRLVGVEAGGEGIDGDRHSATLSMGQPGVL
HGVRTYILQDKAGQIIETHSISAGLDYPGVGPEHAWLKDSKRAEYVVATDEEALRGFRMLTQREGIIPALESSHAIWEAVR
IARTMSKDQDLVVCLSGRGDKDVEQISQLLPKWADILDWHVSSHAVGHTTKF

SEQ. ID NO: 13
ATGGAGCTCACCATGGCGTCGACGATGTCGCTCGCGCTGCTCGTGCTCTCCGCGGCGTACGTGTTGGTCGCGTTGAGGAGG
AGCCGGTCGTCGTCGTCAAAGCCACGGCGGCTGCCGCCGTCGCCGCCGGGGTGGCCGGTGATCGGGCACCTCCACCTCATG

-continued

TCCGGCATGCCGCACCACGCGCTGGCCGAGCTGGCGCGCACCATGCGCGCGCCGCTGTTCCGGATGCGGCTGGGGAGCGTG

CCGGCGGTGGTGATCTCCAAGCCGGACCTCGCCCGCGCCGCGCTCACCACCAACGACGCCGCGCTGGCGTCGCGGCCGCAC

CTGCTCTCCGGCCAGTTCCTGTCGTTCGGCTGCTCCGACGTGACGTTCGCGCCGGCGGGGCCGTACCACCGGATGGCGCGC

CGCGTGGTGGTGTCGGAGCTCCTGTCGGCGCGTCGCGTCGCCACGTACGGCGCCGTCAGGGTCAAGGAGCTCCGCCGCCTG

CTCGCGCACCTCACCAAGAACACCTCGCCGGCGAAGCCCGTCGACCTCAGCGAGTGCTTCCTCAACCTCGCCAACGACGTG

CTCTGCCGCGTCGCGTTCGGCCGCCGGTTCCCGCACGGCGAGGGCGACAAGCTCGGCGCGGTGCTCGCCGAGGCGCAGGAC

CTCTTCGCCGGGTTCACCATCGGCGACTTCTTCCCCGAGCTCGAGCCCGTCGCCAGCACCGTCACCGGACTCCGCCGCCGC

CTCAAGAAGTGCCTCGCCGACCTCCGCGAGGCCTGCGACGTGATCGTGGACGAACACATCAGCGGCAACCGCCAGCGCATC

CCCGGCGACCGCGACGAGGACTTCGTCGACGTCCTCCTCCGCGTCCAGAAATCCCCCGACCTCGAGGTCCCCCTAACCGAC

GACAATCTCAAGGCCCTCGTCCTGGACATGTTCGTCGCCGGCACGGACACCACGTTCGCGACGCTGGAGTGGGTGATGACG

GAGCTAGTCCGCCACCCACGGATCCTCAAGAAGGCGCAGGAGGAGGTCCGGCGAGTCGTCGGCGACAGCGGCCGCGTCGAG

GAGTCCCACCTCGGCGAGCTCCACTACATGCGCGCCATCATCAAGGAGACGTTCCGGCTGCACCCGGCGGTGCCGTTGCTA

GTGCCGCGCGAGTCCGTCGCGCCGTGCACGCTGGGCGGCTACGACATCCCGGCGAGGACGCGGGTGTTCATCAACACGTTC

GCCATGGGGCGCGACCCGGAGATCTGGGACAACCCGCTGGAGTACTCGCCGGAGAGGTTCGAGAGCGCCGGCGGCGGCGGC

GAGATCGACCTCAAGGACCCGGACTACAAGCTGCTGCCGTTCGGCGGCGGGCGGCGAGGGTGCCCCGGCTACACGTTCGCG

CTCGCCACCGTGCAGGTGTCGCTCGCCAGCTTGCTCTACCACTTCGAGTGGGCGCTGCCCGCCGGCGTGCGCGCCGAGGAC

GTCAACCTCGACGAGACGTTCGGCCTCGCCACGAGGAAGAAGGAGCCGCTCTTCGTCGCCGTCAGGAAGAGCGACGCGTAC

GAGTTTAAGGGAGAGGAGCTTAGTGAGGTTTAA

SEQ. ID NO: 14

MELTMASTMSLALLVLSAAYVLVALRRSRSSSSKPRRLPPSPPGWPVIGHLHLMSGMPHHALAELARTMRAPLFRMRLGSV

PAVVISKPDLARAALTTNDAALASRPHLLSGQFLSFGCSDVTFAPAGPYHRMARRVVVSELLSARRVATYGAVRVKELRRL

LAHLTKNTSPAKPVDLSECFLNLANDVLCRVAFGRRFPHGEGDKLGAVLAEAQDLFAGFTIGDFFPELEPVASTVTGLRRR

LKKCLADLREACDVIVDEHISGNRQRIPGDRDEDFVDVLLRVQKSPDLEVPLTDDNLKALVLDMFVAGTDTTFATLEWVMT

ELVRHPRILKKAQEEVRRVVGDSGRVEESHLGELYMRAIIKETFRLHPAVPLLVPRESVAPCTLGGYDIPARTRVFINTFA

MGRDPEIWDNPLEYSPERFESAGGGGEIDLKDPDYKLLPFGGGRRGCPGYTFALATVQVSLASLLYHFEWALPAGVRAEDV

NLDETFGLATRKKEPLFVAVRKSDAYEFKGEELSEV

SEQ. ID NO: 15

ATGATTGAAGACAACAAGGAGAACAAAGACCATTCCTCAGAAAGGGGGAGAGTGACTCTCATCTTTTCCTTGAAGAATGAA

GTTGGAGGACTCATAAAAGCACTGAAAATCTTCCAGGAGAACCACGTGAACCTGTTACATATTGAGTCCCGGAAATCGAAG

CGAAGAAACTCAGAATTTGAGATTTTTGTGGACTGCGACATCAACCGAGAACAGCTGAATGACATCTTTCCCCTGCTGAAG

TCCCACACCACGGTCCTCTCTGTGGACTCGCCCGATCAGCTCCCTGAAAAGGAAGATGTTATGGAGACTGTCCCTTGGTTC

CCAAAGAAGATTTCTGACCTGGACTTCTGCGCCAACAGAGTGCTGTTGTACGGATCCGAACTCGACGCGGACCATCCTGGC

TTCAAAGACAATGTCTACCGTAGAAGACGAAAGTATTTCGCAGAGCTGGCTATGAACTACAAACATGGGGACCCCATTCCC

AAGATTGAATTCACGGAAGAGGAGATTAAGACCTGGGGACCATCTTCCGAGAGCTGAACAAACTCTACCCAACCCACGCC

TGCAGGGAGTACCTCAGAAACCTTCCTCTGCTCTCAAAATACTGTGGCTATCGGAAGACAACGTCCCGCAACTGGAAGAT

GTCTCCAACTTTTTAAAAGAACGCACAGGGTTTTCCATCCGTCCTGTGGCTGGTTACCTCTCACCGAGAGATTTCCTGTCA

GGGTTAGCCTTTCGAGTCTTTCACTGCACTCAGTATGTGAGACACAGTTCGGATCCTCTCTATACCCCAGAGCCAGACACC

TGCCACGAACTCTTAGGCCACGTCCCTCTCTTGGCTGAACCCAGTTTTGCTCAATTCTCCCAAGAAATTGGCCTGGCTTCT

CTTGGAGCTTCAGAGGAGACGGTTCAGAAACTGGCAACGTGCTACTTCTTCACTGTGGAGTTTGGACTGTGCAAGCAAGAT

GGGCAGCTGAGAGTCTTTGGTGCCGGCCTGCTTTCTTCCATCAGTGAGCTCAGACATGCACTTTCTGGACATGCCAAGGTT

AAGCCCTTTGATCCCAAGGTTGCCTGCAAACAGGAATGTCTCATCACAAGCTTCCAGGATGTCTACTTTGTATCGGAGAGC

-continued
TTTGAAGATGCAAAGGAGAAGATGAGAGAATTTGCCAAAACCGTGAAGCGCCCGTTTGGAGTGAAGTACAATCCGTACACA CAGAGCATTCAGGTTCTGAGAGACAGCAAGAGCATAACCAGCGCCATGAATGAGTTGCGGCATGACCTCGATGTCGTCAAT

GATGCCCTTGCTAGAGTCAGCAGGTGGCCCAGTGTGTGA

SEQ. ID NO: 16
MIEDNKENKDHSSERGRVTLIFSLKNEVGGLIKALKIFQENHVNLLHIESRKSKRRNSEFEIFVDCDINREQLNDIFPLLK

SHTTVLSVDSPDQLPEKEDVMETVPWFPKKISDLDFCANRVLLYGSELDADHPGFKDNVYRRRRKYFAELAMNYKHGDPIP

KIEFTEEEIKTWGTIFRELNKLYPTHACREYLRNLPLLSKYCGYREDNVPQLEDVSNFLKERTGFSIRPVAGYLSPRDFLS

GLAFRVFHCTQYVRHSSDPLYTPEPDTCHELLGHVPLLAEPSFAQFSQEIGLASLGASEETVQKLATCYFFTVEFGLCKQD

GQLRVFGAGLLSSISELRHALSGHAKVKPFDPKVACKQECLITSFQDVYFVSESFEDAKEKMREFAKTVKRPFGVKYNPYT

QSIQVLRDSKSITSAMNELRHDLDVVNDALARVSRWPSV

SEQ. ID NO: 17
ATGCCCGCCGTGGCCGGGAGCTTGTACATGGCGAGCCAGCACAAGGGAGTGCCTCCGCCGCTGCCGCCGCCGCCGCGGCCA

TTGCCGGTGATCAACCTGGGCCGGCTCACCATGGACAGTGCCTCGCGGGCGCTCGCCGTGCGGGATATCGTGCTGGCGTGC

CGTGAACGTGGCTGCTTTGAGGTGGTGAACCATGGCATCAGCAGGTCTTGCATGAATGGCGCCCTCGAAGCCGCCTCCGAG

TTCTTCCAGCTATCGACGGAGCGCAAGGAGGAGTTCGCGTCGGACGACATCCGGCAGCCCATCAGGTACGACACGAGCTCG

AGGGACGGGATCAGCATGTCCAGGTCATTTCTGAAGCACTATGCCAATCCCCTGGACGACTGGATCAAGTTCTGGCCGACG

CAGCCACCAACTTACAGGGAGAAAATGGGTGAGTACGCCGTGGAGACGCAGCGAGTGTCAATGCAGCTCATGGAAGCAATC

CTGCAGGGCCTGGGATTAGGGCCATCGTACCTGCAAGAAAAGCTTGAAGGAGGGGTGCAGTTCGTGGCCTTGAACAACTAC

CCGCAGTCATCGGCAAGAAAGCCGACAAGATCGGCTTGGCTCCTCACTCTGATTATGGCTTCCTCACCATCCTGTTGCAG

AGCTCCCCAGGGCTTGAGGTGATGCACCATGAGGATGATGCCTGGACATCTGTCCCTGCTATCCCTGGGGCTCTCCATGTC

CATGTAGGAGACCACCTGGAAGTGTTGAGCAATGGCCAGCTCAAGTCCCTTGTCCATCGAGCCGTTCTCAACCCAAACGAG

GTCAAGGATTTCTATTGCCAGCATCCATGGTCTCTCGATGGATGAAGAGGTCCACTGCGCCGAAGAGCTCGTCGATGAACA

CCACCCCAAAATGTACAGGGGAAGCAGCTTCCAGGACTTCCTGGACTTCCTGCCAGCAGACATGAACAGGTATAGGAGGTA

TGTCGAGAGCCTCAGGATCGACAAACCCTGA

SEQ. ID NO: 18
MPAVAGSLYMASQHKGVPPPLPPPPRPLPVINLGRLTMDSASRALAVRDIVLACRERGCFEVVNHGISRSCMNGALEAASE

FFQLSTERKEEFASDDIRQPIRYDTSSRDGISMSRSFLKHYANPLDDWIKFWPTQPPTYREKMGEYAVETQRVSMQLMEAI

LQGLGLGPSYLQEKLEGGVQFVALNNYPQSSAKKADKIGLAPHSDYGFLTILLQSSPGLEVMHHEDDAWTSVPAIPGALHV

HVGDHLEVLSNGQLKSLVHRAVLNPNESRISIASIHGLSMDEEVHCAEELVDEHHPKMYRGSSFQDFLDFLPADMNRYRRY

VESLRIDKP

SEQ. ID NO: 19
ATGCTGAGTCTCGACCTAGTATTCTCTTTCCCAGCATGGGCGCTCCTCCTAGTCCTAACCCTCTTGTATACACTATACCTA

GCCACAACGCGCCTCCTCCTGAGCCCCATTCGCCATATTCCCGGCCCAACTCTAGCCGCACTGTCGTTTTGGCCTGAATTC

TACTACGACGTCGTCCAGCGGGGACAGTATTTTCGACAAATTGACAAGATGCATCAGACATACGGTCCGCTAGTCCGCATT

AACCCATTCGAAATCCACATCCAAGACCCCTCCTTCTATCCCGTGCTGTACACAGGCCCAACTCGTCGACGACATAAATGG

CTCTGGGCTGCACGAATGTTCGGGAACAACACCTCTGCCTTTGCAACCGTCCGGCACGAACACCACAGACTAAGAAGGAGT

GCATTGAACCCTCTCTTCTCAAAGAGCGCTATCCAGCGGCTAACACCGCACCTGCAACATACCCTAGCGCGGCTATGTAGT

CGGCTCGATGGGTTCGCTTTTACAAGACAGGATGTGGACTTGGGGATCGGACTTACAGCGTTCGCGGCCGACGTCATCACA

GAGTACTGTTTCGGACAGTCACTGGAGTTGATTGGGAAAGATAACTTTGGAAAGGAGTGGATTGATATGGTAAGCGCTCCG

TCAGAGCTCGGCCATCTGGTAAAGCAGTGTCCGTGGATCTTGGTGGTTTGTAAATGGGCGCCGAAAGCTCTTGTTAGGGCT

TTGCTGCCGGGGGTTGCGTTGTTGTTTCAAATACAAGAGAGAATGAGCGCCCAGATTCAACCGCTTGTTGATCGAGCCGCC

GCCGTTGACAAGCCAGCTGACCCTTTGACCGTCTTCGACTTCCTCCTCTCGAGTACCCTCCCACAGCACGAAAGACAGTG

GACCGACTCAAGGGCGAAGGGCAGACGCTCATCGGCGCGGGGACATTAACGACCGGGAATGCATTGAAGACGATAATCTTC

-continued

```
CACGTCCTCAATGATCCCGACATCTTTCGGAAACTTCGAGCAGAGGTCGACGGTGCTCTAGAAAATATGGATATTCTGTCC
ATGTCTGATACGGCCTACCTCGAACGCCTCCCGTACCTGTCAGCGTGCATAAAGGAAGGTCTACGGATTTCCTACGGCGTC
ACGCATAGACTCCAACTGATCGCCGAAGAGCCCCTAATATACTCAGGAGTGACCATCCCAGCAGGAACACCAGTTGGAATG
ACATCGATCTTCATGCACGACAATCCAGTAGTATTCCCTCAGCCGCGGGAATTCCGTCCAGAGCGCTGGTTCGAGGCAGAT
TTTGAGACTGTGCAGGCAATGAATCGCCACTTCGTCCCCTTCAGCAAGGGCAGCCGCATGTGTCTGGGAATGAACCTGGCG
TATGCGGAGATTTACTTGGTGCTGGCAGTACTTTTTCGACGGTATGAGATTTCTCTGAGCGGGGTGACGAGGGAGGATATT
GAGATGGCACATGATTTTTTCGATCCTGCGCCAAAGGAGGGGGCAAGAGGATTGATCGTTCAACTGCAGAAGAGGGGGTGA
```

SEQ. ID NO: 20

```
MLSLDLVFSFPAWALLLVLTLLYTLYLATTRLLLSPIRHIPGPTLAALSFWPEFYYDVVQRGQYFRQIDKMHQTYGPLVRI
NPFEIHIQDPSFYPVLYTGPTRRRHKWLWAARMFGNNTSAFATVRHEHHRLRRSALNPLFSKSAIQRLTPHLQHTLARLCS
RLDGFAFTRQDVDLGIGLTAFAADVITEYCFGQSLELIGKDNFGKEWIDMVSAPSELGHLVKQCPWILVVCKWAPKALVRA
LLPGVALLFQIQERMSAQIQPLVDRAAAVDKPADPLTVFDFLLSSTLPQHEKTVDRLKGEGQTLIGAGTLTTGNALKTIIF
HVLNDPDIFRKLRAEVDGALENMDILSMSDTAYLERLPYLSACIKEGLRISYGVTHRLQLIAEEPLIYSGVTIPAGTPVGM
TSIFMHDNPVVFPQPREFRPERWFEADFETVQAMNRHFVPFSKGSRMCLGMNLAYAEIYLVLAVLFRRYEISLSGVTREDI
EMAHDFFDPAPKEGARGLIVQLQKRG
```

SEQ. ID NO: 21

```
GCTAACAGCGCGATTTGCTGGTGACCCAATGCGACCAGATGCTCCACGCCCAGTCGCGTACCGTCTTCATGGGAGAAAATA
ATACTGTTGATGGGTGTCTGGTCAGAGACATCAAGAAATAACGCCGGAACATTAGTGCAGGCAGCTTCCACAGCAATGGCA
TCCTGGTCATCCAGCGGATAGTTAATGATCAGCCCACTGACGCGTTGCGCGAGAAGATTGTGCACCGCCGCTTTACAGGCT
TCGACGCCGCTTCGTTCTACCATCGACACCACCACGCTGGCACCCAGTTGATCGGCGCGAGATTTAATCGCCGCGACAATT
TGCGACGGCGCGTGCAGGGCCAGACTGGAGGTGGCAACGCCAATCAGCAACGACTGTTTGCCCGCCAGTTGTTGTGCCACG
CGGTTGGGAATGTAATTCAGCTCCGCCATCGCCGCTTCCACTTTTTCCCGCGTTTTCGCAGAAACGTGGCTGGCCTGGTTC
ACCACGCGGGAAACGGTCTGATAAGAGACACCGGCATACTCTGCGACATCGTATAACGTTACTGGTTTCACATTCACCACC
CTGAATTGACTCTCTTCCGGGCGCTATCATGCCATACCGCGAAAGGTTTTGCGCCATTCGATGGTGTCCGGGATCTCGACG
CTCTCCCTTATGCGACTCCTGCATTAGGAAGCAGCCCAGTAGTAGGTTGAGGCCGTTGAGCACCGCCGCCGCAAGGAATGG
TGCATGCAAGGAGATGGCGCCCAACAGTCCCCCGGCCACGGGGCCTGCCACCATACCCACGCCGAAACAAGCGCTCATGAG
CCCGAAGTGGCGAGCCCGATCTTCCCCATCGGTGATGTCGGCGATATAGGCGCCAGCAACCGCACCTGTGGCGCCGGTGAT
GCCGGCCACGATGCGTCCGGCGTAGCCTAGGATCGAGATCGATCTCGATCCCGCGAAATTAATACGACTCACTATAGGGA
ATTGTGAGCGGATAACAATTCCCCTCTAGAAATAATTTTGTTTAACTTTAAGAAGGAGATATACATATGGCAGATCTCAAT
TGGATATCGGCCGGCCACGCGATCGCTGACGTCGGTACCCTCGAGTCTGGTAAAGAAACCGCTGCTGCGAAATTTGAACGC
CAGCACATGGACTCGTCTACTAGTCGCAGCTTAATTAACCTAAACTGCTGCCACCGCTGAGCAATAACTAGCATAACCCCT
TGGGGCCTCTAAACGGGTCTTGAGGGGTTTTTTGCTAGCAAAGGAGGAGTCGACACTGCTTCCGGTAGTCAATAAACCGG
TAAACCAGCAATAGACATAAGCGGCTATTTAACGACCCTGCCCTGAACCGACGACCGGGTCATCGTGGCCGGATCTTGCGG
CCCCTCGGCTTGAACGAATTGTTAGACATTATTTGCCGACTACCTTGGTGATCTCGCCTTTCACGTAGTGGACAAATTCTT
CCAACTGATCTGCGCGCGAGGCCAAGCGATCTTCTTCTTGTCCAAGATAAGCCTGTCTAGCTTCAAGTATGACGGGCTGAT
ACTGGGCCGGCAGGCGCTCCATTGCCCAGTCGGCAGCGACATCCTTCGGCGCGATTTTGCCGGTTACTGCGCTGTACCAAA
TGCGGGACAACGTAAGCACTACATTTCGCTCATCGCCAGCCCAGTCGGGCGGCGAGTTCCATAGCGTTAAGGTTTCATTTA
GCGCCTCAAATAGATCCTGTTCAGGAACCGGATCAAAGAGTTCCTCCGCCGCTGGACCTACCAAGGCAACGCTATGTTCTC
TTGCTTTTGTCAGCAAGATAGCCAGATCAATGTCGATCGTGGCTGGCTCGAAGATACCTGCAAGAATGTCATTGCGCTGCC
ATTCTCCAAATTGCAGTTCGCGCTTAGCTGGATAACGCCACGGAATGATGTCGTCGTGCACAACAATGGTGACTTCTACAG
CGCGGAGAATCTCGCTCTCTCCAGGGGAAGCCGAAGTTTCCAAAAGGTCGTTGATCAAAGCTCGCCGCGTTGTTTCATCAA
```

-continued

GCCTTACGGTCACCGTAACCAGCAAATCAATATCACTGTGTGGCTTCAGGCCGCCATCCACTGCGGAGCCGTACAAATGTA
CGGCCAGCAACGTCGGTTCGAGATGGCGCTCGATGACGCCAACTACCTCTGATAGTTGAGTCGATACTTCGGCGATCACCG
CTTCCCTCATACTCTTCCTTTTTCAATATTATTGAAGCATTTATCAGGGTTATTGTCTCATGAGCGGATACATATTTGAAT
GTATTTAGAAAAATAAACAAATAGCCAGCTCACTCGGTCGCTACGCTCCGGGCGTGAGACTGCGGCGGGCGCTGCGGACAC
ATACAAAGTTACCCACAGATTCCGTGGATAAGCAGGGGACTAACATGTGAGGCAAAACAGCAGGGCCGCGCCGGTGGCGTT
TTTCCATAGGCTCCGCCCTCCTGCCAGAGTTCACATAAACAGACGCTTTTCCGGTGCATCTGTGGGAGCCGTGAGGCTCAA
CCATGAATCTGACAGTACGGGCGAAACCCGACAGGACTTAAAGATCCCCACCGTTTCCGGCGGGTCGCTCCCTCTTGCGCT
CTCCTGTTCCGACCCTGCCGTTTACCGGATACCTGTTCCGCCTTTCTCCCTTACGGGAAGTGTGGCGCTTTCTCATAGCTC
ACACACTGGTATCTCGGCTCGGTGTAGGTCGTTCGCTCCAAGCTGGGCTGTAAGCAAGAACTCCCCGTTCAGCCCGACTGC
TGCGCCTTATCCGGTAACTGTTCACTTGAGTCCAACCCGGAAAAGCACGGTAAAACGCCACTGGCAGCAGCCATTGGTAAC
TGGGAGTTCGCAGAGGATTTGTTTAGCTAAACACGCGGTTGCTCTTGAAGTGTGCGCCAAAGTCCGGCTACACTGGAAGGA
CAGATTTGGTTGCTGTGCTCTGCGAAAGCCAGTTACCACGGTTAAGCAGTTCCCCAACTGACTTAACCTTCGATCAAACCA
CCTCCCCAGGTGGTTTTTTCGTTTACAGGGCAAAAGATTACGCGCAGAAAAAAAGGATCTCAAGAAGATCCTTTGATCTTT
TCTACTGAACCGCTCTAGATTTCAGTGCAATTTATCTCTTCAAATGTAGCACCTGAAGTCAGCCCCATACGATATAAGTTG
TAATTCTCATGTTAGTCATGCCCCGCGCCCACCGGAAGGAGCTGACTGGGTTGAAGGCTCTCAAGGGCATCGGTCGAGATC
CCGGTGCCTAATGAGTGAGCTAACTTACATTAATTGCGTTGCGCTCACTGCCCGCTTTCCAGTCGGGAAACCTGTCGTGCC
AGCTGCATTAATGAATCGGCCAACGCGCGGGGAGAGGCGGTTTGCGTATTGGGCGCCAGGGTGGTTTTTCTTTTCACCAGT
GAGACGGGCAACAGCTGATTGCCCTTCACCGCCTGGCCCTGAGAGAGTTGCAGCAAGCGGTCCACGCTGGTTTGCCCCAGC
AGGCGAAAATCCTGTTTGATGGTGGTTAACGGCGGGATATAACATGAGCTGTCTTCGGTATCGTCGTATCCCACTACCGAG
ATGTCCGCACCAACGCGCAGCCCGGACTCGGTAATGGCGCGCATTGCGCCCAGCGCCATCTGATCGTTGGCAACCAGCATC
GCAGTGGGAACGATGCCCTCATTCAGCATTTGCATGGTTTGTTGAAAACCGGACATGGCACTCCAGTCGCCTTCCCGTTCC
GCTATCGGCTGAATTTGATTGCGAGTGAGATATTTATGCCAGCCAGCCAGACGCAGACGCGCCGAGACAGAACTTAATGGG
CCC

SEQ. ID NO: 22
GACTACAAGGATGACGATGACAAA

SEQ. ID NO: 23
DYKDDDDK

SEQ. ID NO: 24
ATGAACACCTTCAGAACAGCCACTGCCAGAGACATACCTGATGTAGCAGCAACTCTTACGGAAGCCTTCGCAACTGATCCA
CCCACGCAGTGGGTGTTCCCCGACGGTACTGCCGCCGTCAGCAGGTTCTTTACACATGTTGCAGATAGGGTTCACACGGCC
GGTGGTATTGTTGAGCTACTACCAGACAGAGCCGCCATGATTGCATTGCCACCACACGTGAGGCTGCCAGGAGAAGCTGCC
GACGGAAGGCAGGCGGAAATTCAGAGAAGGCTGGCAGACAGGCACCCGCTGACACCTCACTACTACCTGCTGTTTTACGGA
GTTAGAACGGCACACCAGGGTTCGGGATTGGCGGAAGAATGCTGGCCAGATTAACTAGCAGAGCTGATAGGGACAGGGTG
GGTACATATACTGAGGCATCCACCTGGCGTGGCGCTAGACTGATGCTGAGACATGGATTCCATGCTACAAGGCCACTAAGA
TTGCCAGATGGACCCAGCATGTTTCCACTTTGGAGAGATCCAATCCATGATCATTCTGATTAG

SEQ. ID NO: 25
MNTFRTATARDIPDVAATLTEAFATDPPTQWVFPDGTAAVSRFFTHVADRVHTAGGIVELLPDRAAMIALPPHVRLPGEAA
DGRQAEIQRRLADRHPLTPHYYLLFYGVRTAHQGSGLGGRMLARLTSRADRDRVGTYTEASTWRGARLMLRHGFHATRPLR
LPDGPSMFPLWRDPIHDHSD

SEQ. ID NO: 26
ATGAAAGGATATTTCGGACCATACGGTGGCCAGTACGTACCAGAAATATTAATGGGTGCCTTAGAGGAGTTAGAGGCAGCA
TACGAGGAGATTATGAAGGATGAGAGCTTCTGGAAGGAGTTCAACGATCTACTGAGGGATTACGCAGGCAGACCAACGCCA
TTGTACTTTGCCAGGAGATTGTCTGAGAAGTACGGCGCCCGTGTTTACTTGAAGCGTGAGGATCTGCTGCACACTGGAGCA

-continued

CACAAGATAAATAACGCTATCGGACAGGTTTTATTGGCCAAATTAATGGGGAAGACACGTATCATAGCCGAGACGGGAGCT

GGGCAGCATGGAGTCGCTACTGCTACCGCTGCTGCCCTGTTCGGAATGGAATGTGTGATCTACATGGGTGAAGAGGACACA

ATCAGACAGAAGTTGAACGTGGAGCGTATGAAATTATTAGGGGCTAAAGTTGTCCCTGTTAAGTCTGGCAGTAGGACCTTG

AAGGATGCGATAGACGAGGCTTTGAGAGACTGGATTACTAATTTACAGACAACATATTATGTTATCGGATCTGTTGTTGGT

CCCCACCCTTACCCAATTATCGTAAGGAATTTCCAGAAGGTTATCGGTGAGGAGACCAAGAAGCAAATACCAGAAAAGGAA

GGTCGTTTGCCAGACTATATAGTTGCCTGCGTAGGCGGCGGTAGCAATGCCGCAGGTATATTTTACCCATTCATAGACTCT

GGAGTAAAGCTGATAGGTGTTGAGGCAGGTGGCGAGGGATTGGAGACAGGTAAACACGCAGCCTCGTTATTAAAGGGTAAA

ATTGGCTATTTACATGGATCGAAGACCTTTGTTCTACAAGATGACTGGGGTCAAGTCCAAGTGAGCCATTCGGTGTCAGCT

GGTCTTGACTATTCAGGAGTAGGACCTGAGCATGCTTATTGGAGAGAGACAGGGAAGGTTCTGTACGACGCAGTGACTGAC

GAAGAGGCTTTGGACGCATTTATAGAGTTATCAAGACTAGAGGGCATTATACCCGCTTTAGAGTCATCGCATGCTCTAGCA

TATTTGAAGAAGATAAATATAAAAGGTAAGGTTGTGGTGGTCAACCTATCAGGGAGAGGGGATAAAGACCTGGAGTCAGTC

TTAAACCATCCATACGTGAGAGAAAGAATTAGATGA

SEQ. ID NO: 27
MKGYFGPYGGQYVPEILMGALEELEAAYEEIMKDESFWKEFNDLLRDYAGRPTPLYFARRLSEKYGARVYLKREDLLHTGA

HKINNAIGQVLLAKLMGKTRIIAETGAGQHGVATATAAALFGMECVIYMGEEDTIRQKLNVERMKLLGAKVVPVKSGSRTL

KDAIDEALRDWITNLQTTYYVIGSVVGPHPYPIIVRNFQKVIGEETKKQIPEKEGRLPDYIVACVGGGSNAAGIFYPFIDS

GVKLIGVEAGGEGLETGKHAASLLKGKIGYLHGSKTFVLQDDWGQVQVSHSVSAGLDYSGVGPEHAYWRETGKVLYDAVTD

EEALDAFIELSRLEGIIPALESSHALAYLKKINIKGKVVVVNLSGRGDKDLESVLNHPYVRERIR

SEQ. ID NO: 28
GGTAAGCCAATTCCAAATCCTTTGTTGGGTTTGGACTCCACC

SEQ. ID NO: 29
GKPIPNPLLGLDST

SEQ. ID NO: 30
GAAGAATTGTGAGCGGATAACAATTCCCCTCTAGAAATAATTTTGTTTAACTTTAAGAAGGAGATATACATATGGCAGATC

TCAATTGGATATCGGCCGGCCACGCGATCGCTGACGTCGGTACCCTCGAGTCTGGTAAAGAAACCGCTGCTGCGAAATTTG

AACGCCAGCACATGGACTCGTCTACTAGTCGCAGCTTAATTAACCTAAACTGCTGCCACCGCTGAGCAATAACTAGCATAA

CCCCTTGGGGCCTCTAAACGGGTCTTGAGGGGTTTTTTGCTAGCGAAAGGAGGAGTCGACTATATCCGGATTGGCGAATGG

GACGCGCCCTGTAGCGGCGCATTAAGCGCGGCGGGTGTGGTGGTTACGCGCAGCGTGACCGCTACACTTGCCAGCGCCCTA

GCGCCCGCTCCTTTCGCTTTCTTCCCTTCCTTTCTCGCCACGTTCGCCGGCTTTCCCCGTCAAGCTCTAAATCGGGGGCTC

CCTTTAGGGTTCCGATTTAGTGCTTTACGGCACCTCGACCCCAAAAAACTTGATTAGGGTGATGGTTCACGTAGTGGGCCA

TCGCCCTGATAGACGGTTTTTCGCCCTTTGACGTTGGAGTCCACGTTCTTTAATAGTGGACTCTTGTTCCAAACTGGAACA

ACACTCAACCCTATCTCGGTCTATTCTTTTGATTTATAAGGGATTTTGCCGATTTCGGCCTATTGGTTAAAAAATGAGCTG

ATTTAACAAAAATTTAACGCGAATTTTAACAAAATATTAACGTTTACAATTTCTGGCGGCACGATGGCATGAGATTATCAA

AAAGGATCTTCACCTAGATCCTTTTAAATTAAAAATGAAGTTTTAAATCAATCTAAAGTATATATGAGTAAACTTGGTCTG

ACAGTTACCAATGCTTAATCAGTGAGGCACCTATCTCAGCGATCTGTCTATTTCGTTCATCCATAGTTGCCTGACTCCCCG

TCGTGTAGATAACTACGATACGGGAGGGCTTACCATCTGGCCCCAGTGCTGCAATGATACCGCGAGACCCACGCTCACCGG

CTCCAGATTTATCAGCAATAAACCAGCCAGCCGGAAGGGCCGAGCGCAGAAGTGGTCCTGCAACTTTATCCGCCTCCATCC

AGTCTATTAATTGTTGCCGGGAAGCTAGAGTAAGTAGTTCGCCAGTTAATAGTTTGCGCAACGTTGTTGCCATTGCTACAG

GCATCGTGGTGTCACGCTCGTCGTTTGGTATGGCTTCATTCAGCTCCGGTTCCCAACGATCAAGGCGAGTTACATGATCCC

CCATGTTGTGCAAAAAAGCGGTTAGCTCCTTCGGTCCTCCGATCGTTGTCAGAAGTAAGTTGGCCGCAGTGTTATCACTCA

TGGTTATGGCAGCACTGCATAATTCTCTTACTGTCATGCCATCCGTAAGATGCTTTTCTGTGACTGGTGAGTACTCAACCA

AGTCATTCTGAGAATAGTGTATGCGGCGACCGAGTTGCTCTTGCCCGGCGTCAATACGGGATAATACCGCGCCACATAGCA

GAACTTTAAAAGTGCTCATCATTGGAAAACGTTCTTCGGGGCGAAAACTCTCAAGGATCTTACCGCTGTTGAGATCCAGTT

-continued

```
CGATGTAACCCACTCGTGCACCCAACTGATCTTCAGCATCTTTTACTTTCACCAGCGTTTCTGGGTGAGCAAAAACAGGAA
GGCAAAATGCCGCAAAAAAGGGAATAAGGGCGACACGGAAATGTTGAATACTCATACTCTTCCTTTTTCAATCATGATTGA
AGCATTTATCAGGGTTATTGTCTCATGAGCGGATACATATTTGAATGTATTTAGAAAAATAAACAAATAGGTCATGACCAA
AATCCCTTAACGTGAGTTTTCGTTCCACTGAGCGTCAGACCCCGTAGAAAAGATCAAAGGATCTTCTTGAGATCCTTTTTT
TCTGCGCGTAATCTGCTGCTTGCAAACAAAAAAACCACCGCTACCAGCGGTGGTTTGTTTGCCGGATCAAGAGCTACCAAC
TCTTTTTCCGAAGGTAACTGGCTTCAGCAGAGCGCAGATACCAAATACTGTCCTTCTAGTGTAGCCGTAGTTAGGCCACCA
CTTCAAGAACTCTGTAGCACCGCCTACATACCTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAGCTATGAGAAAGCGCCACGCTTCCCGAAGG
GAGAAAGGCGGACAGGTATCCGGTAAGCGGCAGGGTCGGAACAGGAGAGCGCACGAGGGAGCTTCCAGGGGGAAACGCCTG
GTATCTTTATAGTCCTGTCGGGTTTCGCCACCTCTGACTTGAGCGTCGATTTTTGTGATGCTCGTCAGGGGGCGGAGCCT
ATGGAAAAACGCCAGCAACGCGGCCTTTTTACGGTTCCTGGCCTTTTGCTGGCCTTTTGCTCACATGTTCTTTCCTGCGTT
ATCCCCTGATTCTGTGGATAACCGTATTACCGCCTTTGAGTGAGCTGATACCGCTCGCCGCAGCCGAACGACCGAGCGCAG
CGAGTCAGTGAGCGAGGAAGCGGAAGAGCGCCTGATGCGGTATTTTCTCCTTACGCATCTGTGCGGTATTTCACACCGCAT
ATATGGTGCACTCTCAGTACAATCTGCTCTGATGCCGCATAGTTAAGCCAGTATACACTCCGCTATCGCTACGTGACTGGG
TCATGGCTGCGCCCCGACACCCGCCAACACCCGCTGACGCGCCCTGACGGGCTTGTCTGCTCCCGGCATCCGCTTACAGAC
AAGCTGTGACCGTCTCCGGGAGCTGCATGTGTCAGAGGTTTTCACCGTCATCACCGAAACGCGCGAGGCAGCTGCGGTAAA
GCTCATCAGCGTGGTCGTGAAGCGATTCACAGATGTCTGCCTGTTCATCCGCGTCCAGCTCGTTGAGTTTCTCCAGAAGCG
TTAATGTCTGGCTTCTGATAAAGCGGGCCATGTTAAGGGCGGTTTTTTCCTGTTTGGTCACTGATGCCTCCGTGTAAGGGG
GATTTCTGTTCATGGGGGTAATGATACCGATGAAACGAGAGAGGATGCTCACGATACGGGTTACTGATGATGAACATGCCC
GGTTACTGGAACGTTGTGAGGGTAAACAACTGGCGGTATGGATGCGGCGGGACCAGAGAAAAATCACTCAGGGTCAATGCC
AGCGCTTCGTTAATACAGATGTAGGTGTTCCACAGGGTAGCCAGCAGCATCCTGCGATGCAGATCCGGAACATAATGGTGC
AGGGCGCTGACTTCCGCGTTTCCAGACTTTACGAAACACGGAAACCGAAGACCATTCATGTTGTTGCTCAGGTCGCAGACG
TTTTGCAGCAGCAGTCGCTTCACGTTCGCTCGCGTATCGGTGATTCATTCTGCTAACCAGTAAGGCAACCCCGCCAGCCTA
GCCGGGTCCTCAACGACAGGAGCACGATCATGCTAGTCATGCCCCGCGCCCACCGGAAGGAGCTGACTGGGTTGAAGGCTC
TCAAGGGCATCGGTCGAGATCCCGGTGCCTAATGAGTGAGCTAACTTACATTAATTGCGTTGCGCTCACTGCCCGCTTTCC
AGTCGGGAAACCTGTCGTGCCAGCTGCATTAATGAATCGGCCAACGCGCGGGGAGAGGCGGTTTGCGTATTGGGCGCCAGG
GTGGTTTTTCTTTTCACCAGTGAGACGGGCAACAGCTGATTGCCCTTCACCGCCTGGCCCTGAGAGAGTTGCAGCAAGCGG
TCCACGCTGGTTTGCCCCAGCAGGCGAAAATCCTGTTTGATGGTGGTTAACGGCGGGATATAACATGAGCTGTCTTCGGTA
TCGTCGTATCCCACTACCGAGATGTCCGCACCAACGCGCAGCCCGGACTCGGTAATGGCGCGCATTGCGCCCAGCGCCATC
TGATCGTTGGCAACCAGCATCGCAGTGGGAACGATGCCCTCATTCAGCATTTGCATGGTTTGTTGAAAACCGGACATGGCA
CTCCAGTCGCCTTCCCGTTCCGCTATCGGCTGAATTTGATTGCGAGTGAGATATTTATGCCAGCCAGCCAGACGCAGACGC
GCCGAGACAGAACTTAATGGGCCCGCTAACAGCGCGATTTGCTGGTGACCCAATGCGACCAGATGCTCCACGCCCAGTCGC
GTACCGTCTTCATGGGAGAAAATAATACTGTTGATGGGTGTCTGGTCAGAGACATCAAGAAATAACGCCGGAACATTAGTG
CAGGCAGCTTCCACAGCAATGGCATCCTGGTCATCCAGCGGATAGTTAATGATCAGCCCACTGACGCGTTGCGCGAGAAGA
TTGTGCACCGCCGCTTTACAGGCTTCGACGCCGCTTCGTTCTACCATCGACACCACCACGCTGGCACCCAGTTGATCGGCG
CGAGATTTAATCGCCGCGACAATTTGCGACGGCGCGTGCAGGGCCAGACTGGAGGTGGCAACGCCAATCAGCAACGACTGT
TTGCCCGCCAGTTGTTGTGCCACGCGGTTGGGAATGTAATTCAGCTCCGCCATCGCCGCTTCCACTTTTTCCCGCGTTTTC
GCAGAAACGTGGCTGGCCTGGTTCACCACGCGGGAAACGGTCTGATAAGAGACACCGGCATACTCTGCGACATCGTATAAC
GTTACTGGTTTCACATTCACCACCCTGAATTGACTCTCTTCCGGGCGCTATCATGCCATACCGCGAAAGGTTTTGCGCCAT
```

-continued

TCGATGGTGTCCGGGATCTCGACGCTCTCCCTTATGCGACTCCTGCATTAGGAAGCAGCCCAGTAGTAGGTTGAGGCCGTT

GAGCACCGCCGCCGCAAGGAATGGTGCATGCAAGGAGATGGCGCCCAACAGTCCCCGGCCACGGGGCCTGCCACCATACC

CACGCCGAAACAAGCGCTCATGAGCCCGAAGTGGCGAGCCCGATCTTCCCCATCGGTGATGTCGGCGATATAGGCGCCAGC

AACCGCACCTGTGGCGCCGGTGATGCCGGCCACGATGCGTCCGGCGTAGCCTAGGATCGAGATCGATCTCGATCCCGCGAA

ATTAATACGACTCACTACG

SEQ. ID NO: 31
ATGATGTCTGAAAATTTGCAATTGTCAGCTGAAGAAATGAGACAATTGGGTTACCAAGCAGTTGATTTGATCATCGATCAC

ATGAACCATTTGAAGTCTAAGCCAGTTTCAGAAACAATCGATTCTGATATCTTGAGAAATAAGTTGACTGAATCTATCCCA

GAAAATGGTTCAGATCCAAAGGAATTGTTGCATTTCTTGAACAGAAACGTTTTTAATCAAATTACACATGTTGATCATCCA

CATTTCTTGGCTTTTGTTCCAGGTCCAAATAATTACGTTGGTGTTGTTGCAGATTTCTTGGCTTCTGGTTTTAATGTTTTT

CCAACTGCATGGATTGCTGGTGCAGGTGCTGAACAAATCGAATTGACTACAATTAATTGGTTGAAATCTATGTTGGGTTTT

CCAGATTCAGCTGAAGGTTTATTTGTTTCTGGTGGTTCAATGGCAAATTTGACAGCTTTGACTGTTGCAAGACAGGCTAAG

TTGAACAACGATATCGAAAATGCTGTTGTTTACTTCTCTGATCAAACACATTTCTCAGTTGATAGAGCATTGAAGGTTTTA

GGTTTTAAACATCATCAAATCTGTAGAATCGAAACAGATGAACATTTGAGAATCTCTGTTTCAGCTTTGAAGAAACAAATT

AAAGAAGATAGAACTAAGGGTAAAAAGCCATTCTGTGTTATTGCAAATGCTGGTACTACAAATTGTGGTGCTGTTGATTCT

TTGAACGAATTAGCAGATTTGTGTAACGATGAAGATGTTTGGTTGCATGCTGATGGTTCTTATGGTGCTCCAGCTATCTTG

TCTGAAAAGGGTTCAGCTATGTTGCAAGGTATTCATAGAGCAGATTCTTTGACTTTAGATCCACATAAGTGGTTGTTCCAA

CCATACGATGTTGGTTGTGTTTTGATCAGAAACTCTCAATATTTGTCAAAGACTTTTAGAATGATGCCAGAATACATCAAG

GATTCAGAAACTAACGTTGAAGGTGAAATTAATTTCGGTGAATGTGGTATCGAATTGTCAAGAAGATTCAGAGCTTTGAAG

GTTTGGTTGTCTTTTAAAGTTTTCGGTGTTGCTGCTTTTAGACAAGCAATCGATCATGGTATCATGTTAGCAGAACAAGTT

GAAGCATTTTTGGGTAAAGCAAAAGATTGGGAAGTTGTTACACCAGCTCAATTGGGTATCGTTACTTTTAGATACATTCCA

TCTGAATTGGCATCAACAGATACTATTAATGAAATTAATAAGAAATTGGTTAAGGAAATCACACATAGAGGTTTCGCTATG

TTATCTACTACAGAATTGAAGGAAAAGGTTGTTATTAGATTGTGTTCAATTAATCCAAGAACTACAACTGAAGAAATGTTG

CAAATCATGATGAAGATTAAAGCATTGGCTGAAGAAGTTTCTATTTCATACCCATGTGTTGCTGAATAA

SEQ. ID NO: 32
MMSENLQLSAEEMRQLGYQAVDLIIDHMNHLKSKPVSETIDSDILRNKLTESIPENGSDPKELLHFLNRNVFNQITHVDHP

HFLAFVPGPNNYVGVVADFLASGFNVFPTAWIAGAGAEQIELTTINWLKSMLGFPDSAEGLFVSGGSMANLTALTVARQAK

LNNDIENAVVYFSDQTHFSVDRALKVLGFKHHQICRIETDEHLRISVSALKKQIKEDRTKGKKPFCVIANAGTTNCGAVDS

LNELADLCNDEDVWLHADGSYGAPAILSEKGSAMLQGIHRADSLTLDPHKWLFQPYDVGCVLIRNSQYLSKTFRMMPEYIK

DSETNVEGEINFGECGIELSRRFRALKVWLSFKVFGVAAFRQAIDHGIMLAEQVEAFLGKAKDWEVVTPAQLGIVTFRYIP

SELASTDTINEINKKLVKEITHRGFAMLSTTELKEKVVIRLCSINPRTTTEEMLQIMMKIKALAEEVSISYPCVAE

SEQ. ID NO: 33
CATCATCATCATCATCAT

SEQ. ID NO: 34
HHHHHH

SEQ. ID NO: 35
ATCCGGATATAGTTCCTCCTTTCAGCAAAAAACCCCTCAAGACCCGTTTAGAGGCCCCAAGGGGTTATGCTAGTTATTGCT

CAGCGGTGGCAGCAGCCAACTCAGCTTCCTTTCGGGCTTTGTTAGCAGCCGGATCTCAGTGGTGGTGGTGGTGGTGCTCGA

GTGCGGCCGCAAGCTTGTCGACGGAGCTCGAATTCGGATCCGCGACCCATTTGCTGTCCACCAGTCATGCTAGCCATATGG

CTGCCGCGCGGCACCAGGCCGCTGCTGTGATGATGATGATGATGGCTGCTGCCCATGGTATATCTCCTTCTTAAAGTTAAA

CAAAATTATTTCTAGAGGGGAATTGTTATCCGCTCACAATTCCCCTATAGTGAGTCGTATTAATTTCGCGGGATCGAGATC

TCGATCCTCTACGCCGGACGCATCGTGGCCGGCATCACCGGCGCCACAGGTGCGGTTGCTGGCGCCTATATCGCCGACATC

ACCGATGGGGAAGATCGGGCTCGCCACTTCGGGCTCATGAGCGCTTGTTTCGGCGTGGGTATGGTGGCAGGCCCCGTGGCC

-continued

GGGGGACTGTTGGGCGCCATCTCCTTGCATGCACCATTCCTTGCGGCGGCGGTGCTCAACGGCCTCAACCTACTACTGGGC

TGCTTCCTAATGCAGGAGTCGCATAAGGGAGAGCGTCGAGATCCCGGACACCATCGAATGGCGCAAAACCTTTCGCGGTAT

GGCATGATAGCGCCCGGAAGAGAGTCAATTCAGGGTGGTGAATGTGAAACCAGTAACGTTATACGATGTCGCAGAGTATGC

CGGTGTCTCTTATCAGACCGTTTCCCGCGTGGTGAACCAGGCCAGCCACGTTTCTGCGAAAACGCGGGAAAAAGTGGAAGC

GGCGATGGCGGAGCTGAATTACATTCCCAACCGCGTGGCACAACAACTGGCGGGCAAACAGTCGTTGCTGATTGGCGTTGC

CACCTCCAGTCTGGCCCTGCACGCGCCGTCGCAAATTGTCGCGGCGATTAAATCTCGCGCCGATCAACTGGGTGCCAGCGT

GGTGGTGTCGATGGTAGAACGAAGCGGCGTCGAAGCCTGTAAAGCGGCGGTGCACAATCTTCTCGCGCAACGCGTCAGTGG

GCTGATCATTAACTATCCGCTGGATGACCAGGATGCCATTGCTGTGGAAGCTGCCTGCACTAATGTTCCGGCGTTATTTCT

TGATGTCTCTGACCAGACACCCATCAACAGTATTATTTTCTCCCATGAAGACGGTACGCGACTGGGCGTGGAGCATCTGGT

CGCATTGGGTCACCAGCAAATCGCGCTGTTAGCGGGCCCATTAAGTTCTGTCTCGGCGCGTCTGCGTCTGGCTGGCTGGCA

TAAATATCTCACTCGCAATCAAATTCAGCCGATAGCGGAACGGGAAGGCGACTGGAGTGCCATGTCCGGTTTTCAACAAAC

CATGCAAATGCTGAATGAGGGCATCGTTCCCACTGCGATGCTGGTTGCCAACGATCAGATGGCGCTGGGCGCAATGCGCGC

CATTACCGAGTCCGGGCTGCGCGTTGGTGCGGATATCTCGGTAGTGGGATACGACGATACCGAAGACAGCTCATGTTATAT

CCCGCCGTTAACCACCATCAAACAGGATTTTCGCCTGCTGGGGCAAACCAGCGTGGACCGCTTGCTGCAACTCTCTCAGGG

CCAGGCGGTGAAGGGCAATCAGCTGTTGCCCGTCTCACTGGTGAAAAGAAAAACCACCCTGGCGCCCAATACGCAAACCGC

CTCTCCCCGCGCGTTGGCCGATTCATTAATGCAGCTGGCACGACAGGTTTCCCGACTGGAAAGCGGGCAGTGAGCGCAACG

CAATTAATGTAAGTTAGCTCACTCATTAGGCACCGGGATCTCGACCGATGCCCTTGAGAGCCTTCAACCCAGTCAGCTCCT

TCCGGTGGGCGCGGGGCATGACTATCGTCGCCGCACTTATGACTGTCTTCTTTATCATGCAACTCGTAGGACAGGTGCCGG

CAGCGCTCTGGGTCATTTTCGGCGAGGACCGCTTTCGCTGGAGCGCGACGATGATCGGCCTGTCGCTTGCGGTATTCGGAA

TCTTGCACGCCCTCGCTCAAGCCTTCGTCACTGGTCCCGCCACCAAACGTTTCGGCGAGAAGCAGGCCATTATCGCCGGCA

TGGCGGCCCCACGGGTGCGCATGATCGTGCTCCTGTCGTTGAGGACCCGGCTAGGCTGGCGGGGTTGCCTTACTGGTTAGC

AGAATGAATCACCGATACGCGAGCGAACGTGAAGCGACTGCTGCTGCAAAACGTCTGCGACCTGAGCAACAACATGAATGG

TCTTCGGTTTCCGTGTTTCGTAAAGTCTGGAAACGCGGAAGTCAGCGCCCTGCACCATTATGTTCCGGATCTGCATCGCAG

GATGCTGCTGGCTACCCTGTGGAACACCTACATCTGTATTAACGAAGCGCTGGCATTGACCCTGAGTGATTTTCTCTGGT

CCCGCCGCATCCATACCGCCAGTTGTTTACCCTCACAACGTTCCAGTAACCGGGCATGTTCATCATCAGTAACCCGTATCG

TGAGCATCCTCTCTCGTTTCATCGGTATCATTACCCCCATGAACAGAAATCCCCCTTACACGGAGGCATCAGTGACCAAAC

AGGAAAAAACCGCCCTTAACATGGCCCGCTTTATCAGAAGCCAGACATTAACGCTTCTGGAGAAACTCAACGAGCTGGACG

CGGCAGACATCTGTGAATCGCTTCACGACCACGCTGATGAGCTTTACCGCAGCTGCCTCGCGCGTTTCGGTGATGACGGTG

AAAACCTCTGACACATGCAGCTCCCGGAGACGGTCACAGCTTGTCTGTAAGCGGATGCCGGGAGCAGACAAGCCCGTCAGG

GCGCGTCAGCGGGTGTTGGCGGGTGTCGGGGCGCAGCCATGACCCAGTCACGTAGCGATAGCGGAGTGTATACTGGCTTAA

CTATGCGGCATCAGAGCAGATTGTACTGAGAGTGCACCATATATGCGGTGTGAAATACCGCACAGATGCGTAAGGAGAAAA

TACCGCATCAGGCGCTCTTCCGCTTCCTCGCTCACTGACTCGCTGCGCTCGGTCGTTCGGCTGCGGCGAGCGGTATCAGCT

CACTCAAAGGCGGTAATACGGTTATCCACAGAATCAGGGGATAACGCAGGAAAGAACATGTGAGCAAAAGGCCAGCAAAAG

GCCAGGAACCGTAAAAAGGCCGCGTTGCTGGCGTTTTTCCATAGGCTCCGCCCCCCTGACGAGCATCACAAAAATCGACGC

TCAAGTCAGAGGTGGCGAAACCCGACAGGACTATAAAGATACCAGGCGTTTCCCCCTGGAAGCTCCCTCGTGCGCTCTCCT

GTTCCGACCCTGCCGCTTACCGGATACCTGTCCGCCTTTCTCCCTTCGGGAAGCGTGGCGCTTTCTCATAGCTCACGCTGT

AGGTATCTCAGTTCGGTGTAGGTCGTTCGCTCCAAGCTGGGCTGTGTGCACGAACCCCCCGTTCAGCCCGACCGCTGCGCC

TTATCCGGTAACTATCGTCTTGAGTCCAACCCGGTAAGACACGACTTATCGCCACTGGCAGCAGCCACTGGTAACAGGATT

AGCAGAGCGAGGTATGTAGGCGGTGCTACAGAGTTCTTGAAGTGGTGGCCTAACTACGGCTACACTAGAAGGACAGTATTT

GGTATCTGCGCTCTGCTGAAGCCAGTTACCTTCGGAAAAAGAGTTGGTAGCTCTTGATCCGGCAAACAAACCACCGCTGGT

AGCGGTGGTTTTTTTGTTTGCAAGCAGCAGATTACGCGCAGAAAAAAAGGATCTCAAGAAGATCCTTTGATCTTTTCTACG

-continued

```
GGGTCTGACGCTCAGTGGAACGAAAACTCACGTTAAGGGATTTTGGTCATGAACAATAAAACTGTCTGCTTACATAAACAG

TAATACAAGGGGTGTTATGAGCCATATTCAACGGGAAACGTCTTGCTCTAGGCCGCGATTAAATTCCAACATGGATGCTGA

TTTATATGGGTATAAATGGGCTCGCGATAATGTCGGGCAATCAGGTGCGACAATCTATCGATTGTATGGGAAGCCCGATGC

GCCAGAGTTGTTTCTGAAACATGGCAAAGGTAGCGTTGCCAATGATGTTACAGATGAGATGGTCAGACTAAACTGGCTGAC

GGAATTTATGCCTCTTCCGACCATCAAGCATTTTATCCGTACTCCTGATGATGCATGGTTACTCACCACTGCGATCCCCGG

GAAAACAGCATTCCAGGTATTAGAAGAATATCCTGATTCAGGTGAAAATATTGTTGATGCGCTGGCAGTGTTCCTGCGCCG

GTTGCATTCGATTCCTGTTTGTAATTGTCCTTTTAACAGCGATCGCGTATTTCGTCTCGCTCAGGCGCAATCACGAATGAA

TAACGGTTTGGTTGATGCGAGTGATTTTGATGACGAGCGTAATGGCTGGCCTGTTGAACAAGTCTGGAAAGAAATGCATAA

ACTTTTGCCATTCTCACCGGATTCAGTCGTCACTCATGGTGATTTCTCACTTGATAACCTTATTTTTGACGAGGGGAAATT

AATAGGTTGTATTGATGTTGGACGAGTCGGAATCGCAGACCGATACCAGGATCTTGCCATCCTATGGAACTGCCTCGGTGA

GTTTTCTCCTTCATTACAGAAACGGCTTTTTCAAAAATATGGTATTGATAATCCTGATATGAATAAATTGCAGTTTCATTT

GATGCTCGATGAGTTTTTCTAAGAATTAATTCATGAGCGGATACATATTTGAATGTATTTAGAAAAATAAACAAATAGGGG

TTCCGCGCACATTTCCCCGAAAAGTGCCACCTGAAATTGTAAACGTTAATATTTTGTTAAAATTCGCGTTAAATTTTTGTT

AAATCAGCTCATTTTTTAACCAATAGGCCGAAATCGGCAAAATCCCTTATAAATCAAAAGAATAGACCGAGATAGGGTTGA

GTGTTGTTCCAGTTTGGAACAAGAGTCCACTATTAAAGAACGTGGACTCCAACGTCAAAGGGCGAAAAACCGTCTATCAGG

GCGATGGCCCACTACGTGAACCATCACCCTAATCAAGTTTTTTGGGGTCGAGGTGCCGTAAAGCACTAAATCGGAACCCTA

AAGGGAGCCCCCGATTTAGAGCTTGACGGGGAAAGCCGGCGAACGTGGCGAGAAAGGAAGGGAAGAAAGCGAAAGGAGCGG

GCGCTAGGGCGCTGGCAAGTGTAGCGGTCACGCTGCGCGTAACCACCACACCCGCCGCGCTTAATGCGCCGCTACAGGGCG

CGTCCCATTCGCCA

SEQ. ID NO: 36
GAACAAAAGTTAATTTCTGAAGAAGATTTGGAA

SEQ. ID NO: 37
EQKLISEEDL

SEQ. ID NO: 38
ATGGAGTCGTCGGCGGGGCCGATGGAGCTGGTGGCGGCGCTGCTGCGGGGGCTGACGCCGCGGGCGGAGCAGCTGCTGCAG

CTGTCGTCCGGGGGAGGGGAGGCCGCCGCCGGTGGCGCGGCGGAGGCGAGGGCCGCGGTGGCCACGGTGGCCGCCGCGCTG

CTCGGGTGCGCGTTCTTGGTGTTATGGAGGCGGGTCTCGGCGGGGCGGAAGCGGAAGAGGGAGGAGGCAGAGAGGTCGGCG

GCGGCCGTGGCTGGGGTGGGGAAGGGCGGGAAGAATGCCTCCGCGGCGGCCGGGGAGGAGGCCGGCGGCGCCGACGGGAGG

AAGCGGGTCACCGTCTTCTTCGGCACGCAGACCGGCACCGCCGAGGGCTTCGCCAAGGCACTCGCTGAGGAGGCTAAGTCA

AGATACGACAAGGCGATATTCAAAGTTGTGGACTTGGATGAGTATGCGATGGAGGATGAGGAGTACGAGGAGAGATTGAAG

AAGGAGAAGATATCGTTGTTCTTCGTTGCAACGTACGGAGATGGTGAACCGACTGACAATGCTGCTAGGTTCTATAAATGG

TTCACTGAGGGAAATGAGAGGGGTGTTTGGTTGAATGACTTCCAGTATGCTATTTTTGGTCTTGGCAATCGGCAGTATGAG

CATTTCAACAAGGTTGCCAAGGTTGTTGATGAGCTCCTAGTTGAGCAAGGTGGAAAACGTCTTGTTCCGGTTGGTCTTGGA

GATGATGATCAATGCATTGAGGATGACTTCAACGCATGGAAAGAAACTCTCTGGCCAGAATTGGATCAGTTACTTCGGGAT

GAAAATGATGTTTCAACAGGCACTACCTACACAGCTGCCATTCCTGAATACCGGGTTGAATTTGTTAAGCCTGATGAGGCA

GCCCATTTGGAGAGAAATTTCAGTCTTGCAAACGGTTATGCGGTTCATGATGCTCAGCATCCTTGCCGGGCAACGTGGCT

GTGCGACGGGAACTCCACACTCCTGCTTCTGATCGTTCATGCACTCACTTGGAGTTTGACATTGCTGGCACTGGTCTTACG

TATGAAACCGGTGACCATGTTGGTGTATACACAGAGAACTGCCTCGAGGTTGTAGAGGAGGCAGAGAGGTTGTTAGGCTAC

TCCCCAGAGGCTTTTTTCACCATCCATGCAGACAAAGAGGACGGTACACCACTAGGTGGTGGTTCTCTGGCTCCTCCATTC

CCTTCCCCGATTACTGTGAGGAATGCGCTTGCTAGATATGCGGATCTTCTGAATTCGCCGAAGAAGAGTGCTTTGGTTGCA

TTAGCTACTTATGCTTCAGATTCTACTGAAGCTGATCGTCTGAGGTTCTTGGCCTCTCCTGCTGGAAAGGATGAGTATGCT

CAATGGGTTGTTGCGAGTCAAAGAAGTCTATTAGAAGTGATGGCAGAGTTCCCTTCAGCAAAGCCTCCACTAGGAGTCTTC
```

-continued

```
TTTGCAGCCGTTGCTCCTCGTCTTCAGCCGAGATACTACTCAATTTCATCTTCACCTAGCATGGCACCTACCAGAATTCAT

GTTACATGTGCACTTGTCCATGAAAAAACACCTGCTGGAAGGGTACATAAGGGAGTCTGCTCAACATGGATTAAGAATGCT

ATTCCATCAGAAGAGACAAAGGACTGCAGCTGGGCTCCAGTTTTTGTGAGACAATCAAACTTCAAACTGCCTGCTGATCCT

TCAGTACCGGTTATCATGATTGGCCCAGGAACTGGTCTTGCTCCTTTCCGCGGATTCTTGCAGGAGAGGCTGTCTCAAAAA

CAATCAGGAGCTGAGCTTGGTCGCTCCGTATTCTTCTTTGGATGCAGAAACAGCAAGATGGACTTCATCTATGAGGATGAG

CTGAACACTTTCCTTGAGGAAGGAGCATTGTCCGAGCTGGTTCTCGCCTTCTCTCGTGAGGGCCCTACGAAGGAATACGTG

CAGCACAAAATGTCGCAGAAAGCTTCCGAAATCTGGGACATGATCTCCCAGGGTGGTTACATTTACGTCTGTGGTGATGCC

AAAGGCATGGCCAGAGATGTACATAGAGTTCTCCACACCATTGTACAGGAACAGGGATCACTTGACAGCTCTAAGGCTGAG

AGCTTTGTGAAGAGCCTCCAAACGGAGGGTAGGTATCTGAGAGATGTGTGGTGA
```

SEQ. ID NO: 39
```
MESSAGPMELVAALLRGLTPRAEQLLQLSSGGGEAAAGGAAEARAAVATVAAALLGCAFLVLWRRVSAGRKRKREEAERSA

AAVAGVGKGGKNASAAAGEEAGGADGRKRVTVFFGTQTGTAEGFAKALAEEAKSRYDKAIFKVVDLDEYAMEDEEYEERLK

KEKISLFFVATYGDGEPTDNAARFYKWFTEGNERGVWLNDFQYAIFGLGNRQYEHFNKVAKVVDELLVEQGGKRLVPVGLG

DDDQCIEDDFNAWKETLWPELDQLLRDENDVSTGTTYTAAIPEYRVEFVKPDEAAHLERNFSLANGYAVHDAQHPCRANVA

VRRELHTPASDRSCTHLEFDIAGTGLTYETGDHVGVYTENCLEVVEEAERLLGYSPEAFFTIHADKEDGTPLGGGSLAPPF

PSPITVRNALARYADLLNSPKKSALVALATYASDSTEADRLRFLASPAGKDEYAQWVVASQRSLLEVMAEFPSAKPPLGVF

FAAVAPRLQPRYYS1SSSPSMAPTRIHVTCALVHEKTPAGRVHKGVCSTWIKNAIPSEETKDCSWAPVFVRQSNFKLPADP

SVPVIMIGPGTGLAPFRGFLQERLSQKQSGAELGRSVFFFGCRNSKMDFIYEDELNTFLEEGALSELVLAFSREGPTKEYV

QHKMSQKASEIWDMISQGGYIYVCGDAKGMARDVHRVLHTTVQEQGSLDSSKAESFVKSLQTEGRYLRDVW
```

SEQ. ID NO: 40
```
TACCCATACGACGTTCCAGACTACGCC
```

SEQ. ID NO: 41
```
YPYDVPDYA
```

SEQ. ID NO: 42
```
ATGTCCCCTATACTAGGTTATTGGAAAATTAAGGGCCTTGTGCAACCCACTCGACTTCTTTTGGAATATCTTGAAGAAAAA

TATGAAGAGCATTTGTATGAGCGCGATGAAGGTGATAAATGGCGAAACAAAAAGTTTGAATTGGGTTTGGAGTTTCCCAAT

CTTCCTTATTATATTGATGGTGATGTTAAATTAACACAGTCTATGGCCATCATACGTTATATAGCTGACAAGCACAACATG

TTGGGTGGTTGTCCAAAAGAGCGTGCAGAGATTTCAATGCTTGAAGGAGCGGTTTTGGATATTAGATACGGTGTTTCGAGA

ATTGCATATAGTAAAGACTTTGAAACTCTCAAAGTTGATTTTCTTAGCAAGCTACCTGAAATGCTGAAAATGTTCGAAGAT

CGTTTATGTCATAAAACATATTTAAATGGTGATCATGTAACCCATCCTGACTTCATGTTGTATGACGCTCTTGATGTTGTT

TTATACATGGACCCAATGTGCCTGGATGCGTTCCCAAAATTAGTTTGTTTTAAAAAACGTATTGAAGCTATCCCACAAATT

GATAAGTACTTGAAATCCAGCAAGTATATAGCATGGCCTTTGCAGGGCTGGCAAGCCACGTTTGGTGGTGGCGACCATCCT

CCAAAATCGGATCTGGAAGTTCTGTTCCAGGGGCCCCTGGGATCCCCGATGCTGCCGCCGTCGCCGCCGGGGTGGCCGGTG

ATCGGGCACCTCCACCTCATGTCCGGCATGCCGCACCACGCGCTGGCCGAGCTGGCGCGCACCATGCGCGCGCCGCTGTTC

CGGATGCGGCTGGGGAGCGTGCCGGCGGTGGTGATCTCCAAGCCGGACCTCGCCCGCGCCGCTCACCACCAACGACGCC

GCGCTGGCGTCGCGGCCGCACCTGCTCTCCGGCCAGTTCCTGTCGTTCGGCTGCTCCGACGTGACGTTCGCGCCGGCGGGG

CCGTACCACCGGATGGCGCGCCGCGTGGTGGTGTCGGAGCTCCTGTCGGCGCGTCGCGTCGCCACGTACGGCGCCGTCAGG

GTCAAGGAGCTCCGCCGCCTGCTCGCGCACCTCACCAAGAACACCTCGCCGGCGAAGCCCGTCGACCTCAGCGAGTGCTTC

CTCAACCTCGCCAACGACGTGCTCTGCCGCGTCGCGTTCGGCCGCCGGTTCCCGCACGGCGAGGGCGACAAGCTCGGCGCG

GTGCTCGCCGAGGCGCAGGACCTCTTCGCCGGGTTCACCATCGGCGACTTCTTCCCCGAGCTCGAGCCCGTCGCCAGCACC

GTCACCGGACTCCGCCGCCGCCTCAAGAAGTGCCTCGCCGACCTCCGCGAGGCCTGCGACGTGATCGTGGACGAACACATC

AGCGGCAACCGCCAGCGCATCCCCGGCGACCGCGACGAGGACTTCGTCGACGTCCTCCTCCGCGTCCAGAAATCCCCCGAC
```

-continued

CTCGAGGTCCCCCTAACCGACGACAATCTCAAGGCCCTCGTCCTGGACATGTTCGTCGCCGGCACGGACACCACGTTCGCG
ACGCTGGAGTGGGTGATGACGGAGCTAGTCCGCCACCCACGGATCCTCAAGAAGGCGCAGGAGGAGGTCCGGCGAGTCGTC
GGCGACAGCGGCCGCGTCGAGGAGTCCCACCTCGGCGAGCTCCACTACATGCGCGCCATCATCAAGGAGACGTTCCGGCTG
CACCCGGCGGTGCCGTTGCTAGTGCCGCGCGAGTCCGTCGCGCCGTGCACGCTGGGCGGCTACGACATCCCGGCGAGGACG
CGGGTGTTCATCAACACGTTCGCCATGGGGCGCGACCCGGAGATCTGGGACAACCCGCTGGAGTACTCGCCGGAGAGGTTC
GAGAGCGCCGGCGGCGGCGGCGAGATCGACCTCAAGGACCCGGACTACAAGCTGCTGCCGTTCGGCGGCGGGCGGCGAGGG
TGCCCCGGCTACACGTTCGCGCTCGCCACCGTGCAGGTGTCGCTCGCCAGCTTGCTCTACCACTTCGAGTGGGCGCTGCCC
GCCGGCGTGCGCGCCGAGGACGTCAACCTCGACGAGACGTTCGGCCTCGCCACGAGGAAGAAGGAGCCGCTCTTCGTCGCC
GTCAGGAAGAGCGACGCGTACGAGTTTAAGGGAGAGGAGCTTAGTGAGGTTTACCCATACTGA

SEQ. ID NO: 43
MSPILGYWKIKGLVQPTRLLLEYLEEKYEEHLYERDEGDKWRNKKFELGLEFPNLPYYIDGDVKLTQSMAIIRYIADKHNM
LGGCPKERABISMLEGAVLDIRYGVSRIAYSKDFETLKVDFLSKLPEMLKMFEDRLCHKTYLNGDHVTHPDFMLYDALDVV
LYMDPMCLDAFPKLVCFKKRIEAIPQIDKYLKSSKYIAWPLQGWQATFGGGDHPPKSDLEVLFQGPLGSPMLPPSPPGWPV
IGHLHLMSGMPHHALAELARTMRAPLFRMRLGSVPAVVISKPDLARAALTTNDAALASRPHLLSGQFLSFGCSDVTFAPAG
PYHRMARRVVVSELLSARRVATYGAVRVKELRRLLAHLTKNTSPAKPVDLSECFLNLANDVLCRVAFGRRFPHGEGDKLGA
VLAEAQDLFAGFTIGDFFPELEPVASTVTGLRRRLKKCLADLREACDVIVDEHISGNRQRIPGDRDEDFVDVLLRVQKSPD
LEVPLTDDNLKALVIDMFVAGTDTTFATLEWVMTELVRHPRILKKAQEEVRRVVGDSGRVEESHLGELHYMRAIIKETFRL
HPAVPLLVPRESVAPCTLGGYDIPARTRVFINTFAMGRDPEIWDNPLEYSPERFESAGGGGEIDLKDPDYKLLPFGGGRRG
CPGYTFALATVQVSLASLLYHFEWALPAGVRAEDVNLDETFGLATRKKEPLFVAVRKSDAYEFKGEELSEVYPY

SEQ. ID NO: 44
GGGGAATTGTGAGCGGATAACAATTCCCCTGTAGAAATAATTTTGTTTAACTTTAATAAGGAGATATACCATGGGCAGCAG
CCATCACCATCATCACCACAGCCAGGATCCGAATTCGAGCTCGGCGCGCCTGCAGGTCGACAAGCTTGCGGCCGCATAATG
CTTAAGTCGAACAGAAAGTAATCGTATTGTACACGGCCGCATAATCGAAATTAATACGACTCACTATAGGGGAATTGTGAG
CGGATAACAATTCCCCATCTTAGTATATTAGTTAAGTATAAGAAGGAGATATACATATGGCAGATCTCAATTGGATATCGG
CCGGCCACGCGATCGCTGACGTCGGTACCCTCGAGTCTGGTAAAGAAACCGCTGCTGCGAAATTTGAACGCCAGCACATGG
ACTCGTCTACTAGCGCAGCTTAATTAACCTAGGCTGCTGCCACCGCTGAGCAATAACTAGCATAACCCCTTGGGGCCTCTA
AACGGGTCTTGAGGGGTTTTTTGCTGAAACCTCAGGCATTTGAGAAGCACACGGTCACACTGCTTCCGGTAGTCAATAAAC
CGGTAAACCAGCAATAGACATAAGCGGCTATTTAACGACCCTGCCCTGAACCGACGACCGGGTCATCGTGGCCGGATCTTG
CGGCCCCTCGGCTTGAACGAATTGTTAGACATTATTTGCCGACTACCTTGGTGATCTCGCCTTTCACGTAGTGGACAAATT
CTTCCAACTGATCTGCGCGCGAGGCCAAGCGATCTTCTTCTTGTCCAAGATAAGCCTGTCTAGCTTCAAGTATGACGGGCT
GATACTGGGCCGGCAGGCGCTCCATTGCCCAGTCGGCAGCGACATCCTTCGGCGCGATTTTGCCGGTTACTGCGCTGTACC
AAATGCGGGACAACGTAAGCACTACATTTCGCTCATCGCCAGCCCAGTCGGGCGGCGAGTTCCATAGCGTTAAGGTTTCAT
TTAGCGCCTCAAATAGATCCTGTTCAGGAACCGGATCAAAGAGTTCCTCCGCCGCTGGACCTACCAAGGCAACGCTATGTT
CTCTTGCTTTTGTCAGCAAGATAGCCAGATCAATGTCGATCGTGGCTGGCTCGAAGATACCTGCAAGAATGTCATTGCGCT
GCCATTCTCCAAATTGCAGTTCGCGCTTAGCTGGATAACGCCACGGAATGATGTCGTCGTGCACAACAATGGTGACTTCTA
CAGCGCGGAGAATCTCGCTCTCTCCAGGGGAAGCCGAAGTTTCCAAAAGGTCGTTGATCAAAGCTCGCCGCGTTGTTTCAT
CAAGCCTTACGGTCACCGTAACCAGCAAATCAATATCACTGTGTGGCTTCAGGCCGCCATCCACTGCGGAGCCGTACAAAT
GTACGGCCAGCAACGTCGGTTCGAGATGGCGCTCGATGACGCCAACTACCTCTGATAGTTGAGTCGATACTTCGGCGATCA
CCGCTTCCCTCATACTCTTCCTTTTTCAATATTATTGAAGCATTTATCAGGGTTATTGTCTCATGAGCGGATACATATTTG
AATGTATTTAGAAAAATAAACAAATAGCTAGCTCACTCGGTCGCTACGCTCCGGGCGTGAGACTGCGGCGGGCGCTGCGGA
CACATACAAAGTTACCCACAGATTCCGTGGATAAGCAGGGGACTAACATGTGAGGCAAAACAGCAGGGCCGCGCCGGTGGC
GTTTTTCCATAGGCTCCGCCCTCCTGCCAGAGTTCACATAAACAGACGCTTTTCCGGTGCATCTGTGGGAGCCGTGAGGCT

-continued

```
CAACCATGAATCTGACAGTACGGGCGAAACCCGACAGGACTTAAAGATCCCCACCGTTTCCGGCGGGTCGCTCCCTCTTGC
GCTCTCCTGTTCCGACCCTGCCGTTTACCGGATACCTGTTCCGCCTTTCTCCCTTACGGGAAGTGTGGCGCTTTCTCATAG
CTCACACACTGGTATCTCGGCTCGGTGTAGGTCGTTCGCTCCAAGCTGGGCTGTAAGCAAGAACTCCCCGTTCAGCCCGAC
TGCTGCGCCTTATCCGGTAACTGTTCACTTGAGTCCAACCCGGAAAAGCACGGTAAAACGCCACTGGCAGCAGCCATTGGT
AACTGGGAGTTCGCAGAGGATTTGTTTAGCTAAACACGCGGTTGCTCTTGAAGTGTGCGCCAAAGTCCGGCTACACTGGAA
GGACAGATTTGGTTGCTGTGCTCTGCGAAAGCCAGTTACCACGGTTAAGCAGTTCCCCAACTGACTTAACCTTCGATCAAA
CCACCTCCCCAGGTGGTTTTTTCGTTTACAGGGCAAAAGATTACGCGCAGAAAAAAAGGATCTCAAGAAGATCCTTTGATC
TTTTCTACTGAACCGCTCTAGATTTCAGTGCAATTTATCTCTTCAAATGTAGCACCTGAAGTCAGCCCCATACGATATAAG
TTGTAATTCTCATGTTAGTCATGCCCCGCGCCCACCGGAAGGAGCTGACTGGGTTGAAGGCTCTCAAGGGCATCGGTCGAG
ATCCCGGTGCCTAATGAGTGAGCTAACTTACATTAATTGCGTTGCGCTCACTGCCCGCTTTCCAGTCGGGAAACCTGTCGT
GCCAGCTGCATTAATGAATCGGCCAACGCGCGGGGAGAGGCGGTTTGCGTATTGGGCGCCAGGGTGGTTTTTCTTTTCACC
AGTGAGACGGGCAACAGCTGATTGCCCTTCACCGCCTGGCCCTGAGAGAGTTGCAGCAAGCGGTCCACGCTGGTTTGCCCC
AGCAGGCGAAAATCCTGTTTGATGGTGGTTAACGGCGGGATATAACATGAGCTGTCTTCGGTATCGTCGTATCCCACTACC
GAGATGTCCGCACCAACGCGCAGCCCGGACTCGGTAATGGCGCGCATTGCGCCCAGCGCCATCTGATCGTTGGCAACCAGC
ATCGCAGTGGGAACGATGCCCTCATTCAGCATTTGCATGGTTTGTTGAAAACCGGACATGGCACTCCAGTCGCCTTCCCGT
TCCGCTATCGGCTGAATTTGATTGCGAGTGAGATATTTATGCCAGCCAGCCAGACGCAGACGCGCCGAGACAGAACTTAAT
GGGCCCGCTAACAGCGCGATTTGCTGGTGACCCAATGCGACCAGATGCTCCACGCCCAGTCGCGTACCGTCTTCATGGGAG
AAAATAATACTGTTGATGGGTGTCTGGTCAGAGACATCAAGAAATAACGCCGGAACATTAGTGCAGGCAGCTTCCACAGCA
ATGGCATCCTGGTCATCCAGCGGATAGTTAATGATCAGCCCACTGACGCGTTGCGCGAGAAGATTGTGCACCGCCGCTTTA
CAGGCTTCGACGCCGCTTCGTTCTACCATCGACACCACCACGCTGGCACCCAGTTGATCGGCGCGAGATTTAATCGCCGCG
ACAATTTGCGACGGCGCGTGCAGGGCCAGACTGGAGGTGGCAACGCCAATCAGCAACGACTGTTTGCCCGCCAGTTGTTGT
GCCACGCGGTTGGGAATGTAATTCAGCTCCGCCATCGCCGCTTCCACTTTTTCCCGCGTTTTCGCAGAAACGTGGCTGGCC
TGGTTCACCACGCGGGAAACGGTCTGATAAGAGACACCGGCATACTCTGCGACATCGTATAACGTTACTGGTTTCACATTC
ACCACCCTGAATTGACTCTCTTCCGGGCGCTATCATGCCATACCGCGAAAGGTTTTGCGCCATTCGATGGTGTCCGGGATC
TCGACGCTCTCCCTTATGCGACTCCTGCATTAGGAAATTAATACGACTCACTATA
```

Hereinafter are provided examples of specific implementations for performing the methods of the present disclosure, as well as implementations representing the compositions of the present disclosure. The examples are provided for illustrative purposes only, and are not intended to limit the scope of the present disclosure in any way.

EXAMPLES

Example 1—Process for Biosynthetically Making a First Hydroxylated Psilocybin Derivative from Hydroxylated Indole Feedstock E. coli strain Ec-1 was constructed as follows. For plasmid cloning, Top10 or XL1-blue strains were used depending on antibiotic markers. Standard LB media was used for culturing. For gene expression and feeding experiments, the parent host strain employed was BL21 (DE3). From plasmid pCDM4 (SEQ. ID NO: 21), the plasmid pCDM4-PsmF-FLAG was created by inserting an in-frame, C-terminally FLAG-tagged (SEQ. ID NO: 22; SEQ. ID NO: 23) PsmF gene (SEQ. ID NO: 24) into the NdeI/XhoI site of pCDM4. The plasmid pETM6-H10-TmTrpB-2F3-V5-BaTDC-FLAG was created by first cloning the in-frame, C-terminally V5-tagged (SEQ. ID NO: 28) TmTrpB-2F3 (SEQ. ID NO: 26) into the NdeI/XhoI site of pETM6-110 (SEQ. ID NO: 30) to create pETM6-H$_{10}$-TmTrpB-2F3-V5. This intermediate plasmid was digested with SpeI and SalI, and in-frame, C-terminally FLAG tagged (SEQ. ID NO: 22) BaTDC (SEQ. ID NO: 31) was cloned into the site with XbaI and SalI, nullifying the SpeI restriction site. In this setup, the T7 polymerase was able to drive the expression of the polycistronic DNA containing both TmTrpB-2F3 and BaTDC, The two target plasmids pCDM4-PsmF-FLAG and pETM6-H10-TmTrpB-2F3-V5-BaTDC-FLAG were transformed into BL21 (DE3) cells, and antibiotics ampicillin plus streptomycin were used to select for the correct clones containing both plasmids. Scaled-up culturing of engineered E. coli was conducted as follows: seed cultures were inoculated in AMM (Jones et al. 2015, Sci Rep. 5: 11301) medium overnight. The overnight culture was then divided into two flasks containing 500 mL each of AMM medium additionally containing 0.5% (w/v) serine, 1M IPTG, 50 ug/L ampicillin and streptomyces, and 100 mg/L 4-hydroxy-7-methylindole (BLDPharm, www.bldpharm.com) for conversion by Ec-1. Cultures were grown for 24 h. Cultures were then centrifuged (10,000 g×5 minutes) to remove cellular content, and culture broth containing secreted derivative was stored at −80° C. until further processing. The N-[2-(4-hydroxy-7-methyl-1H-indol-3-yl)ethyl]acetamide product having chemical formula (IV):

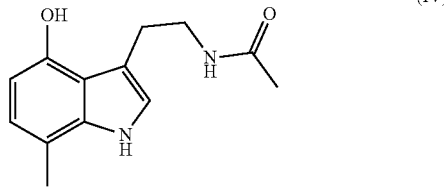

contained in 1 L of E. coli culture was extracted by ethyl acetate (3×600 ml). The organic layer was dried over $Na_2SO_4$, followed by concentration under reduced pressure. The residue was purified by flash chromatography on silica gel using ethyl acetate-hexane (50→70%) as eluent, followed by crystallization from acetone/hexane to give the compound as a pink solid (80 mg). Following purification, high-resolution MS (HRMS), $^1H$ NMR, and selective $^{13}C$ NMR were performed to assess purity, estimate total quantity, and confirm molecular structure. $^1H$ NMR (400 MHz, $CD_3OD$): δ=1.89 (s, 3H), 2.38 (s, 3H), 3.14 (t, J=6.7 Hz, 2H), 3.49 (t, J=6.9 Hz, 2H), 6.28 (d, J=7.6 Hz, 1H), 6.68 (dd, J=7.6, 0.6 Hz, 1H), 6.91 (s, 1H). $^{13}C$ NMR (100 MHz, $CD_3OD$): δ=14.8, 21.2, 25.9, 41.7, 102.7, 111.9, 112.7, 116.3, 120.9, 121.8, 138.1, 149.4, 171.8. HRMS (ESI) m/z: calcd. for $C_{13}H_{16}N_2O_2$ [M+H]$^+$ 233.1284, found 233.1283. The purity of compound (IV) was determined to be 95% (w/w).

Cell lines for pharmacology assays. CHO-K1/Galpha15 (GenScript, M00257) (−5-$HT_{2A}$) and CHO-K1/5-$HT_{2A}$ (GenScript, M00250) (+5-$HT_{2A}$) cells lines were used in both toxicology/growth inhibition (MTT) and calcium release assays. Briefly, CHO-K1/Galpha15 is a control cell line that constitutively expresses Galpha15 which is a promiscuous Gq protein. It is engineered as a host cell, allowing transfected receptor(s) to signal through the Gq signal transduction pathway and mobilize intracellular calcium from the endoplasmic reticulum (ER). These control cells lack any transgene encoding 5-$HT_{2A}$ receptors, thus preventing calcium mobilization in response to 5-$HT_{2A}$ activation. Conversely, CHO-K1/5-$HT_{2A}$ cells stably express 5-$HT_{2A}$ receptor in the CHO-K1 host background. This design enables Gq-11 expressed in CHO-K1 cells to mobilize intracellular calcium changes when 5-$HT_{2A}$ receptors are activated by ligands.

Cell lines were maintained in Ham's F12 media plus 10% FBS in the presence of 100 ug/ml hygromycin for CHO-K1/Ga15 or 400 ug/ml G418 for CHO-K1/5-$HT_{2A}$ unless indicated otherwise for specific assays. Cell maintenance was carried out as recommended by the cell supplier. Briefly, vials with cells were removed from the liquid nitrogen and thawed quickly in 37° C. water bath. Just before cells were completely thawed, vial exteriors were decontaminated with 70% ethanol spray. Cell suspension was then retrieved from the vial and added to warm (37° C.), 'complete' (non-dropout) growth media, and centrifuged at 1,000 rpm for 5 minutes. The supernatant was discarded and the cell pellet was then resuspended in another 10 ml of complete growth media, and added to a 10 cm cell culture dish (Greiner Bio-One #664160). The media was changed every third day until the cells reached ~90% confluence. The ~90% confluent cells were then split 10:1, and used either for maintenance or pharmacological study.

Figure 8A:
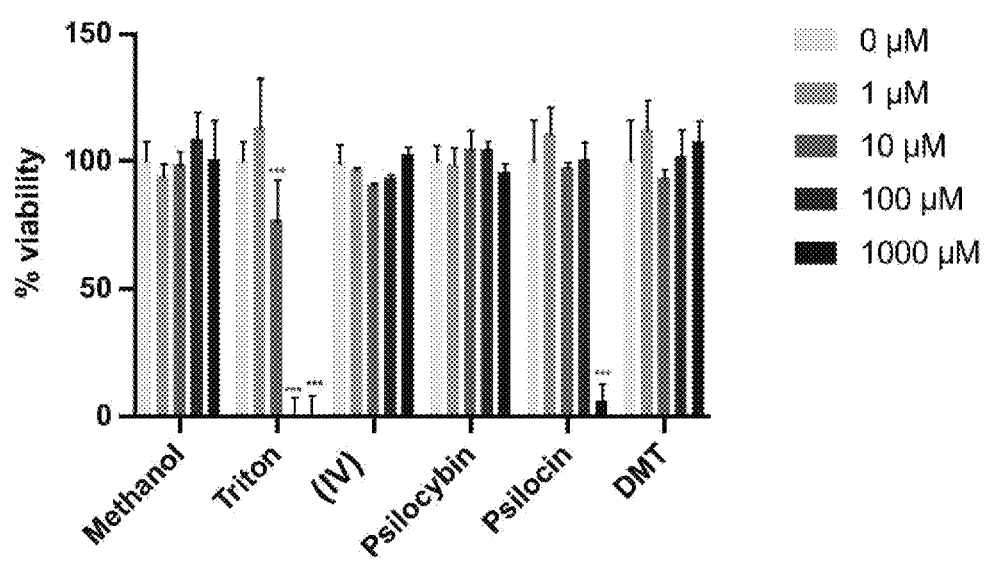
FIGS. 8A, 8B, 8C, and 8D depict various graphs obtained in the performance of an experimental assay to evaluate the efficacy of an example hydroxylated psilocybin derivative having the chemical formula (IV) set forth herein, notably a cell viability assay (FIG. 8A), a serotonin positive allosteric modulation assay in +5-$HT_{2a}$ cells (FIG. 8B), a serotonin calcium flux assay (FIG. 8C), and control assays: serotonin response in −5-$HT_{2a}$ cells (FIG. 8D—panel A) and methanol response in +5-$HT_{2a}$ cells (FIG. 8D—panel B).

Assessment of cell viability upon treatment of hydroxylated psilocybin derivatives. To establish suitable ligand concentrations for the calcium release assays, MTT (3-(4,5-dimethylthiazol-2-yl)-2,5-diphenyltetrazolium) assays were first performed. Results of these assays were conducted using both control ligands (e.g. psilocybin, psilocin, DMT) and novel derivatives, in part as a pre-screen for any remarkable toxic effects on cell cultures up to concentrations of 1 mM. A known cellular toxin (Triton X-100, Pyrgiotakis G. et al., 2009, Ann. Biomed. Eng. 37: 1464-1473) was included as a general marker of toxicity. Modified Chinese Hamster Ovary cells (CHO-K1/Ga15) were cultured using standard procedures using the manufacture's protocols (Genscript, M00257). Briefly, cells were cultured in Ham's F12 medium supplemented with 10% fetal bovine serum and 100 mg/ml hygromycin B, and grown at 37° C. in the presence of 5% $CO_2$. To test the various compounds with the cell line, cells were seeded in a clear 96-well culture plate at 10,000 cells per well. After allowing cells to attach and grow for 24 hours, assay compounds were added at 1 μM, 10 μM, 100 μM, and 1 mM final concentrations. Methanol concentrations used are 0.001, 0.01, 0.1, and 1%. Triton concentrations used are 0.0001, 0.001, 0.01 and 0.1%. Cells were incubated with compounds for 48 hours before accessing cell viability with the MTT assay following the manufacture's protocol (MTT Cell Growth Assay Kit; Millipore Sigma, CT02). MTT reagent was added to cells and allowed to incubate for 4 hours before solubilization with isopropanol plus 0.04 N HCl. Absorbance readings were performed at 570 nm with the reference at 630 nm on a SpectraMax iD3 plate reader. Non-treated cells were assigned 100% viability. Results of the cell viability assays are shown in FIG. 8A. Bar graphs show the mean +/−SD (n=3). Significance (P<0.0001), as indicated by (***) was determined using 2-way ANOVA with Dunnett's multiple comparisons test. The results using compound with formula (IV) are indicated as "(IV)" on the x-axis.

Figure 8B:
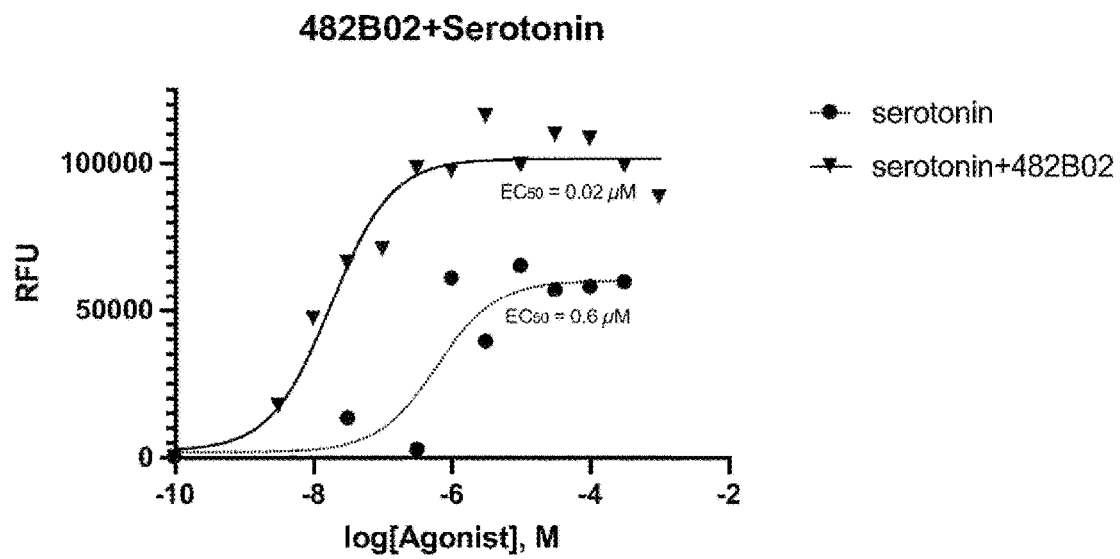

Increase in cytosolic calcium concentration by 5-$HT_{2A}$ activation and assessment of modulation. Changes in intracellular calcium concentration due to the treatment with assay compounds was measured using Fluo-8 dye (Abcam, #ab112129) according to the manufacturer's instructions. Briefly, CHO-K1 cells stably expressing 5-$HT_{2A}$ (Genscript #M00250) (+5-$HT_{2A}$) or lacking 5-$HT_{2A}$ (Genscript, M00257) (−5-$HT_{2A}$) were seeded on black walled clear bottom 96-well plates (Thermo Scientific #NUNC165305), allowing 70,000 cells/well in 100 ul media (HAM's F12, GIBCO #11765-047) with 1% FBS (Thermo Scientific #12483020). Cultures were maintained in a humidified incubator at 37° C. and 5% $CO_2$. Fluo-8 dye was loaded into the cultures for 30 min at 37° C., followed by 30 min additional incubation at room temperature. Next, different dilutions of novel molecules and controls were prepared in serum-free culture media and added to the cells. Fluorescence (ex 490 nm/em 525 nm) obtained after the addition of molecules was expressed relative to values obtained before addition of the molecules (relative Fluo-8 fluorescence=Fmax/F0, where Fmax=maximum fluorescence and F0=baseline fluorescence). Fluorescence intensities were measured using a Spectramax ID3 plate reader (www.moleculardevices.com). Relative fluorescence (RFU) data was subjected to four parameter logistic curve fittings to determine $EC_{50}$ for serotonin with the aid of GraphPad Prism (Version 9.2.0). Serotonin (5-hydroxytryptamine, 5-HT) is a known agonist with binding activity to 5$HT_{2A}$ (Göthert, 2013, M. Pharmacol. Rep 65: 771-786; Kim K. et al., 2020, Cell 182: 1574-1588). Serotonin was assayed with and without compound (IV) in +5-$HT_{2A}$ cells to evaluate potential for positive allosteric modulation (PAM) Fasciani, I. et al., 2020, Pharmaceuticals 13: 388; Gao Z. and Jacobsen K. A., 2013, Drug Discov. Today Technol. 10: e237-e243). FIG. 8B shows a shift in serotonin $EC_{50}$ in the presence of compound (IV), which is referred to in FIG. 8B as "482602".

Figure 8C:
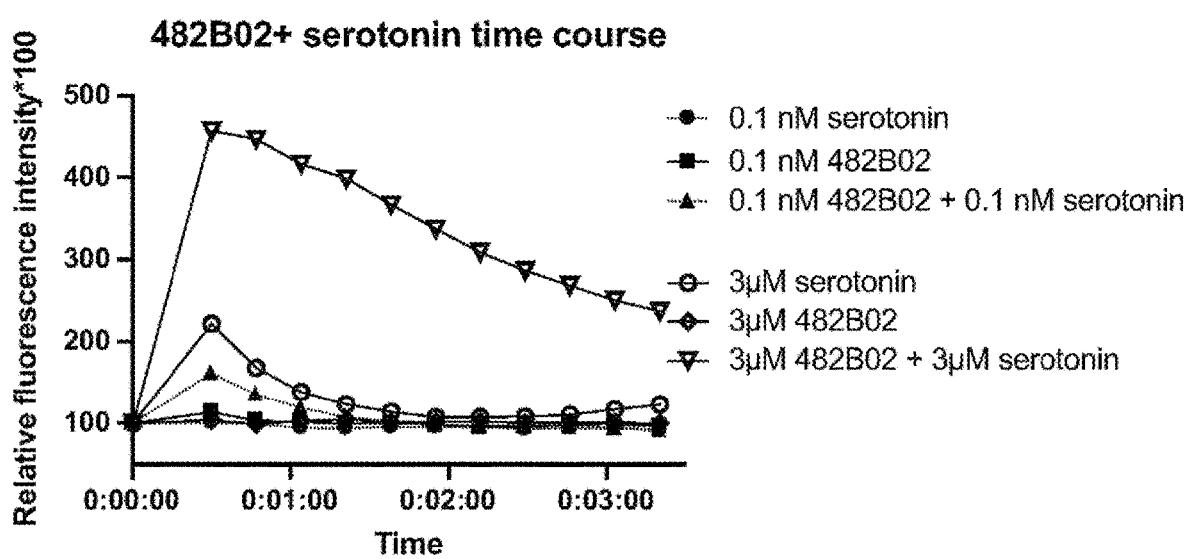

Relative fluorescence (RFU) was then evaluated with respect to time (seconds) illustrating time-dependent calcium flux in response to serotonin with, or without, compound (IV). Results shown in FIG. 8C illustrate elevated flux in response to serotonin (3 uM) with compound (IV) (3 uM) compared to serotonin (3 uM) alone. Compound (IV) is referred to as "482602" in FIG. 8C.

Figure 8D:
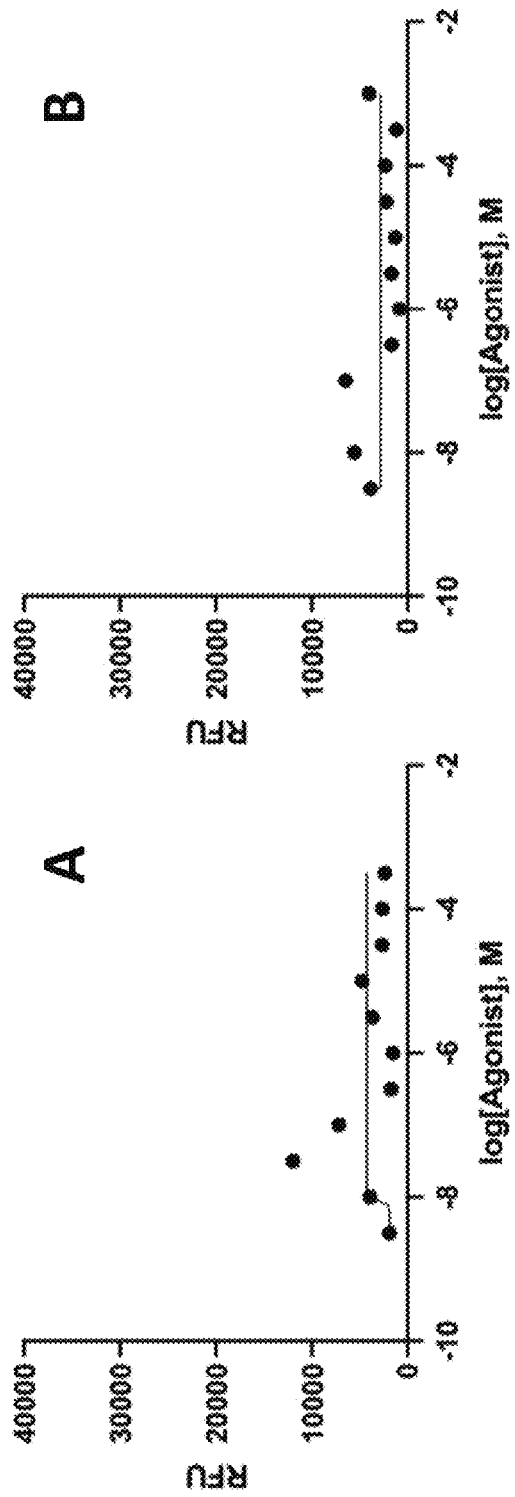

Conversely, −5-$HT_{2A}$ cells (CHO-K1/Galpha15, GenScript, M00257) did not exhibit a response to serotonin (FIG. 8D (panel A), serotonin is "Agonist") and application of methanol vehicle did not elicit a response in +5-$HT_{2A}$ cells (FIG. 8D (Panel B), vehicle is "Agonist").

Example 2—Process for Biosynthetically Making a Second Hydroxylated Psilocybin Derivative from Hydroxylated Indole Feedstock

*Escherichia coli* strain Ec-1 was used to biosynthesize hydroxylated tryptamine derivative with formula (III) from hydroxylated indole feedstock. The construction of Ec-1 is described in Example 1. Scaled-up culturing and material storage of engineered *E. coli* was conducted as described in Example 1, except that 4-hydroxy-5-methylindole (Combi-Blocks, www.combi-blocks.com) was used in place of 4-hydroxy-7-methylindole. N-[2-(4-Hydroxy-5-methyl-1H-indol-3-yl)ethyl]acetamide product having chemical formula (III):

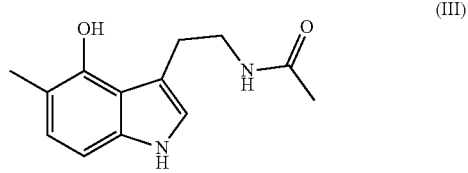 [SMILES: CC(=O)NCCc1c[nH]c2ccc(C)c(O)c12]

(III)

contained in 0.5 litre of broth was extracted by ethyl acetate (3×300 ml). The organic layer was dried over $Na_2SO_4$, followed by concentration under reduced pressure. The residue was purified by flash chromatography on silica gel using ethyl acetate-hexane (50→70%) as eluent, followed by crystallization from acetone/hexane to give the compound as a light yellow solid (8 mg). Following purification, high-resolution MS (HRMS), $^1$H NMR, and selective $^{13}$C NMR were performed to assess purity, estimate total quantity, and confirm molecular structure. $^1$H NMR (400 MHz, $CD_3OD$): δ=1.90 (s, 3H), 2.28 (s, 3H), 3.08 (t, J=6.5 Hz, 2H), 3.49 (t, J=7.1 Hz, 2H), 6.79 (d, J=0.9 Hz, 2H), 6.86 (s, 1H). $^{13}$C NMR (100 MHz, $CD_3OD$): δ=14.4, 21.1, 26.1, 41.7, 103.3, 111.4, 111.7, 117.7, 121.2, 124.5, 137.9, 147.8, 171.9. HRMS (ESI) m/z: calcd. for $C_{13}H_{16}N_2O_2$ [M+H]+ 233.1284, found 233.1283. The purity of compound (III) was determined to be 95% (w/w).

Figure 9A:
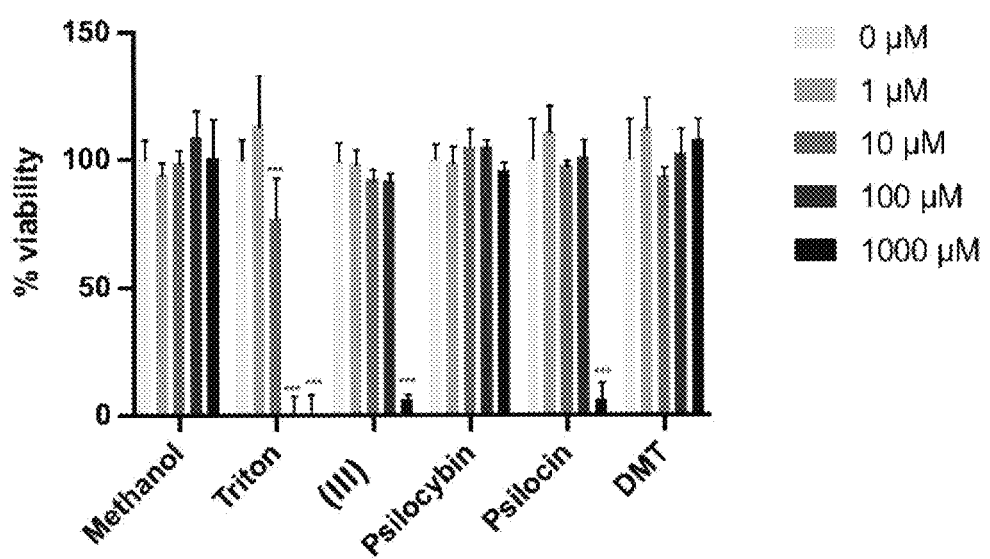
FIGS. 9A, 9B and 9C depict various graphs obtained in the performance of an experimental assay to evaluate the efficacy of an example hydroxylated psilocybin derivative having the chemical formula (III) set forth herein, notably a cell viability assay (FIG. 9A), a serotonin positive allosteric modulation assay in +5-$HT_{2a}$ cells (FIG. 9B), and a serotonin calcium flux assay (FIG. 9C).
Figure 9B:
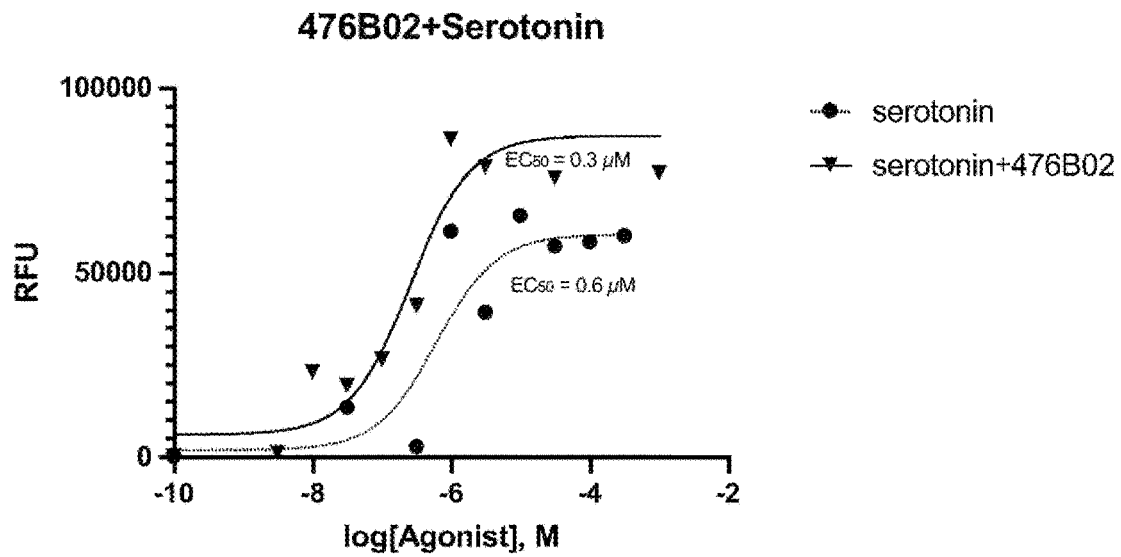
Figure 9C:
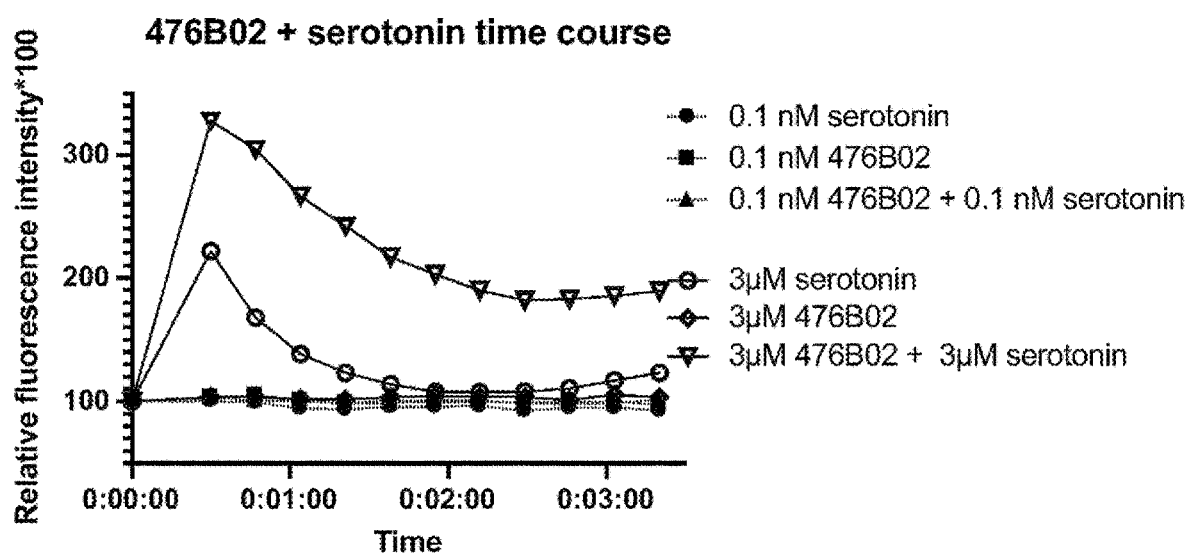

Efficacy testing was carried out as described in Example 1. MTT assay results are shown in FIG. 9A, and calcium mobility assay results are shown in FIGS. 9B and 9C. In the MTT assay, the example compound of the chemical formula (III) is shown as "III". In the calcium mobility assays, the Example compound of the chemical formula (III) is referred to as "476602".

Example 3—Process for Biosynthetically Making a Third Hydroxylated Psilocybin Derivative from Hydroxylated Indole Feedstock

*E. coli* strain Ec-2 was constructed as follows. For plasmid cloning, Top10 or XL1-blue strains were used depending on antibiotic markers. Standard LB media was used for culturing. For gene expression and feeding experiments, the parent host strain employed was BL21 (DE3). For this Example, heterologous expression of a non-native or engineered TrpB gene was not necessary, as endogenous tryptophan synthase activity proved sufficient. The plasmid pET28a(+)-BaTDC-HIS was created by inserting the HIS tagged (SEQ. ID NO: 33) BaTDC gene (SEQ. ID NO: 31) into the NdeIIXhoI site of pET28a(+) (SEQ. ID NO: 35). The plasmid pCDFDuet-OsCPR2-Myc-GST-d37OsCYP71p-HA was created by first cloning the c-MYC tagged (SEQ. ID NO: 36) OsCPR2 gene (SEQ. ID NO: 38) into the MCS1 of pCDFDuet (SEQ. ID NO: 44) and then cloning HA tagged (SEQ. ID NO: 40) GST-d37OsCYP71p (SEQ. ID NO: 42) into the MCS2 of the same plasmid. In this setup, two different genes are driven in tandem by two different T7 promoters on the same plasmid. Scaled-up culturing and material storage of engineered *E. coli* was conducted as described in Example 1, except that 7-ethylindole (Combi-Blocks, www.combi-blocks.com) was used in place of 4-hydroxy-7-methylindole. Analysis was carried out using high-resolution LC-HESI-LTQ-Orbitrap-XL MS (Thermo Fisher Scientific), employing a modified version of a method described previously (Chang et al., 2015, Plant Physiol. 169: 1127-1140), with the exception that liquid chromatography was carried out using an UltiMate 3000 HPLC (Thermo Fisher Scientific) equipped with a Poroshell 120 SB-C18 column (Agilent Technologies) instead of an Accela HPLC system (Thermo Fisher Scientific) equipped with a Zorbax C18 column (Agilent Technologies). Briefly, 10 microliters of culture media was injected at a flow rate of 0.5 mL/min and a gradient of solvent A (water with 0.1% of formic Acid) and solvent B (ACN with 0.1% formic Acid) as follows: 100% to 0% (v/v) solvent A over 5 min; isocratic at 0% (v/v) for 1 min; 0% to 100% (v/v) over 0.1 min; and isocratic at 100% (v/v) for 1.9 min. Total run time was 8 minutes. Heated ESI source and interface conditions were operated in positive ion mode as follows: vaporizer temperature, 400° C., source voltage, 3 kV; sheath gas, 60 au; auxiliary gas, 20 au; capillary temperature, 380° C.; capillary voltage, 6 V; tube lens, 45 V. Instrumentation was performed as a single, HR scan event using Orbitrap detection of m/z in the range of 100-700 m/z. Ion injection time was 300 ms with scan time of 1 s. External and internal calibration procedures ensured <2 ppm error to facilitate elemental formulae predictions. Singly protonated product with exact m/z and expected elemental formula matching protonated 3-(2-aminoethyl)-7-ethyl-1H-indol-5-ol having chemical formula (XXXII):

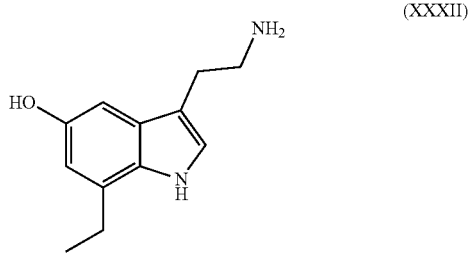

Figure 10:
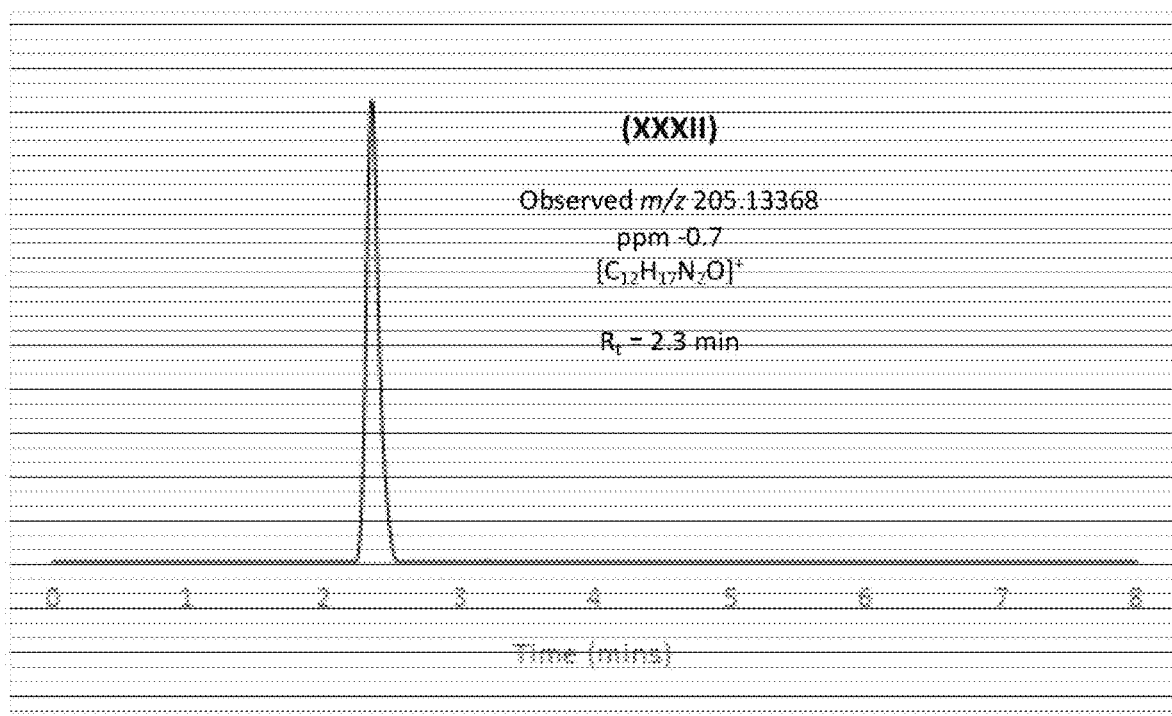
FIG. 10 depicts a representation of mass spectrometry data in the form of a chromatogram, notably a chromatogram obtained in the performance of an experiment to synthesize an example hydroxylated psilocybin derivative compound having the chemical formula (XXXII) set forth herein.

(XXXII)

eluted at 2.3 minutes (EIC, see: FIG. 10).

Figure 11:
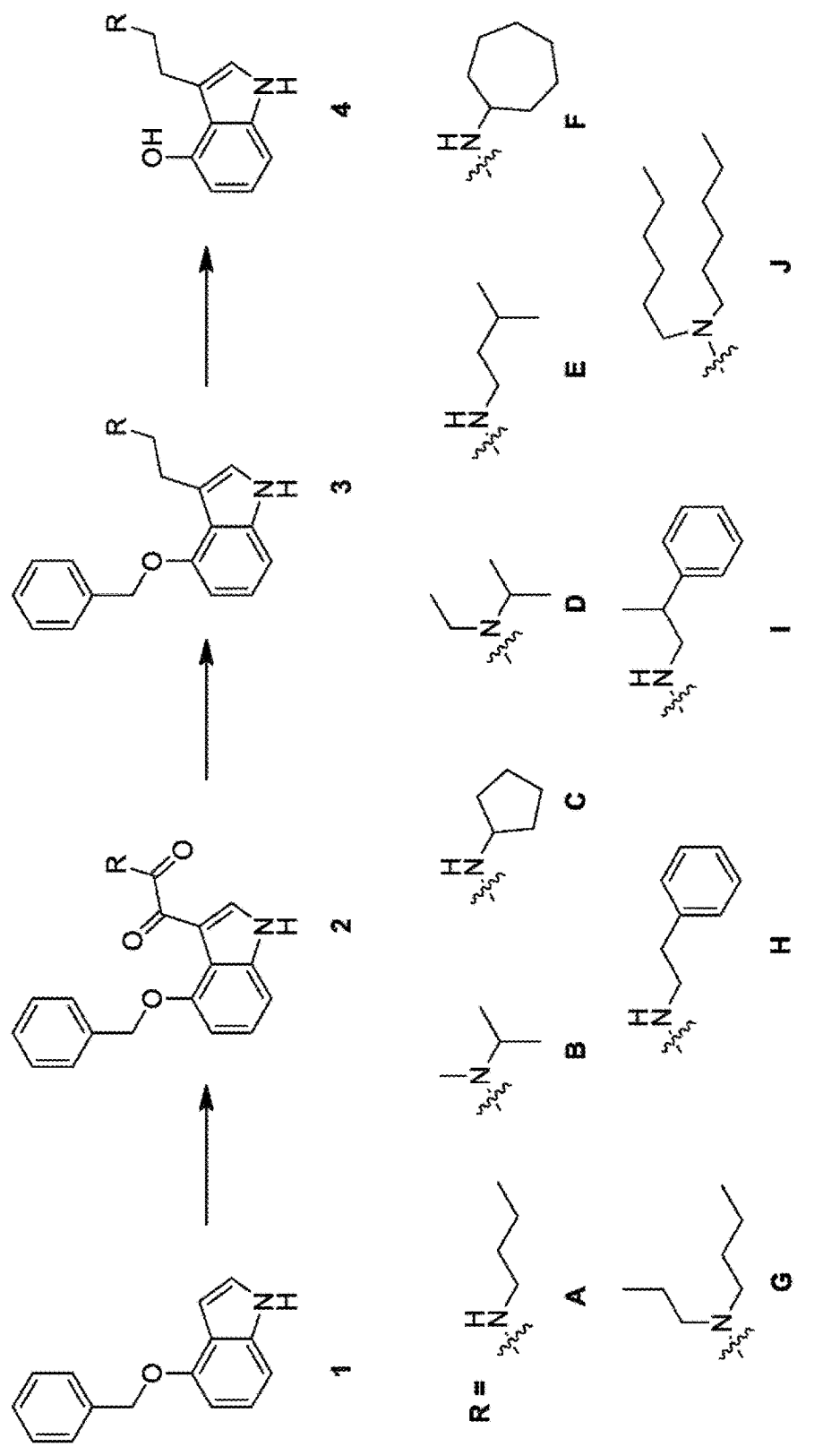
FIG. 11 depicts an example process for chemically example synthesizing hydroxylated psilocybin compounds

Example 4—Process for Making a Fourth Hydroxylated Psilocybin Derivative Using Synthetic Chemistry This example describes an example process for chemically synthesizing hydroxylated psilocybins. The general synthetic procedure shown in FIG. 11 was followed.

To a solution of 4-benzyloxyindole 1 (1.00 mmol, 1.00 eq) dissolved in anhydrous diethyl ether (10 mL) under argon sparging at 0° C., was added oxalyl chloride (2.05 mmol, 2.05 eq) dropwise over the course of 30 minutes, and the reaction was continued at 0-5° C. for 3 hours. A solution of N-ethyl(isopropyl)amine (9.00 total eq, required for R group "D" in FIG. 11) in anhydrous diethyl ether (5 mL) was added dropwise over the course of 1 hour. The diethyl ether was removed in vacuo, and the residue was redissolved in dichloromethane (30 mL). The organic solution was washed with water (4×10 mL) and brine (10 mL), then dried with $MgSO_4$ and concentrated under vacuo to yield 2, which was used without purification in the following step. A solution of lithium aluminum hydride in anhydrous THF (1 M, 5.20 eq) in dry 1,4-dioxane (2.0 mL) was brought to 60° C. under argon. A solution of 2 in a mixture of anhydrous THF (2.0 mL) and 1,4-dioxane (3.5 mL) was added dropwise over 30 minutes, and the reaction mixture was brought to 70° C. for 2 hours, then to reflux at 95° C. for 20 hours. After cooling to 0° C., excess lithium aluminum hydride was quenched through the dropwise addition of a mixture of water (0.4 mL)-THF (2.0 mL), yielding a flocculant precipitate. Diethyl ether (10 mL) was added, and the reaction mixture was allowed to stir at room temperature for 30 minutes. The precipitate was removed via vacuum filtration, the filtrate was dried over $MgSO_4$, and concentrated under vacuo to yield 3 which was used without purification. The above obtained 3 was dissolved in 95% EtOH (10 mL), and 10% palladium on activated charcoal (0.110 eq) was added. The reaction flask was evacuated then backfilled with hydrogen. After stirring at room temperature for 2 hours, the catalyst was removed through filtration and solvent removed in vacuo to yield 4, which was purified by liquid chromatography on C18 silica gel using a water–acetonitrile+0.1% formic acid eluent system.

Analysis was carried out using high-resolution LC-HESI-LTQ-Orbitrap-XL MS (Thermo Fisher Scientific), employing a modified version of a method described previously (Chang et al., 2015, Plant Physiol. 169: 1127-1140), with the exception that liquid chromatography was carried out using an UltiMate 3000 HPLC (Thermo Fisher Scientific) equipped with a Poroshell 120 SB-C18 column (Agilent Technologies) instead of an Accela HPLC system (Thermo Fisher Scientific) equipped with a Zorbax C18 column (Agilent Technologies). Briefly, 10 microliters of final reaction product was injected at a flow rate of 0.5 mL/min and a gradient of solvent A (water with 0.1% of formic acid) and solvent B (ACN with 0.1% formic Acid) as follows: 100% to 0% (v/v) solvent A over 5 min; isocratic at 0% (v/v) for 1 min; 0% to 100% (v/v) over 0.1 min; and isocratic at 100% (v/v) for 1.9 min. Total run time was 8 minutes. Heated ESI source and interface conditions were operated in positive ion mode as follows: vaporizer temperature, 400° C., source voltage, 3 kV; sheath gas, 60 au, auxiliary gas, 20 au; capillary temperature, 380° C.; capillary voltage, 6 V; tube lens, 45 V. Instrumentation was performed as a single, HR scan event using Orbitrap detection of m/z in the range of 100-700 m/z. Ion injection time was 300 ms with scan time of 1 s. External and internal calibration procedures ensured <2 ppm error to facilitate elemental formulae predictions. Singly protonated product with exact m/z and expected elemental formula matching protonated 3-(2-[N-ethyl(isopropyl)amino]ethyl)-1H-indol-4-ol (R-group "D" in FIG. 11) having chemical formula (V):

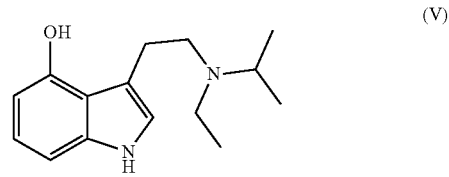 [SMILES: CCN(CCc1c[nH]c2cccc(O)c12)C(C)C]

Figure 12:
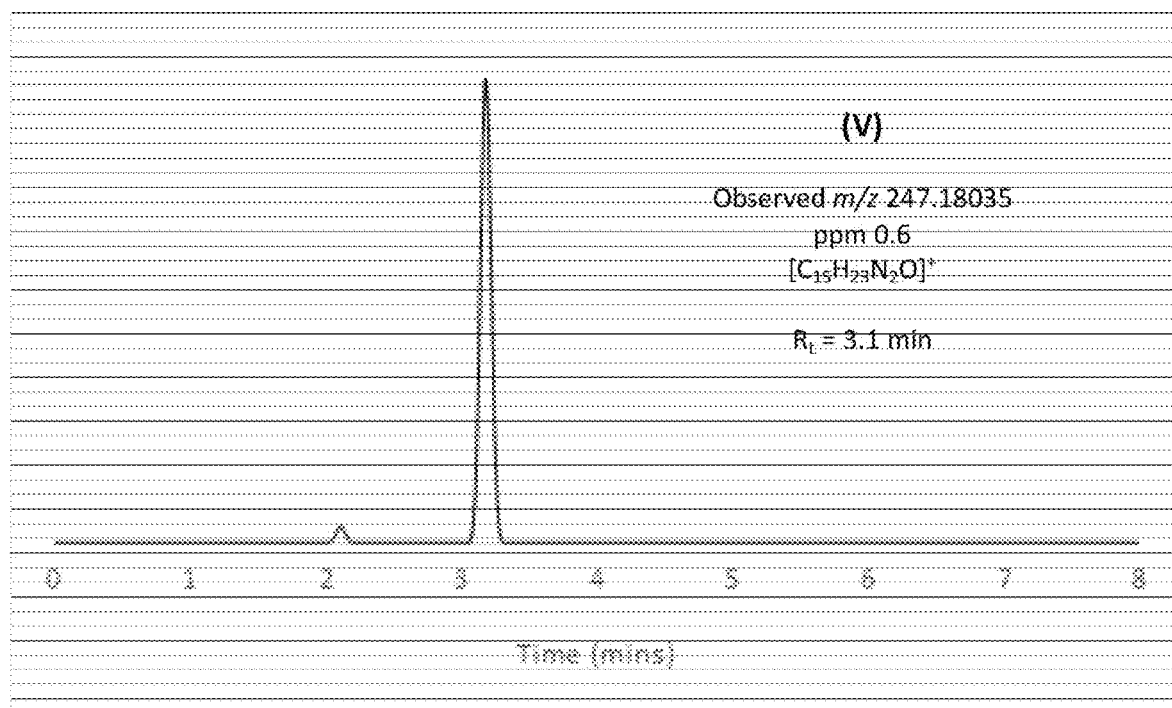
FIG. 12 depicts a representation of mass spectrometry data in the form of a chromatogram, notably a chromatogram obtained in the performance of an experiment to synthesize an example hydroxylated psilocybin derivative compound having the chemical formula (V) set forth herein.

(V)

eluted at 3.1 minutes (EIC, see: FIG. 12).

Figure 13:
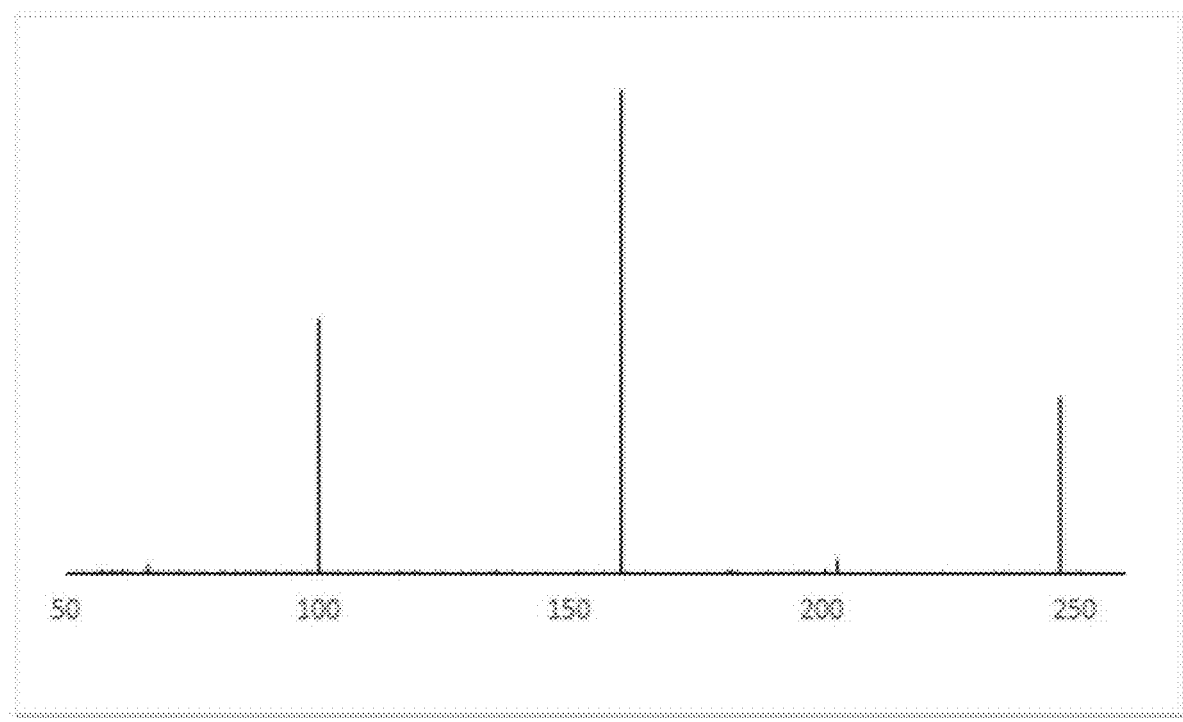
FIG. 13 depicts a representation of mass spectrometry data in the form of a mass spectrometry spectrum obtained in the performance of an experiment to identify a hydroxylated psilocybin derivative compound having the chemical formula (V) set forth herein.

As per standard procedures (Menéndez-Perdomo et al. 2021, Mass Spectrom 56: e4683) high energy collisions (HCD) were achieved in a dedicated, post-LTQ, nitrogen collision cell. Orbitrap-based, HR fragment detection was employed (normalized collision energy, NCE 35), enabling opportunity to assign elemental formulae to subsequent diagnostic ion species characteristic of a compound of formula (V) (FIG. 13, Table I) ((Servillo L. et al., J. Agric. Food Chem 61: 5156-5162).

TABLE I relative abundance of molecular species in a sample containing compound (V)

| m/z | % Relative abundance | Fragment | Empirical formula |
|---|---|---|---|
| 160.0755 | 100. | $[M + H - NH_2C_5H_{10}]^+$ | $C_{10}H_{11}NO$ |
| 100.1117 | 53 |  | $C_6H_{14}N$ |
| 247.1805 | 36 | $[M + H]^+$ | $C_{15}H_{22}N_2O$ |
| 202.9303 | 2 |  |  |
| 66.1250 | 1 |  |  |
| 200.5065 | 0.9 |  |  |
| 56.9876 | 0.7 |  |  |

Example 5—Process for Making a Fifth Hydroxylated Psilocybin Derivative Using Synthetic Chemistry Chemical synthesis was conducted as described in Example 4, except that cycloheptylamine (9.00 total eq, required for R group "F" in FIG. 11) was used in place of N-ethyl(isopropyl)amine. Analysis was carried out using high-resolution LC-HESI-LTQ-Orbitrap-XL MS (Thermo Fisher Scientific) as described in Example 4. Singly protonated product with exact m/z and expected elemental formula matching protonated 3-[2-(cycloheptylamino)ethyl]-1H-indol-4-ol (R-group "F" in FIG. 11) and having chemical formula (IX):

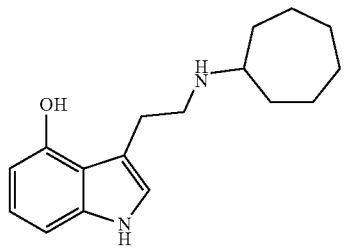

Figure 14:
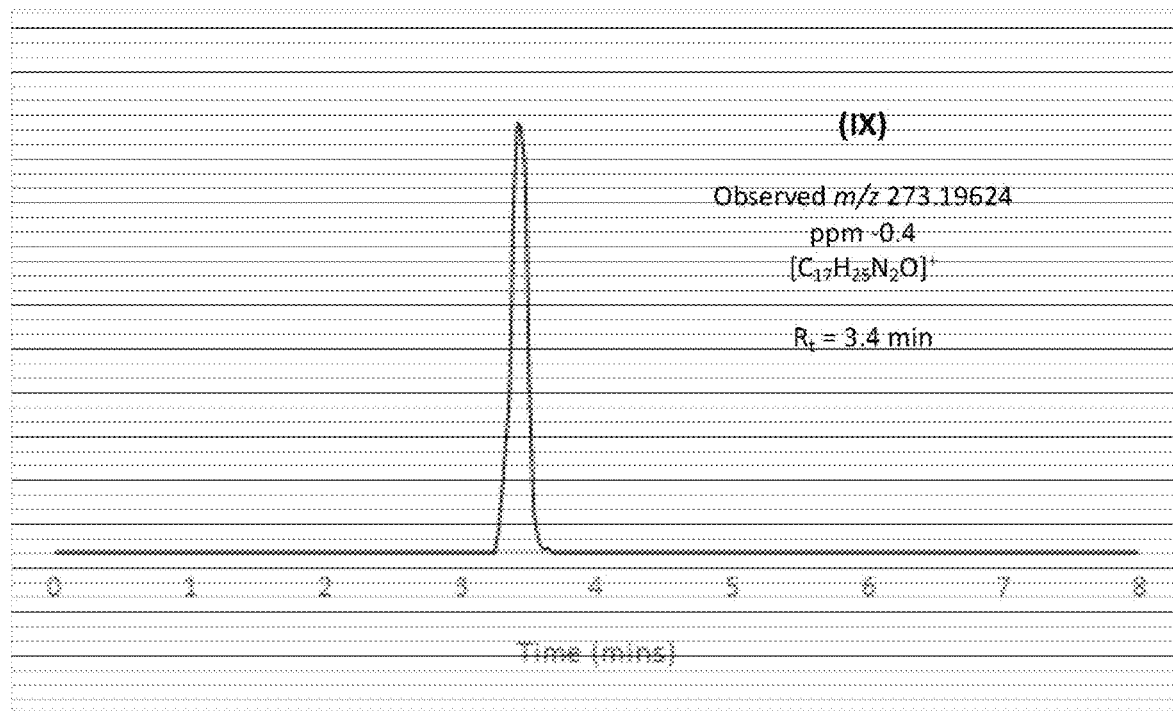
FIG. 14 depicts a representation of mass spectrometry data in the form of a chromatogram, notably a chromatogram obtained in the performance of an experiment to synthesize an example hydroxylated psilocybin derivative compound having the chemical formula (IX) set forth herein.

(IX)

eluted at 3.4 minutes (EIC, see: FIG. 14).

Example 6—Process for Making a Sixth Hydroxylated Psilocybin Derivative Using Synthetic Chemistry Chemical synthesis was conducted as described in Example 4, except that dioctylamine (9.00 total eq, required for R group "K" in FIG. 11) was used in place of N-ethyl(isopropyl)amine. Analysis was carried out using high-resolution LC-HESI-LTQ-Orbitrap-XL MS (Thermo Fisher Scientific) as described in Example 4. Singly protonated product with exact m/z and expected elemental formula matching protonated 3-[2-(dioctylamino)ethyl]-1H-indol-4-ol (R-group "K" in FIG. 11) and having chemical formula (X):

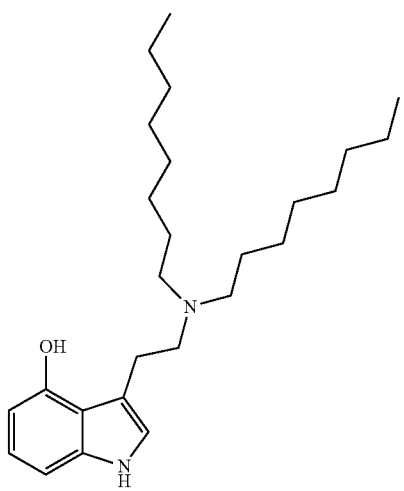

Figure 15A:
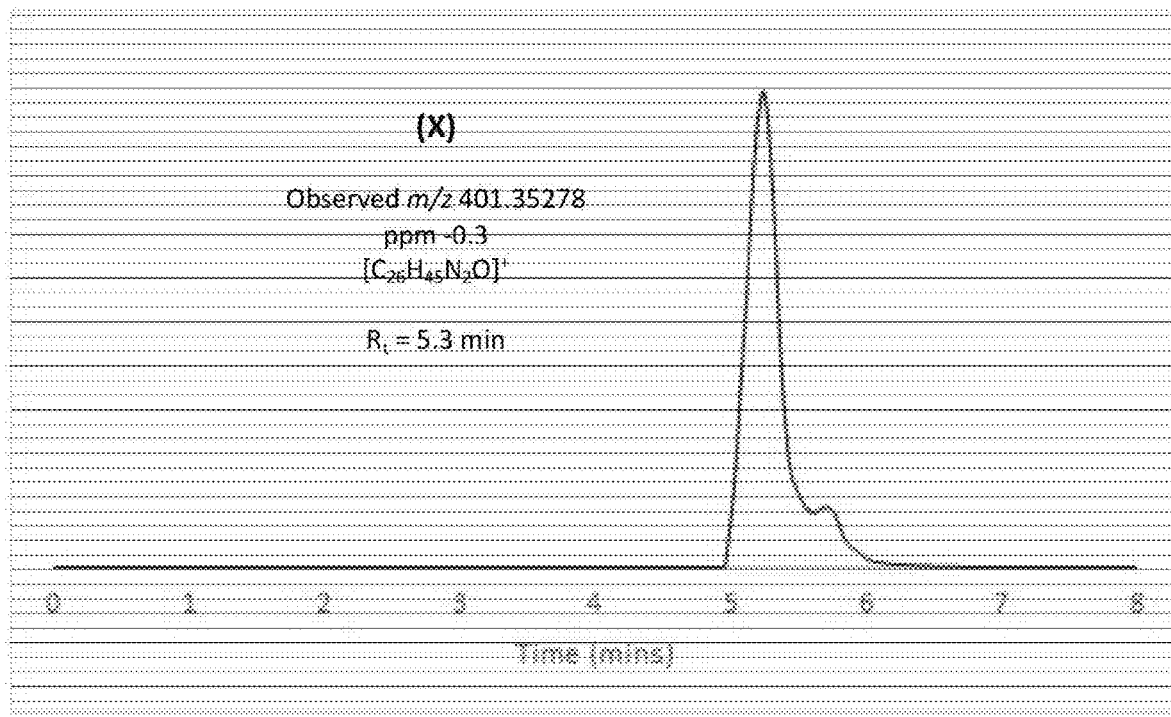
FIGS. 15A and 15B depict a representation of mass spectrometry data in the form of a chromatogram, notably a chromatogram obtained in the performance of an experiment to synthesize an example hydroxylated psilocybin derivative compound having the chemical formula (X) set forth herein (FIG. 15A), and in the form of a mass spectrometry spectrum obtained in the performance of an experiment to identify a hydroxylated psilocybin derivative compound having the chemical formula (X) set forth herein (FIG. 15B).

(X)

eluted at 5.3 minutes (EIC, see: FIG. 15A).

Figure 15B:
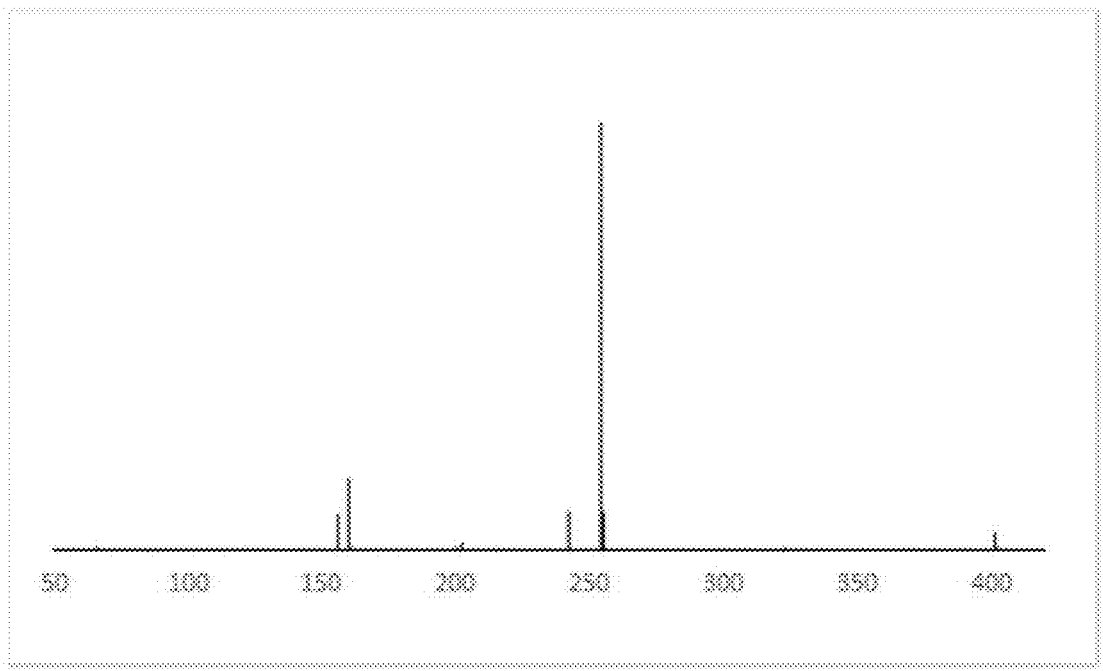

High energy collisions (HCD) were achieved as described in Example 4. Elemental formulae were assigned to subsequent diagnostic ion species characteristic of a compound of formula (X) (FIG. 15B, Table II).

TABLE II relative abundance of molecular species in a sample containing compound (X)

| m/z | % Relative Abundance | Fragment | Empirical formula |
|---|---|---|---|
| 254.2842 | 100 | | |
| 160.0755 | 16 | $[M + H - NH_2C_{16}H_{33}]^+$ | $C_{10}H_{11}NO$ |
| 242.2842 | 9 | | |
| 255.2875 | 9 | | |
| 156.1745 | 8 | $[M + H - C_8H_{18}]^+$ | $C_{16}H_{27}N_2O$ |
| 401.3524 | 4 | $[M + H]^+$ | $C_{26}H_{45}N_2O$ |
| 202.4264 | 1.7 | | |
| 66.1240 | 0.6 | | |
| 200.0434 | 0.6 | | |

Example 7—Process for Making a Seventh Hydroxylated Psilocybin Derivative Using Synthetic Chemistry Chemical synthesis was conducted as described in Example 4, except that phenethylamine (9.00 total eq, required for R group "H" in FIG. 11) was used in place of N-ethyl(isopropyl)amine. Analysis was carried out using high-resolution LC-HESI-LTQ-Orbitrap-XL MS (Thermo Fisher Scientific) as described in Example 4. Singly protonated product with exact m/z and expected elemental formula matching protonated 3-[2-(phenethylamino)ethyl]-1H-indol-4-ol (R-group "H" in FIG. 11) and having chemical formula (XIII):

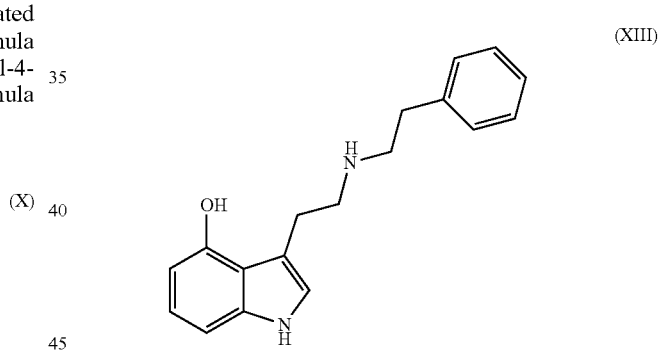

Figure 16A:
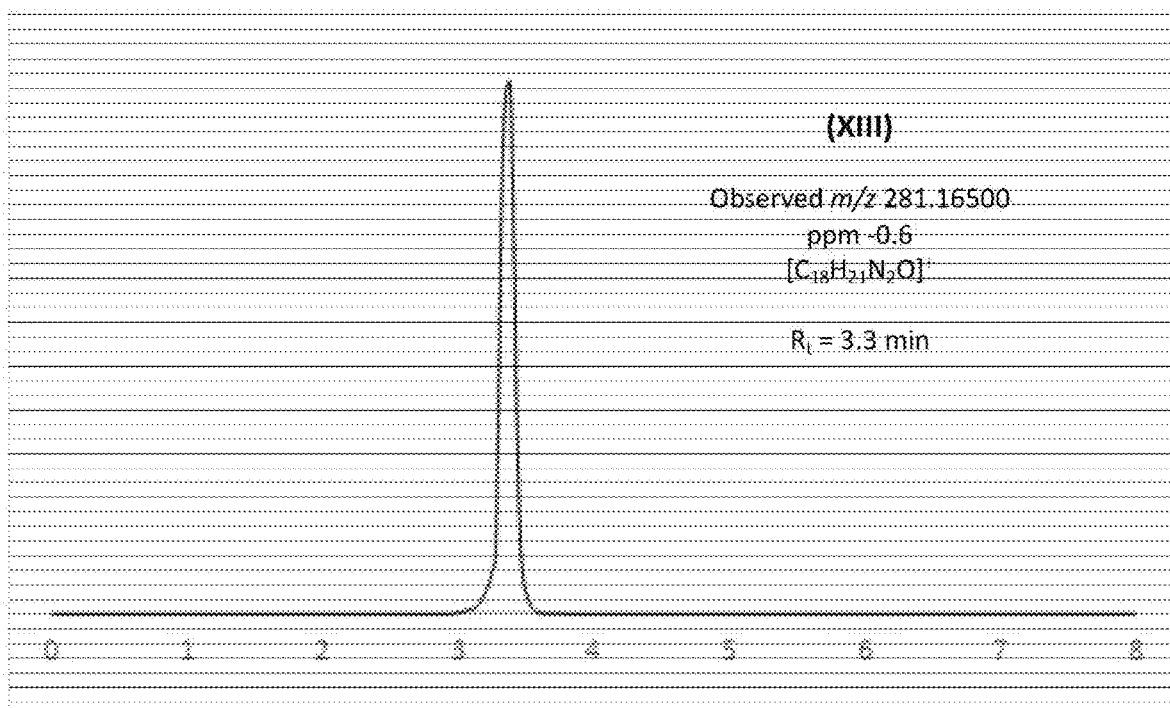
FIGS. 16A and 16B depict a representation of mass spectrometry data in the form of a chromatogram, notably a chromatogram obtained in the performance of an experiment to synthesize an example hydroxylated psilocybin derivative compound having the chemical formula (XIII) set forth herein (FIG. 16A), and in the form of a mass spectrometry spectrum obtained in the performance of an experiment to identify a hydroxylated psilocybin derivative compound having the chemical formula (XIII) set forth herein (FIG. 16B).

(XIII)

eluted at 3.3 minutes (EIC, see: FIG. 16A).

Figure 16B:
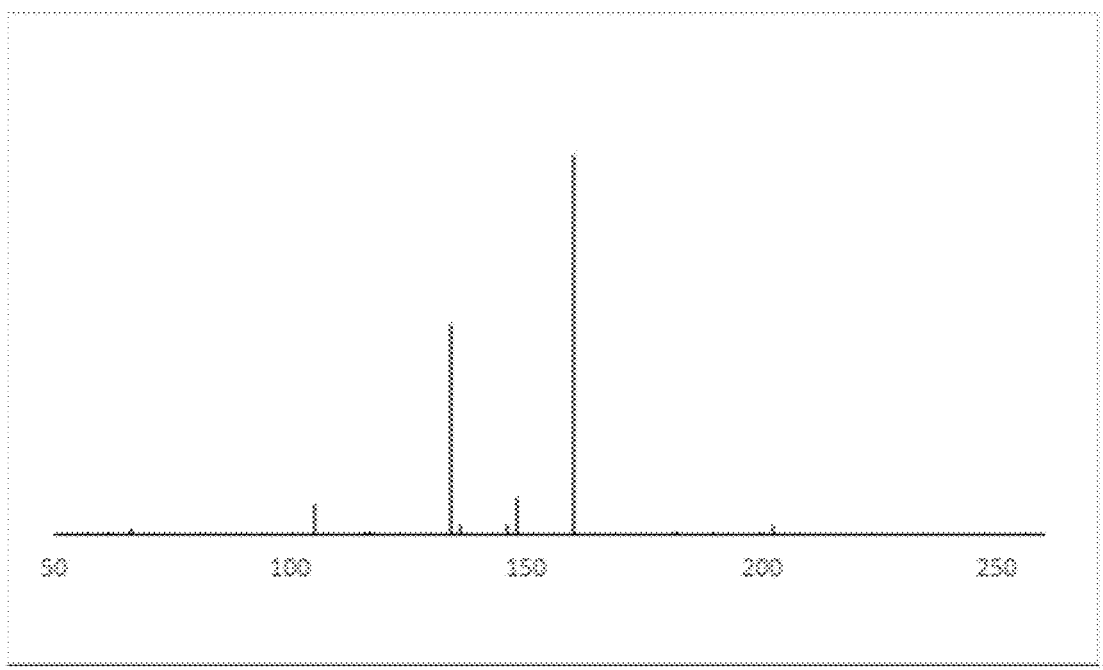

High energy collisions (HOD) were achieved as described in Example 4. Elemental formulae were assigned to subsequent diagnostic ion species characteristic of a compound of formula (XIII) (FIG. 16B, Table III).

TABLE III relative abundance of molecular species in a sample containing compound (XIII)

| m/z | % Relative abundance | Fragment | Empirical formula |
|---|---|---|---|
| 160.0755 | 100 | $[M + H - NH_2C_2H_4Ben]^+$ | $C_{10}H_{11}NO$ |
| 134.0962 | 6 | | $C_9H_{12}N$ |
| 148.0755 | 10 | $[M + H - CH_2NH_2C_3H_6Ben]^+$ | $C_9H_9NO$ |
| 281.1649 | 9 | $[M + H]^+$ | $C_{18}H_{20}N_2O$ |
| 105.0696 | 8 | | $C_8H_9$ |
| 146.0598 | 3 | | |
| 136.1118 | 2 | | |
| 202.4219 | 2 | | |

Example 8—Process for Making an Eighth Hydroxylated Psilocybin Derivative Using Synthetic Chemistry Chemical synthesis was conducted as described in Example 4, except that 2-phenylpropylamine (9.00 total eq, required for R group "I" in FIG. 11) was used in place of N-ethyl(isopropyl)amine. Analysis was carried out using high-resolution LC-HESI-LTQ-Orbitrap-XL MS (Thermo Fisher Scientific) as described in Example 4. Singly protonated product with exact m/z and expected elemental formula matching protonated 3-[2-(2-phenylpropylamino)ethyl]-1H-indol-4-ol (R-group "I" in FIG. 11) and having chemical formula (XIV):

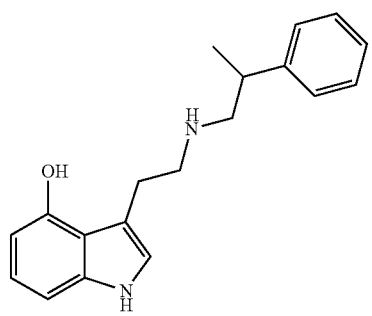

Figure 17A:
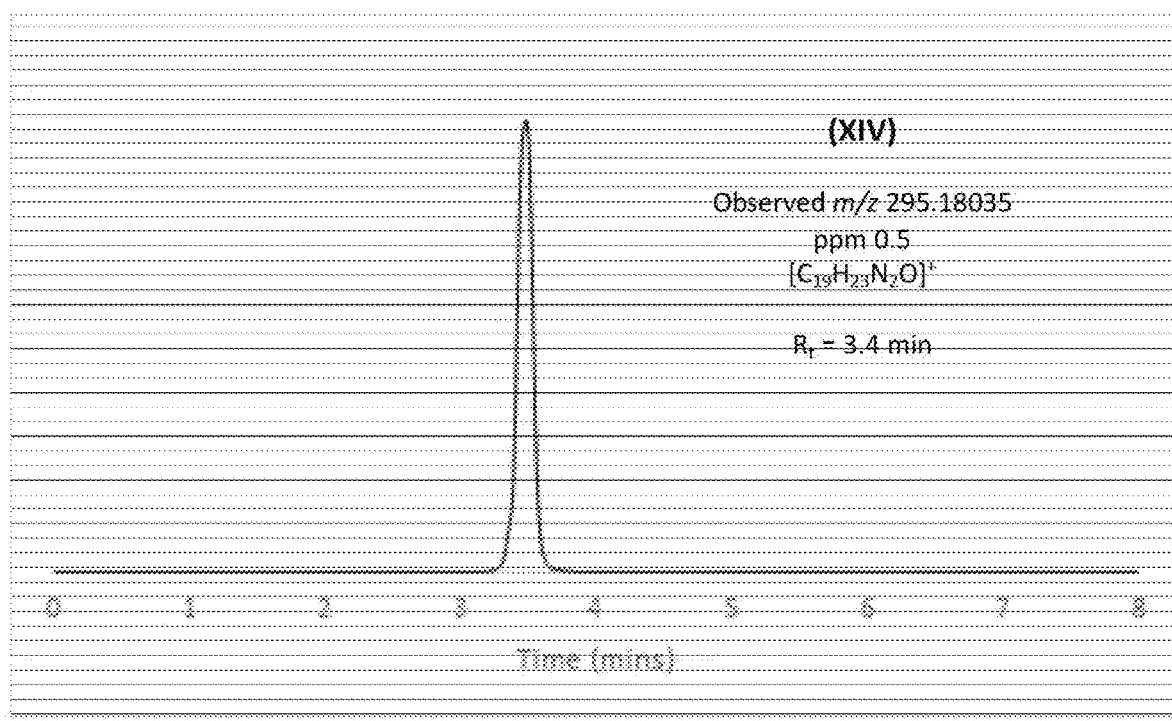
FIGS. 17A and 17B depict a representation of mass spectrometry data in the form of a chromatogram, notably a chromatogram obtained in the performance of an experiment to synthesize an example hydroxylated psilocybin derivative compound having the chemical formula (XIV) set forth herein (FIG. 17A), and in the form of a mass spectrometry spectrum obtained in the performance of an experiment to identify a hydroxylated psilocybin derivative compound having the chemical formula (XIV) set forth herein (FIG. 17B).

(XIV)

eluted at 3.4 minutes (EIC, see: FIG. 17A).

Figure 17B:
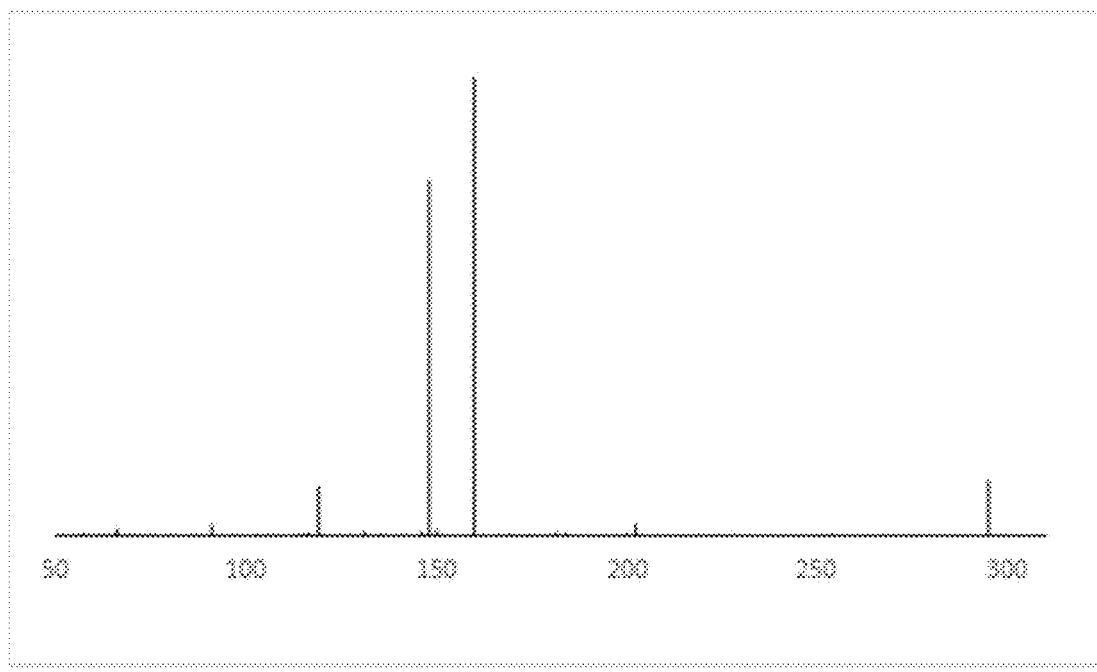

High energy collisions (HOD) were achieved as described in Example 4. Elemental formulae were assigned to subsequent diagnostic ion species characteristic of a compound of formula (XIV) (FIG. 17B; Table IV).

TABLE IV

| | relative abundance of molecular species in a sample containing compound (XIV) | | |
|---|---|---|---|
| m/z | % Relative abundance | Fragment | Empirical formula |
| 160.0755 | 100 | [M + H − OH − C$_3$H$_6$Ben]$^+$ | C$_{10}$H$_{11}$N$_2$ |
| 148.1119 | 77 | [M + H − CH$_2$NH$_2$C$_3$H$_6$Ben]$^+$ | C$_9$H$_9$NO |
| 295.1806 | 12 | [M + H]$^+$ | C$_{19}$H$_{23}$N$_2$O |
| 119.0852 | 11 | | C$_9$H$_{11}$ |
| 148.0755 | 4 | | |
| 202.4136 | 3 | | |
| 91.0539 | 2 | | C$_7$H$_7$ |
| 160.0736 | 2 | | |
| 148.1102 | 2 | | |

Example 9—Process for Making a Ninth Hydroxylated Psilocybin Derivative Using Synthetic Chemistry Chemical synthesis was conducted as described in Example 4, except that N-propylbutylamine (9.00 total eq, required for R group "G" in FIG. 11) was used in place of N-ethyl(isopropyl)amine. Analysis was carried out using high-resolution LC-HESI-LTQ-Orbitrap-XL MS (Thermo Fisher Scientific) as described in Example 4. Singly protonated product with exact m/z and expected elemental formula matching protonated 3-[2-(N-butyl-N-propylamino)ethyl]-1H-indol-4-ol (R-group "G" in FIG. 11) and having chemical formula (XV):

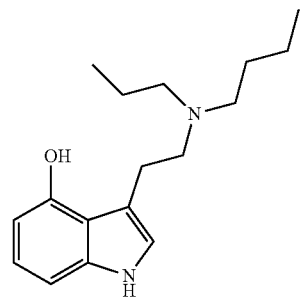

Figure 18A:
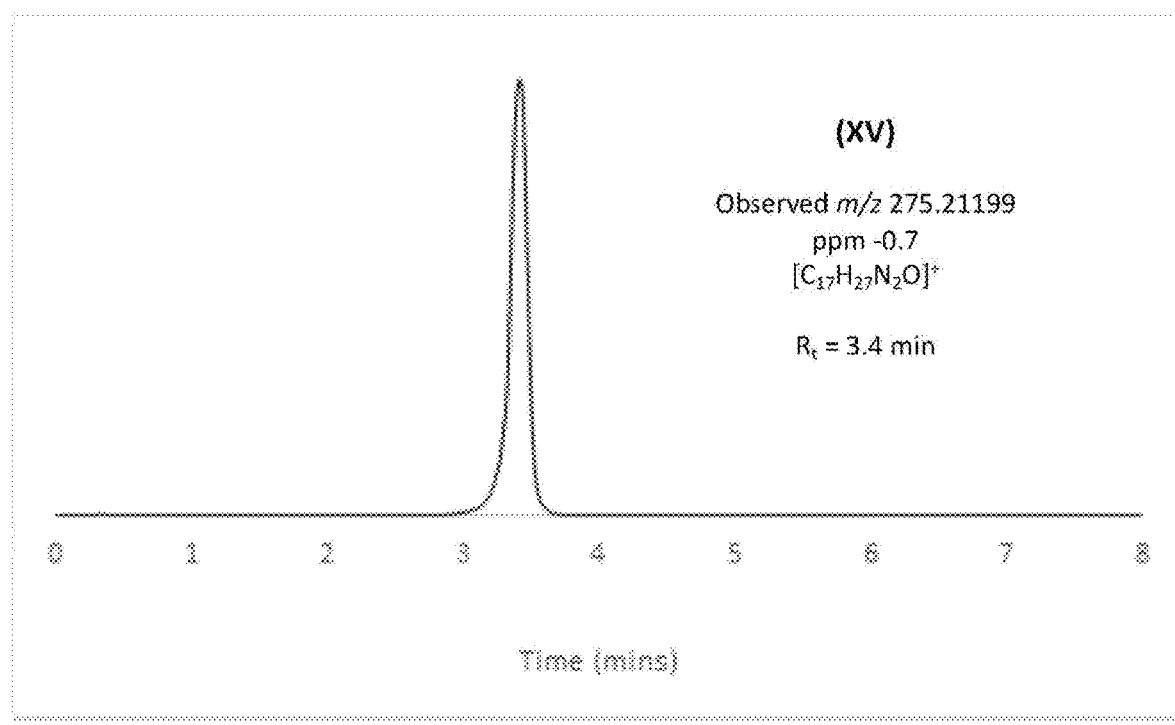
FIGS. 18A and 18B depict a representation of mass spectrometry data in the form of a chromatogram, notably a chromatogram obtained in the performance of an experiment to synthesize an example hydroxylated psilocybin derivative compound having the chemical formula (XV) set forth herein (FIG. 18A), and in the form of a mass spectrometry spectrum obtained in the performance of an experiment to identify a hydroxylated psilocybin derivative compound having the chemical formula (XV) set forth herein (FIG. 18B).

(XV)

eluted at 3.4 minutes (EIC, see: FIG. 18A).

Figure 18B:
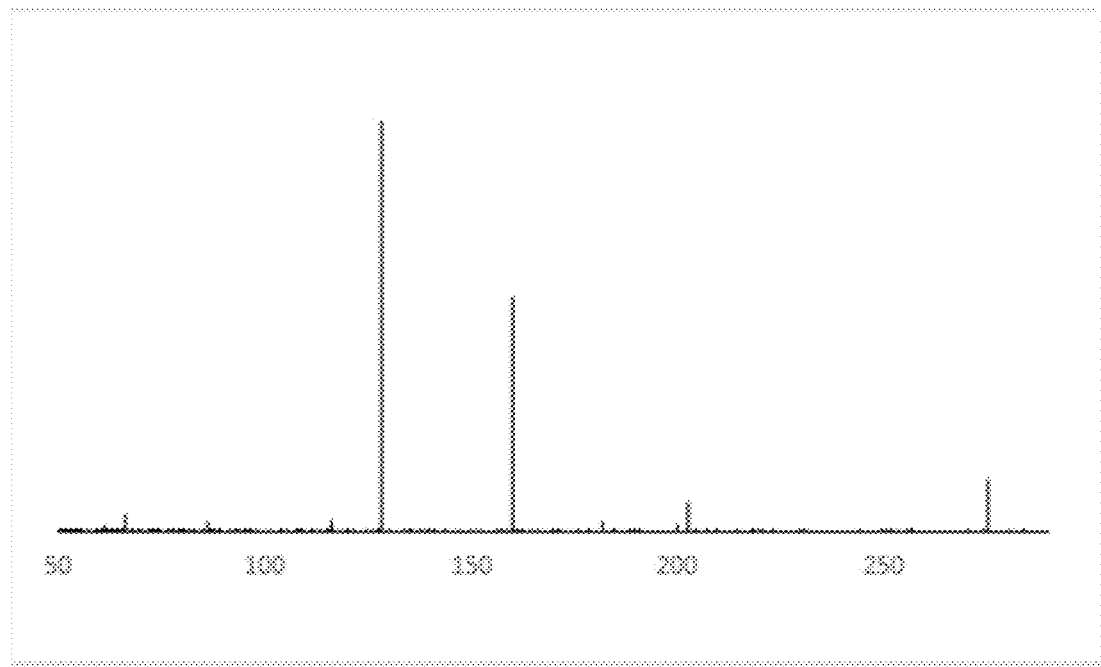

High energy collisions (HOD) were achieved as described in Example 4. Elemental formulae were assigned to subsequent diagnostic ion species characteristic of a compound of formula (XV) (FIG. 18B, Table V).

TABLE V

| | relative abundance of molecular species in a sample containing compound (XV) | | |
|---|---|---|---|
| m/z | % Relative abundance | Fragment | Empirical formula |
| 128.1431 | 100 | [M + H − OH − CH$_2$NH$_2$C$_7$H$_{16}$]$^+$ | C$_8$H$_{18}$N |
| 160.0755 | 58 | [M + H − NH$_2$C$_7$H$_{16}$]$^+$ | C$_{10}$H$_{11}$NO |
| 275.2119 | 13 | [M + H]$^+$ | C$_{17}$H$_{27}$N$_2$O |
| 202.4525 | 7 | | |
| 66.1247 | 4 | | |
| 116.1430 | 3 | | C$_7$H$_{18}$N |
| 86.0960 | 3 | | C$_5$H$_{12}$N |
| 181.7339 | 2 | | |
| 200.0026 | 2 | | |

Example 10—Process for Making a Tenth Hydroxylated Psilocybin Derivative Using Synthetic Chemistry Chemical synthesis was conducted as described in Example 4, except that isopentylamine (9.00 total eq, required for R group "E" in FIG. 11) was used in place of N-ethyl(isopropyl)amine. Analysis was carried out using high-resolution LC-HESI-LTQ-Orbitrap-XL MS (Thermo Fisher Scientific) as described in Example 4. Singly protonated product with exact m/z and expected elemental formula matching protonated 3-[2-(isopentylamino)ethyl]-1H-indol-4-ol (R-group "E" in FIG. 11) and having chemical formula (XVI):

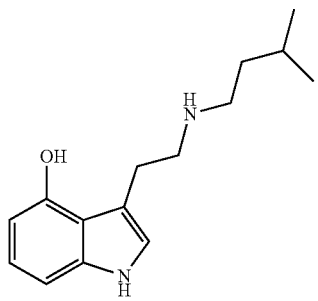

Figure 19A:
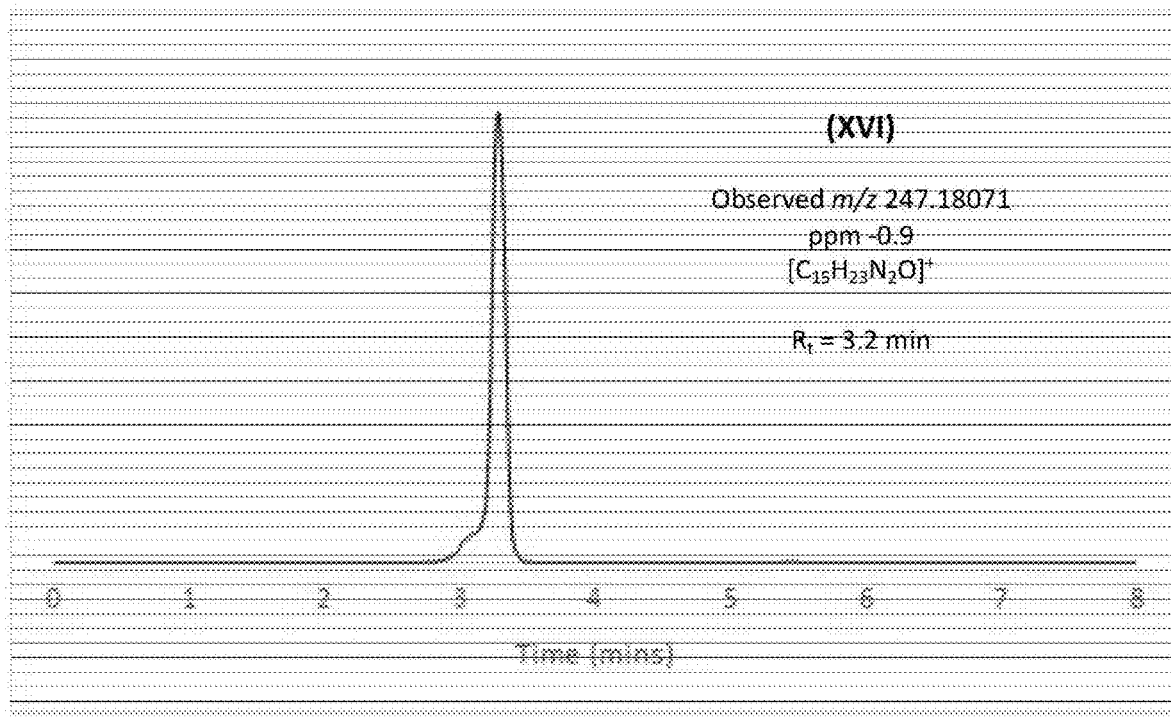
FIGS. 19A and 19B depict a representation of mass spectrometry data in the form of a chromatogram, notably a chromatogram obtained in the performance of an experiment to synthesize an example hydroxylated psilocybin derivative compound having the chemical formula (XVI) set forth herein (FIG. 19A), and in the form of a mass spectrometry spectrum obtained in the performance of an experiment to identify a hydroxylated psilocybin derivative compound having the chemical formula (XVI) set forth herein (FIG. 19B).

(XVI)

eluted at 3.2 minutes (EIC, see: FIG. 19A).

Figure 19B:
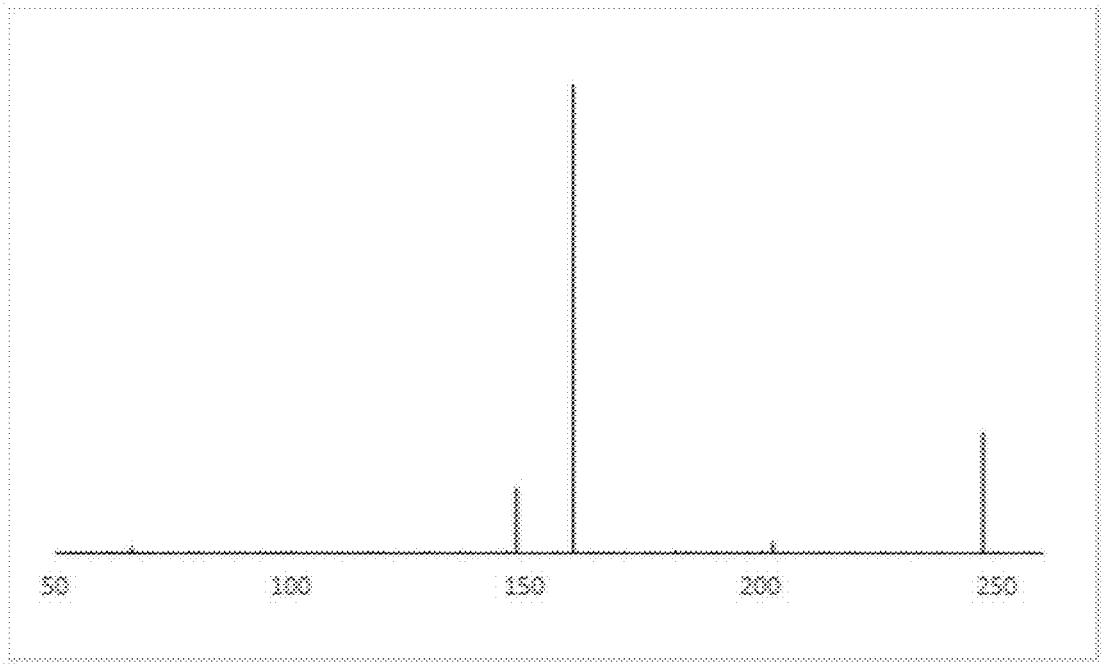

High energy collisions (HOD) were achieved as described in Example 4. Elemental formulae were assigned to subsequent diagnostic ion species characteristic of a compound of formula (XVI), (FIG. 19B, Table VI).

TABLE VI relative abundance of molecular species in a sample containing compound (XVI)

| m/z | % Relative abundance | Fragment | Empirical formula |
|---|---|---|---|
| 160.0755 | 100 | $[M + H - NH_2C_5H_{11}]^+$ | $C_{10}H_{11}NO$ |
| 247.1805 | 26 | $[M + H]^+$ | $C_{15}H_{22}N_2O$ |
| 148.0755 | 14 | $[M + H - CH_2NH_2C_5H_{11}]^+$ | $C_9H_9NO$ |
| 202.5658 | 2 | | |
| 160.0736 | 2 | | |
| 66.1248 | 1 | | |
| 160.0727 | 0.7 | | |
| 200.1163 | 0.6 | | |
| 181.7336 | 0.6 | | |

Example 11—Process for Making an Eleventh Hydroxylated Psilocybin Derivative Using Synthetic Chemistry Chemical synthesis was conducted as described in Example 4, except that cyclopentylamine (9.00 total eq, required for R group "C" in FIG. 11) was used in place of N-ethyl(isopropyl)amine. Analysis was carried out using high-resolution LC-HESI-LTQ-Orbitrap-XL MS (Thermo Fisher Scientific) as described in Example 4. Singly protonated product with exact m/z and expected elemental formula matching protonated 3-[2-(cyclopentylamino)ethyl]-1H-indol-4-ol (R-group "C" in FIG. 11) and having chemical formula (XVIII):

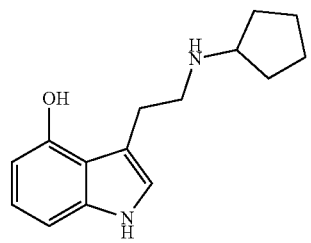

Figure 20A:
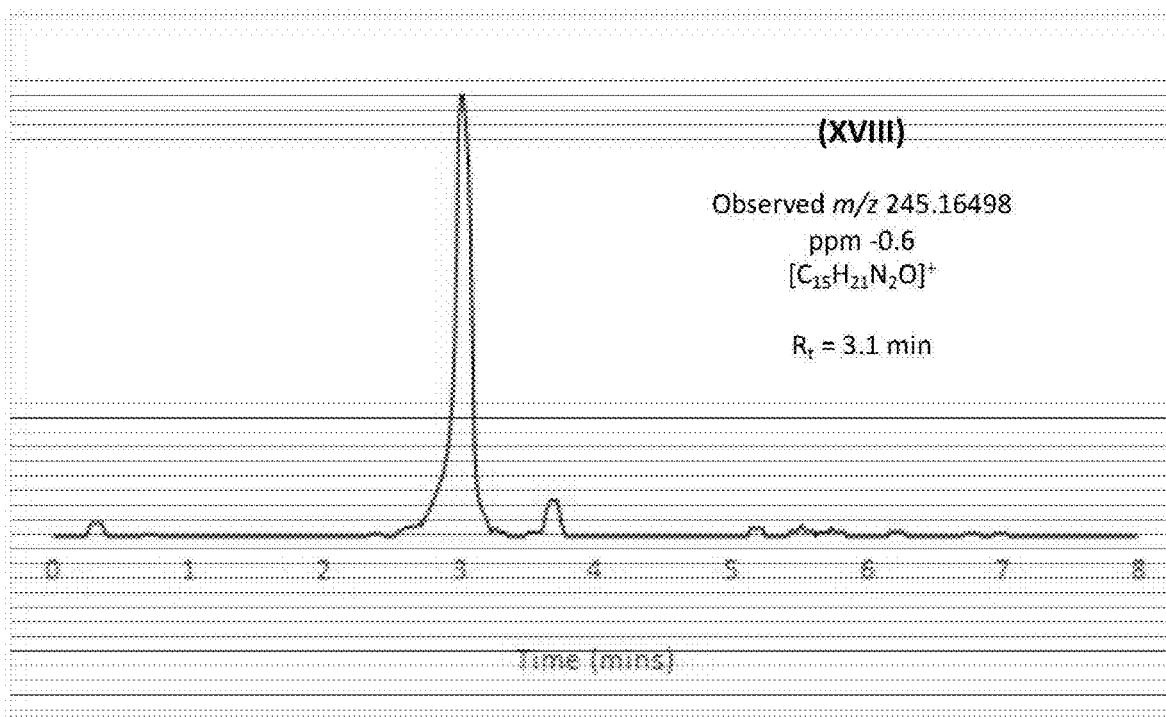
FIGS. 20A and 20B depict a representation of mass spectrometry data in the form of a chromatogram, notably a chromatogram obtained in the performance of an experiment to synthesize an example hydroxylated psilocybin derivative compound having the chemical formula (XVIII) set forth herein (FIG. 20A), and in the form of a mass spectrometry spectrum obtained in the performance of an experiment to identify a hydroxylated psilocybin derivative compound having the chemical formula (XVIII) set forth herein (FIG. 20B).

(XVIII)

eluted at 3.1 minutes (EIC, see: FIG. 20A).

Figure 20B:
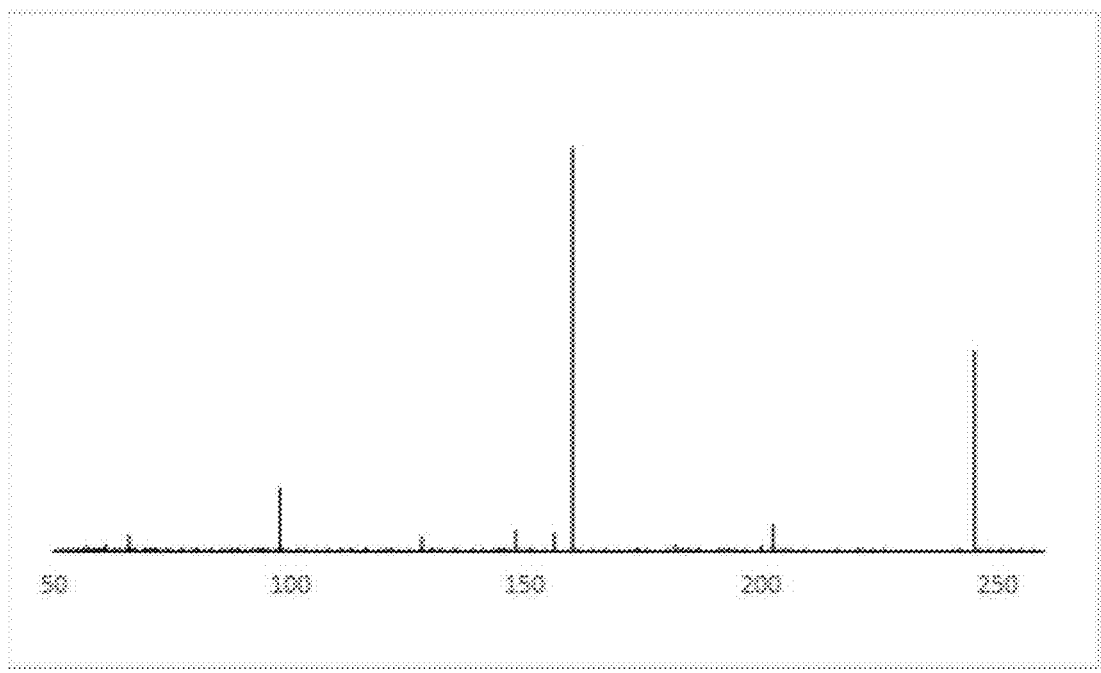

High energy collisions (HOD) were achieved as described in Example 4. Elemental formulae were assigned to subsequent diagnostic ion species characteristic of a compound of formula (XVIII) (FIG. 20B, Table VII).

TABLE VII relative abundance of molecular species in a sample containing compound (XVIII)

| m/z | % Relative abundance | Fragment | Empirical formula |
|---|---|---|---|
| 160.0755 | 100 | $[M + H - NH_2C_5H_9]^+$ | $C_{10}H_{11}NO$ |
| 245.1658 | 49 | $[M + H]^+$ | $C_{15}H_{21}N_2O$ |
| 98.0960 | 16 | | $C_6H_{12}N$ |
| 202.5918 | 7 | | |
| 148.0754 | 5 | | $C_9H_{10}ON$ |

TABLE VII-continued relative abundance of molecular species in a sample containing compound (XVIII)

| m/z | % Relative abundance | Fragment | Empirical formula |
|---|---|---|---|
| 156.1745 | 5 | | |
| 66.1249 | 4 | | |
| 128.1432 | 4 | | $C_8H_{18}N$ |

Example 12—Process for Making a Twelfth Hydroxylated Psilocybin Derivative Using Synthetic Chemistry Chemical synthesis was conducted as described in Example 4, except that butylamine (9.00 total eq, required for R group "A" in FIG. 11) was used in place of N-ethyl(isopropyl)amine. Analysis was carried out using high-resolution LC-HESI-LTQ-Orbitrap-XL MS (Thermo Fisher Scientific) as described in Example 4. Singly protonated product with exact m/z and expected elemental formula matching protonated 3-[2-(butylamino)ethyl]-1H-indol-4-ol (R-group "A" in FIG. 11) and having chemical formula (XXVI):

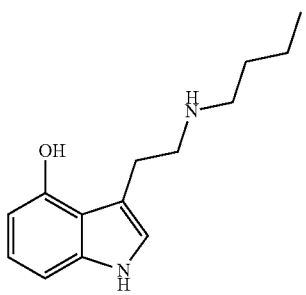

Figure 21A:
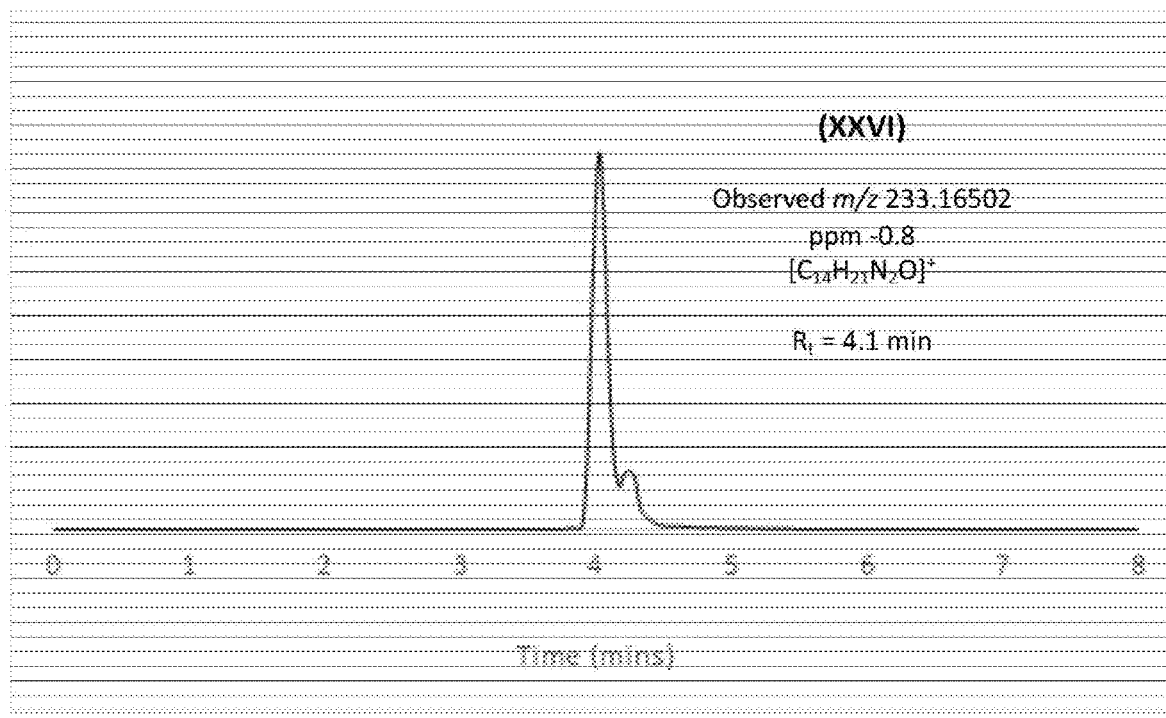
FIGS. 21A and 21B depict a representation of mass spectrometry data in the form of a chromatogram, notably a chromatogram obtained in the performance of an experiment to synthesize an example hydroxylated psilocybin derivative compound having the chemical formula (XXVI) set forth herein (FIG. 21A), and in the form of a mass spectrometry spectrum obtained in the performance of an experiment to identify a hydroxylated psilocybin derivative compound having the chemical formula (XXVI) set forth herein (FIG. 21B).

(XXVI)

eluted at 4.1 minutes (EIC, see: FIG. 21A).

Figure 21B:
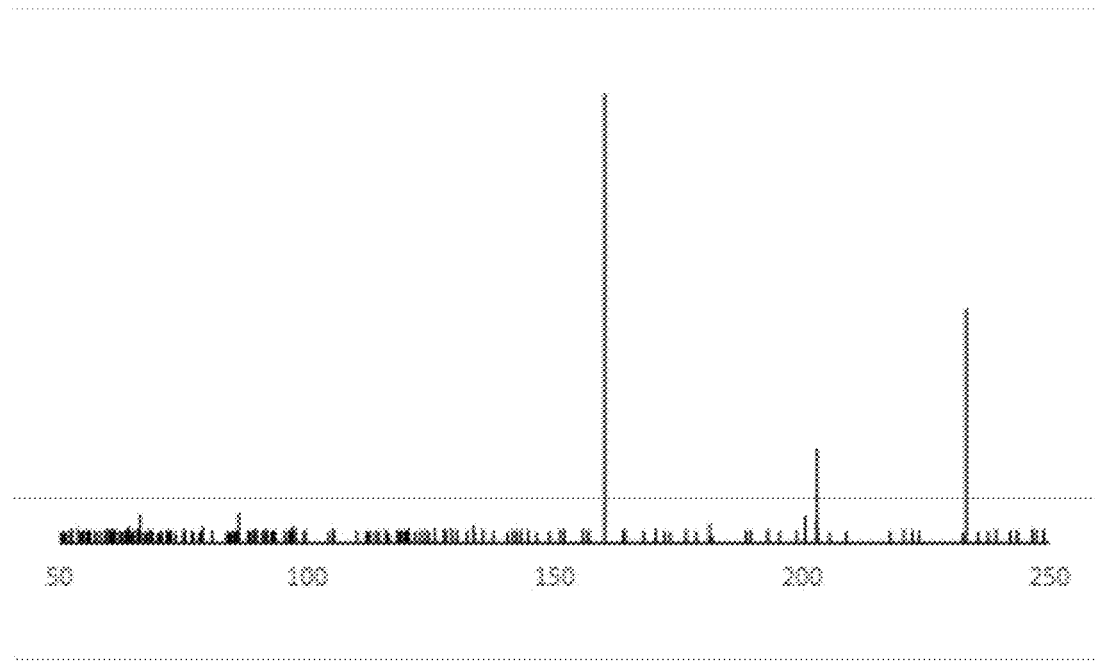

High energy collisions (HOD) were achieved as described in Example 4. Elemental formulae were assigned to subsequent diagnostic ion species characteristic of a compound of formula (XXVI) (FIG. 21B, Table VIII).

TABLE VIII relative abundance of molecular species in a sample containing compound (XXVI)

| m/z | % Relative abundance | Fragment | Empirical formula |
|---|---|---|---|
| 160.0755 | 100 | $[M + H - NH_2C_4H_9]^+$ | $C_{10}H_{11}NO$ |
| 233.1649 | 51 | $[M + H]^+$ | $C_{14}H_{21}N_2O$ |
| 203.0414 | 21 | $[M + H - C_2H_6]^+$ | $C_{12}H_{15}N_2O$ |
| 86.0962 | 6 | | $C_5H_{12}N$ |
| 66.1252 | 6 | | |
| 200.6570 | 6 | | |
| 202.9407 | 5 | | |

Example 13—Process for Making a Thirteenth Hydroxylated Psilocybin Derivative Using Synthetic Chemistry Chemical synthesis was conducted as described in Example 4, except that dodecylamine (9.00 total eq, required for R group "L" in FIG. 11) was used in place of N-ethyl(isopropyl)amine. Analysis was carried out using high-resolution LC-HESI-LTQ-Orbitrap-XL MS (Thermo Fisher Scientific) as described in Example 4. Singly protonated product with exact m/z and expected elemental formula matching protonated 3-[2-(dodecylamino)ethyl]-1H-indol-4-ol (R-group in FIG. 11) and having chemical formula (XXVII):

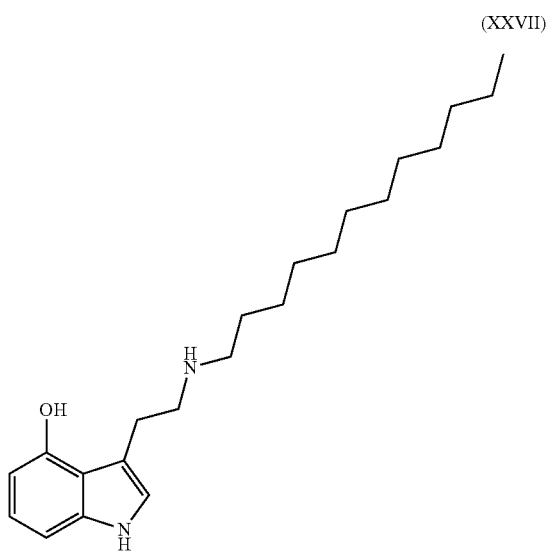

Figure 22A:
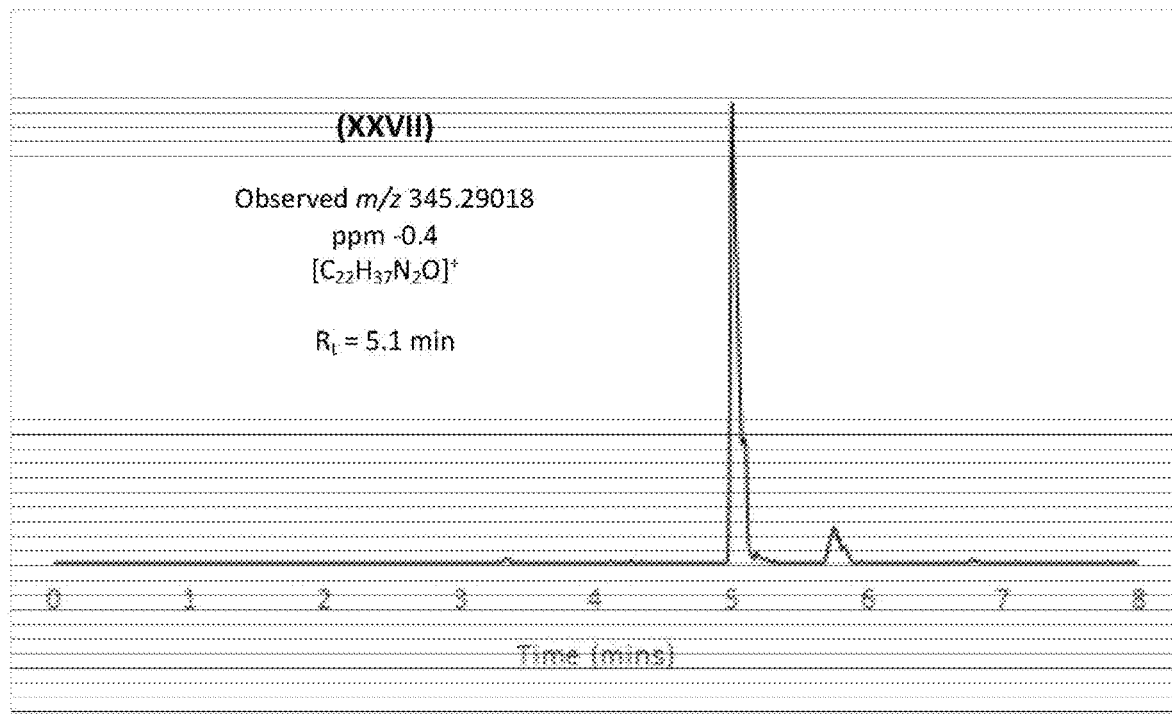
FIGS. 22A and 22B depict a representation of mass spectrometry data in the form of a chromatogram, notably a chromatogram obtained in the performance of an experiment to synthesize an example hydroxylated psilocybin derivative compound having the chemical formula (XXVII) set forth herein (FIG. 22A), and in the form of a mass spectrometry spectrum obtained in the performance of an experiment to identify a hydroxylated psilocybin derivative compound having the chemical formula (XXVII) set forth herein (FIG. 22B).

(XXVII)

eluted at 5.1 minutes (EIC, see: FIG. 22A).

Figure 22B:
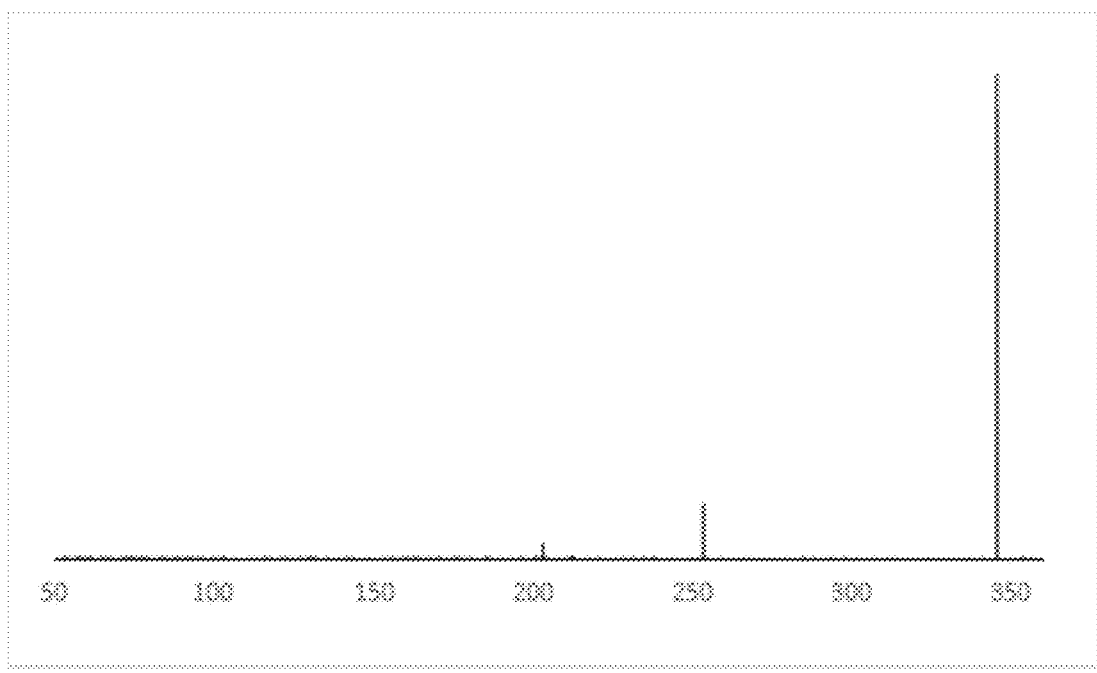

High energy collisions (HOD) were achieved as described in Example 4. Elemental formulae were assigned to subsequent diagnostic ion species characteristic of a compound of formula (XXVII), (FIG. 22B, Table IX).

TABLE IX relative abundance of molecular species in a sample containing compound (XXVII)

| m/z | % Relative abundance | Fragment | Empirical formula |
|---|---|---|---|
| 345.3265 | 100 | [M + H]$^+$ | $C_{22}H_{36}N_2O$ |
| 253.2640 | 12 | | $C_{16}H_{33}N_2$ |
| 203.0388 | 3 | | |
| 345.2809 | 1 | | |
| 200.6552 | 0.8 | | |
| 345.3366 | 0.7 | | |
| 56.9881 | 0.6 | | |

Example 14—Process for Making a Fourteenth Hydroxylated Psilocybin Derivative Using Synthetic Chemistry Chemical synthesis was conducted as described in Example 4, except that dihexylamine (9.00 total eq, required for R group "J" in FIG. 11) was used in place of N-ethyl (isopropyl)amine. Analysis was carried out using high-resolution LC-HESI-LTQ-Orbitrap-XL MS (Thermo Fisher Scientific) as described in Example 4. Singly protonated product with exact m/z and expected elemental formula matching protonated 3-[2-(dihexylamino)ethyl]-1H-indol-4-ol (R-group "J" in FIG. 11) and having chemical formula (XXIX):

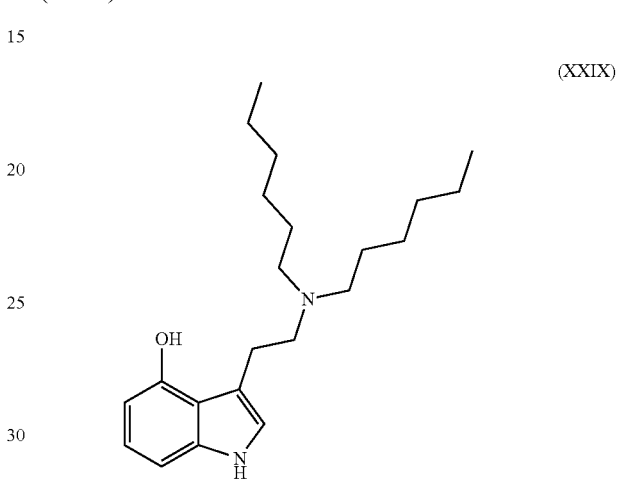

Figure 23A:
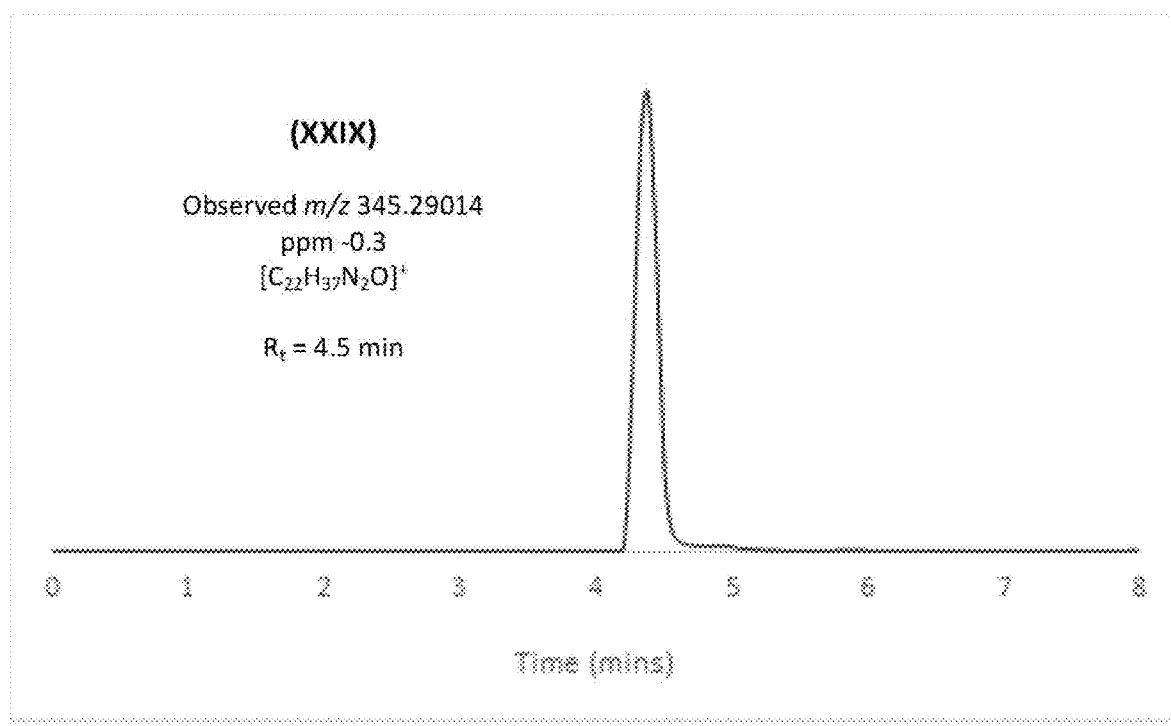
FIGS. 23A and 23B depict a representation of mass spectrometry data in the form of a chromatogram, notably a chromatogram obtained in the performance of an experiment to synthesize an example hydroxylated psilocybin derivative compound having the chemical formula (XXIX) set forth herein (FIG. 23A), and in the form of a mass spectrometry spectrum obtained in the performance of an experiment to identify a hydroxylated psilocybin derivative compound having the chemical formula (XXIX) set forth herein (FIG. 23B).

(XXIX)

eluted at 4.5 minutes (EIC, see: FIG. 23A).

Figure 23B:
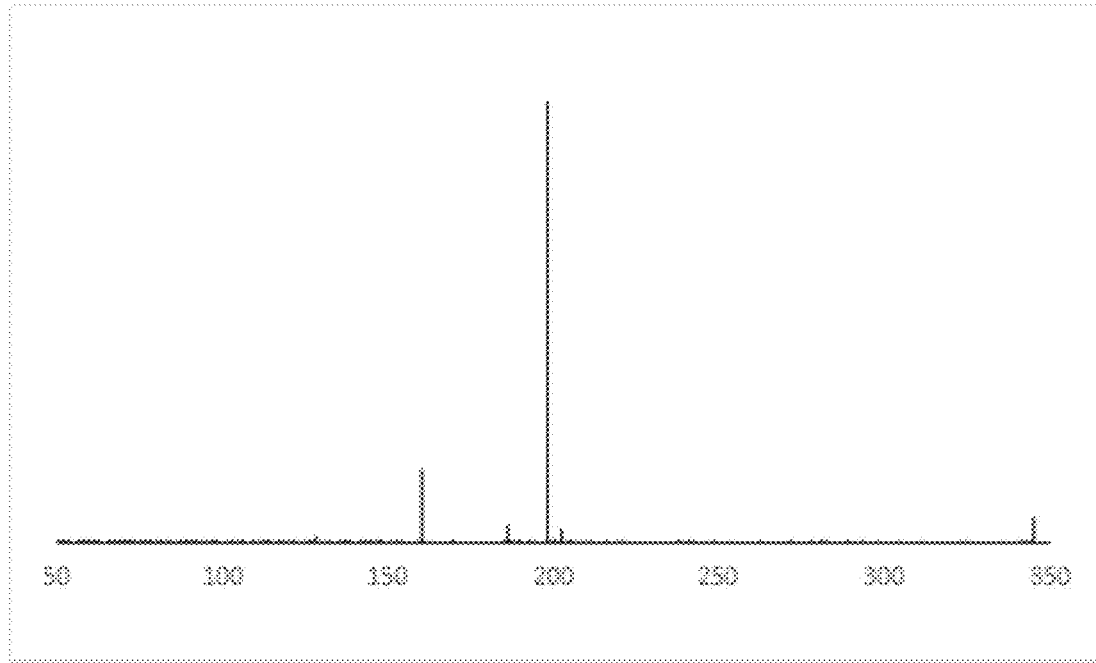

High energy collisions (HOD) were achieved as described in Example 4. Elemental formulae were assigned to subsequent diagnostic ion species characteristic of a compound of formula (XXIX), (FIG. 23B, Table X).

TABLE X relative abundance of molecular species in a sample containing compound (XXIX)

| m/z | % Relative abundance | Fragment | Empirical formula |
|---|---|---|---|
| 198.2215 | 100 | | |
| 160.0755 | 17 | [M + H − $NH_2C_{12}H_{26}$]$^+$ | $C_{10}H_{11}NO$ |
| 345.2904 | 6 | [M + H]$^+$ | $C_{22}H_{37}N_2O$ |
| 186.2215 | 4 | | |
| 202.4168 | 3 | | |
| 128.1431 | 2 | | |
| 200.0211 | 1 | | |
| 202.5173 | 0.8 | | |
| 198.2173 | 0.8 | | |

The invention claimed is:

1. A chemical compound of formula (I):

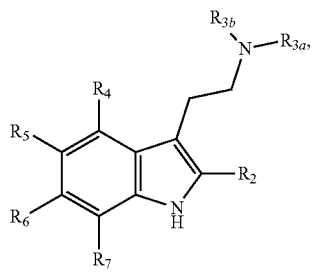

or a salt thereof
wherein
$R_4$ is a hydroxy group, $R_5$ is an alkyl group, $R_2$, $R_6$, or $R_7$ are a hydrogen atom or an alkyl group, and wherein $R_{3a}$ is a $C_2$-$C_{20}$ alkyl group, a cycloalkyl group, an alkaryl group, an aryl group, or an acyl group, and $R_{3b}$ is an alkyl group, a cycloalkyl group, an alkaryl group, an aryl group, an acyl group, or a hydrogen atom.

2. A chemical compound according to claim 1, wherein one of $R_2$, $R_6$, or $R_7$ is an alkyl group, and the remaining $R_2$, $R_6$, or $R_7$ are a hydrogen atom.

3. A chemical compound according to claim 1, wherein $R_5$, $R_6$, or $R_7$ are independently a $C_1$-$C_6$ alkyl group.

4. A chemical compound according to claim 1, wherein $R_5$, $R_6$, or $R_7$ are independently a $C_1$-$C_3$ alkyl group.

5. A chemical compound according to claim 1, wherein all of $R_2$, $R_6$, and $R_7$ are a hydrogen atom.

6. A chemical compound according to claim 1, wherein $R_{3a}$ is a $C_2$-$C_{20}$ alkyl group, a cycloalkyl group, an alkaryl group, an aryl group, or an acyl group, and $R_{3b}$ is a hydrogen atom.

7. A chemical compound according to claim 1, wherein $R_{3a}$ and $R_{3b}$ are independently a $C_2$-$C_{20}$ alkyl group, a cycloalkyl group, an alkaryl group, an aryl group, or an acyl group.

8. A chemical compound according to claim 1, wherein $R_{3a}$ and $R_{3b}$ are each independently a $C_2$-$C_{20}$ alkyl group.

9. A chemical compound according to claim 1, wherein $R_{3a}$ is an acyl group and $R_{3b}$ is a hydrogen atom.

10. A chemical compound according to claim 9, wherein the acyl group is a —C(=O)($C_1$-$C_6$)-alkyl group.

11. A chemical compound according to claim 9, wherein the acyl group is —C(=O)(CH$_3$).

12. A chemical compound according to claim 1, wherein $R_{3a}$ is an acyl group and $R_{3b}$ is a hydrogen atom, wherein $R_5$ is a $C_1$-$C_3$ alkyl group.

13. A chemical compound according to claim 12, wherein the acyl group is a —C(=O)($C_1$-$C_6$)-alkyl group.

14. A chemical compound according to claim 13, wherein the acyl group is —C(=O)(CH$_3$).

15. A chemical compound according to claim 1, wherein when $R_{3a}$ is a $C_2$-$C_{12}$ alkyl group, and $R_{3b}$ is a hydrogen atom.

16. A chemical compound according to claim 1, wherein $R_{3a}$ is a cycloalkyl group, and the cycloalkyl group is a cyclopentyl, cyclohexyl or cycloheptyl group, and $R_{3b}$ is a hydrogen atom.

17. A chemical compound according to claim 1, wherein when one of $R_{3a}$ is an alkaryl group, wherein the alkaryl group is a ($C_1$-$C_6$)-alk-($C_6$-$C_{10}$) aryl, and $R_{3b}$ is a hydrogen atom.

18. A chemical compound according to claim 17, wherein the ($C_1$-$C_6$)-alk-($C_6$-$C_{10}$) aryl is ($C_1$-$C_6$)-alk-phenyl.

19. A chemical compound according to claim 17, wherein ($C_1$-$C_6$)-alk-($C_6$-$C_{10}$) aryl is —(CH$_2$)-phenyl or —(CH$_2$CH$_2$)-phenyl.

20. A chemical compound according to claim 17, wherein ($C_1$-$C_6$)-alk-($C_6$-$C_{10}$) aryl group is —(CH$_2$CH(CH$_3$))-phenyl or —(CH(CH$_3$))-phenyl.

21. A chemical compound according to claim 1, wherein the chemical compound is a compound having formula (III):

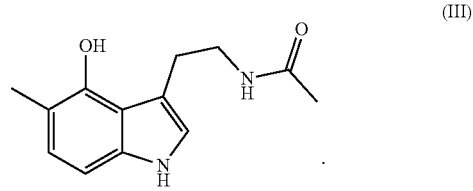 [SMILES: CC(=O)NCCc1c[nH]c2ccc(C)c(O)c12]

22. A chemical compound or salt thereof according to claim 1, wherein the compound is at least about 95% pure.

23. A pharmaceutical drug formulation comprising an effective amount of a chemical compound according to claim 1, together with a pharmaceutically acceptable diluent, carrier, or excipient.

24. A method for treating a psychiatric disorder, the method comprising administering to a subject in need thereof a pharmaceutical formulation comprising a chemical compound according to claim 1, wherein the pharmaceutical formulation is administered in an effective amount to treat the psychiatric disorder in the subject.

25. A chemical compound or salt thereof according to claim 21, wherein the compound is at least about 95% pure.

26. A pharmaceutical drug formulation comprising an effective amount of a chemical compound according to claim 21, together with a pharmaceutically acceptable diluent, carrier, or excipient.

* * * * *